United States Patent
Olson et al.

(10) Patent No.: US 6,525,044 B2
(45) Date of Patent: Feb. 25, 2003

(54) SUCCINOYLAMINO CARBOCYCLES AND HETEROCYCLES AS INHIBITORS OF A-β PROTEIN PRODUCTION

(75) Inventors: Richard E Olson, Wilmington, DE (US); Thomas P Maduskuie, Wilmington, DE (US); Lorin Andrew Thompson, Wilmington, DE (US); Andrew J Tebben, Wallingford, PA (US); Nenghui Wang, Newark, DE (US); Wei Deng, Wilmington, DE (US); Hong Liu, Glen Mills, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/788,227

(22) Filed: Feb. 16, 2001

(65) Prior Publication Data

US 2002/0055501 A1 May 9, 2002

Related U.S. Application Data

(60) Provisional application No. 60/183,186, filed on Feb. 17, 2000.

(51) Int. Cl.[7] ..................... C07D 487/04; C07D 471/04; C07D 471/08; A61K 31/55; A61P 25/28

(52) U.S. Cl. ........................ 514/220; 540/496

(58) Field of Search ........................ 540/496; 514/220

(56) References Cited

U.S. PATENT DOCUMENTS

| | | | | |
|---|---|---|---|---|
| 4,929,614 A | * | 5/1990 | Calvet et al. ............... | 540/214 |
| 5,283,241 A | | 2/1994 | Bochis et al. ............... | 514/183 |
| 5,532,359 A | | 7/1996 | Marsters et al. ............ | 540/522 |
| 5,550,126 A | | 8/1996 | Horwell et al. .......... | 514/237.5 |
| 5,578,629 A | | 11/1996 | Ciccarone et al. .......... | 514/397 |
| 5,595,990 A | | 1/1997 | Baldwin et al. ............ | 514/221 |
| 5,602,145 A | | 2/1997 | Samanen .................... | 514/309 |
| 5,602,156 A | | 2/1997 | Kohn et al. ................. | 514/359 |
| 5,618,812 A | | 4/1997 | Pineiro et al. .............. | 514/221 |
| 5,672,596 A | | 9/1997 | Wyvratt et al. ............. | 514/183 |
| 5,703,129 A | | 12/1997 | Felsenstein ................. | 514/613 |
| 5,710,153 A | | 1/1998 | Ohmoto et al. .......... | 514/236.2 |
| 5,710,171 A | | 1/1998 | Dinsmore et al. .......... | 514/396 |
| 5,756,528 A | | 5/1998 | Anthony et al. ............ | 514/399 |
| 5,763,437 A | | 6/1998 | Sato et al. ................... | 514/221 |
| 5,770,573 A | | 6/1998 | Arrhenius et al. .......... | 514/183 |
| 5,852,010 A | | 12/1998 | Graham et al. ............ | 514/221 |
| 5,856,326 A | | 1/1999 | Anthony et al. ............ | 514/252 |
| 5,859,012 A | | 1/1999 | Dinsmore et al. .......... | 514/252 |
| 5,869,682 A | | 2/1999 | DeSolms ................. | 548/335.5 |
| 5,872,135 A | | 2/1999 | DeSolms .................... | 514/326 |
| 5,885,995 A | | 3/1999 | Dinsmore .................... | 514/326 |
| 5,891,889 A | | 4/1999 | Anthony et al. ............ | 514/326 |
| 5,905,077 A | | 5/1999 | Jungheim et al. ........ | 514/222.2 |
| 5,919,785 A | | 7/1999 | Dinsmore et al. .......... | 514/255 |
| 5,936,089 A | | 8/1999 | Carpino et al. ............. | 546/143 |
| 5,965,578 A | | 10/1999 | Graham et al. ............ | 514/326 |
| 5,985,900 A | | 11/1999 | Abreo et al. ................ | 514/336 |

FOREIGN PATENT DOCUMENTS

| | | |
|---|---|---|
| EP | 0421802 | 4/1991 |
| EP | 0434360 | 6/1991 |
| EP | 0842944 | 5/1998 |
| WO | WO 9217460 | 10/1992 |
| WO | WO 9403437 | 2/1994 |
| WO | WO 9405634 | 3/1994 |
| WO | WO 9414776 | 7/1994 |
| WO | WO 9509633 | 4/1995 |
| WO | WO 9617833 | 6/1996 |
| WO | WO 9618602 | 6/1996 |
| WO | WO 9620918 | 7/1996 |
| WO | WO 9629313 | 9/1996 |
| WO | WO 9633165 | 10/1996 |
| WO | WO 9639137 | 12/1996 |
| WO | WO 9942889 | 2/1997 |
| WO | WO 9712861 | 4/1997 |
| WO | WO 9719053 | 5/1997 |
| WO | WO 9727852 | 8/1997 |
| WO | WO 9736877 | 10/1997 |
| WO | WO 9736879 | 10/1997 |
| WO | WO 9736900 | 10/1997 |
| WO | WO 9738664 | 10/1997 |
| WO | WO 9745412 | 12/1997 |
| WO | WO 9816523 | 4/1998 |
| WO | WO 9822430 | 5/1998 |
| WO | WO 9822433 | 5/1998 |
| WO | WO 9822441 | 5/1998 |
| WO | WO 9822493 | 5/1998 |
| WO | WO 9827053 | 6/1998 |

(List continued on next page.)

OTHER PUBLICATIONS

Dingwall; J. Clinical Invest., 108, Nov. 2001, 1243–1246.

Selkoe; J. Alzheimer's Disease, 3, 2001, p. 75–81.

Tanzi and Parson, "Decoding Darkness, The Search for the Genetic Causes of Alzheimer's Disease", Perseus Publishing, 2000, pp. xvii–xviii.

Olson et al., Current Opinion Drug Discovery and Development, 4, 2001, p. 390–401.

Su San Mok et al, A Novel Metalloprotease in Rat rain cleaves. .Biochemistry, vol. 36, No. 1, 1997, pp. 156–63 XP002177252.

Primary Examiner—Bruck Kifle
(74) Attorney, Agent, or Firm—Scott K. Larsen

(57) ABSTRACT

This invention relates to novel carbocycles and heterocycles having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

18 Claims, No Drawings

FOREIGN PATENT DOCUMENTS

| | | |
|---|---|---|
| WO | WO 9828268 | 7/1998 |
| WO | WO 9828980 | 7/1998 |
| WO | WO 9837079 | 8/1998 |
| WO | WO 9841510 | 9/1998 |
| WO | WO 9844797 | 10/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9918951 | 4/1999 |
| WO | WO 9919305 | 4/1999 |
| WO | WO 9932453 | 7/1999 |
| WO | WO 9966934 | 12/1999 |
| WO | WO 9967219 | 12/1999 |
| WO | WO 9967220 | 12/1999 |
| WO | WO 9967221 | 12/1999 |
| WO | WO 0002903 | 1/2000 |
| WO | WO 0007995 | 2/2000 |
| WO | WO 0028331 | 5/2000 |
| WO | WO 0038618 | 7/2000 |
| WO | WO 0160826 | 8/2001 |

* cited by examiner

SUCCINOYLAMINO CARBOCYCLES AND HETEROCYCLES AS INHIBITORS OF A-β PROTEIN PRODUCTION

This application claims the benefit of U.S. Provisional Application No. 60/183,186, filed Feb. 17, 2000.

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotional stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to deposition of Aβ in amyloid plaques, Aβ is also found in the walls of meningeal and parenchymal arterioles, small arteries, capillaries, and sometimes, venules. Aβ was first purified, and a partial amino acid reported, in 1984 (Glenner and Wong, Biochem. Biophys. Res. Commun. 120: 885-890). The isolation and sequence data for the first 28 amino acids are described in U.S. Pat. No 4,666,829.

Compelling evidence accumulated during the last decade revealed that Aβ is an internal polypeptide derived from a type 1 integral membrane protein, termed b amyloid precursor protein (APP). β APP is normally produced by many cells both in vivo and in cultured cells, derived from various animals and humans. AP is derived from cleavage of β APP by as yet unknown enzyme (protease) system(s), collectively termed secretases.

The existence of at least four proteolytic activities has been postulated. They include β secretase(s), generating the N-terminus of Aβ, a secretase(s) cleaving around the 16/17 peptide bond in Aβ, and y secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other b APP mutations have been described in familiar forms of AD. Fourthly, similar neuropathological changes have been observed in transgenic animals overexpressing mutant forms of human β APP. Fifthly, individuals with Down's syndrome have an increased gene dosage of b APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

PCT publication number WO 96/29313 discloses the general formula:

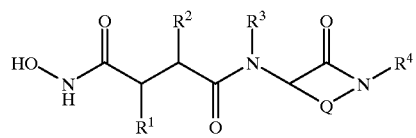

covering metalloprotease inhibiting compounds useful for the treatment of diseases associated with excess and/or unwanted matrix metalloprotease activity, particularly collagenase and or stromelysin activity.

Compounds of general formula:

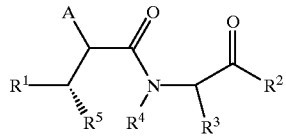

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer.

European Patent Application number EP 0652009A1 relates to the general formula:

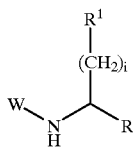

and discloses compounds that are protease inhibitors that inhibit AD production.

U.S. Pat. No. 5703129 discloses the general formula:

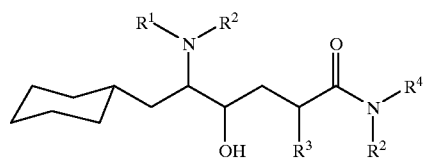

which covers 5-amino-6-cyclohexyl-4-hydroxy-hexanamide derivatives that inhibit AD production and are useful in the treatment of Alzheimer's disease.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

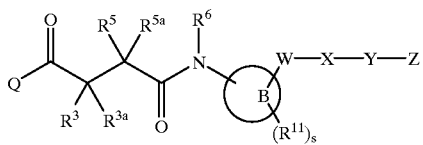

or pharmaceutically acceptable salt or prodrug forms thereof, wherein $R^3$, $R^{3a}$, $R^5$, $R^{5a}$, $R^6$, Q, B, W, X, Y, and Z are defined below, are effective inhibitors of the production of Aβ.

DETAILED DESCRIPTION OF PREFERRED EMBODIMENTS

Thus, in a first embodiment, the present invention provides a novel compound of Formula (I):

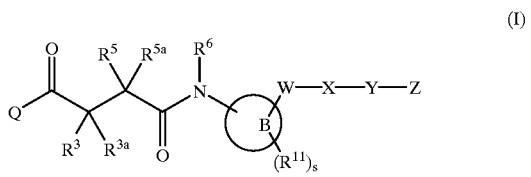

or a pharmaceutically acceptable salt or prodrug thereof, wherein:

Q is $-OR^1$ or $-NR^1R^2$;

ring B is selected from the group consisting of:
- a carbocyclic group of 3 to 8 carbon atoms wherein the carbocyclic group is saturated, partially saturated or unsaturated;
- a heterocycle of 3 to 8 atoms containing a heteroatom selected from the group consisting of $-O-$, $-S-$, $-S(=O)-$, $-S(=O)_2-$, and $-N(R^{10})-$;
- a bicyclic ring system selected from the group consisting of:

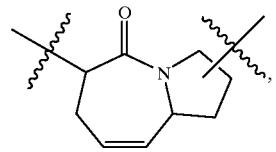

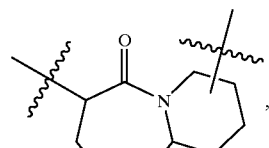

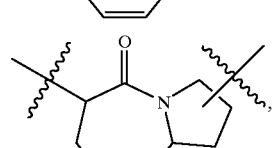

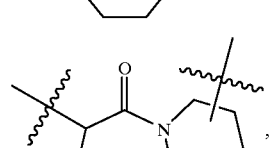

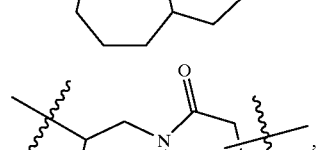

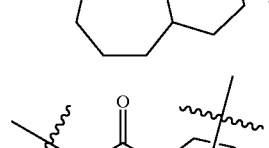

-continued
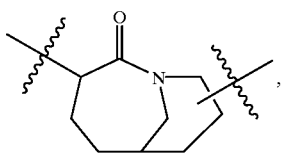,
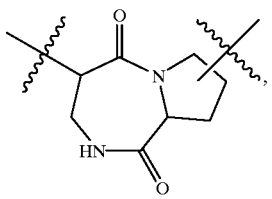,
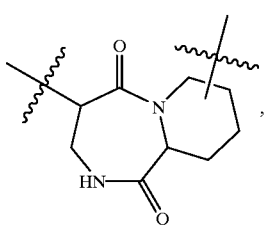,
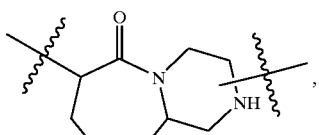,
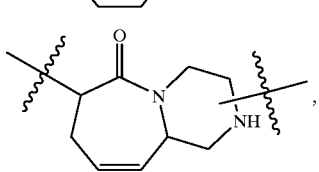,
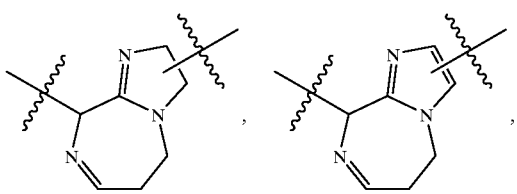,
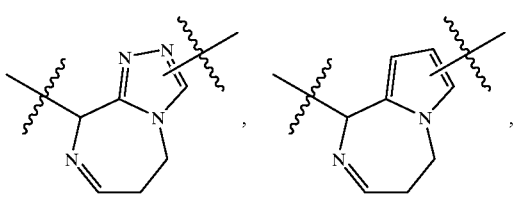,
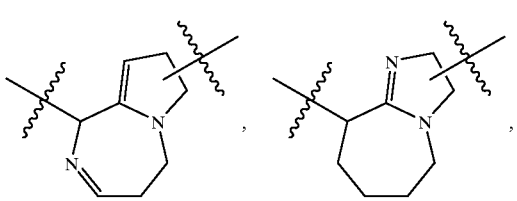,
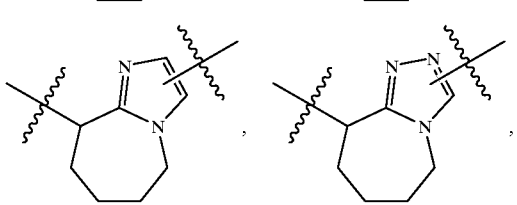,
-continued
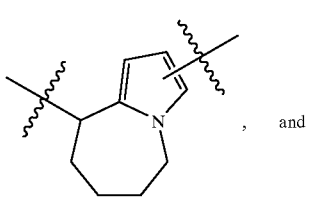, and
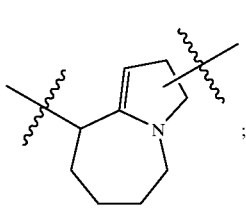;
a tricyclic ring system selected from the group consisting of:
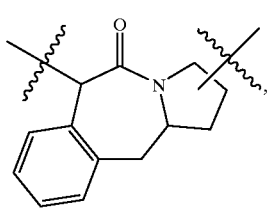,
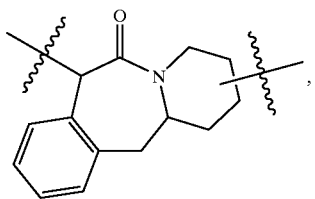,
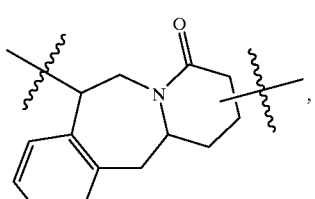,
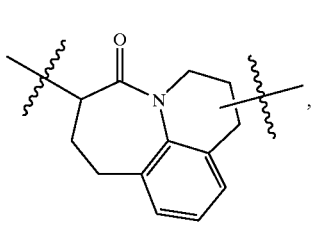,
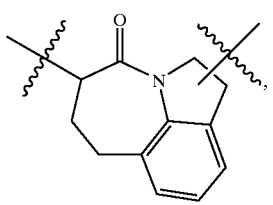, -continued
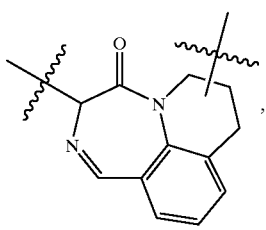,
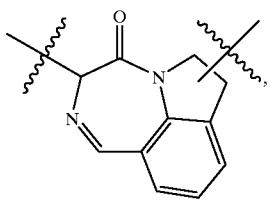,
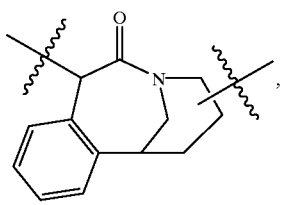,
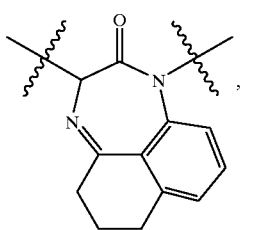,
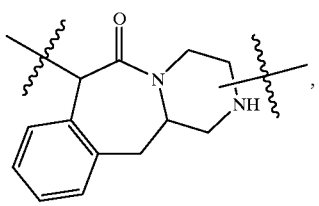,
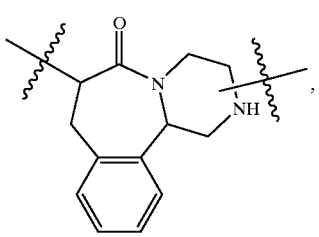,
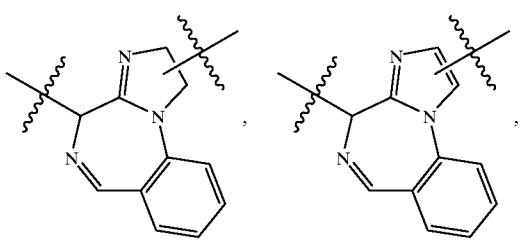,
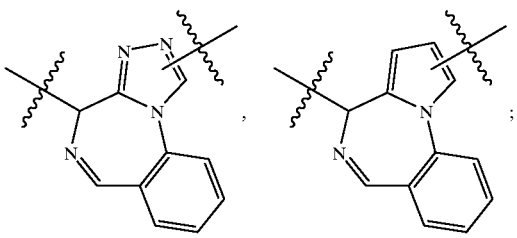,
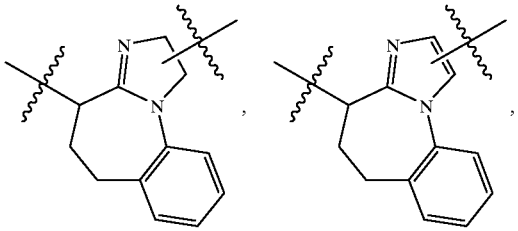;
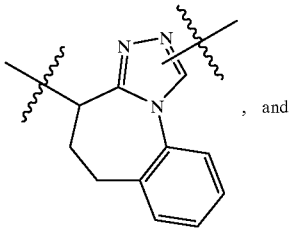, and
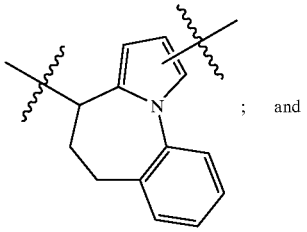;
a tetracyclic ring system selected from the group consisting of:
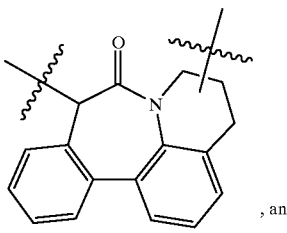, and
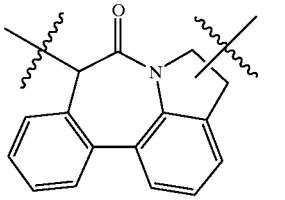;
s is 0, 1, 2, 3, 4, 5, or 6;
$R^1$, at each occurrence, is independently selected from: H;
$C_1$–$C_6$ alkyl substituted with 0–3 $R^{1a}$;
$C_2$–$C_6$ alkenyl substituted with 0–3 $R^{1a}$;

$C_3–C_{10}$ carbocycle substituted with 0–3 $R^{1b}$;

$C_6–C_{10}$ aryl substituted with 0–3 $R^{1b}$; and 5 to 10 membered heterocycle substituted with 0–3 $R^{1b}$;

$R^{1a}$, at each occurrence, is independently selected from H, $C_1–C_6$ alkyl, $OR^{14}$, Cl, F, Br, I, =O, CN, $NO_2$, $NR^{15}R^{16}$, $CF_3$;

$C_3–C_{10}$ carbocycle substituted with 0–3 $R^{1b}$;

$C_6–C_{10}$ aryl substituted with 0–3 $R^{1b}$; and 5 to 6 membered heterocycle substituted with 0–3 $R^{1b}$;

$R^{1b}$, at each occurrence, is independently selected from H, OH, Cl, F, Br, I, CN, $NO_2$, $NR^{15}R^{16}$, $CF_3$, $C_1–C_6$ alkyl, $C_1–C_4$ alkoxy, $C_1–C_4$ haloalkyl, and $C_1–C_4$ haloalkoxy;

$R^2$ is independently selected from H, $NH_2$, OH, $C_1–C_6$ alkyl, $C_1–C_6$ alkoxy, phenoxy, benzyloxy, $C_3–C_{10}$ carbocycle, $C_6–C_{10}$ aryl and 5 to 10 membered heterocycle;

$R^3$ is —$(CR^7R^{7a})_n$—$R^4$,

—$(CR^7R^{7a})$-S -$(CR^7R^{7a})_m$—$R^4$,

—$(CR^7R^{7a})_n$—O-$(CR^7R^{7a})_m$—$R^4$,

—$(CR^7R^{7a})_n$—$N(R^{7b})$—$(CR^7R^{7a})_m$—$R^4$,

—$(CR^7R^{7a})_n$—S(=O)—$(CR^7R^{7a})_m$—$R^4$,

—$(CR^7R^{7a})_n$—$S(=O)_2$—$(CR^7R^{7a})_m$—$R^4$,

—$(CR^7R^{7a})_n$—C(=O)—$(CR^7R^{7a})_m$—$R^4$,

—$(CR^7R^{7a})_n$—$N(R^{7b})C(=O)$—$(CR^7R^{7a})_m$—$R^4$,

—$(CR^7R^{7a})_n$—$C(=O)N(R^{7b})$—$(CR^7R^{7a})_m$—$R^4$

—$(CR^7R^{7a})_n$—$N(R^{7b})S(=O)_2$—$(CR^7R^{7a})_m$—$R^4$, or

—$(CR^7R^{7a})_n$—$S(=O)_2N(R^{7b})$—$(CR^7R^{7a})_m$—$R^4$;

n is 0, 1, 2, or 3;

m is 0, 1, 2, or 3;

$R^{3a}$ is H, OH, $C_1–C_4$ alkyl, $C_1–C_4$ alkoxy, or $C_2–C_4$ alkenyloxy;

alternatively, $R^3$ and $R^{3a}$ may be combined to form a 3–7 membered carbocyclic moiety;

wherein said 3–7 membered carbocyclic moiety is saturated or partially unsaturated;

wherein said 3–7 membered carbocyclic moiety may optionally contain a heteroatom selected from —O—, —S—, —S(=O)—, —$S(=O)_2$—, —N=, —NH—, and —$N(R^{20})$—, and wherein said 3–7 membered carbocyclic moiety is substituted with 0–4 $R^4$;

additionally, two $R^4$ substituents on adjacent atoms may be combined to form a benzo fused radical; wherein said benzo fused radical is substituted with 0–4 $R^{23}$;

additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$; additionally, two $R^4$ substituents on the same or adjacent carbon atoms may be combined to form a $C_3–C_6$ carbocycle substituted with 0–3 $R^{23}$;

$R^4$ is H, OH, $OR^{14a}$, $C_1–C_6$ alkyl substituted with 0–3 $R^{4a}$, $C_2–C_6$ alkenyl substituted with 0–3 $R^{4a}$, $C_2–C_6$ alkynyl substituted with 0–3 $R^{4a}$, $C_3–C_{10}$ carbocycle substituted with 0–3 $R^{4b}$, $C_6–C_{10}$ aryl substituted with 0–3 $R^{4b}$, or 5 to 10 membered heterocycle substituted with 0–3 $R^{4b}$;

$R^{4a}$, at each occurrence, is independently selected from is H, F, Cl, Br, I, $CF_3$, $C_3–C_{10}$ carbocycle substituted with 0–3 $R^{4b}$, $C_6–C_{10}$ aryl substituted with 0–3 $R^{4b}$, or 5 to 10 membered heterocycle substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1–C_6$ alkyl, $C_1–C_4$ alkoxy, $C_1–C_4$ haloalkyl, $C_1–C_4$ haloalkoxy, and $C_1–C_4$ halothioalkoxy;

$R^5$ is H, $OR^{14}$;

$C_1–C_6$ alkyl substituted with 0–3 $R^{5b}$;

$C_1–C_6$ alkoxy substituted with 0–3 $R^{5b}$;

$C_2–C_6$ alkenyl substituted with 0–3 $R^{5b}$;

$C_2–C_6$ alkynyl substituted with 0–3 $R^{5b}$;

$C_3–C_{10}$ carbocycle substituted with 0–3 $R^{5c}$;

$C_6–C_{10}$ aryl substituted with 0–3 $R^{5c}$; or 5 to 10 membered heterocycle substituted with 0–3$R^{5c}$;

$R^{5a}$ is H, OH, $C_1–C_4$ alkyl, $C_1–C_4$ alkoxy, $C_2–C_4$ alkenyl, or $C_2–C_4$ alkenyloxy;

$R^{5b}$, at each occurrence, is independently selected from:

H, $C_1–C_6$ alkyl, $CF_3$, $OR^{14}$, Cl, F, Br, I, =O, CN, $NO_2$, $NR^{15}R^{16}$;

$C_3–C_{10}$ carbocycle substituted with 0–3 $R^{5c}$;

$C_6–C_{10}$ aryl substituted with 0–3 $R^{5c}$; or 5 to 10 membered heterocycle substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1–C_6$ alkyl, $C_1–C_4$ alkoxy, $C_1–C_4$ haloalkyl, $C_1–C_4$ haloalkoxy, and $C_1–C_4$ halothioalkoxy;

alternatively, $R^5$ and $R^{5a}$ may be combined to form a 3–7 membered carbocyclic ring substituted with 0–3 $R^{5c}$; optionally the carbocyclic ring formed by combining $R^5$ and $R^{5a}$ may be benzo fused, wherein the benzo fused ring may be substituted with 0–3 $R^{5c}$;

$R^6$ is H;

$C_1–C_6$ alkyl substituted with 0–3 $R^{6a}$;

$C_3–C_{10}$ carbocycle substituted with 0–3 $R^{6b}$; or $C_6–C_{10}$ aryl substituted with 0–3$R^{6b}$;

$R^{6a}$, at each occurrence, is independently selected from H, $C_1–C_6$ alkyl, $OR^{14}$, Cl, F, Br, I, =O, CN, $NO_2$, $NR^{15}R^{16}$, phenyl or $CF_3$;

$R^{6b}$, at each occurrence, is independently selected from H, OH, Cl, F, Br, I, CN, $NO_2$, $NR^{15}R^{16}$, $CF_3$, $C_1–C_6$ alkyl, $C_1–C_4$ alkoxy, $C_1–C_4$ haloalkyl, and $C_1–C_4$ haloalkoxy;

$R^7$, at each occurrence, is independently selected from H, OH, Cl, F, Br, I, CN, $NO_2$, $CF_3$, and $C_1–C_4$ alkyl;

$R^{7a}$, at each occurrence, is independently selected from H, OH, Cl, F, Br, I, CN, $NO_2$, $CF_3$, aryl and $C_1–C_4$ alkyl;

$R^{7b}$ is independently selected from H and $C_1–C_4$ alkyl;

W is —$(CR^8R^{8a})_p$—;

p is 0, 1, 2, 3, or 4;

$R^8$ and $R^{8a}$, at each occurrence, are independently selected from H, F, $C_1–C_4$ alkyl, $C_2–C_4$ alkenyl, $C_2–C_4$ alkynyl and $C_3–C_8$ cycloalkyl;

X is a bond;

$C_6–C_{10}$ aryl substituted with 0–3 $R^{Xb}$;

$C_3–C_1O$ carbocycle substituted with 0–3 $R^{Xb}$; or 5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1–C_6$ alkyl, $C_1–C_4$ alkoxy, $C_1–C_4$ haloalkyl, $C_1–C_4$ haloalkoxy, and $C_1–C_4$ halothioalkoxy;

Y is a bond or —$(CR^9R^{9a})_t$—V—$(CR^9R^{9a})_u$—;

t is 0, 1, 2, or 3;

u is 0, 1, 2, or 3;

$R^9$ and $R^{9a}$, at each occurrence, are independently selected from H, F, $C_1$-$C_6$ alkyl or $C_3$-$C_8$ cycloalkyl;

V is a bond, —C(=O)—, —O—, —S—, —S(=O)—, —S(=O)$_2$—, —N($R^{19}$)—, —C(=O)N$R^{19b}$—, —N$R^{19b}$C(=O)—, —N$R^{19b}$S(=O)$_2$—, —S(=O)$_2$N$R^{19b}$—, —N$R^{19b}$S(=O)—, —S(=O)N$R^{19b}$—C(=O)O—, or —OC(=O)—;

Z is H;

$C_1$-$C_8$ alkyl substituted with 0–3 $R^{12a}$;
  $C_2$-$C_4$ alkenyl substituted with 0–3 $R^{12a}$;
  $C_2$-$C_4$ alkynyl substituted with 0–3 $R^{12a}$;
  $C_6$-$C_{10}$ aryl substituted with 0–4 $R^{12a}$;
  $C_3$-$C_{10}$ carbocycle substituted with 0–4 $R^{12a}$; or
  5 to 10 membered heterocycle substituted with 0–3 $R^{12a}$;

$R^{12a}$ at each occurrence, is independently selected from
  H, OH, Cl, F, Br, I, CN, NO$_2$, N$R^{15}R^{16}$, —C(=O)N$R^{15}R^{16}$, CF$_3$, acetyl,
  SCH$_3$, S(=O)CH$_3$, S(=O)$_2$CH$_3$, $C_1$-$C_6$ alkyl, $C_1$-$C_4$ alkoxy, $C_1$-$C_4$ haloalkyl,
  $C_1$-$C_4$ haloalkoxy, $C_1$-$C_4$ haloalkyl-S—,
  $C_1$-$C_3$ alkyl substituted with 0–1 $R^{12c}$;
  $C_6$-$C_{10}$ aryl substituted with 0–4 $R^{12b}$;
  $C_3$-$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R_{12b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S-;

$R^{12c}$, at each occurrence, is independently selected from
  $C_6$-$C_{10}$ aryl substituted with 0–4 $R^{12b}$;
  $C_3$-$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{10}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;
  $C_1$-$C_6$ alkyl substituted with 0–2 $R^{10a}$;
  $C_6$-$C_{10}$ aryl substituted with 04 $R^{10b}$;
  $C_3$-$C_{10}$ carbocycle substituted with 0–3 $R^{10b}$; or
  5 to 10 membered heterocycle optionally substituted with 0–3 $R^{10b}$;

$R^{10a}$, at each occurrence, is independently selected from H, $C_1$-$C_6$ alkyl, O$R^{14}$, Cl, F, Br, I, =O, CN, NO$_2$, N$R^{15}R^{16}$, CF$_3$, or aryl substituted with 0–4 $R^{10b}$;

$R^{10b}$, at each occurrence, is independently selected from H, OH, $C_1$-$C_6$ alkyl, $C_1$-$C_4$ alkoxy, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ halothioalkoxy;

alternatively, $R^{10}$ may be —W—X—Y—Z;

$R^{11}$, at each occurrence, is independently selected from H, $C_1$-$C_4$ alkoxy, Cl, F, Br, I, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$;
  $C_1$-$C_6$ alkyl substituted with 0–1 $R^{11a}$;
  $C_6$-$C_{10}$ aryl substituted with 0–3 $R^{11b}$;
  $C_3$-$C_{10}$ carbocycle substituted with 0–3 $R^{11b}$; or
  5 to 10 membered heterocycle substituted with 0–3 $R^{11b}$;

alternatively, two $R^{11}$ substituents on the same or adjacent carbon atoms may be combined to form a $C_3$-$C_6$ carbocycle or a benzo fused radical; wherein said benzo fused radical is substituted with 0–4 $R^{13}$;

$R_{11a}$, at each occurrence, is independently selected from H, $C_1$-$C_6$ alkyl, O$R^{14}$, Cl, F, Br, I, =O, CN, NO$_2$, N$R^{15}R^{16}$, CF$_3$, or phenyl substituted with 0–3 $R^{11b}$;

$R^{11b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ halothioalkoxy;

$R^{13}$, at each occurrence, is independently selected from
  H, OH, $C_1$-$C_6$ alkyl, $C_1$-$C_4$ alkoxy, Cl, F, Br, I, CN, NO$_2$, N$R^{15}R^{16}$, and CF$_3$;

$R^{14}$, at each occurrence, is independently selected from H, phenyl, benzyl, $C_1$-$C_6$ alkyl, or $C_2$-$C_6$ alkoxyalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl);

$R^{16}$, at each occurrence, is independently selected from H, OH, $C_1$-$C_6$ alkyl, benzyl, phenethyl, —C(=O)—($C_1$-$C_6$ alkyl) and —S(=O)$_2$—($C_1$-$C_6$ alkyl);

$R^{17}$ is H, aryl, aryl-CH$_2$—, $C_1$-$C_6$ alkyl, or $C_2$-$C_6$ alkoxyalkyl;

$R^{18}$, at each occurrence, is independently selected from H, $C_1$-$C_6$ alkyl, benzyl, phenethyl, —C(=O)—($C_1$-$C_6$ alkyl) and —S(=O)$_2$—($C_1$-$C_6$ alkyl); and $R^{19}$, at each occurrence, is independently selected from H, OH, $C_1$-$C_6$ alkyl, phenyl, benzyl, phenethyl, —C(=O)—($C_1$-$C_6$ alkyl) and —S(=O)$_2$—($C_1$-$C_6$ alkyl); and $R^{19b}$ is H, $C_1$-$C_6$ alkyl, $C_3$-$C_8$ cycloalkyl, phenyl, benzyl or phenethyl; additionally, $R^{18}$ and $R^{19}$, when substituents on the same atom, may be combined to form a 3 to 7 membered heterocyclic ring;

$R^{20}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;
  $C_1$-$C_6$ alkyl optionally substituted with 0–3 $R^{20a}$; or
  $C_6$-$C_{10}$ aryl substituted with 0–4 $R^{20b}$;

$R^{20a}$, at each occurrence, is independently selected from H, $C_1$-$C_4$ alkyl, O$R^{14}$, Cl, F, Br, I, =O, CN, NO$_2$, N$R^{15}R^{16}$, CF$_3$, or aryl substituted with 0–4 $R^{20b}$;

$R^{20b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_4$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{23}$, at each occurrence, is independently selected from
  H, OH, $C_1$-$C_6$ alkyl, $C_1$-$C_4$ alkoxy, Cl, F, Br, I, CN, NO$_2$, N$R^{15}R^{16}$ and CF$_3$.

[2] In a preferred embodiment the present invention provides a compound of Formula (Ia):

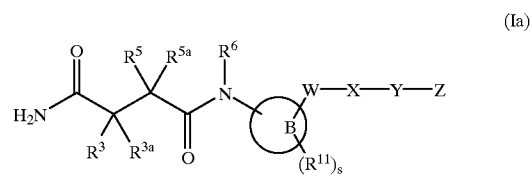

or a pharmaceutically acceptable salt or prodrug thereof, wherein:

ring B is selected from the group consisting of:
- a carbocyclic group of 5 to 7 carbon atoms wherein the carbocyclic group is saturated, partially saturated or unsaturated;
- a heterocycle of 5 to 7 atoms containing a heteroatom selected from the group consisting of —O—, —S—, —S(=O)—, —S(=O)$_2$—, and —N(R$^{10}$)—;
- a bicyclic ring system selected from the group consisting of:
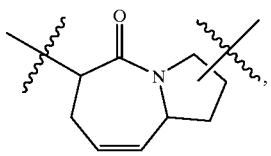
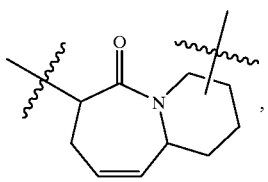
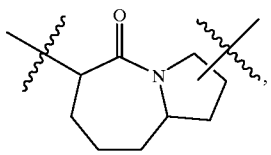
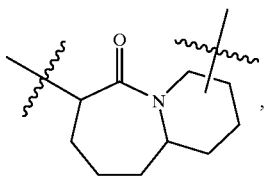
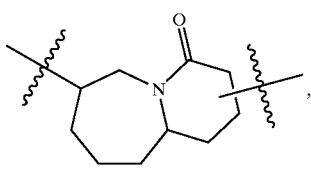
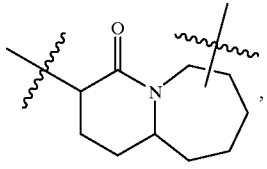
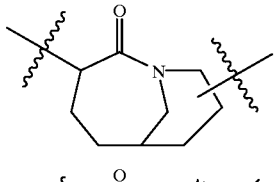
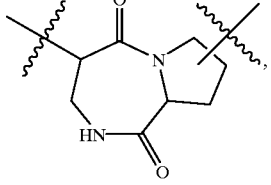
-continued
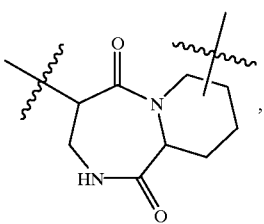
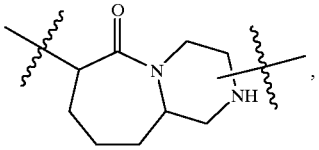
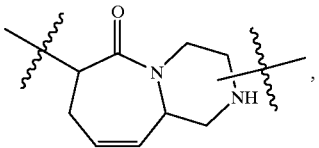
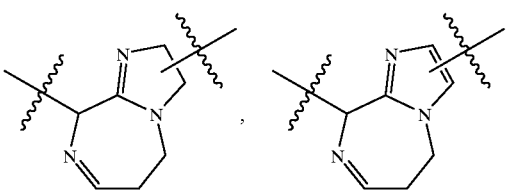
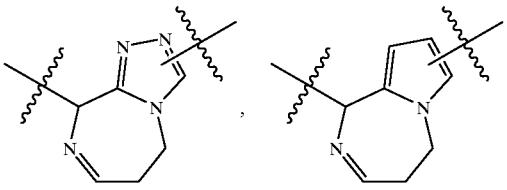
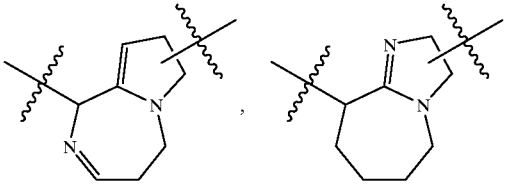
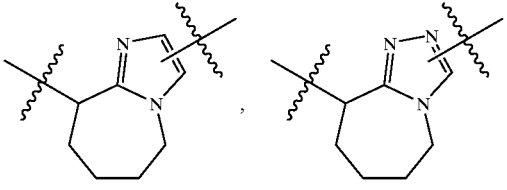
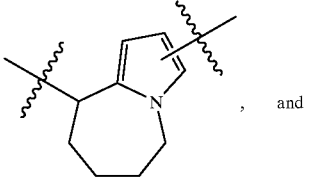, and

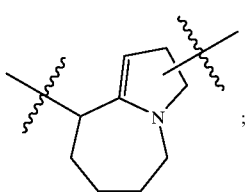;
a tricyclic ring system selected from the group consisting of:
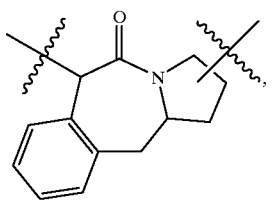,
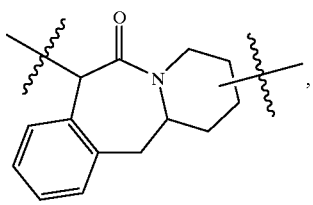,
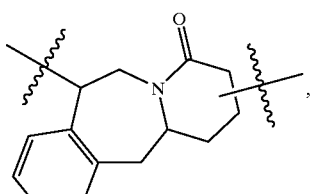,
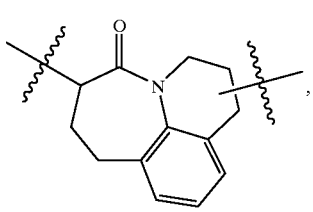,
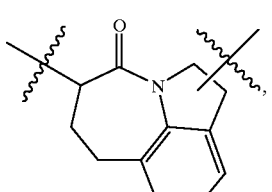,
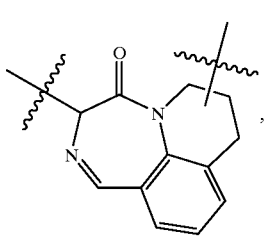,
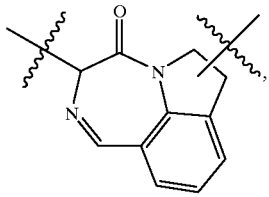,
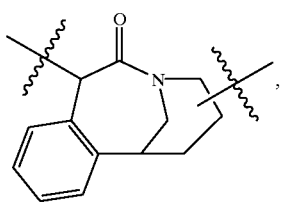,
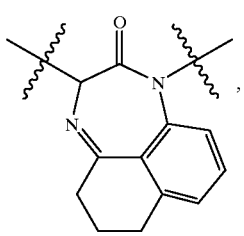,
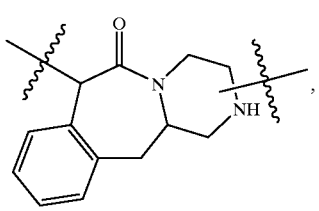,
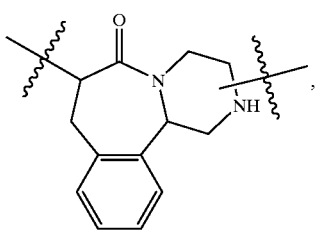,
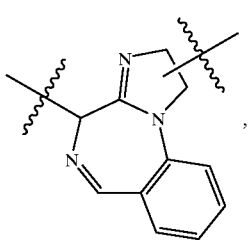, 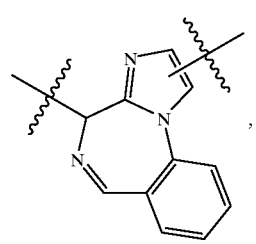,
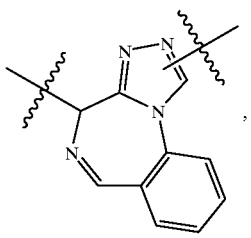, 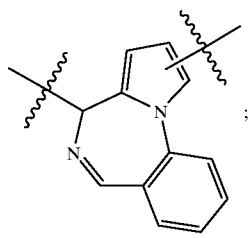;

-continued

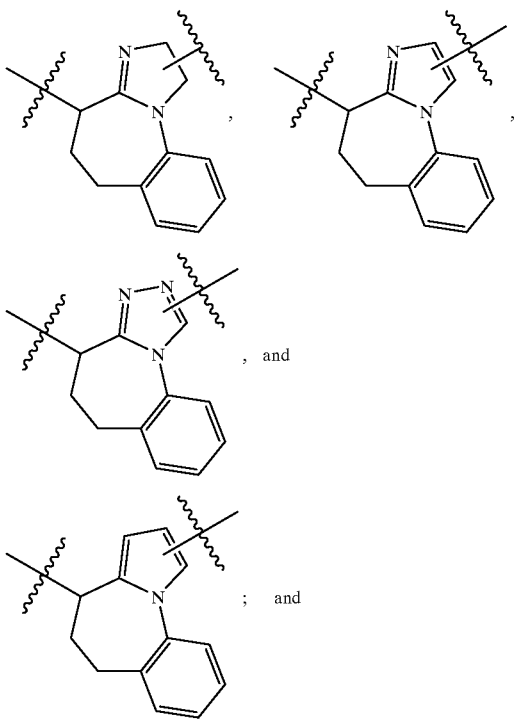

a tetracyclic ring system selected from the group consisting of:

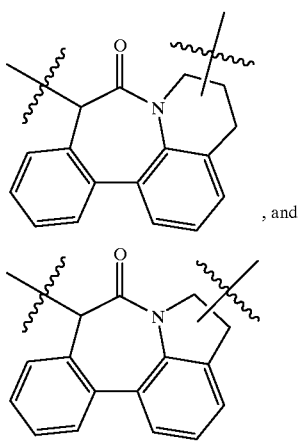

s is, 1, 2, 3, or 4;
$R^3$ is —$(CR^7R^{7a})_n$—$R^4$,
 —$(CR^7R^{7a})_n$—S—$R^4$,
 —$(CR^7R^{7a})_n$—$OR^4$,
 —$(CR^7R^{7a})_n$—$N(R^{7b})_n$—$R^4$,
 —$(CR^7R^{7a})_n$—S(=O)—$R^4$,
 —$(CR^7R^{7a})_n$—S(=O)$_2$—$R^4$, or
 —$(CR^7R^{7a})_n$—C(=O)—$R^4$;
n is 0, 1, or 2;
$R^{3a}$ is H, OH, $C_1$–$C_4$ alkyl, $C_1$–$C_4$ alkoxy, or $C_2$–$C_4$ alkenyloxy;
alternatively, $R^3$ and $R^{3a}$ may be combined to form a 3–7 membered carbocyclic moiety;
  wherein said 3–7 membered carbocyclic moiety is saturated or partially unsaturated;
  wherein said 3–7 membered carbocyclic moiety may optionally contain a heteroatom selected from —O—, —S—, —S(=O)—, —S(=O)$_2$—, —N=, —NH—, and —N($R^{20}$)—, and
  wherein said 3–7 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$ is H, OH, $OR^{14a}$,
 $C_1$–$C_6$ alkyl substituted with 0–3 $R^{4a}$,
 $C_2$–$C_6$ alkenyl substituted with 0–3 $R^{4a}$,
 $C_2$–$C_6$ alkynyl substituted with 0–3 $R^{4a}$,
 $C_3$–$C_{10}$ carbocycle substituted with 0–3 $R^{4b}$,
 $C_6$–$C_{10}$ aryl substituted with 0–3 $R^{4b}$, or
 5 to 10 membered heterocycle substituted with 0–3 $R^{4b}$;
$R^{4a}$, at each occurrence, is independently selected from is H, F, Cl, Br, I, $CF_3$,
 $C_3$–$C_{10}$ carbocycle substituted with 0–3 $R^{4b}$,
 $C_6$–$C_{10}$ aryl substituted with 0–3 $R^{4b}$, or 5 to 10 membered heterocycle substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;
$R^5$ is H;
 $C_1$–$C_6$ alkyl substituted with 0–3 $R^{5b}$;
 $C_2$–$C_6$ alkenyl substituted with 0–3 $R^{5b}$;
 $C_2$–$C_6$ alkynyl substituted with 0–3 $R^{5b}$;
 $C_3$–$C_{10}$ carbocycle substituted with 0–3 $R^{5c}$; or $C_6$–$C_{10}$ aryl substituted with 0–3 $R^{5c}$;
$R^{5a}$ is H, $C_1$–$C_4$ alkyl, or $C_2$–$C_4$ alkenyl;
$R^{5b}$, at each occurrence, is independently selected from:
 H, $C_1$–$C_6$ alkyl, $CF_3$, $OR^{14}$, Cl, F, Br, I, =O, CN, $NO_2$, $NR^{15}R^{16}$;
 $C_3$–$C_{10}$ carbocycle substituted with 0–3 $R^{5c}$;
 $C_6$–$C_{10}$ aryl substituted with 0–3 $R^{5c}$; or
 5 to 10 membered heterocycle substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;
alternatively, $R^5$ and $R^{5a}$ may be combined to form a 3–7 membered carbocyclic ring substituted with 0–3 $R^{5c}$; optionally the carbocyclic ring formed by combining $R^5$ and $R^{5a}$ may be benzo fused, wherein the benzo fused ring may be substituted with 0–3 $R^{5c}$;
$R^6$ is H;
 $C_1$–$C_6$ alkyl substituted with 0–3 $R^{6a}$;
 $C_3$–$C_{10}$ carbocycle substituted with 0–3 $R^{6b}$; or
 $C_6$–$C_{10}$ aryl substituted with 0–3$R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;

$R^{6b}$, at each occurrence, is independently selected from H, OH, Cl, F, Br, I, CN, NO$_2$, NR$^{15}$R$^{16}$, CF$_3$, C$_1$–C$_6$ alkyl, C$_1$–C$_4$ alkoxy, C$_1$–C$_4$ haloalkyl, and C$_1$–C$_4$ haloalkoxy;

$R^7$, at each occurrence, is independently selected from H, OH, Cl, F, Br, I, CN, NO$_2$, CF$_3$, and C$_1$–C$_4$ alkyl;

$R^{7a}$, at each occurrence, is independently selected from H, OH, Cl, F, Br, I, CN, NO$_2$, CF$_3$, aryl and C$_1$–C$_4$ alkyl;

$R^{7b}$ is independently selected from H and C$_1$–C$_4$ alkyl;

W is —(CR$^8$R$^{8a}$)$_p$—;

p is 0, 1, 2, or 3;

$R^8$ and $R^{8a}$, at each occurrence, are independently selected from H, F, C$_1$–C$_4$ alkyl, C$_2$–C$_4$ alkenyl, C$_2$–C$_4$ alkynyl and C$_3$–C$_8$ cycloalkyl;

X is a bond;

C$_6$–C$_{10}$ aryl substituted with 0–3 R$^{Xb}$;

C$_3$–C$_{10}$ carbocycle substituted with 0–3 R$^{Xb}$; or 5 to 10 membered heterocycle substituted with 0–2 R$^{Xb}$;

$R^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

Y is a bond or —(CR$^9$R$^{9a}$)$_t$—V—(CR$^9$R$^{9a}$)$_u$—;

t is 0, 1, 2, or 3;

u is 0, 1, 2, or 3;

$R^9$ and $R^{9a}$, at each occurrence, are independently selected from H, F, C$_1$–C$_6$ alkyl or C$_3$–C$_8$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;

C$_1$–C$_8$ alkyl substituted with 0–3 R$^{12a}$;

C$_2$–C$_4$ alkenyl substituted with 0–3 Rl$^{2a}$;

C$_2$–C$_4$ alkynyl substituted with 0–3 R$^{12a}$;

C$_6$–C$_{10}$ aryl substituted with 0–4 R$^{12a}$;

C$_3$–C$_{10}$ carbocycle substituted with 0–4 R$^{12a}$; or 5 to 10 membered heterocycle containing 1 to 4 heteroatoms selected from nitrogen, oxygen, and sulphur, wherein said 5 to 10 membered heterocycle is substituted with 0–3 R$^{12a}$; or $R^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$,

S(=O)CH$_3$, S(=O)$_2$CH$_3$,

C$_1$–C$_6$ alkyl, C$_1$–C$_4$ alkoxy, C$_1$–C$_4$ haloalkyl,

C$_1$–C$_4$ haloalkoxy, C$_1$–C$_4$ haloalkyl-S—,

C$_1$–C$_3$ alkyl substituted with 0–1 R$^{12c}$;

C$_6$–C$_{10}$ aryl substituted with 0–4 R$^{12b}$;

C$_3$–C$_{10}$ carbocycle substituted with 0–4 R$^{12b}$; or 5 to 10 membered heterocycle containing 1 to 4 heteroatoms selected from nitrogen, oxygen, and sulphur, wherein said 5 to 10 membered heterocycle is substituted with 0–3 R$^{12b}$;

$R^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

$R^{12c}$, at each occurrence, is independently selected from

C$_6$–C$_{10}$ aryl substituted with 0–4 R$^{12b}$;

C$_3$–C$_{10}$ carbocycle substituted with 0–4 R$^{12b}$; or 5 to 10 membered heterocycle containing 1 to 4 heteroatoms selected from nitrogen, oxygen, and sulphur, wherein said 5 to 10 membered heterocycle is substituted with 0–3 R$^{12b}$;

$R^{10}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;

C$_1$–C$_6$ alkyl substituted with 0–2 R$^{10a}$;

C$_6$–C$_{10}$ aryl substituted with 0–4 R$^{10b}$;

C$_3$–C$_{10}$ carbocycle substituted with 0–3 R$^{10b}$; or 5 to 10 membered heterocycle optionally substituted with 0–3 R$^{10b}$;

$R^{10a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or aryl substituted with 0–4 R$^{10b}$;

$R^{10b}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

alternatively, $R^{10}$ may be —W—X—Y—Z;

$R^{11}$, at each occurrence, is independently selected from H, C$_1$–C$_4$ alkoxy, Cl, F, Br, I, CN, NO$_2$, NR$^{18}$R$^{19}$, C(=O) Rl$^7$, C(=O)OR$^{17}$, C(=O)NR$^{18}$R$^{19}$, S(=O)$_2$NR$^{18}$R$^{19}$, CF$_3$;

C$_1$–C$_6$ alkyl substituted with 0–1 R$^{11a}$;

C$_6$–C$_{10}$ aryl substituted with 0–3 R$^{11b}$;

C$_3$–C$_{10}$ carbocycle substituted with 0–3 R$^{11b}$; or 5 to 10 membered heterocycle substituted with 0–3 R$^{11b}$;

alternatively, two R$^{11}$ substituents on the same or adjacent carbon atoms may be combined to form a C$_3$–C$_6$ carbocycle or a benzo fused radical; wherein said benzo fused radical is substituted with 0–4 R$^{13}$;

$R^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or phenyl substituted with 0–3 R$^{11b}$;

$R^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

$R^{13}$, at each occurrence, is independently selected from

H, OH, C$_1$–C$_6$ alkyl, C$_1$–C$_4$ alkoxy, Cl, F, Br, I, CN, NO$_2$, NR$^{15}$Rl$^6$, and CF$_3$;

$R^{14}$, at each occurrence, is independently selected from H, phenyl, benzyl, C$_1$–C$_6$ alkyl, or C$_2$–C$_6$ alkoxyalkyl;

$R^{14a}$ is H, phenyl, benzyl, or C$_1$–C$_4$ alkyl;

$R^{15}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl);

$R^{16}$, at each occurrence, is independently selected from H, OH, C$_1$–C$_6$ alkyl, benzyl, phenethyl, —C(=O)—(C$_1$–C$_6$ alkyl) and —S(=O)$_2$—(C$_1$–C$_6$ alkyl);

$R^{17}$ is H, aryl, aryl-CH$_2$—, C$_1$–C$_6$ alkyl, or C$_2$–C$_6$ alkoxyalkyl;

$R^{18}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl); and $R^{19}$, at each occurrence, is independently selected from H, OH, C$_1$–C$_6$ alkyl, phenyl, benzyl, phenethyl, —C(=O)—(C$_1$–C$_6$ alkyl) and —S(=O)$_2$—(C$_1$–C$_6$ alkyl); and $R^{19b}$ is H, C$_1$–C$_6$ alkyl, C$_3$–C$_8$ cycloalkyl, phenyl, benzyl or phenethyl;

additionally, $R^{18}$ and $R^{19}$, when substituents on the same atom, may be combined to form a 3 to 7 membered heterocyclic ring;

$R^{20}$ is H, $C(=O)R^{17}$, $C(=O)OR^{17}$, $C(=O)NR^{18}R^{19}$, $S(=O)_2NR^{18}R^{19}$, $S(=O)_2R^{17}$;

$C_1$–$C_6$ alkyl optionally substituted with 0–3 $R^{20a}$; or $C_6$–$C_{10}$ aryl substituted with 0–4 $R^{20b}$;

$R^{20a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, or aryl substituted with 0–4 $R^{20b}$;

$R^{20b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

[3] In another preferred embodiment the present invention provides a compound of Formula (Ia):

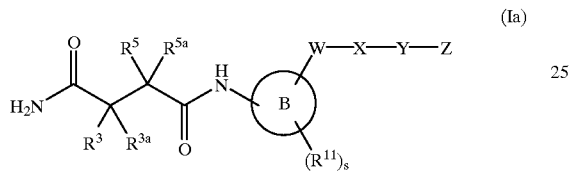

(Ia)

or a pharmaceutically acceptable salt or prodrug thereof, wherein:

ring B is selected from the group consisting of:

a carbocyclic group of 5, 6, or 7 carbon atoms selected from -cyclopentylene-, -cyclohexylene-, -cycloheptylene-, -cyclopentenylene-, -cyclohexenylene-, and -phenylene-;

a heterocycle of 5, 6, or 7 atoms selected from -pyrrolidinylene-, -piperidinylene-, -homopiperidinylene-, and -thiophenylene-;

a bicyclic ring system selected from the group consisting of:

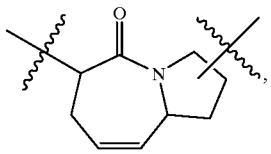

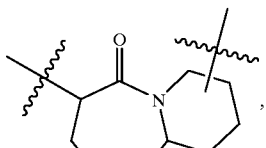

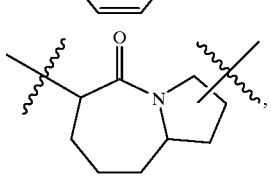

-continued

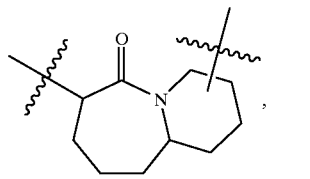

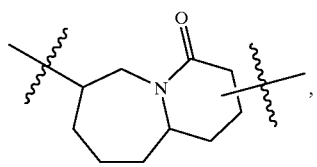

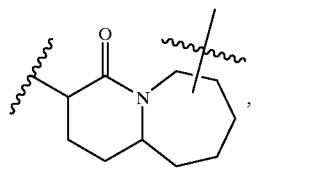

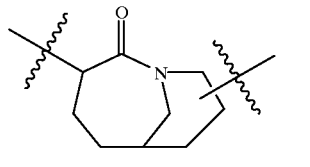

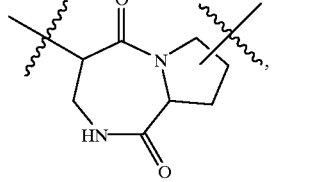

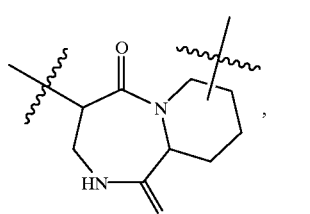

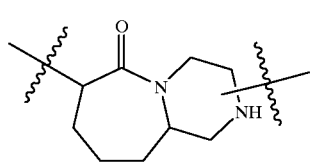

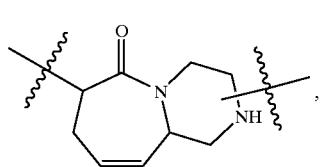

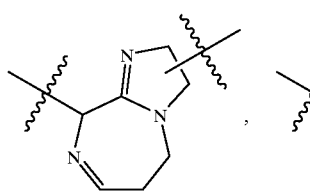

-continued
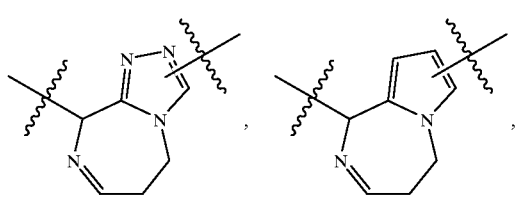
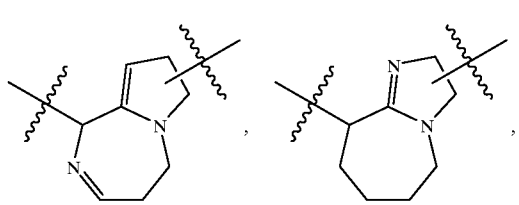
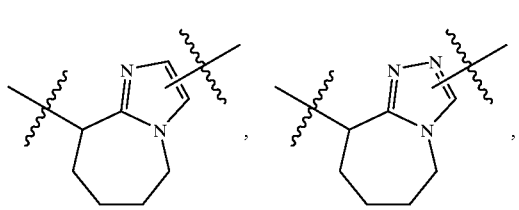
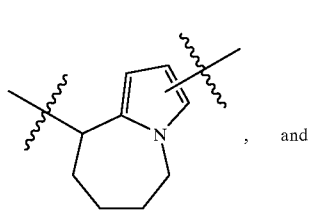, and
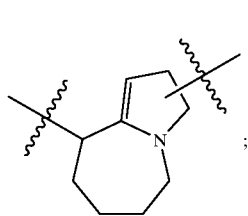;
a tricyclic ring system selected from the group consisting of:
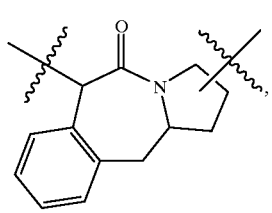,
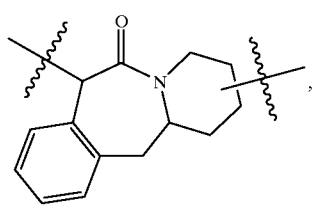,
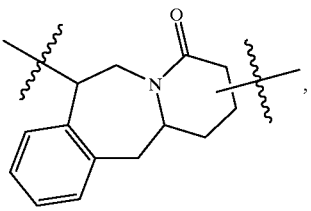,
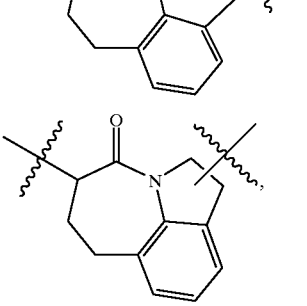,
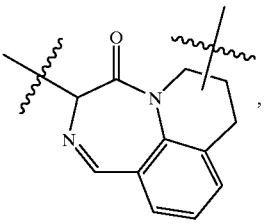,
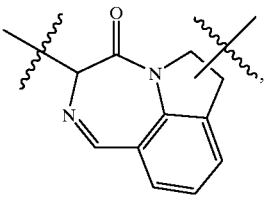,
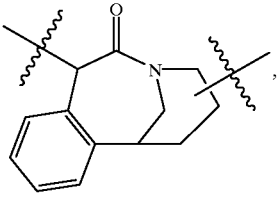,
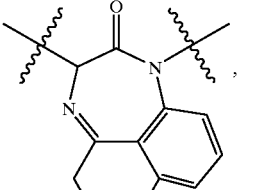,
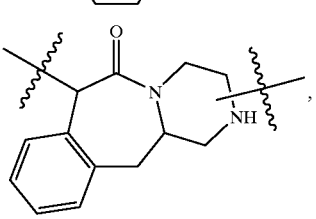, -continued

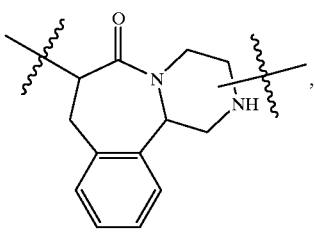

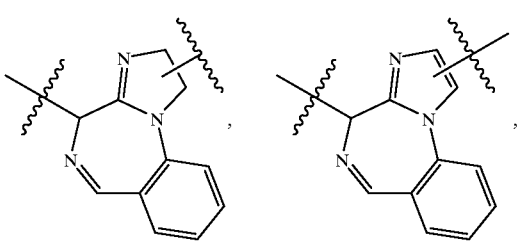

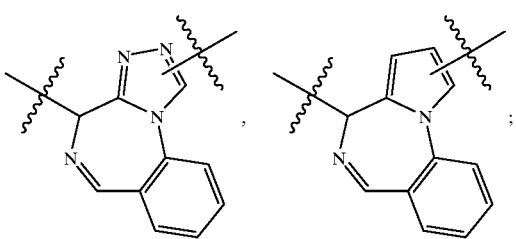

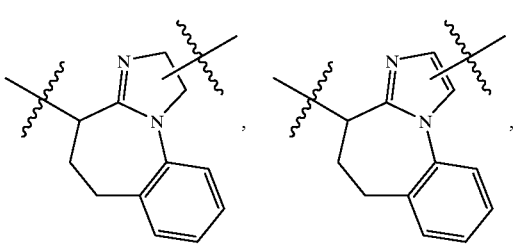

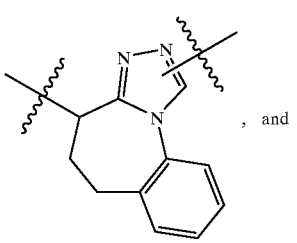, and

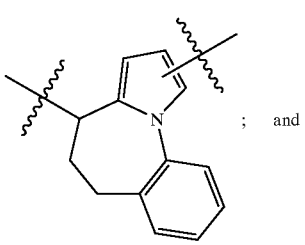;    and a tetracyclic ring system selected from the group consisting of:

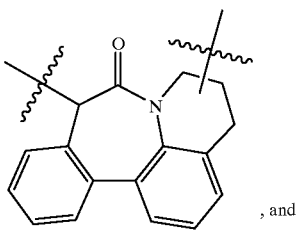, and

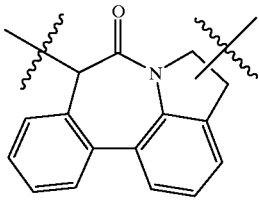

s is 0, 1, 2, 3, or 4;
$R^3$ is —$(CH_2)_n$—$R^4$;
n is 0, 1, or 2;
$R^{3a}$ is H, OH, methyl, ethyl, propyl, butyl, methoxy, ethoxy, propoxy, or butoxy;
alternatively, $R^3$ and $R^{3a}$ may be combined to form a 3–7 membered carbocyclic moiety;
 wherein said 3–7 membered carbocyclic moiety is saturated or partially unsaturated;
 wherein said 3–7 membered carbocyclic moiety is substituted with 0–2 $R^4$;
$R^4$ is H, OH,
 $C_1$–$C_4$ alkyl substituted with 0–2 $R^{4a}$,
 $C_2$–$C_4$ alkenyl substituted with 0–2 $R^{4a}$,
 $C_2$–$C_4$ alkynyl substituted with 0–1 $R^{4a}$,
 $C_3$–$C_6$ cycloklyl substituted with 0–3 $R^{4b}$,
 $C_6$–$C_{10}$ aryl substituted with 0–3 $R^{4b}$, or
 5 to 6 membered heterocycle substituted with 0–3 $R^{4b}$;
$R^{4a}$, at each occurrence, is independently selected from is H, F, Cl, $CF_3$,
 $C_3$–$C_6$ cycloalkyl substituted with 0–3 $R^{4b}$,
 phenyl substituted with 0–3 $R^{4b}$, or
 5 to 6 membered heterocycle substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;
$R^5$ is H;
 $C_1$–$C_4$ alkyl substituted with 0–2 $R^{5b}$;
 $C_2$–$C_4$ alkenyl substituted with 0–2 $R^{5b}$;
 $C_2$–$C_4$ alkynyl substituted with 0–2 $R^{5b}$;
 $C_3$–$C_6$ cycloalkyl substituted with 0–2 $R^{5c}$; or
 phenyl substituted with 0–3 $R^{5c}$;
$R^{5a}$ is H, methyl, ethyl, propyl, butyl, or allyl;
$R^{5b}$, at each occurrence, is independently selected from:
 H, methyl, ethyl, propyl, butyl, $CF_3$, $OR^{14}$,
 $C_3$–$C_6$ cycloalkyl substituted with 0–2 $R^{5c}$;
 phenyl substituted with 0–3 $R^{5c}$; or
 5 to 6 membered heterocycle substituted with 0–2 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

alternatively, $R^5$ and $R^{5a}$ may be combined to form a 3–7 membered carbocyclic ring substituted with 0–3 $R^{5c}$;

W is a bond, —$CH_2$—, —$CH(CH_3)$—, —$CH_2CH_2$— or —$CH(CH_3)CH_2$—;

X is a bond;
  phenyl substituted with 0–2 $R^{Xb}$;
  $C_3$–$C_6$ cycloalkyl substituted with 0–2 $R^{Xb}$; or
  5 to 6 membered heterocycle substituted with 0–2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Y is a bond, —$CH_2CH_2$—V—, —$CH_2$—V—, or —V—;

V is a bond, —$C(=O)$—, —O—, —S—, —$S(=O)$—, —$S(=O)_2$—, —$N(R^{19})$—, —$C(=O)NR^{19b}$—, —$NR^{19b}C(=O)$—, —$C(=O)O$—, or —$OC(=O)$—;

Z is H;
  $C_1$–$C_8$ alkyl substituted with 0–3 $R^{12a}$;
  $C_2$–$C_4$ alkenyl substituted with 0–3 $R^{12a}$;
  $C_2$–$C_4$ alkynyl substituted with 0–3 $R^{12a}$;
  $C_6$–$C_{10}$ aryl substituted with 0–4 $R^{12a}$;
  $C_3$–$C_{10}$ carbocycle substituted with 0–4 $R^{12a}$; or
  5 to 10 membered heterocycle containing 1 to 4 heteroatoms selected from nitrogen, oxygen, and sulphur, wherein said 5 to 10 membered heterocycle is substituted with 0–3 $R^{12a}$; or $R^{12a}$, at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$,
  $C_1$–$C_6$ alkyl, $C_1$–$C_4$ alkoxy, $C_1$–$C_4$ haloalkyl,
  $C_1$–$C_4$ haloalkoxy, $C_1$–$C_4$ haloalkyl-S—,
  $C_1$–$C_3$ alkyl substituted with 0–1 $R^{12c}$;
  $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$ at each occurrence, is independently selected from H, OH, Cl, F, $NR^{15}R^{16}$ $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{12c}$ at each occurrence, is independently selected from
  $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{11}$, at each occurrence, is independently selected from H, $C_1$–$C_4$ alkoxy, Cl, F, $NR^{18}R^{19}$, $C(=O)R^{17}$, $C(=O)OR^{17}$, $CF_3$;
  $C_1$–$C_4$ alkyl substituted with 0–1 $R^{11a}$;
  phenyl substituted with 0–3 $R^{11b}$;
  $C_3$–$C_6$ carbocycle substituted with 0–3 $R^{11b}$; or
  5 to 6 membered heterocycle substituted with 0–3 $R^{11b}$;

alternatively, two $R^{11}$ substituents on the same or adjacent carbon atoms may be combined to form a cyclopropyl, cyclobutyl, cyclopentyl, cyclohexyl, or a benzo fused radical;

$R^{11a}$, at each occurrence, is independently selected from H, $C_1$–$C_4$ alkyl, $OR^{14}$, F, =O, $NR^{15}R^{16}$, $CF_3$, or phenyl substituted with 0–3 $R^{11b}$;

$R^{11b}$, at each occurrence, is independently selected from H, OH, Cl, F, $NR^1SR^{16}$, $CF_3$, $C_1$–$C_4$ alkyl, $C_1$–$C_3$ alkoxy, $C_1$–$C_2$ haloalkyl, and $C_1$–$C_2$ haloalkoxy;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, —$C(=O)$—($C_1$–$C_4$ alkyl) and —$S(=O)_2$—($C_1$–$C_4$ alkyl);

$R^{16}$, at each occurrence, is independently selected from H, OH, $C_1$–$C_4$ alkyl, benzyl, phenethyl, —$C(=O)$—($C_1$–$C_4$ alkyl) and —$S(=O)_2$—($C_1$–$C_4$ alkyl);

$R^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;

$R^{19b}$ is H, mehyl, ethyl, propyl, butyl, cyclopropyl, cyclobutyl, cyclopentyl, phenyl, benzyl or phenethyl;

additionally, $R^{18}$ and $R^{19}$, when substituents on the same atom, may be combined to form a 3 to 7 membered heterocyclic ring.

[4] In another preferred embodiment the present invention provides a compound of Formula (Ia):

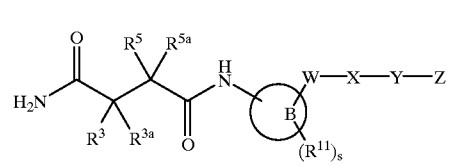

(Ia)

or a pharmaceutically acceptable salt or prodrug thereof, wherein:

ring B is selected from the group consisting of: -cyclopent-1,2-diyl-, -cyclopent-1,3-diyl-, -cyclohex-1,2-diyl-, -cyclohex-1,3-diyl-, -cyclohex-1,4-diyl-, -cyclohept-1,3-diyl-, -cyclopenten-3,5-diyl-, -phen-1,2-diyl-, -phen-1,3-diyl-, -phen-1,4-diyl-, -pyrrolidin-1,4-diyl-, -pyrrolidin-2,4-diyl-, -piperidin-1,4-diyl-, -piperidin-1,3-diyl-, -thiophen-2,3-diyl-, and

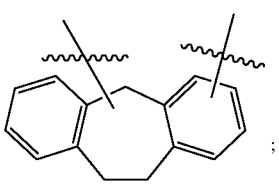

a bicyclic ring system selected from the group consisting of:
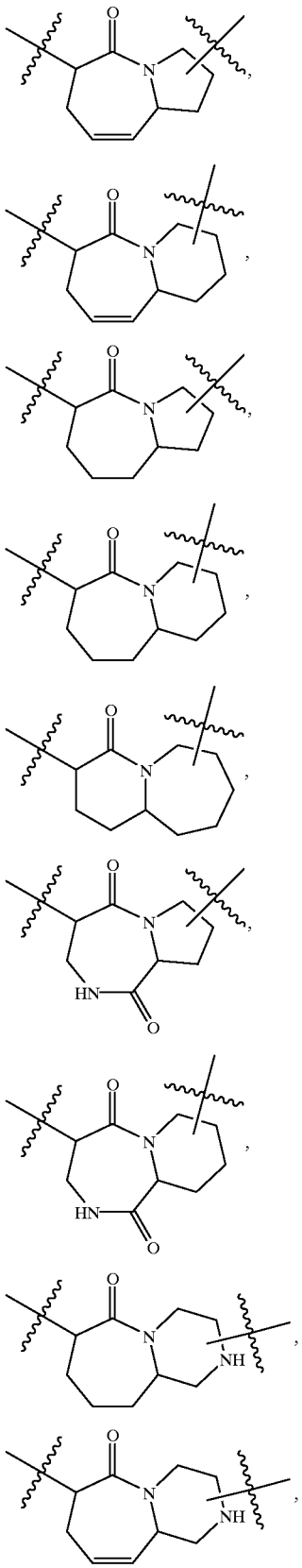
-continued
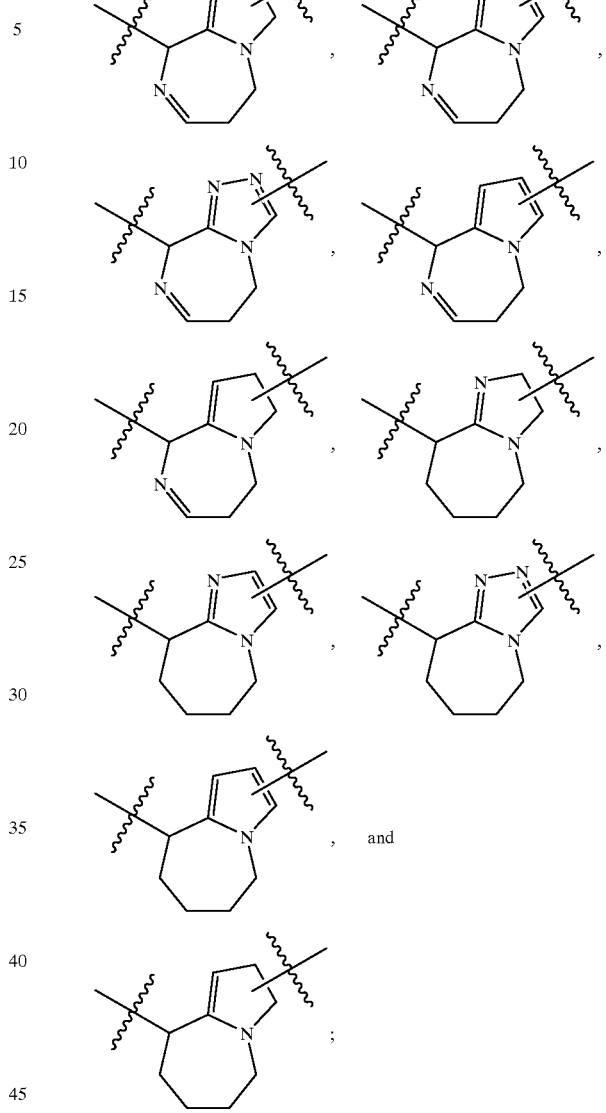
a tricyclic ring system selected from the group consisting of:
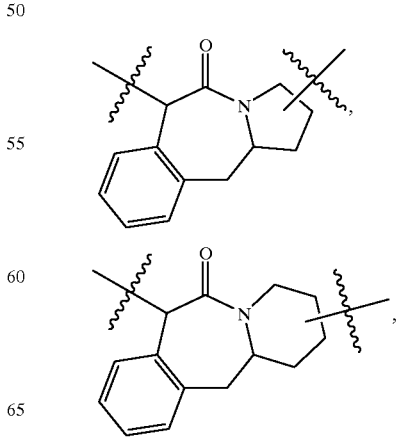

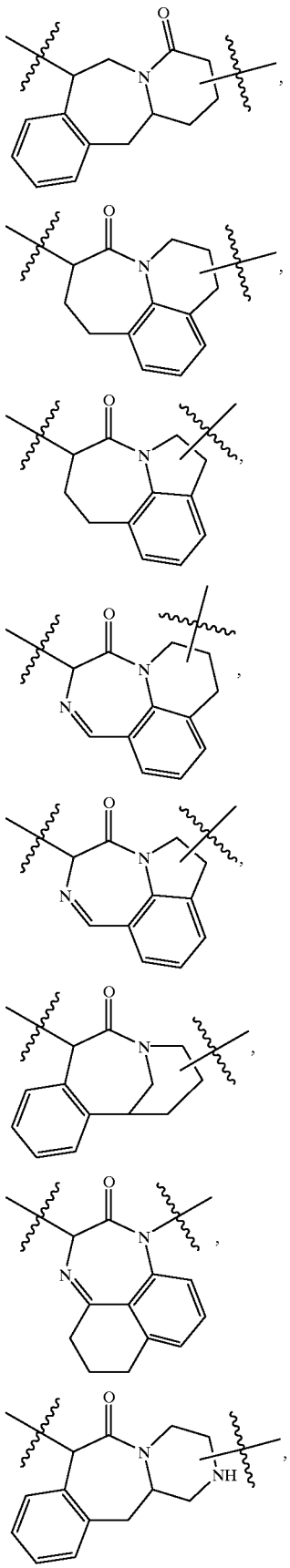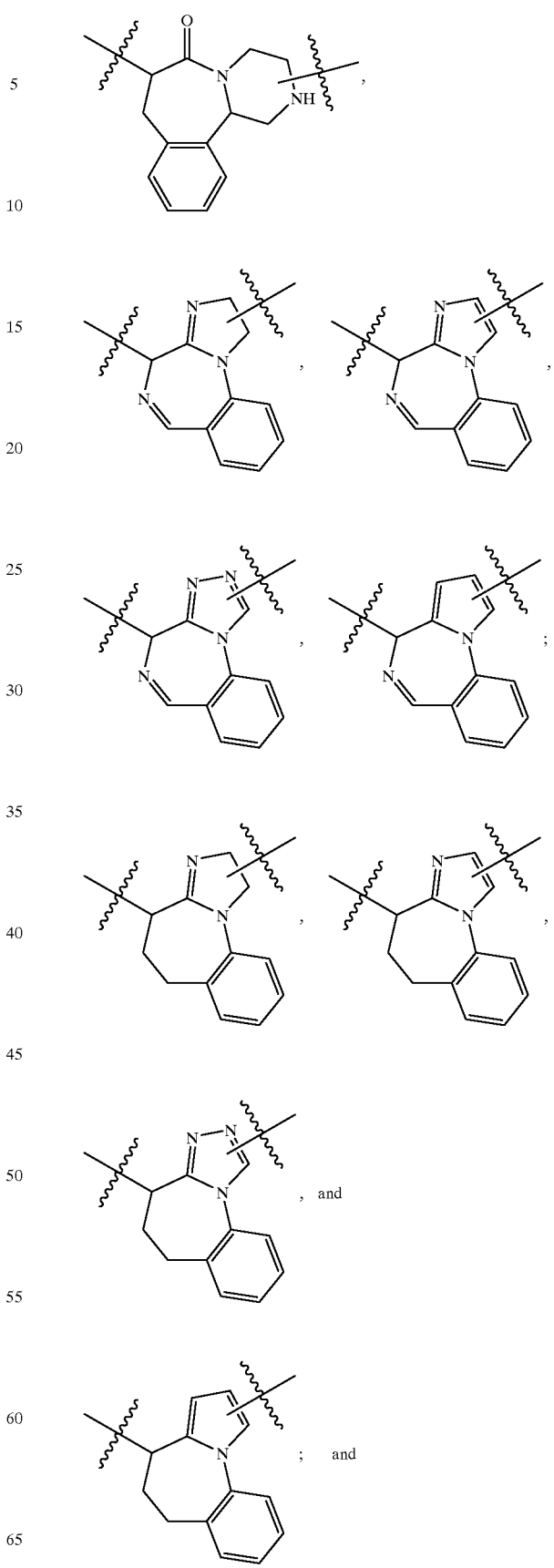

a tetracyclic ring system selected from the group consisting of:

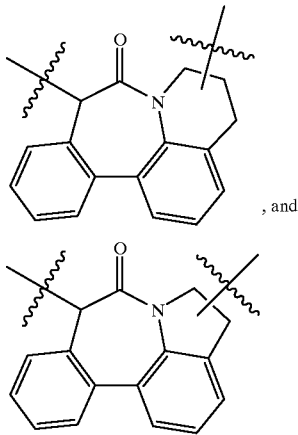, and s is 0, 1, or 2;
$R^3$ is $-R^4$, $-CH_2-R^4$, or $-CH_2CH_2-R^4$;
$R^{3a}$ is H;
alternatively, $R^3$ and $R^{3a}$ may be combined to form a cyclopropyl, cyclobutyl, cyclopentyl, or cyclohexyl moiety;
$R^4$ is H, $C_1-C_4$ alkyl, $C_2-C_4$ alkenyl, or $C_2-C_4$ alkynyl;
$R^5$ is $C_1-C_4$ alkyl substituted with 0–1 $R^{5b}$;
$C_2-C_4$ alkenyl substituted with 0–1 $R^{5b}$; or
$C_2-C_4$ alkynyl substituted with 0–1 $R^{5b}$;
$R^{5a}$ is H;
$R^{5b}$, at each occurrence, is independently selected from:
H, methyl, ethyl, propyl, butyl, $CF_3$, $OR^{14}$,
$C_3-C_6$ cycloalkyl substituted with 0–2 $R^{5c}$;
phenyl substituted with 0–3 $R^{5c}$; or
5 to 6 membered heterocycle substituted with 0–2 $R^{5c}$;
alternatively, $R^5$ and $R^{5a}$ may be combined to form a cyclopropyl, cyclobutyl, cyclopentyl, or cyclohexyl ring;
W is a bond, $-CH_2-$, $-CH(CH_3)-$, $-CH_2CH_2-$ or $-CH(CH_3)CH_2-$;
X is a bond, phenyl, pyridyl, cyclopentyl, cyclohexyl, piperidinyl, or pyrrolidinyl;
Y is a bond, $-CH_2CH_2-V-$, $-CH_2-V-$, or $-V-$;
V is a bond, $-C(=O)-$, $-O-$, $-S-$, $-S(=O)-$, $-S(=O)_2-$, $-N(R^{19})-$, $-C(=O)NR^{19b}-$, $-NR^{19b}C(=O)-$, $-C(=O)O-$, or $-OC(=O)-$;
Z is H;
$C_1-C_8$ alkyl substituted with 0–3 $R^{12a}$;
5 $C_2-C_4$ alkenyl substituted with 0–3 $R^{12a}$;
$C_2-C_4$ alkynyl substituted with 0–3 $R^{12a}$;
$C_6-C_{10}$ aryl substituted with 0–2 $R^{12a}$;
$C_3-C_{10}$ carbocycle substituted with 0–4 $R^{12a}$; or
5 to 10 membered heterocycle containing 1 to 4 heteroatoms selected from nitrogen, oxygen, and sulphur, wherein said 5 to 10 membered heterocycle is substituted with 0–3 $R^{12a}$; or
$R^{12a}$, at each occurrence, is independently selected from
H, OH, Cl, F, Br, I, CN, $NO_2$, $NR^{15}R^{16}$, $-C(=O)NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl,
$C_1-C_4$ haloalkoxy, $C_1-C_4$ haloalkyl-S—,
$C_1-C_3$ alkyl substituted with 0–1 $R^{12c}$;
$C_6-C_{10}$ aryl substituted with 0–4 $R^{12b}$;
$C_3-C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1-C_4$ alkyl, $C_1-C_3$ alkoxy, $C_1-C_2$ haloalkyl, and $C_1-C_2$ haloalkoxy;
$R^{12c}$, at each occurrence, is independently selected from
$C_6-C_{10}$ aryl substituted with 0–4 $R^{12b}$;
$C_3-C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{11}$, at each occurrence, is independently selected from H, $C_1-C_4$ alkoxy, Cl, F, =O, $NR^{18}R^{19}$, $C(=O)R^{17}$, $C(=O)OR^{17}$, $CF_3$; $C_1-C_4$ alkyl substituted with 0–1 $R^{11a}$;
phenyl substituted with 0–3 $R^{11b}$;
$C_3-C_6$ carbocycle substituted with 0–3 $R^{11b}$; or
5 to 6 membered heterocycle substituted with 0–3 $R^{11b}$;
alternatively, two $R^{11}$ substituents on the same or adjacent carbon atoms may be combined to form a cyclopropyl, cyclobutyl, cyclopentyl, cyclohexyl, or a benzo fused radical;
$R^{11a}$, at each occurrence, is independently selected from H, $C_1-C_4$ alkyl, $OR^{14}$, F, =O, $NR^{15}R^{16}$, $CF_3$, or phenyl substituted with 0–3 $R^{11b}$;
$R^{11b}$, at each occurrence, is independently selected from H, OH, Cl, F, $NR^{15}R^{16}$, $CF_3$, $C_1-C_4$ alkyl, $C_1-C_3$ alkoxy, $C_1-C_2$ haloalkyl, and $C_1-C_2$ haloalkoxy;
$R^{14}$ is H, phenyl, benzyl, $C_1-C_4$ alkyl, or $C_2-C_4$ alkoxyalkyl;
$R^{15}$, at each occurrence, is independently selected from H, $C_1-C_4$ alkyl, benzyl, phenethyl, $-C(=O)-(C_1-C_4$ alkyl$)$ and $-S(=O)_2-(C_1-C_4$ alkyl$)$;
$R^{16}$, at each occurrence, is independently selected from H, OH, $C_1-C_4$ alkyl, benzyl, phenethyl, $-C(=O)-(C_1-C_4$ alkyl$)$ and $-S(=O)_2-(C_1-C_4$ alkyl$)$;
$R^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;
$R^{18}$, at each occurrence, is independently selected from H, methyl, ethyl, propyl, butyl, phenyl, benzyl, and phenethyl; and
$R^{19}$, at each occurrence, is independently selected from H, methyl, and ethyl; $R^{19b}$ is H, mehyl, ethyl, propyl, butyl, cyclopropyl, cyclobutyl, cyclopentyl, phenyl, benzyl or phenethyl;
additionally, $R^{18}$ and $R^{19}$, when substituents on the same atom, may be combined to form a 3 to 7 membered heterocyclic ring.

[5] In another preferred embodiment the present invention provides a compound of Formula (Ic):
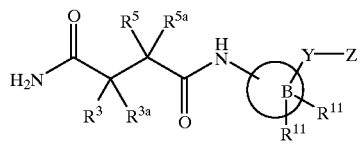
(Ic)
or a pharmaceutically acceptable salt or prodrug thereof, wherein:
ring B is selected from the group consisting of:
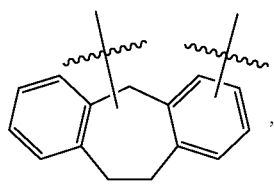,
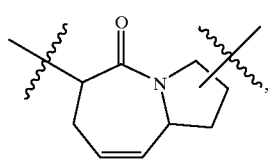,
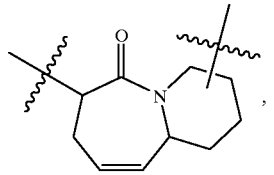,
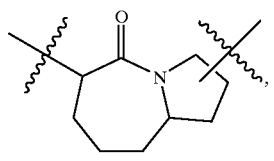,
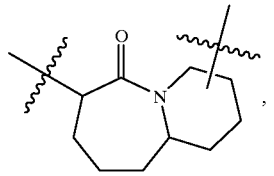,
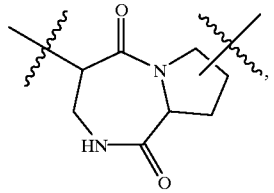,
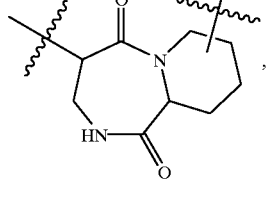,
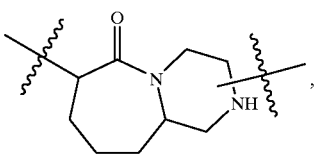,
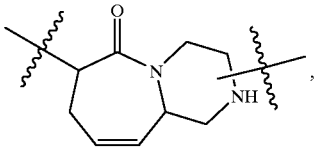,
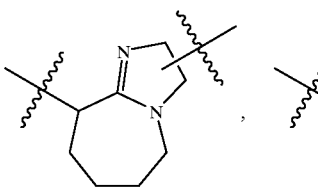,
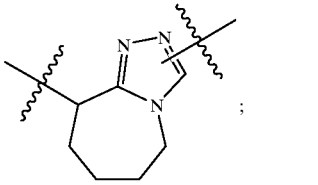;
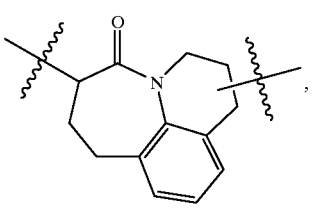,
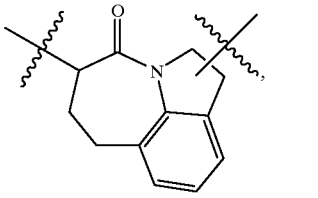,
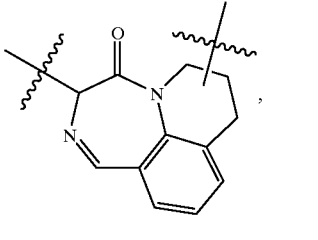, -continued

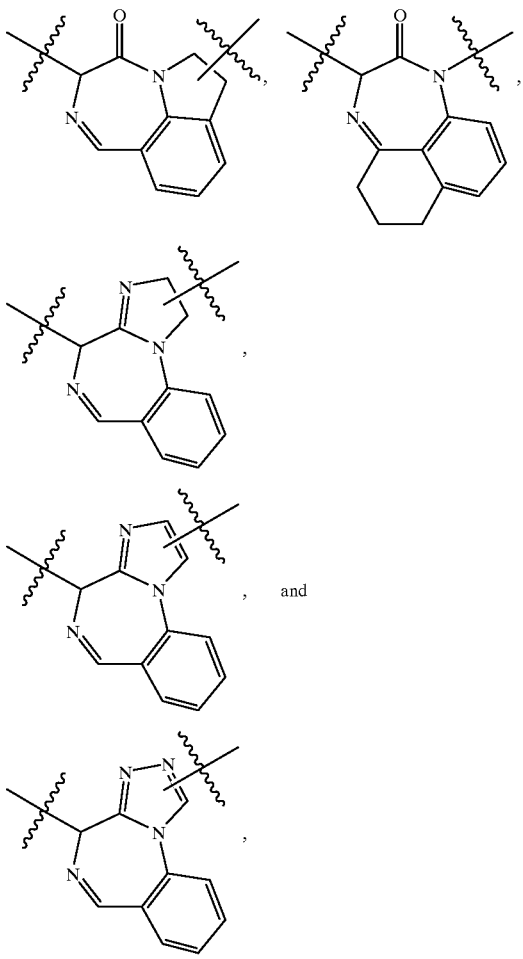

R³ is —CH₃, —CH₂CH₃, —CH₂CH₂CH₃, —CH₂CH₂CH₂CH₃, —CH₂(CH₃)₂, —CH(CH₃)CH₂CH₃, —CH₂CH(CH₃)₂, —CH₂C(CH₃)₃, —CH=CH₂, —CH₂CH=CH₂, —CH₂C(CH₃)=CH₂, —CH₂CH=C(CH₃)₂, —CH₂CH₂CH=CH₂, —CH₂CH₂C(CH₃)=CH₂, —CH₂CH₂CH=C(CH₃)₂, cis-CH₂CH=CH(CH₃), cis-CH₂CH₂CH=CH(CH₃), trans-CH₂CH=CH(CH₃), trans-CH₂CH₂CH=CH(CH₃), —C≡CH, —CH₂C≡CH, or —CH₂C≡C(CH₃);

R³ᵃ is H;

alternatively, R³ and R³ᵃ may be combined to form a cyclopropyl, cyclobutyl, cyclopentyl, or cyclohexyl moiety;

R⁵ is —CH₃, —CH₂CH₃, —CH₂CH₂CH₃, —CH₂(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CH=CH₂, —CH₂CH=CH₂, —CH=CHCH₃, —CH₂CH₂CH=CH(CH₃), trans-CH₂CH=CH(CH₃), —CH₂CH=C(CH₃)₂, cis-CH₂CH=CHCH₂CH₃, trans-CH₂CH=CHCH₂CH₃, cis-CH₂CH₂CH=CH(CH₃), trans-CH₂CH₂CH=CH(CH₃), —C≡CH, —CH₂C≡CH, —CH₂C≡C(CH₃), —CH₂CH₂C≡CH, or -CH₂CH₂C≡C(CH₃);

R⁵ᵃ is H;

alternatively, R⁵ and R⁵ᵃ may be combined to form a cyclopropyl, cyclobutyl, cyclopentyl, or cyclohexyl ring;

Y is a bond, —CH₂CH₂—V—, —CH₂—V—, or —V—;

V is a bond, —C(=O)—, —O—, —S—, —S(=O)—, —S(=O)₂—, —N(R¹⁹)—, —C(=O)NR¹⁹ᵇ—, —NR¹⁹ᵇC(=O)—, —C(=O)O—, or —OC(=O)—;

Z is H;

C₁–C₄ alkyl substituted with 0–1 R¹²ᵃ;

C₂–C₄ alkenyl substituted with 0–1 Rl²ᵃ;

C₂–C₄ alkynyl substituted with 0–1 R¹²ᵃ;

phenyl substituted with 0–2 R¹²ᵃ;

C₃–C₆ cycloalkyl, selected from cyclopropyl, cyclobutyl, cyclopentyl, and cyclohexyl; substituted with 0–2 R¹²ᵃ; or 5 to 10 membered heterocycle selected from pyridinyl, pyrimidinyl, triazinyl, furanyl, thienyl, thiazolyl, pyrrolyl, pyrrolidinyl, piperidinyl, N-piperinyl, pyrazolyl, imidazolyl, oxazolyl, isoxazolyl, tetrazolyl, morpholinyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl; wherein said 5 to 10 membered heterocycle is substituted with 0–2 R¹²ᵃ;

R¹²ᵃ, at each occurrence, is independently selected from H, OH, Cl, F, Br, CN, NO₂, NR¹⁵R¹⁶, —C(=O)NR¹⁵R¹⁶, CF₃, acetyl, SCH₃, SCF₃, S(=O)CH₃, S(=O)₂CH₃, methyl, ethyl, propyl, butyl, methoxy, ethoxy, propoxy, cyclopropyl, cyclobutyl, cyclopentyl, cyclohexyl, C₁–C₂ haloalkyl, C₁–C₂ haloalkoxy, C₁–C₃ alkyl substituted with R¹²ᶜ;

phenyl substituted with 0–3 R¹²ᵇ;

5 to 10 membered heterocycle selected from pyridinyl, pyrimidinyl, triazinyl, furanyl, thienyl, thiazolyl, pyrrolyl, pyrrolidinyl, piperidinyl, N-piperinyl, pyrazolyl, imidazolyl, oxazolyl, isoxazolyl, tetrazolyl, morpholinyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl; wherein said 5 to 10 membered heterocycle is substituted with 0–3 R¹²ᵇ;

R¹²ᵇ, at each occurrence, is independently selected from H, OH, Cl, F, NR¹⁵R¹⁶, CF₃, acetyl, SCH₃, S(=O)CH₃, S(=O)₂CH₃, methyl, ethyl, propyl, butyl, methoxy, ethoxy, propoxy, C₁–C₂ haloalkyl, and C₁–C₂ haloalkoxy;

R¹²ᶜ, at each occurrence, is independently selected from phenyl substituted with 0–4 R¹²ᵇ;

C₃–C₁₀ cycloalkyl, selected from cyclopropyl, cyclobutyl, cyclopentyl, and cyclohexyl; substituted with 0–4 R¹²ᵇ; or 5 to 10 membered heterocycle selected from pyridinyl, pyrimidinyl, triazinyl, furanyl, thienyl, thiazolyl, pyrrolyl, pyrrolidinyl, piperidinyl, N-piperinyl, pyrazolyl, imidazolyl, oxazolyl, isoxazolyl, tetrazolyl, morpholinyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl; wherein said 5 to 10 membered heterocycle is substituted with 0–3 R¹²ᵇ;

R¹¹, at each occurrence, is independently selected from H, Cl, F, NR¹⁸R¹⁹, methyl, ethyl, methoxy, ethoxy, phenyl, benzyl, phenethyl, 4-F-phenyl, (4-F-phenyl)CH₂—, (4-F-phenyl)CH₂CH₂—, 4-Cl-phenyl, (4-Cl-phenyl)CH₂—, (4-Cl-phenyl)CH₂CH₂—, 4—CH₃-phenyl, (4-CH₃-phenyl)CH₂—, (4-CH₃-phenyl)CH₂CH₂—, 4-CF₃-phenyl, (4-CF₃-phenyl)CH₂—, or (4-CF₃-phenyl)CH₂CH₂—; and $R^{15}$, at each occurrence, is independently selected from
H, methyl, ethyl, propyl, butyl, benzyl, phenethyl, methyl-C(=O)—, ethyl-C(=O)—, propyl-C(=O)—, butyl-C(=O)—, methyl-S(=O)$_2$—, ethyl-S(=O)$_2$—, propyl-S(=O)$_2$—, and butyl-S(=O)$_2$—;

$R^{16}$, at each occurrence, is independently selected from
H, OH, methyl, ethyl, propyl, butyl, benzyl, phenethyl, methyl-C(=O)—, ethyl-C(=O)—, propyl-C(=O)—, butyl-C(=O)—, methyl-S(=O)$_2$—, ethyl-S(=O)$_2$—, propyl-S(=O)$_2$—, and butyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;

$R^{19b}$ is H, mehyl, ethyl, propyl, butyl, cyclopropyl, cyclobutyl, cyclopentyl, phenyl, benzyl or phenethyl;

additionally, $R^{18}$ and $R^{19}$, when substituents on the same atom, may be combined to form a 3 to 7 membered heterocyclic ring selected from pyrrolidinyl, piperidinyl, homopiperidinyl, piperazinyl, and morpholinyl.

[6] In another embodiment the present invention provides a compound of Formula (I):

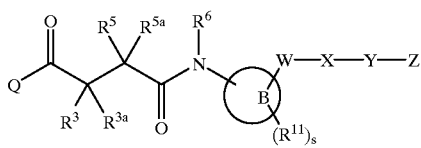

(I)

or a pharmaceutically acceptable salt or prodrug thereof, wherein:

Q is NH$_2$;

ring B is cycloalkyl group of 3 to 8 carbon atoms wherein the cycloalkyl group is saturated, partially saturated or unsaturated; a heterocycle of 3 to 8 atoms containing a heteroatom selected from —O—, —S—, —S(=O)—, —S(=O)$_2$—, and —N(R$^{10}$)—;

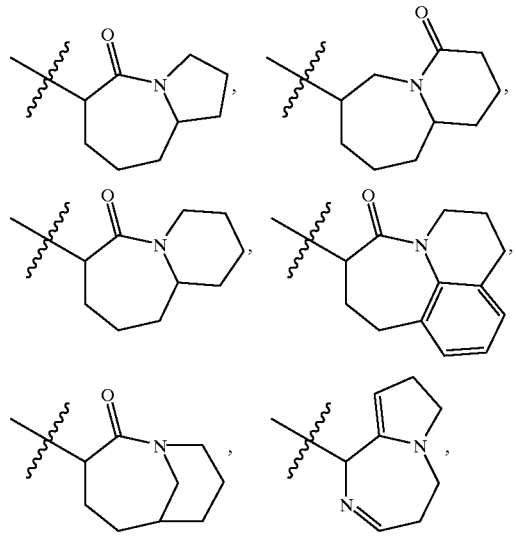

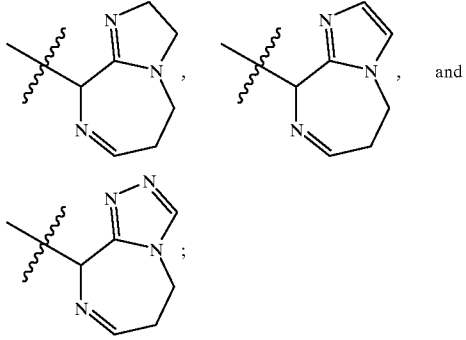

s is 0, 1, 2, 3, 4, 5, or 6;

$R^3$ is —(CR$^7$R$^{7a}$)$_n$—R$^4$,
—(CR$^7$R$^{7a}$)$_n$—S—(CR$^7$R$^{7a}$)$_m$—R$^4$,
—(CR$^7$R$^{7a}$)$_n$—O—(CR$^7$R$^{7a}$)$_m$—R$^4$, or
—(CR$^7$R$^{7a}$)$_n$—N(R$^{7b}$)—(CR$^7$R$^{7a}$)$_m$—R$^4$;

n is 0, 1, or 2;

m is 0, 1, or 2;

$R^{3a}$ is H, OH, methyl, ethyl, propyl, butyl, methoxy, ethoxy, propoxy, or butoxy;

$R^4$ is H, OH, OR$^{14a}$,
C$_1$–C$_4$ alkyl substituted with 0–2 R$^{4a}$,
C$_2$–C$_4$ alkenyl substituted with 0–2 R$^{4a}$,
C$_2$–C$_4$ alkynyl substituted with 0–2 R$^{4a}$,
C$_3$–C$_6$ cycloalkyl substituted with 0–3 R$^{4b}$,
C$_6$–C$_{10}$ aryl substituted with 0–3 R$^{4b}$, or
5 to 10 membered heterocycle substituted with 0–3 R$^{4b}$;

$R^{4a}$, at each occurrence, is independently selected from is H, F, Cl, Br, I, CF$_3$,
C$_3$–C$_{10}$ carbocycle substituted with 0–3 R$^{4b}$,
C$_6$–C$_{10}$ aryl substituted with 0–3 R$^{4b}$, or
5 to 10 membered heterocycle substituted with 0–3 R$^{4b}$;

$R^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, and C$_1$–C$_4$ haloalkoxy;

$R^5$ is H, OR$^{14}$;
C$_1$–C$_6$ alkyl substituted with 0–3 R$^{5b}$;
C$_2$–C$_6$ alkenyl substituted with 0–3R$^{5b}$;
C$_2$–C$_6$ alkynyl substituted with 0–3 R$^{5b}$;
C$_3$–C$_{10}$ carbocycle substituted with 0–3 R$^{5c}$;
C$_6$–C$_{10}$ aryl substituted with 0–3 RsC; or
5 to 10 membered heterocycle substituted with 0–3R$^{5c}$;

$R^{5a}$ is H, OH, C$_1$–C$_4$ alkyl, C$_1$–C$_4$ alkoxy, C$_2$–C$_4$ alkenyl, or C$_2$–C$_4$ alkenyloxy; R$^{5b}$, at each occurrence, is independently selected from:
H, C$_1$–C$_6$ alkyl, CF$_3$, OR$^{14}$, Cl, F, Br, I, =O, CN, NO$_2$, NR$^{15}$R$^{16}$;
C$_3$–C$_{10}$ carbocycle substituted with 0–3 R$^{5c}$;
C$_6$–C$_{10}$ aryl substituted with 0–3 R$^5$C; or
5 to 10 membered heterocycle substituted with 0–3 R$^{5c}$;

$R^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, and C$_1$–C$_4$ haloalkoxy;

$R^6$ is H, methyl, or ethyl;

$R^7$, at each occurrence, is independently selected from H, OH, Cl, F, Br, I, CN, NO$_2$, CF3, and C$_1$–C$_4$ alkyl;

$R^{7a}$, at each occurrence, is independently selected from H, OH, Cl, F, Br, I, CN, NO$_2$, CF$_3$, phenyl and C$_1$–C$_4$ alkyl;

$R^{7b}$ is independently selected from H, methyl, ethyl, propyl, and butyl;

W is —(CR$^8$R$^{8a}$)$_p$—;

p is 0, 1, or 2;

R$^8$ and R$^{8a}$, at each occurrence, are independently selected from H, F, C$_1$–C$_3$ alkyl, C$_2$–C$_3$ alkenyl, C$_2$–C$_3$ alkynyl and C$_3$–C$_6$ cycloalkyl;

X is a bond;
C$_6$–C$_{10}$ aryl substituted with 0–3 R$^{Xb}$;
C$_3$–C$_{10}$ carbocycle substituted with 0–2 R$^{Xb}$; or 5 to 10 membered heterocycle substituted with 0–2 R$^{Xb}$;

R$^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, and C$_1$–C$_4$ haloalkoxy; Y is a bond or —(CR$^9$R$^{9a}$)$_t$—V—(CR$^9$R$^{9a}$)$_u$—;

t is 0, 1, or 2;

u is 0, 1, or 2;

R$^9$ and R$^{9a}$, at each occurrence, are independently selected from H, F, C$_1$–C$_4$ alkyl or C$_3$–C$_6$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, or —S(=O)NR$^{19b}$—;

Z is C$_1$–C$_3$ alkyl substituted with 1–2 R$^{12}$;
C$_6$–C$_{10}$ aryl substituted with 0–4 R$^{12b}$;
C$_3$–C$_{10}$ carbocycle substituted with 0–4 R$^{12b}$; or
5 to 10 membered heterocycle substituted with 0–3 R$^{12b}$;

R$^{12}$ is C$_6$–C$_{10}$ aryl substituted with 0–4 R$^{12b}$;
C$_3$–C$_{10}$ carbocycle substituted with 0–4 R$^{12b}$; or
5 to 10 membered heterocycle substituted with 0–3 R$^{12b}$;

R$^{12b}$ at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, and C$_1$–C$_4$ haloalkoxy;

R$^{10}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
C$_1$–C$_6$ alkyl substituted with 0–1 R$^{10a}$;
C$_6$–C$_{10}$ aryl substituted with 0–4 R$^{10b}$;
C$_3$–C$_{10}$ carbocycle substituted with 0–3 R$^{10b}$; or
5 to 10 membered heterocycle optionally substituted with 0–3 R$^{10b}$;

R$^{10a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or phenyl substituted with 0–4 R$^{10b}$;

R$^{10b}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, or CF$_3$; R$^{11}$, at each occurrence, is independently selected from
C$_1$–C$_4$ alkoxy, Cl, F, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$–C$_6$ alkyl substituted with 0–1 R$^{11a}$;
C$_6$–C$_{10}$ aryl substituted with 0–3 R$^{11b}$;
C$_3$–C$_{10}$ carbocycle substituted with 0–3 R$^{11b}$; or
5 to 10 membered heterocycle substituted with 0–3 R$^{11b}$;

alternatively, two R$^{11}$ substituents on the same or adjacent carbon atoms may be combined to form a C$_3$–C$_6$ carbocycle or a benzo fused radical;

R$^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or phenyl substituted with 0–3 R$^{11b}$;

R$^{11b}$, at each occurrence, is independently selected from H, OH, Cl, F, Br, I, CN, NO$_2$, NR$^{15}$R$^{16}$, CF$_3$, C$_1$–C$_6$ alkyl, C$_1$–C$_4$ alkoxy, C$_1$–C$_4$ haloalkyl, and C$_1$–C$_4$ haloalkoxy;

R$^{14}$ is H, phenyl, benzyl, C$_1$–C$_6$ alkyl, or C$_2$–C$_6$ alkoxyalkyl;

R$^{15}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl);

R$^{16}$, at each occurrence, is independently selected from H, OH, C$_1$–C$_6$ alkyl, benzyl, phenethyl, —C(=O)—(C$_1$–C$_6$ alkyl) and —S(=O)$_2$—(C$_1$–C$_6$ alkyl);

R$^{17}$ is H, aryl, (aryl)CH$_2$—, C$_1$–C$_6$ alkyl, or C$_2$–C$_6$ alkoxyalkyl;

R$^{18}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl); and R$^{19}$, at each occurrence, is independently selected from H, OH, C$_1$–C$_6$ alkyl, phenyl, benzyl, phenethyl, —C(=O)—(C$_1$–C$_6$ alkyl) and —S(=O)$_2$—(C$_1$–C$_6$ alkyl); and R$^{19b}$ is H, C$_1$–C$_6$ alkyl, C$_3$–C$_8$ cycloalkyl, phenyl, benzyl or phenethyl.

[7] In another preferred embodiment the present invention provides a compound of Formula (Ia) wherein:

R$^3$ is —(CR$^7$R$^{7a}$)$_n$—R$^4$,
—(CR$^7$R$^{7a}$)$_n$—S—(CR$^7$R$^{7a}$)$_m$—R$^4$,
—(CR$^7$R$^{7a}$)$_n$—O—(CR$^7$R$^{7a}$)$_m$—R$^4$, or
—(CR$^7$R$^{7a}$)$_n$—N(R$^{7b}$)—(CR$^7$R$^{7a}$)$_m$—R$^4$;

n is 0 or 1;

m is 0 or 1;

R$^{3a}$ is H, OH, methyl, ethyl, propyl, butyl, methoxy, ethoxy, propoxy, or butoxy;

R$^4$ is H, OH,
C$_1$–C$_4$ alkyl substituted with 0–2 R$^{4a}$,
C$_2$–C$_4$ alkenyl substituted with 0–2 R$^{4a}$,
C$_2$–C$_4$ alkynyl substituted with 0–1 R$^{4a}$,
C$_3$–C$_6$ cycloalkyl substituted with 0–3 R$^{4b}$,
C$_6$–C$_{10}$ aryl substituted with 0–3 R$^{4b}$, or
5 to 10 membered heterocycle substituted with 0–3 R$^{4b}$;

R$^{4a}$, at each occurrence, is independently selected from is H, F, Cl, CF$_3$,
C$_3$–C$_6$ cycloalkyl substituted with 0–3 R$^{4b}$,
phenyl substituted with 0–3 R$^{4b}$, or
5 to 6 membered heterocycle substituted with 0–3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_2$ haloalkyl, and C$_1$–C$_2$ haloalkoxy;

R$^5$ is H, OR$^{14}$;
C$_1$–C$_4$ alkyl substituted with 0–3 R$^{5b}$;
C$_2$–C$_4$ alkenyl substituted with 0–2 R$^{5b}$; or
C$_2$–C$_4$ alkynyl substituted with 0–2 R$^{5b}$;

R$^{5a}$ is H, OH, methyl, ethyl, propyl, butyl, methoxy, ethoxy, propoxy, butoxy, or allyl;

R$^{5b}$, at each occurrence, is independently selected from:
H, methyl, ethyl, propyl, butyl, CF$_3$, OR$^{14}$, =O;
C$_3$–C$_6$ cycloalkyl substituted with 0–2 R$^{5c}$;
phenyl substituted with 0–3 R$^{5c}$; or
5 to 6 membered heterocycle substituted with 0–2 R$^5$C;

R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_2$ haloalkyl, and C$_1$–C$_2$ haloalkoxy;

R$^6$ is H;

R$^7$, at each occurrence, is independently selected from H, F, CF$_3$, methyl, and ethyl;

R$^{7a}$, at each occurrence, is independently selected from H, F, CF$_3$, methyl, and ethyl;

$R^{7b}$ is independently selected from H, methyl, and ethyl;

W is a bond, —$CH_2$—, —$CH(CH_3)$—, —$CH_2CH_2$— or —$CH(CH_3)CH_2$—;

X is a bond;
  phenyl substituted with 0–2 $R^{Xb}$;
  $C_3$–$C_6$ cycloalkyl substituted with 0–2 $R^{Xb}$; or
  5 to 6 membered heterocycle substituted with 0–2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Y is a bond, —$CH_2$—V—, —V—, or —V—$CH_2$—;

V is a bond, —C(=O)—, —O—, —O—, —S(=O)—, —S(=O)_2—, —NH—, —N(CH_3)—, or —N(CH_2CH_3)—;

Z is $C_1$–$C_2$ alkyl substituted with 1–2 $R^{12}$;
  $C_6$–$C_{10}$ aryl substituted with 0–4 $R^{12b}$;
  $C_3$–$C_6$ carbocycle substituted with 0–3 $R^{12b}$; or
  5 to 10 membered heterocycle substituted with 0–3 $R^{12b}$;

$R^{12}$ is $C_6$–$C_{10}$ aryl substituted with 0–4 $R^{12b}$;
  $C_3$–$C_6$ carbocycle substituted with 0–3 $R^{12b}$; or
  5 to 10 membered heterocycle substituted with 0–3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{10}$ is H, $C(=O)R^{17}$, $C(=O)OR^{17}$;
  $C_1$–$C_4$ alkyl substituted with 0–1 $R^{10a}$;
  phenyl substituted with 0–4 $R^{10b}$;
  $C_3$–$C_6$ carbocycle substituted with 0–3 $R^{10b}$; or
  5 to 6 membered heterocycle optionally substituted with 0–3 $R^{10b}$;

$R^{10a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, or phenyl substituted with 0–4 $R^{10b}$;

$R^{10b}$, at each occurrence, is independently selected from H, OH, $C_1$–$C_4$ alkyl, $C_1$–$C_3$ alkoxy, Cl, F, Br, I, CN, $NO_2$, $NR^{15}R^{16}$, or $CF_3$;

$R^{11}$, at each occurrence, is independently selected from
  $C_1$–$C_4$ alkoxy, Cl, F, =O, $NR^{18}R^{19}$, $C(=O)R^{17}$, $C(=O)OR^{17}$, $CF_3$;
  $C_1$–$C_4$ alkyl substituted with 0–1 $R^{11a}$;
  phenyl substituted with 0–3 $R^{11b}$;
  $C_3$–$C_6$ carbocycle substituted with 0–3 $R^{11b}$; or 5 to 6 membered heterocycle substituted with 0–3 $R^{11b}$;

alternatively, two $R^{11}$ substituents on the same or adjacent carbon atoms may be combined to form a cyclopropyl, cyclobutyl, cyclopentyl, cyclohexyl, or a benzo fused radical;

$R^{11a}$, at each occurrence, is independently selected from H, $C_1$–$C_4$ alkyl, $OR^{14}$, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, —C(=O)—($C_1$–$C_4$ alkyl) and —S(=O)_2—($C_1$–$C_4$ alkyl);

$R^{16}$, at each occurrence, is independently selected from H, OH, $C_1$–$C_4$ alkyl, benzyl, phenethyl, —C(=O)—($C_1$–$C_4$ alkyl) and —S(=O)_2—($C_1$–$C_4$ alkyl);

$R^{17}$ is H, phenyl, 4-fluorophenyl, 4-chlorophenyl, 4-methylphenyl, 4-trifluorophenyl, (4-fluorophenyl) methyl, (4-chlorophenyl)methyl, (4-methylphenyl) methyl, (4-trifluorophenyl)methyl, methyl, ethyl, propyl, butyl, methoxymethyl, methyoxyethyl, ethoxymethyl, or ethoxyethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

[8] In another preferred embodiment the present invention provides a compound of Formula (Ib):

(Ib)

or a pharmaceutically acceptable salt or prodrug thereof, wherein:

$R^3$ is —$CH_3$, —$CH_2CH_3$, —$CH_2CH_2CH_3$, —$CH_2CH_2CH_2CH_3$, —$CH_2(CH_3)_2$, —$CH(CH_3)CH_2CH_3$, —$CH_2CH(CH_3)_2$, —$CH_2C(CH_3)_3$, —$CF_3$, —$CH_2CF_3$, —$CH_2CH_2CF_3$, —$CH_2CH_2CH_2CF_3$, —CH=$CH_2$, —$CH_2$CH=$CH_2$, —$CH_2$C($CH_3$)=$CH_2$, —$CH_2$CH=C($CH_3$)_2, —$CH_2CH_2$CH=$CH_2$, —$CH_2CH_2$C($CH_3$)=$CH_2$, —$CH_2CH_2$CH=C($CH_3$)_2, cis-$CH_2$CH=CH($CH_3$), cis-$CH_2CH_2$CH=CH($CH_3$), trans-$CH_2$CH=CH($CH_3$), trans-$CH_2CH_2$CH=CH($CH_3$); —C≡CH, —$CH_2$C≡CH, —$CH_2$C≡C($CH_3$), cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, or (3-F-5-Cl-phenyl)$CH_2CH_2$—;

$R^5$ is -$CH_3$, —$CH_2CH_3$, —$CH_2CH_2CH_3$, —$CH_2(CH_3)_2$, —$CH_2CH_2CH_2CH_3$, —CH($CH_3$)$CH_2CH_3$, —$CH_2$CH($CH_3$)_2, —$CH_2$C($CH_3$)_3, —$CH_2CH_2CH_2CH_3$, —CH($CH_3$)$CH_2CH_2CH_3$, —$CH_2$CH($CH_3$)$CH_2CH_3$, —$CH_2CH_2$CH($CH_3$)_2, —CH($CH_2CH_3$)_2, -$CF_3$, —$CH_2CF_3$, —$CH_2CH_2CF_3$, —$CH_2CH_2CH_2CF_3$, —$CH_2CH_2CH_2CH_2CF_3$, —CH=$CH_2$, —$CH_2$CH=$CH_2$, —CH=CH$CH_3$, cis-$CH_2$CH=CH($CH_3$), trans-$CH_2$CH=CH($CH_3$), trans-$CH_2$CH=CH($C_6H_5$), —$CH_2$CH=C($CH_3$)_2, cis-$CH_2$CH=CH$CH_2CH_3$, trans- CH$_2$CH=CHCH$_2$CH$_3$, cis-CH$_2$CH$_2$CH=CH(CH$_3$), trans-CH$_2$CH$_2$CH=CH(CH$_3$), trans-CH$_2$CH=CHCH$_2$ (C$_6$H$_5$), —C≡CH, —CH$_2$C≡CH, —CH$_2$C≡C(CH$_3$), —CH$_2$C≡C(C$_6$H$_5$), —CH$_2$CH$_2$C≡CH, —CH$_2$CH$_2$C≡C(CH$_3$), —CH$_2$CH$_2$C≡C(C$_6$H$_5$), —CH$_2$CH$_2$CH$_2$C≡CH, —CH$_2$CH$_2$CH$_2$C≡C(CH$_3$), —CH$_2$CH$_2$CH$_2$C≡C(C$_6$H$_5$), cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, furanyl-CH$_2$—, thienyl-CH$_2$—, pyridyl-CH$_2$—, 1-imidazolyl-CH$_2$—, oxazolyl-CH$_2$—, isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, or isoxazolyl-CH$_2$CH$_2$—;

W is a bond, —CH$_2$—, or —CH(CH$_3$)—;
X is a bond;

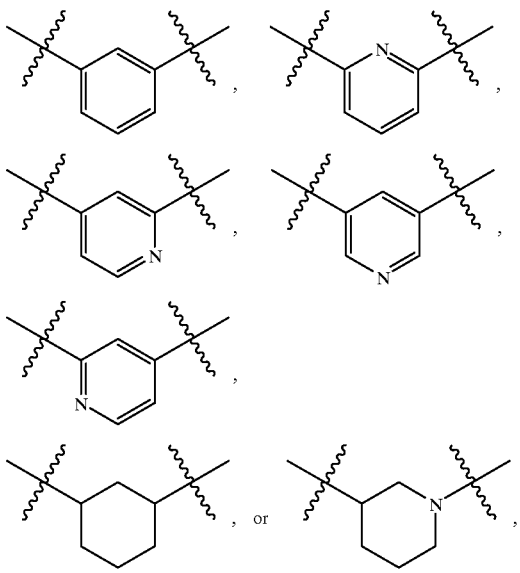

Y is a bond, —CH$_2$—V—, —V—, or —V—CH$_2$—;
V is a bond, —C(=O)—, —O—, —S—, —S(=O)—, —S(=O)$_2$—, —NH—, or —N(CH$_3$)—,
Z is phenyl 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino,N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—,(cyclopropyl)CH$_2$CH$_2$—, (cyclobutyl)CH$_2$CH$_2$—,(cyclopentyl)CH$_2$CH$_2$—, (cyclohexyl)CH$_2$CH$_2$—, (morpholino)CH$_2$CH$_2$—, (N-pipridinyl)CH$_2$CH$_2$—, methyl, ethyl, i-propyl, n-propyl, n-butyl, i-butyl, s-butyl, t-butyl, or allyl;

$R^{10}$ is H, methyl, ethyl, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—;

$R^{11}$, at each occurrence, is independently selected from H, methyl, ethyl, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—; and alternatively, two $R^{11}$ substituents on the same or adjacent carbon atoms may be combined to form a cyclopropyl, cyclobutyl, cyclopentyl, cyclohexyl, or a benzo fused radical.

[9] In another preferred embodiment the present invention provides a compound of Formula (Ib) wherein:
ring B, along with up to 2 R[11]s, is

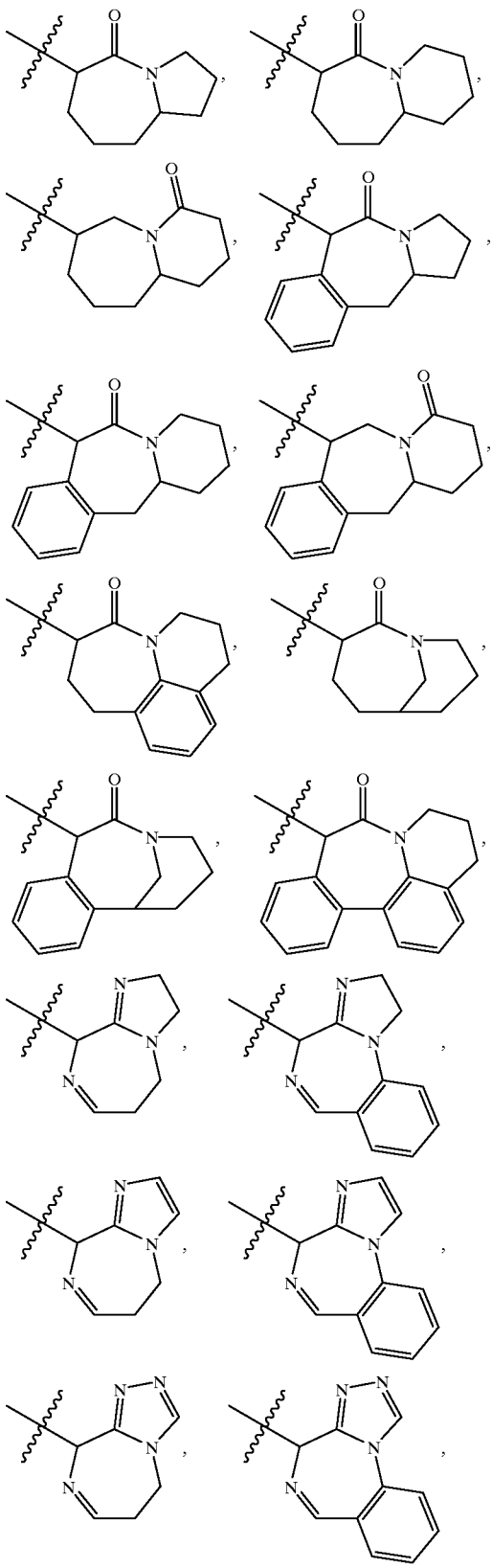

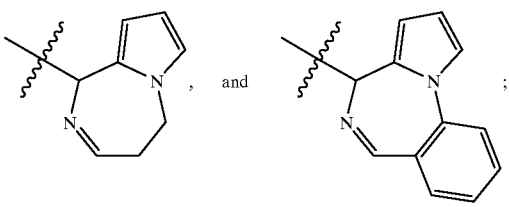

wherein ring B is further substituted with 0, 1, 2, 3, or 4 R[11].

[10] In another preferred embodient the present invention provides a compound selected from:

(2R,3S)-3-allyl-2-isobutyl-N[1]-(4-butyl-3-oxo-2,3,4,8,9,10-hexahydronaphtho[1,8-ef] [1,4]diazepin-2-yl)butanediamide;

(2R,3S)-3-allyl-2-isobutyl-N[1]-(4-methyl-3-oxo-2,3,4,8,9,10-hexahydronaphtho[1,8-ef] [1,4]diazepin-2-yl)butanediamide;

(2R, 3S)-3-allyl-2-isobutyl-N[1]-(4-(pyrid-2-ylmethyl)-3-oxo-2,3,4,8,9,10-hexahydronaphtho[1,8-ef] [1,4]diazepin-2-yl)butanediamide;

(2R, 3S)-3-allyl-2-isobutyl-N[1]-(4-(2-(diethylamino)ethyl)-3-oxo-2,3,4,8,9,10-hexahydronaphtho[1,8-ef] [1,4]diazepin-2-yl)butanediamide;

N1-(2-benzylcarbamoyl-4-oxo-1,2,4,5,6,7-hexahydro-azepino[3,2,1-hi]indol-5-yl)-2-isobutyl-3-propyl-succinamide;

N1-[2-(1-benzyl-pyrrolidin-3-ylcarbamoyl)-4-oxo-1,2,4,5,6,7-hexahydro-azepino[3,2,1-hi] indol-5-yl]-2-isobutyl-3-propyl-succinamide;

N1-[2-(1-benzyl-pyrrolidin-3-ylcarbamoyl)-4-oxo-1,2,4,5,6,7-hexahydro-azepino[3,2,1-hi]indol-5-yl]-2-isobutyl-3-propyl-succinamide;

2-isobutyl-N1-[2-(4-methoxy-benzylcarbamoyl)-4-oxo-1,2,4,5,6,7-hexahydro-azepino[3,2,1-hi]indol-5-yl]-3-propyl-succinamide;

2-isobutyl-N 1-[2-(3-methoxy-benzylcarbamoyl)-4-oxo-1,2,4,5,6,7-hexahydro-azepino[3,2,1-hi]indol-5-yl]-3-propyl-succinamide;

N1-[2-(cyclohexylmethyl-carbamoyl)-4-oxo-1,2,4,5,6,7-hexahydro-azepino[3,2,1-hi]indol-5-yl]-2-isobutyl-3-propyl-succinamide;

2-isobutyl-N1-(2-isopropylcarbamoyl-4-oxo-1,2,4,5,6,7-hexahydro-azepino[3,2,1-hi]indol-5-yl)-3-propyl-succinamide;

2-isobutyl-N 1-(4-oxo-2-phenylcarbamoyl-1,2,4,5,6,7-hexahydro-azepino[3,2,1-hi]indol-5-yl)-3-propyl-succinamide;

(2R,3S)-3-allyl-N[1]-[(7S)-2-benzyl-6-oxo-1,2,3,4,6,7,8,10a-octahydropyrazino[1,2-a]azepin-7-yl]-2-isobutylbutanediamide;

N[1]-(1,5-dioxo-octahydro-pyrrolo[1,2-a] [1,4]diazepin-4-yl)-2-isobutyl-3-propyl-succinamide;

N1-(2-benzyloxy-5-oxo-2,3,5,6,7,9a-hexahydro-1H-pyrrolo[1,2-a]azepin-6-yl)-2-isobutyl-3-propyl-succinamide;

N1-(2-benzyloxy-5-oxo-octahydro-pyrrolo[1,2-a]azepin-6-yl)-2-isobutyl-3-propyl-succinamide;

N1-(2-hydroxy-5-oxo-octahydro-pyrrolo[1,2-a]azepin-6-yl)-2-isobutyl-3-propyl-succinamide;

3-allyl-N[1]-[3 -(4-bromo-phenyl)-6,7,8,9-tetrahydro-5H-[1,2,4]triazolo[4,3-a]azepin-9-yl]-2-isobutyl-succinamide;

3-allyl-N[1]-[3-(4-phenyl-phenyl)-6,7,8,9-tetrahydro-5H-[1,2,4]triazolo[4,3-a]azepin-9-yl]-2-isobutyl-succinamide;

3-allyl-N[1]-[3-(4-benzofuran-2-yl-phenyl)-6,7,8,9-tetrahydro-5H-[1,2,4]triazolo[4,3-a]azepin-9-yl]-2-isobutyl-succinamide;

3-allyl-N¹-[3-(4-(4-chloro-phenyl)-phenyl)-6,7,8,9-tetrahydro-5H-[1,2,4]triazolo[4,3-a]azepin-9-yl]-2-isobutyl-succinamide;

3-allyl-N¹-[3-(4-(3,5-dimethylisoxazol-4-yl)phenyl)-6,7,8,9-tetrahydro-5H-[1,2,4]triazolo[4,3-a]zepin-9-yl]-2-isobutyl-succinamide;

3-allyl-N¹-[3-(3-bromo-phenyl)-6,7,8,9-tetrahydro-5H-[1,2,4]triazolo[4,3-a]azepin-9-yl]-2-isobutyl-succinamide;

3-allyl-N¹-[3-(3-phenyl-phenyl)-6,7,8,9-tetrahydro-5H-[1,2,4]triazolo[4,3-a]azepin-9-yl]-2-isobutyl-succinamide; and 3-allyl-N¹-[3-(3-benzofuran-2-yl-phenyl)-6,7,8,9-tetrahydro-5H-[1,2,4]triazolo[4,3-a]azepin-9-yl]-2-isobutyl-succinamide.

In another preferred embodiment of the present invention, Q is NH2.

In another preferred embodiment $R^3$ is $R^4$, $R^{3a}$ is H, methyl, ethyl, propyl, or butyl;

$R^4$ is $C_1$–$C_6$ alkyl, $C_2$–$C_6$ alkenyl, $C_2$–$C_6$ alkynyl $R^5$ is $C_1$–$C_6$ alkyl, $C_2$–$C_6$ alkenyl, $C_2$–$C_6$ alkynyl $R^{5a}$ is H, methyl, ethyl, propyl, or butyl; and the total number of carbon atoms in $R^3$, $R^{3a}$, $R^5$ and $R^{5a}$ equals seven or more.

In another preferred embodiment $R^3$ is $R^4$;

$R^{3a}$ is H;

$R^4$ is $C_1$–$C_4$ alkyl substituted with 1–2 $R^{4a}$, $R^{4a}$, at each occurrence, is independently selected from $C_3$–$C_6$ cycloalkyl substituted with 0–3 $R^{4b}$, phenyl substituted with 0–3 $R^{4b}$, or 5 to 6 membered heterocycle substituted with 0–3 $R^{4b}$;

$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^5$ is $C_2$–$C_4$ alkyl substituted with 0–3 $R^{5b}$;

$C_2$–$C_4$ alkenyl substituted with 0–2 $R^{5b}$; or $C_2$–$C_4$ alkynyl substituted with 0–2 $R^{5b}$;

$R^{5b}$, at each occurrence, is independently selected from:

H, methyl, ethyl, propyl, butyl, $CF_3$, $OR^{14}$, =O;

$C_3$–$C_6$ cycloalkyl substituted with 0–2 $R^{5c}$;

phenyl substituted with 0–3 $R^{5c}$; or 5 to 6 membered heterocycle substituted with 0–2 $R^{5c}$; and $R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy.

In another preferred embodiment $R^3$ is $R^4$;

$R^{3a}$ is H;

$R^4$ is $C_2$–$C_4$ alkyl substituted with 0–2 $R^{4a}$, $C_2$–$C_4$ alkenyl substituted with 0–2 $R^{4a}$, $C_2$–$C_4$ alkynyl substituted with 0–2 $R^{4a}$, $R^{4a}$, at each occurrence, is independently selected from is H, F, $CF_3$, $C_3$–$C_6$ cycloalkyl substituted with 0–3 $R^{4b}$, phenyl substituted with 0–3 $R^{4b}$, or 5 to 6 membered heterocycle substituted with 0–3 $R^{4b}$;

$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^5$ is $C_1$–$C_4$ alkyl substituted with 1–2 $R^{5b}$;

$R^{5b}$, at each occurrence, is independently selected from:

$C_3$–$C_6$ cycloalkyl substituted with 0–2 $R^{5c}$;

phenyl substituted with 0–3 $R^{5c}$; or 5 to 6 membered heterocycle substituted with 0–2 $R^{5c}$; and $R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy.

In another preferred embodiment

W is —$(CH_2)_p$—;

p is 1, 2, or 3;

X is a bond;

phenyl substituted with 0–2 $R^{Xb}$;

$C_3$–$C_6$ cycloalkyl substituted with 0–2 $R^{Xb}$; or 5 to 6 membered heterocycle substituted with 0–2 $R^{Xb}$;

wherein the 5 to 6 membered heterocycle does not contain an oxo or imino substitued ring atom; and $R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy.

In a preferred embodiment of ring B, ring B is selected from the group consisting of a carbocyclic group of 5, 6, or 7 carbon atoms selected from -cyclopentylene-, -cyclohexylene-, -cycloheptylene-, -cyclopentenylene-, -cyclohexenylene-, and -phenylene-; a heterocycle of 5, 6, or 7 atoms selected from -pyrrolidinylene-, -piperidinylene-, -homopiperidinylene-, and -thiophenylene-; a bicyclic ring system selected from the group consisting of:

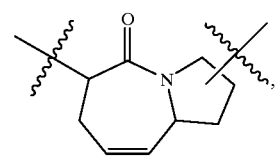,

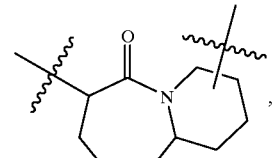,

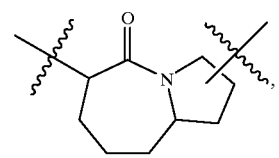,

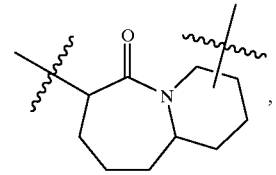,

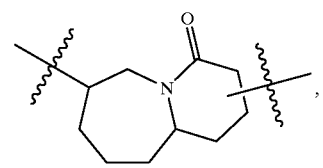,

-continued
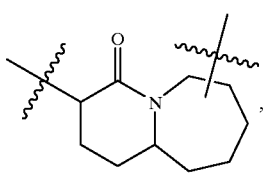
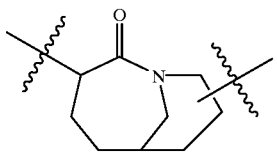
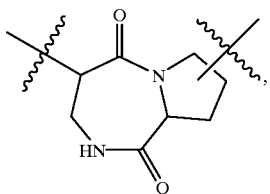
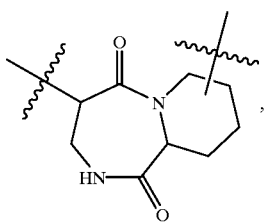
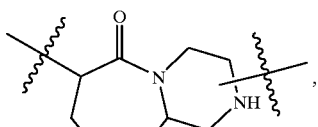
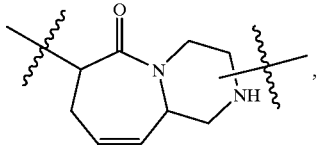
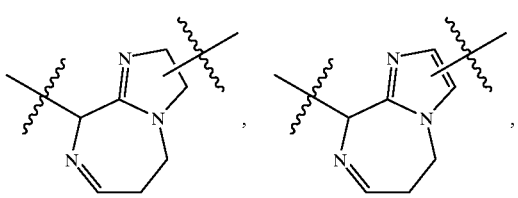
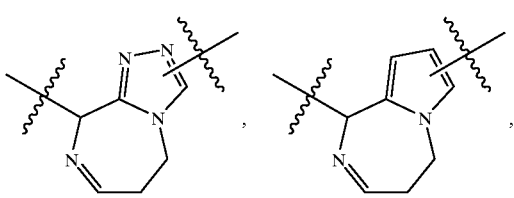
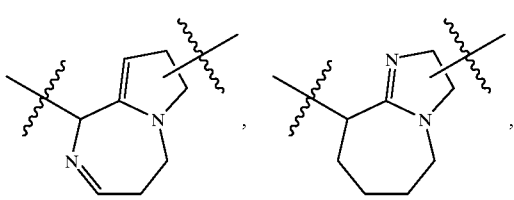
-continued
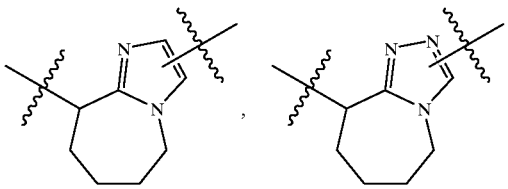
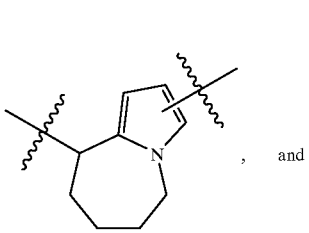
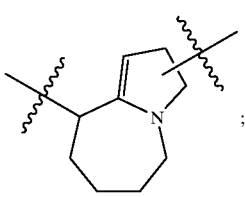
a tricyclic ring system selected from the group consisting of:
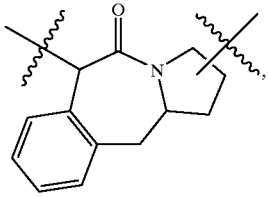
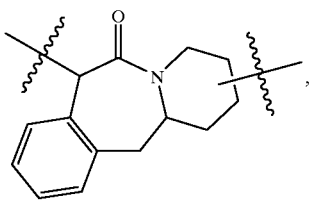
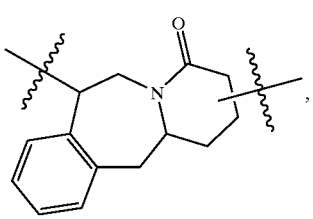
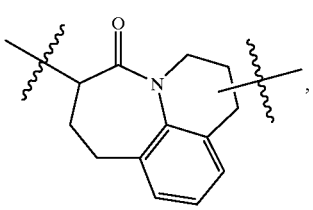

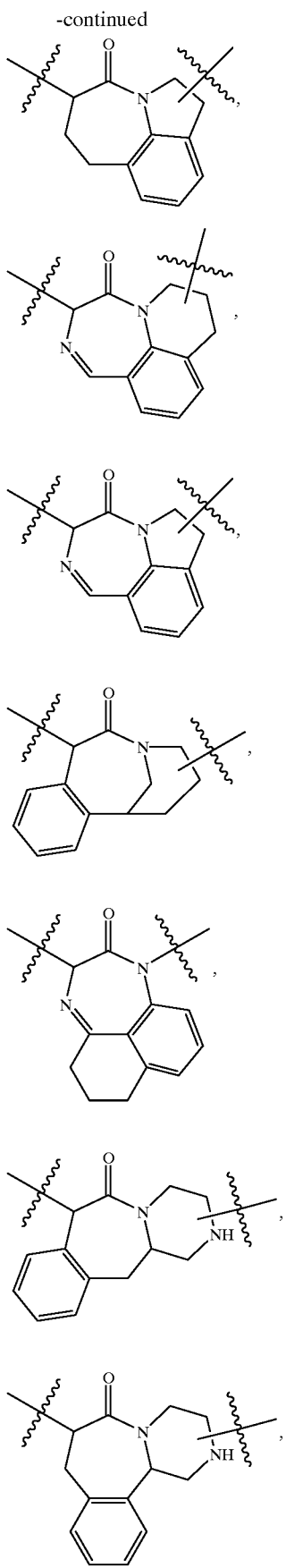
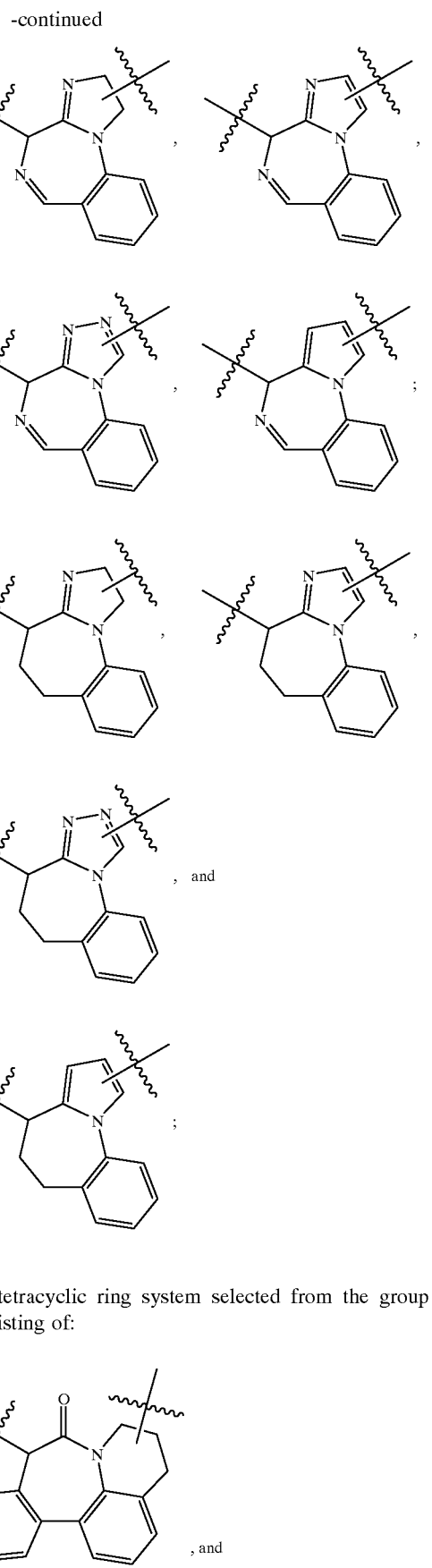
and a tetracyclic ring system selected from the group consisting of:
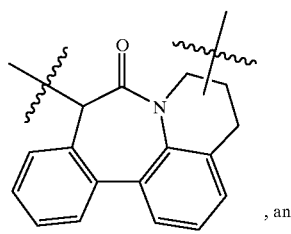
, and

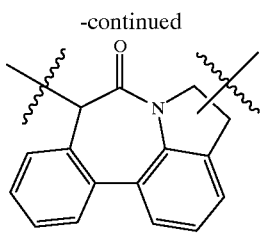

and Ring B is substituted with 0, 1, 2, 3, or 4 $R^{11}$ groups.

In another preferred embodiment of ring B, ring B is selected from the group consisting of -cyclopent-1,2-diyl-, -cyclopent-1,3-diyl-, -cyclohex-1,2-diyl-, -cyclohex-1,3-diyl-, -cyclohex-1,4-diyl-, -cyclohept-1,3-diyl-, -cyclopenten-3,5-diyl-, -phen-1,2-diyl-, -phen-1,3-diyl-, -phen-1,4-diyl-, -pyrrolidin-1,4-diyl-, -pyrrolidin-2,4-diyl-, -piperidin-1,4-diyl-, -piperidin-1,3-diyl-, -thiophen-2,3-diyl-, and

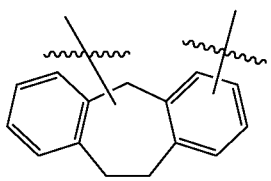

;

a bicyclic ring system selected from the group consisting of:

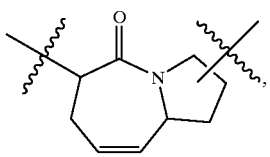

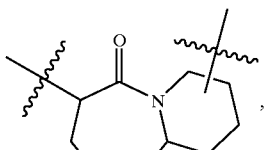

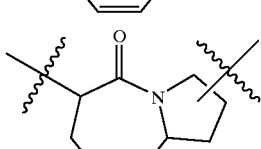

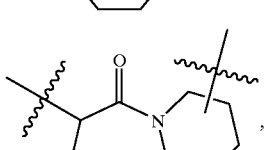

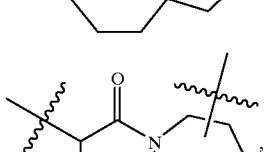

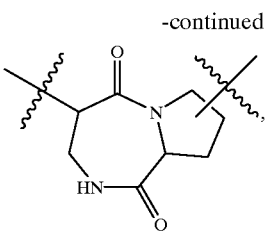

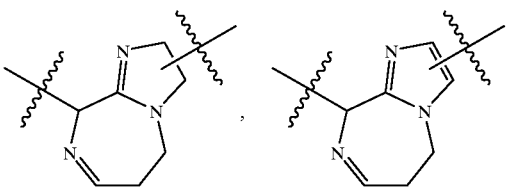

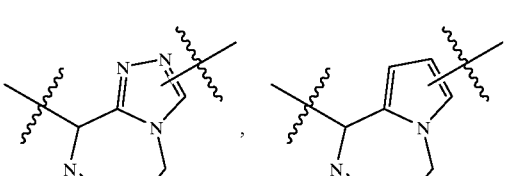

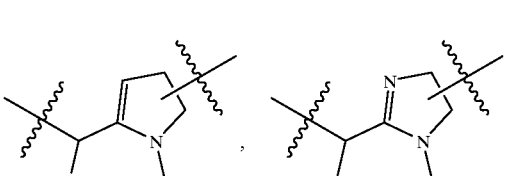

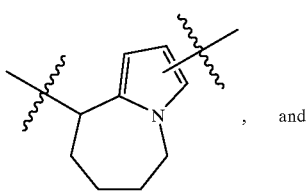, and
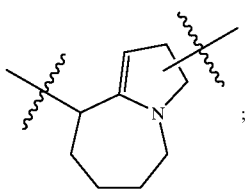;
a tricyclic ring system selected from the group consisting of:
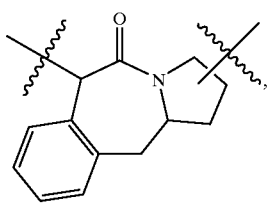,
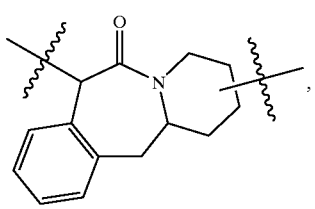,
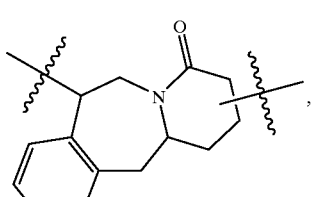,
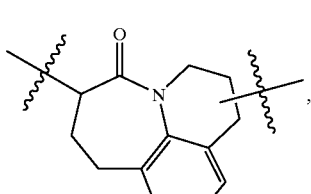,
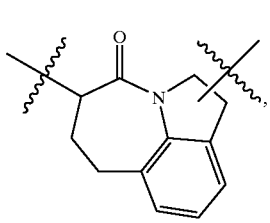,
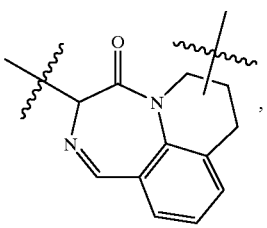,
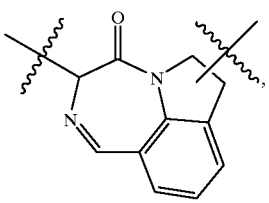,
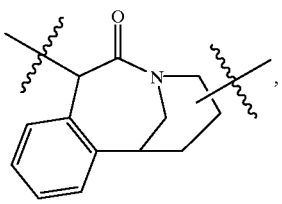,
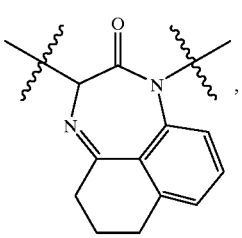,
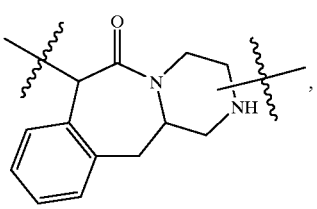,
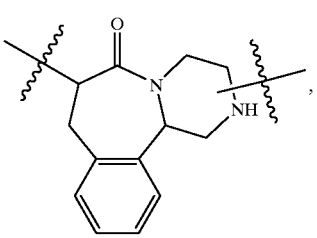,
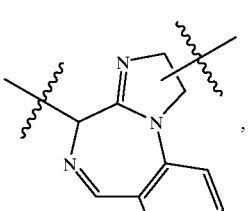, 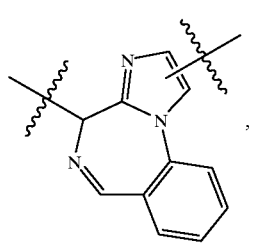, -continued

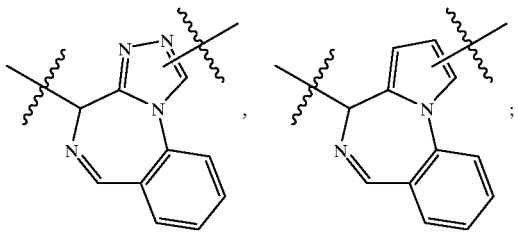
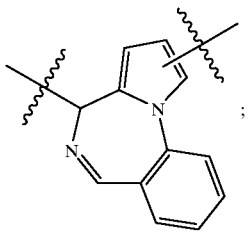

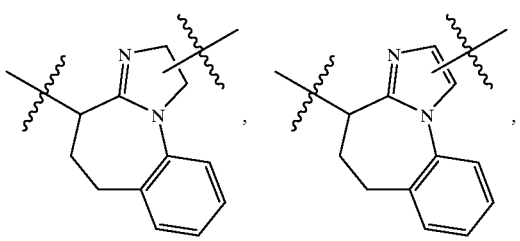
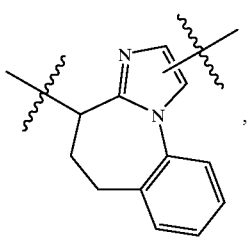

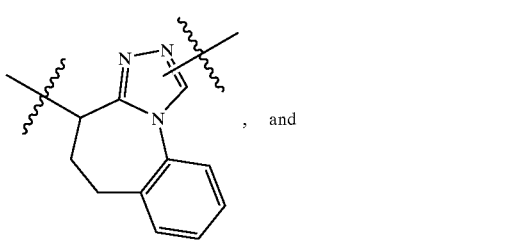

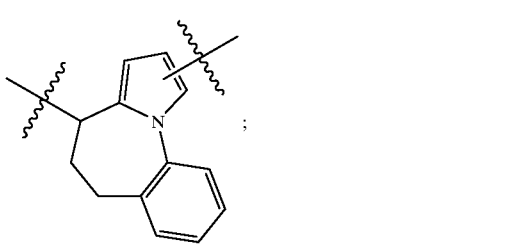

and a tetracyclic ring system selected from the group consisting of:

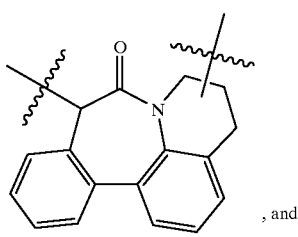
, and

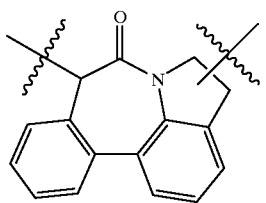

and Ring B is substituted with 0, 1, or 2 $R^{11}$ groups.

In another preferred embodiment of ring B, ring B is selected from the group consisting of:

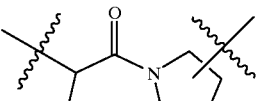
,

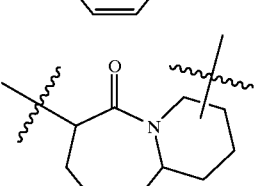
,

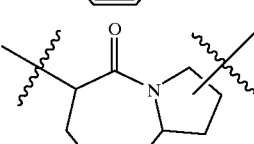
, and

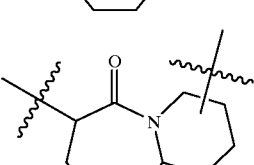
;

and Ring B is substituted with 0–1 $R^{11}$.

In another preferred embodiment of ring B, ring B is selected from the group consisting of:

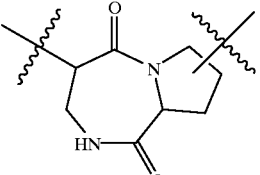
and

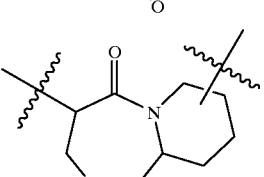
;

and Ring B is substituted with 0 –1 $R^{11}$.

In another preferred embodiment of ring B, ring B is selected from the group consisting of:

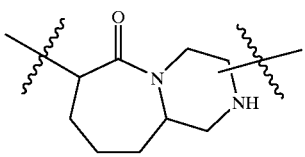
and

-continued

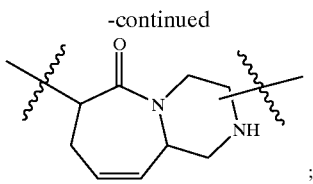

and Ring B is substituted with 0–1 $R^{11}$.

In another preferred embodiment of ring B, ring B is selected from the group consisting of:

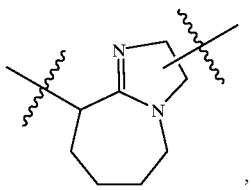
,

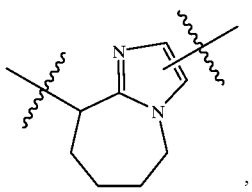
, and

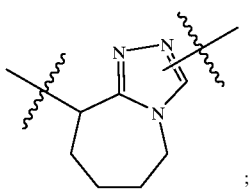
;

and Ring B is substituted with 0–1 $R^{11}$.

In another preferred embodiment of ring B, ring B is selected from the group consisting of:

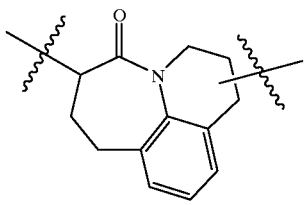
and

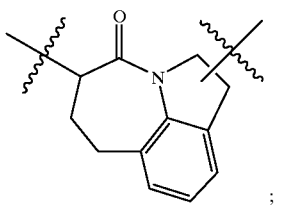
;

and Ring B is substituted with 0–1 $R^{11}$.

In another preferred embodiment of ring B, ring B is selected from the group consisting of:

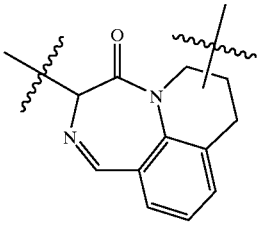
and

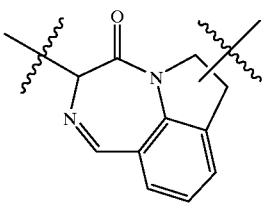
;

and Ring B is substituted with 0–1 $R^{11}$.

In another preferred embodiment of ring B, ring B is:

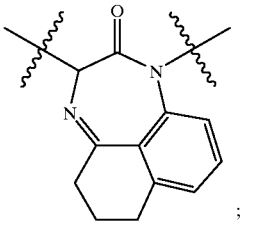
;

and Ring B is substituted with 0–1 $R^{11}$.

In another preferred embodiment of ring B, ring B is selected from the group consisting of:

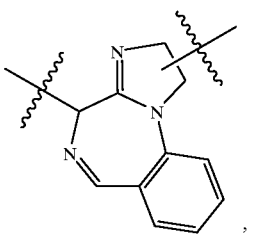
,

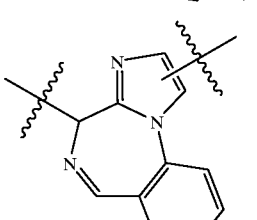
, and

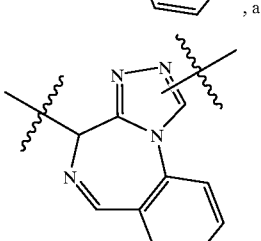
;

and Ring B is substituted with 0–1 $R^{11}$.

In a preferred embodiment of $R^3$ and $R^{3a}$, $R^3$ is selected from $C_1$–$C_4$ alkyl, $C_2$–$C_4$ alkenyl, and $C_2$–$C_4$ alkynyl; and $R^{3a}$ is H.

In another preferred embodiment of $R^3$ and $R^{3a}$, $R^3$ and $R^{3a}$ may be combined to form a cyclopropyl, cyclobutyl, cyclopentyl, or cyclohexyl moiety.

In another preferred embodiment of $R^3$ and $R^{3a}$, $R^3$ and $R^{3a}$ may be combined to form a cyclopropyl, cyclobutyl, cyclopentyl, or cyclohexyl moiety.

In another preferred embodiment of $R^3$, $R^3$ may be selected from the corresponding substituents depicted in Group B of Table 1.

In a preferred embodiment of $R^5$ and $R^{5a}$, $R^5$ is selected from $C_1$–$C_4$ alkyl, $C_2$–$C_4$ alkenyl, and $C_2$–$C_4$ alkynyl; and $R^{5a}$ is H.

In another preferred embodiment of $R^5$ and $R^{5a}$, $R^5$ and $R^{5a}$ may be combined to form a cyclopropyl, cyclobutyl, cyclopentyl, or cyclohexyl moiety.

In another preferred embodiment of $R^5$, $R^5$ may be selected from the corresponding substituents depicted in Group B of Table 1.

It is understood that any and all embodiments of the present invention may be taken in conjunction with any other embodiment to descibe additional even more preferred embodiments of the present invention.

In a second embodiment, the present invention provides a pharmaceutical composition comprising a compound of Formula (I) and a pharmaceutically acceptable carrier.

In a third embodiment, the present invention provides a method for the treatment of neurological disorders associated with P-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for the treatment of neurological disorders associated with β-amyloid production comprising administering to a host in need of such treatment a therapeutically effective amount of a metalloprotease inhibitor which inhibits γ secretase activity.

In a preferred embodiment the neurological disorder associated with β∇amyloid production is Alzheimer's Disease.

In a preferred embodiment, the metalloprotease inhibitor is a hydroxamic acid.

In a more preferred embodiment, the metalloprotease inhibitor is a hydroxamic acid with an $IC_{50}$ value of less than 10 μM in the Aβ immunoprecipation assay.

In a fifth embodiment, the present invention provides a method for inhibiting γ secretase activity for the treatment of a physiological disorder associated with inhibiting γ secretase activity comprising administering to a host in need of such inhibition a therapeutically effective amount of a compound of Formula (I) that inhibits γ secretase activity.

In a preferred embodiment the physiological disorder associated with inhibiting γ secretase activity is Alzheimer's Disease.

In a sixth embodiment, the present invention provides a compound of Formula (I) for use in therapy.

In a preferred embodiment the present invention provides a compound of Formula (I) for use in therapy of Alzheimer's Disease.

In a seventh embodiment, the present invention provides for the use of a compound of Formula (I) for the manufacture of a medicament for the treatment of Alzheimer's Disease.

DEFINITIONS

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No 4,666,829. The 43 amino acid sequence is:

```
 1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr.
```

However, a skilled artisan knows that fragments generated by enzymatic degradation can result in loss of amino acids 1–10 and/or amino acids 39–43. Thus, an amino acid sequence 1–43 represents the maximum sequence of amino acids for Aβ peptide.

The term "APP", as used herein, refers to the protein known in the art as β∇amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, a secretase cleaving around the 16/17 peptide bond in Aβ, and "γ secretases", as used herein, generating C-terminal Aβ fragments ending at position 38, 39, 40, 41, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{5b}$) occurs more than one time in any constituent or formula for a compound, its definition at each occurrence is independent of its definition at every other occurrence. Thus, for example, if a group is shown to be substituted with 0–2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl".

As used herein, "alkenyl" or "alkenylene" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms, preferably 1, 2, or 3 heteroatoms, independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and 0 atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Unless otherwise specified, "aryl" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The compounds herein described may have asymmetric centers. One enantiomer of a compound of Formula (I) may display superior biological activity over the opposite enantiomer. Both of the configurations are considered part of the invention. For example, the amino attachment to ring B may exist in either an S or R configuration. An example of such configuration includes,

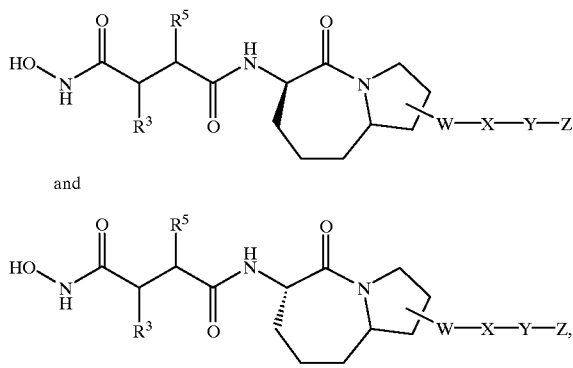

and but is not intended to be limited to this example of ring B. When required, separation of the racemic material can be achieved by methods known in the art. Additionally, the connection point of —W—X—Y—Z or other substituents to ring B may exist in two enantiomers. Both enantiomers are considered part of this invention. Additionally, the carbon atoms to which $R^3$ and $R^5$ are attached may describe chiral carbons which may display superior biological activity over the opposite enantiomer. For example, where $R^3$ and $R^5$ are not H, then the configuration of the two centers may be described as (2R,3R), (2R,3S), (2S,3R), or (2S,3 S). All configurations are considered part of the invention; however, the (2R,3S) and the (2S,3R) are preferred and the (2R,3S) is more preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharnaceutical Sciences,* 17th ed., Mack Publishing Company, Easton, Pa., 1985, p. 1418, the disclosure of which is hereby incorporated by reference. "Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Methods for the synthesis of succinylamino lactams are known in the art and are disclosed in a number of references including PCT publication number WO 96/29313, which is hereby incorporated by reference.

Disubstituted succinate derivatives can be prepared by a number of known procedures. The procedure of Evans (D. A. Evans et al, Org. Synth. 86, p83 (1990)) is outlined in Scheme 1 where acylation of an oxazolidinone with an acylating agent such as an acid chloride provides structures 1. Alkylation to form 2 followed by cleavage of the chiral auxiliary and subsequent alkylation of the dianion of the carboxylic acid 3 provides a variety of disubstituted succinates which can be separated and incorporated into structures of Formula (I) by those skilled in the art. Additional examples are found in P. Becket, M. J. Crimmin, M. H. Davis, Z. Spavold, Synlett, (1993), 137–138, incorporated herein by reference.

Scheme 1

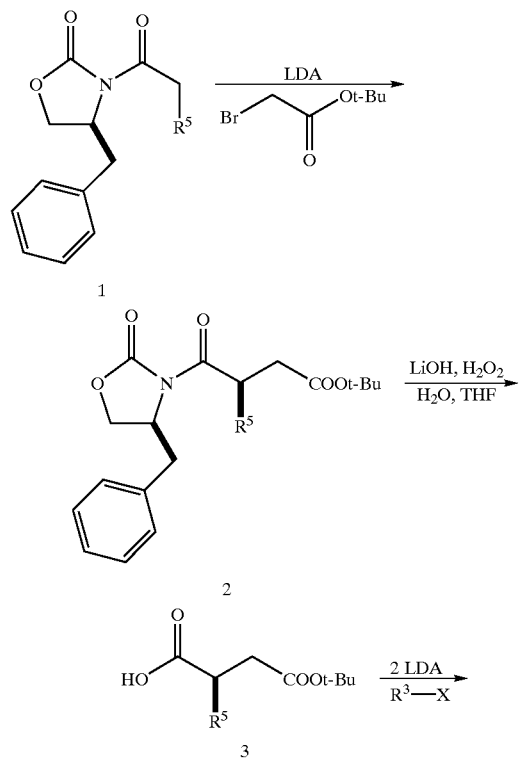

-continued

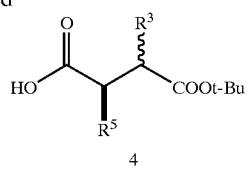

4

Diastereomerically pure succinate derivatives can be accessed using the chemistry outlined below, adapted from P. Becket, M. J. Crimmin, M. H. Davis, Z. Spavold, Synlett, (1993), 137–138 incorporated herein by reference. This reference provides the synthesis below to obtain compound 9. Compound 11 is used as an intermediate and is prepared from 9 by hydrogenation of the allyl group followed by coupling of 9-fluorenemethanol under standard conditions using DCC and DMAP in $CH_2Cl_2$. Deprotection of the tert-butyl ester is accomplished by treatment with 50% trifluoroacetic acid.

Additional methods useful for the preparation of succinate derivatives are known by those skilled in the art. Such references include, McClure and Axt, Bioorganic & Medicinal Chemistry Letters, 8 (1998) 143–146; Jacobson and Reddy, Tetrahedron Letters, Vol 37, No. 46, 8263–8266 (1996); Pratt et al., SYNLETT, May 1998, p. 531; WO 97/18207; and WO 98/51665. The synthetic disclosures of WO97/18207 and WO 98/51665 are hereby incorporated by reference.

Additional methods useful for the preparation of succinate derivatives are disclosed in WO00/07995 and WO 00/38618, which are hereby incorporated in their entirety by reference.

Scheme 2

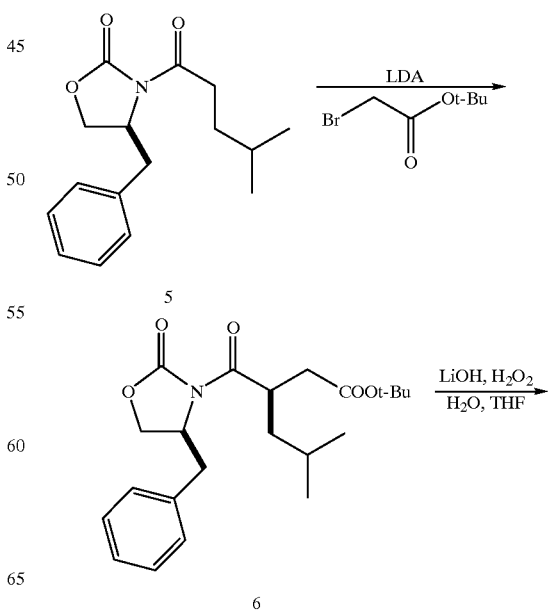

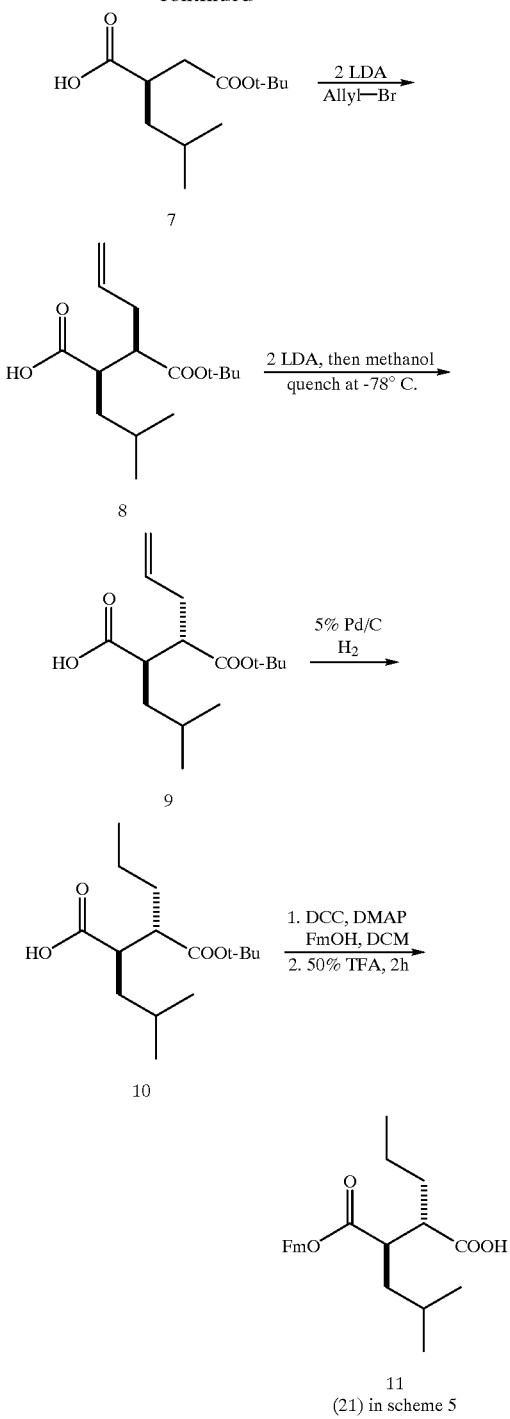

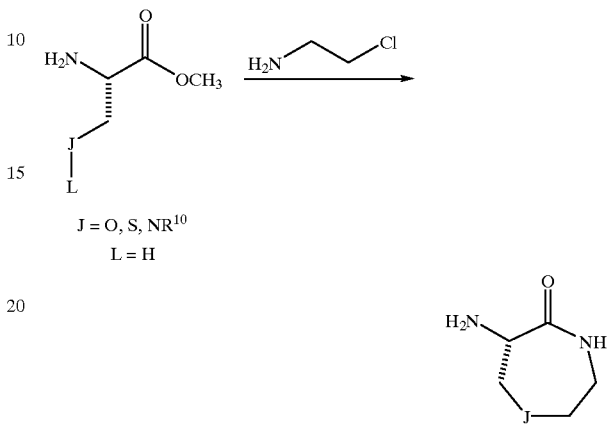

Scheme 3

$J = O, S, NR^{10}$
$L = H$

One skilled in the art can extend this methodology to the synthesis of β amino and oxygen containing rings by analogy. The sulfur-containing molecules can also be oxidized to the sulfoxide and sulfone by methods known to one skilled in the art.

The lactam nitrogen of compound 13 can be alkylated by generating the anion with bases such as LDA, lithium bis(trimethylsilyl)amide or sodium hydride in solvents like THF, with or without cosolvents such as DMPU or HMPA and reacting this with a variety of groups containing leaving groups (X") like bromide, iodide, mesylate or tosylate. Alkylating agents such as a bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304–305, 342–347, 695–698.

The N-Boc protecting group can be removed by any number of methods well known in the literature like TFA in methylene chloride to give the compound 15. The amine 15 can be coupled to an appropriately substituted carboxylic acid or acid chloride by methods well described in the literature for making amide bonds, like TBTU in DMF with a base like NMM to give the elaborated compound 16. Compounds 16 can be alkylated using standard bases like LDA, NaH, or NaHMDS to deprotonate the amide followed by addition of an alkylating agent with an appropriate leaving group like halide, mesylate, or triflate in an appropriate solvent to provide compounds 17 with an $R^6$ substituent. The t-butyl ester is then removed by treatment with TFA in methylene chloride to give the carboxylic acid 17.

It is understood that methods useful for the preparation of W—X—Y—Z derivatives, on a non-commercial scale, are known by those skilled in the art or readily ascertainable from the literature. Such methods useful for the preparation of W—X—Y—Z derivatives are disclosed in WO00/07995 and WO 00/38618, which are hereby incorporated in their entirety by reference.

A variety of compounds of Formula (I) can be prepared by methods described in Scheme 4. The protected α amine 3 of the a amino-e caprolactam can be prepared by methods well known in the literature for amino protecting groups as discussed in Theodora W. Greene's book "Protective Groups in Organic Synthesis", like N-Boc using di-t-butyldicarbonate in an appropriate solvent like DMSO. A sulfur atom can be introduced into the ring providing L-α amino-β thio-ε caprolactam according to the procedure in S. A. Ahmed et al, FEBS Letters, (1984), vol. 174, pages 76–9 (Scheme 3).

Scheme 4

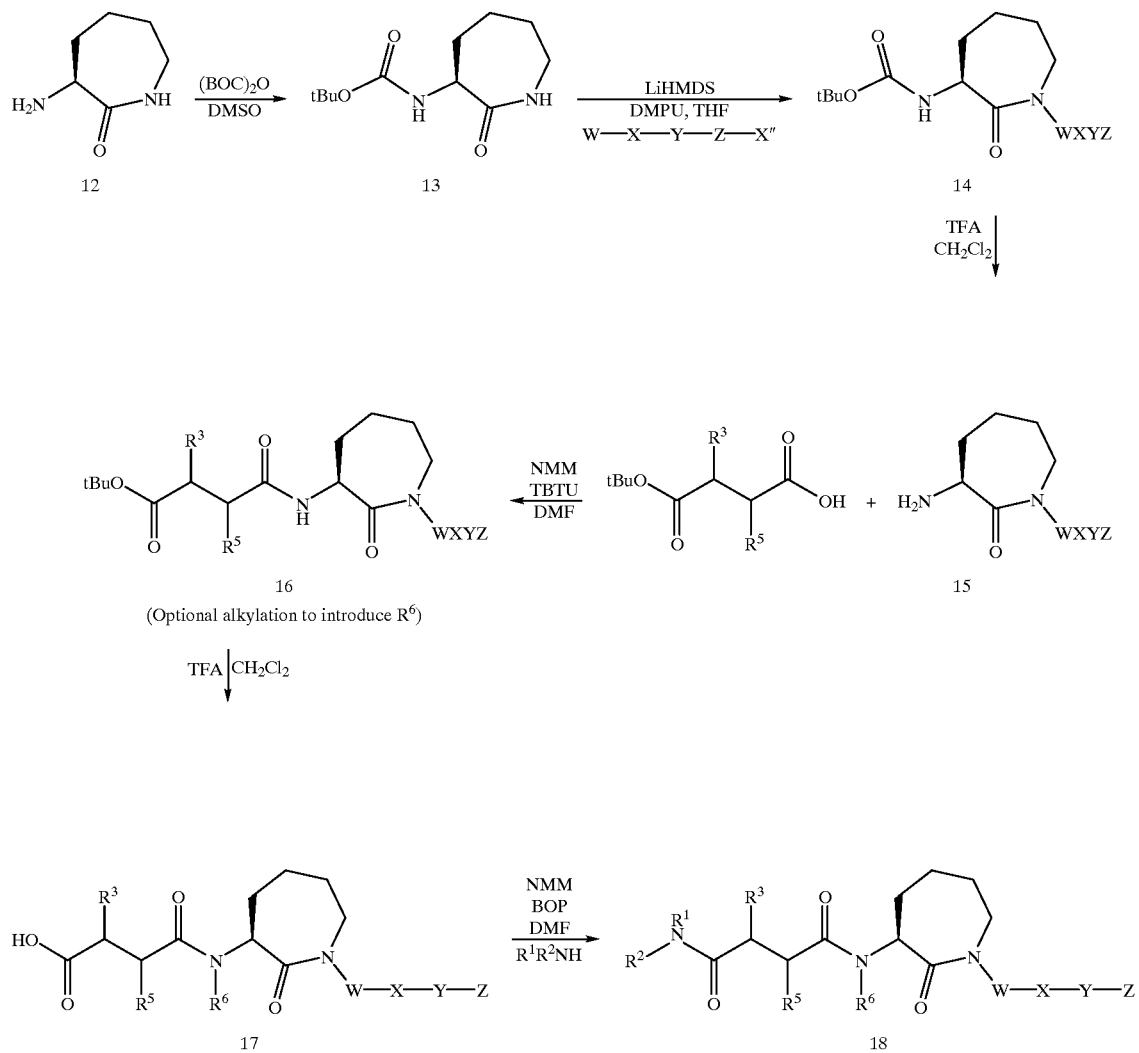

The final compounds 18 were prepared by treating the activated carboxylic acid of 17 with an appropriately substituted amine. For instance, activation of the carboxylic acid with HATU (O—(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) or other coupling agents known to those skilled in the art allows condensation with ammonia to form primary amides. Similarly, condensation of the activated acid with hydroxylamine hydrochloride provides the hydroxamic acid, or reaction with a primary or secondary amine provides the substituted amine derivative. Activation of the acid with PyBrOP (bromo-tris-pyrrolidino-phosphonium hexafluorophosphate) followed by addition of an alcohol and 4-dimethylaminopyridine allows formation of the ester directly. For additional acylation reactions see for example Carey, F. A. and Sundberg, R. J., Advanced Organic Chemistry, Part A, New York: Plenum Press, 1990, pages 475–479.

Additional Examples of compounds of Formula (I) can be prepared as shown in Scheme 5. A suitable resin for solid phase synthesis such as Fmoc (Fluorenylmethylcarbonyl)-protected hydroxylamine bound to polystyrene beads can be purchased from Novabiochem, Inc. Deprotection of the Fmoc group under standard conditions using 20% piperidine in DMF provides trityl-linked hydroxylamine resin. Coupling of a fluorenylmethyl-protected succinic acid derivative such as 20 with a coupling agent such as HATU in a suitable solvent like DMF or N-methylpyrrolidinone provides the support-bound hydroxamate 21. The Fluorenylmethyl ester can be removed using 20% piperidine in DMF to provide the free carboxylic acid which can be coupled to amines like the caprolactam 22 (which is available using chemistry outlined in Scheme 4) using PyBOP (benzotriazole-1-yl-oxy-tris-pyrrolidino-phosphonium hexafluorophosphate) and a suitable base like DIEA in DMF or NMP. The support-bound intermediate 23 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing dilute (5%) trifluoroacetic acid in $CH_2Cl_2$ and purified by conventional chromatography.

Scheme 5

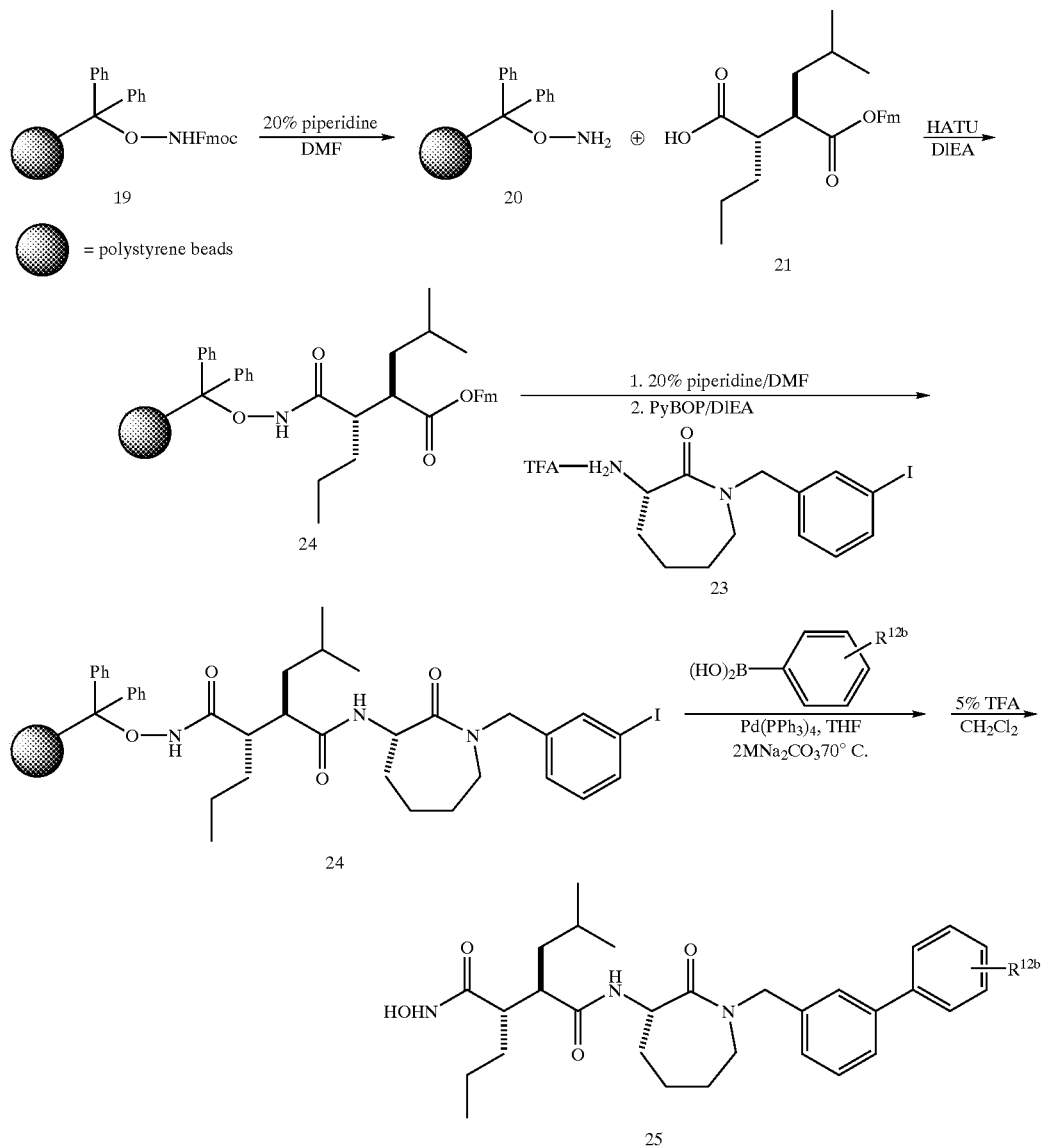

General Procedure for Solid-phase Synthesis According to Scheme 5.

Resin 20 of Scheme 5:

Fmoc-protected resin 19 (2.0 g, 0.78 mmol/g, 1.56 mmol) is purchased from Novabiochem and swelled in 20 ml of $CH_2Cl_2$ for 1 hour. The $CH_2Cl_2$ is removed and the resin is then treated with 25% v/v piperidine in DMF (8 mL) and allowed to shake slowly for 16 h. The solvent was removed by filtration and the resin was shaken with an additional 8 mL of 25% v/v piperidine in DMF for 2 h at room temperature. The solvents were removed by filtration, and the resin 20 was rinsed 3× with 20 mL of DMF, 3× with 20 mL of methanol, and 3× with 20 mL of $CH_2Cl_2$ and dried in vacuo.

Succinate 10 of Scheme 2:

Succinate 9 is prepared according to the literature procedure (P. Becket, M. J. Crimmin, M. H. Davis, Z. Spavold, Synlett, (1993), 137–138; WO 97/18207; WO 98/51665). Succinate 9 (17.8 g, 66 mmol) is dissolved in 250 mL of ethyl acetate and placed in a Parr shaker bottle. To the solution is added 890 mg of 5% palladium on carbon, and the bottle is pressurized to 40 psi with hydrogen gas and shaken for 2.5 h at room temperature. The hydrogen is removed and the palladium catalyst is removed by filtration through a pad of celite. Concentration of the ethyl acetate solution provides 17.5 g (98%) of succinate 10. No further purification is necessary. MS $(M-H)^+=271$.

Succinate 21 of Scheme 5:

Succinate 10 (6.3 g, 23.1 mmol) is dissolved in 125 mL of $CH_2Cl_2$ and 4.8 g (23.3 mmol) of dicyclohexylcarbodiimide is added. The solution is stirred at room temperature for 30 min and then 4.6 g (23.4 mmol) of 9-fluorenemethanol is added followed by 122 mg (1 mmol) of 4-dimethylaminopyridine. After 5 h of stirring at room temperature, the reaction solution was diluted with an additional 100 mL of $CH_2Cl_2$ and filtered through a pad of celite to remove precipitated dicyclohexylurea. The solution was then washed 3× with 50 mL of a 1N HCl solution, 3 × with 50 mL of a saturated sodium bicarbonate solution, and 2× with 50 mL of brine. The crude product was dried over MgSO$_4$ and soncentrated onto 15 g of silica gel. Chromatography eluting with a gradient of 2.5% to 5% ethyl acetate/hexanes provided 6.4 g (61%) of the diester as an oil. The purified diester (6.4 g 14.2 mmol) is then dissolved in 25 mL of CH$_2$Cl$_2$, 25 mL of trifluoroacetic acid is added, and the reaction solution is stirred at room temperature for 2 h. The reaction solution is directly concentrated in vacuo to an oil which is then redissolved in 25 mL of toluene and reconcentrated, followed by drying in vacuo to provide 6.3 g (98%) of the desired succinate 9 as an oil which solidifies on standing. MS (M+Na)$^+$=471, (M+2Na)$^+$=439.

Caprolactam 23 of Scheme 5:

Boc-caprolactam 14 (5.0 g, 21.9 mmol) is dissolved in 60 mL of THF and chilled to -78° C. To the chilled solution is added 24 mL of a 1.0 M solution of lithium bis(trimethylsilyl)amide in THF, and the solution was brounght to 0° C. and stirred for 15 min. To the anion solution was added 6.5 g (22 mmol) of 3-iodobenzyl bromide (Aldrich) and the the solution was allowed to warm to room temperature and stirred for 18 h. The reaction solution was diluted with 50 mL of water and extracted 3× with ethyl acetate. The combined organic layers were dried over MgSO$_4$ and concentrated in vacuo. The crude product was purified by chromatography eluting with a gradient of 5–20% ethyl acetate/hexanes to afford 7.0 g (72%) of the title compound as a white solid. MS (M+Na)$^+$=467.

Resin 22 of Scheme 5:

Resin 22 (2.0 g, 0.78 mmol/g, 1.56 mmol) was swollen in 3 mL of DMF. In a separate flask, 1.85 g (4.68 mmol) of succinate 21 was dissolved in 3 mL of DMF and 2.5 mL of N,N-diisopropylethylamine (14 mmol) wsa added, followed by 1.81 g (4.68 mmol) of HATU. The solution containing the active ester was added to the slurried resin and the reaction suspension was slowly shaken for 18 h. The resin was then washed 3× with 20 mL of DMF, 3× with 20 mL of methanol, and 3× with 20 mL of CH$_2$Cl$_2$. Loading of the resin was determined by Fmoc quantitation to be 0.25 mmol/g, see Reddy, M. P.; Voelker, P.J. *Int. J. Pept. Protein Res.* 1998, 31, 345-348.

Resin 24 of Scheme 5:

Resin 22 (2.0 g, 0.25 mmol/g, 0.5 mmol) was suspended in 10 mL of 25% piperidine in DMF. The suspended resin was shaken for 30 min at room temperature, and then the resin was washed 3× with 20 mL of DMF, 3× with 20 mL of methanol, and 3× with 20 mL of CH$_2$Cl$_2$. Deprotected resin (1.0 g, 0.25 mmol) was swollen in 2 mL of DMF. To the slurry was added 650 mg (1.25 mmol) of PyBOP and 217 mL (1.25 mmol) of DIEA. Separately, 443 mg (0.97 mmol) of caprolactam 23 was dissolved in 2 mL of DMF and 436 mL (2.5 mmol) of DIEA was added. The caprolactam solution was added to the resin slurry and the resin was mixed for 18 h at room temperature. The solvents were then removed and the coupling was repeated, with shaking at room temperature for 6 h. The resin was then washed 3× with 10 mL of DMF, 3× with 10 mL of methanol, and 3× with 10 mL of CH$_2$Cl$_2$.

Products 25 of Scheme 5:

A 70 mg (17.5 mmol) portion of resin 24 was suspended in 1 mL of THF in a screw-cap vial. To the slurry was added a boronic acid (0.15 mmol), 150 mL of a 2 M solution of sodium carbonate, and 15 mg (13 mmol) of tetrakis(triphenylphosphine)palladium. The vial was tightly closed and heated to 60° C. for 16 h using a dry heater on a shaker table. The solvents were then removed by filtration and the resin was washed 3× with THF (2 mL), 3× with methanol (2 mL), 3× with water, and 3× with CH$_2$Cl$_2$. The resins were then placed in a glass vial and cleaved with 1 mL of 5% trifluoroacetic acid in CH$_2$Cl$_2$ for 30 min. The solution ws filtered off and the resin was washed with an additional 2 mL of CH$_2$Cl$_2$ and the combined filtrates were evaporated to dryness to yield the crude products 25. The products were purified by chromatography eluting with 10–100% ethyl acetate in hexanes to yield 13.0 to 6.0 mg (14–60%) of the final products.

Additional Examples of compounds of Formula (I) can be prepared as shown in Scheme 6. A suitable resin for solid phase synthesis such as Fmoc (Fluorenylmethylcarbonyl)-protected peptide amide linker (PAL)-derivatized polystyrene beads can be purchased from Perkin Elmer Biosystems, Inc. Deprotection of the Fmoc group under standard conditions using 20% piperidine in DMF provides the free benzylamine. Coupling of a succinic acid derivative such as 28 (which is available using chemistry outlined in Scheme 4) with a coupling agent such as HATU in a suitable solvent like DMF or N-methylpyrrolidinone provides the support-bound amide 29. The support-bound intermediate 29 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing 50% trifluoroacetic acid in CH$_2$Cl$_2$ and can be purified by conventional chromatography or preparative HPLC.

Scheme 6

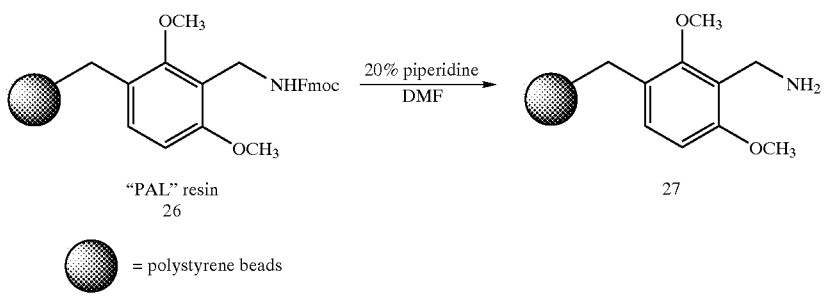

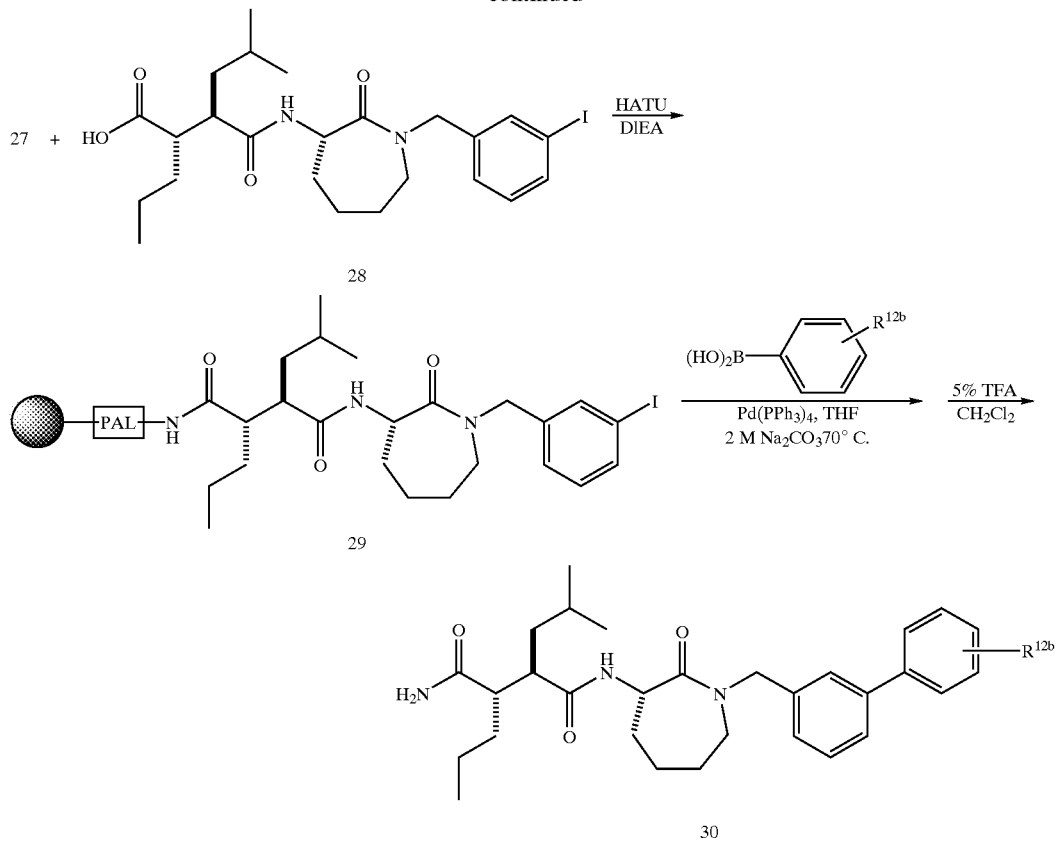

General Procedure for Solid-phase Synthesis According to Scheme 6:

Resin 27 of Scheme 6:

Fmoc-protected PAL resin 26 (0.80 g, 0.50 mmol/g, 0.40 mmol) is purchased from Advanced Chemtech and swelled in 20 ml of $CH_2Cl_2$ for 1 hour. The $CH_2Cl_2$ is removed and the resin is then treated with 25% v/v piperidine in DMF (6 mL) and allowed to shake slowly for 1 h. The solvents were removed by filtration, and the resin 27 was rinsed 3× with 20 mL of DMF, 3× with 20 mL of methanol, and 3× with 20 mL of $CH_2Cl_2$. and dried in vacuo.

Acid 28 of Scheme 6:

To a solution of 0.100 g (367 mmol) of succinate 10 dissolved in 2.0 mL of dry DMF was added 0.120 mL (1.10 mmol) of N-methylmorpholine. A second solution containing 0.139 g (0.403 mmol) of caprolactam 23 of Scheme 5 dissolved in 2.0 mL of DMF was then added. To the mixed solution was added 229 mg (0.440 mmol) of PyBop and the reaction solution was stirred for 16 h at room temperature. The reaction solution was diluted with water (20 mL) and extracted 3 × with 100 mL of ethyl acetate. The combined organic layers were dried with $Na_2SO_4$ and concentrated under reduced pressure. The resulting oil was purified by chromatography eluting with a gradient of 5–20% ethyl acetate in hexanes to provide 0.195 g (0.360 mmol, 98%) of the tert-butyl ester of Acid 28 (MS M+Na=621). The purified ester (0.195 g, 0.360 mmol) was dissolved in 10 mL of 25% trifluoroacetic acid in $CH_2Cl_2$ and stirred for 2 h at room temperature. The solvents were removed under reduced pressure and the acid was redissolved in 5 mL of toluene and reconcentrated 2× to remove residual TFA. The crude acid was found to be pure by $^1H$ NMR and was used in Scheme 6 without further purification.

Resin 29 of Scheme 6:

Resin 27 (800 mg, 0.40 mmol) was solvated in 4.0 mL of dry DMF and and 0.63 mL (3.6 mmol) of diisopropylethylamine was addedfollowed by a solution of Acid 28 dissolved in 4 mL of DMF. To the slurry was then added 0.465 g (1.2 mmol) of HATU and the slurry was shaken for 26 h at room temperature. The solvents were removed by filtration, and the resin 29 was rinsed 3× with 20 mL of DMF, 3× with 20 mL of methanol, and 3× with 20 mL of $CH_2Cl_2$. and dried in vacuo.

Products 30 of Scheme 6:

A 75 mg (0.38 mmol/g, 28.8 mmol) portion of resin 24 was suspended in 1 mL of THF in a screw-cap vial. To the slurry was added a boronic acid (0.33 mmol), 150 mL of a 2 M solution of sodium carbonate, and 15 mg (13 mmol) of tetrakis(triphenylphosphine)palladium. The vial was tightly closed and heated to 60° C. for 16 h using a dry heater on a shaker table. The solvents were then removed by filtration and the resin was washed 3× with THF (2 mL), 3× with methanol (2 mL), 3 x with water, and 3× with $CH_2Cl_2$. The resins were then placed in a glass vial and cleaved with 1 mL of 5% trifluoroacetic acid in $CH_2Cl_2$ for 2 h. The solution was filtered off and the resin was washed with an additional 2 mL of $CH_2Cl_2$ and the combined filtrates were evaporated to dryness to yield the crude products 25. The products were purified by chromatography eluting with 10–100% ethyl acetate in hexanes to yield 0.5 to 2.0 mg (14–60%) of the final products.

The internal phenyl ring can be exchanged for a pyridine ring using chemistry outlined in Scheme 7. The chloromethyl pyidine 33 is prepared using a known procedure reported in Nutaitis, Charles F.; Ledeboer, Mark W. Org.

Prep. Proced. Int. (1992), 24(2), 143–6 Incorporated herein by reference. After freebasing the pyridine, alkylation with the Boc-caprolactam provides pyridine intermediate 34, which can be elaborated to the protected amide 35 with succinate 10. Substitution can then be introduced using Suzuki methodology employing a palladium source such as tetrakis(triphenylphosphine) palladium(0) or bis (diphenylphosphinoferrocene) palladium(II) dichloride and a suitable base such as sodium carbonate or triethylamine in a solvent such as THF or toluene containing 10% methanol. Stille chemistry is also possible using a suitable palladium source such as tetrakis(triphenylphosphine)palladium(0) and an aryl or vinyl tin derivative in a solvent such as benzene, toluene, or xylenes. The tert-butyl ester is then deprotected under standard acidic conditions using trifluoroacetic acid and the amide is formed under standard conditions to provide products 36.

extracted with 30 mL of $CH_2Cl_2$ 3× followed by concentration of the organic layers to provide the free base. Separately, 1.8 g (7.8 mmol) of caprolactam 13 is dissolved in 40 mL of dry THF and chilled to −78° C. To the solution was added 8.7 mL of a 1M solution of sodium bis (trimethylsilyl) amide. The solution was brought to 0° C. and stirred for 30 min. To the resultant anion was added a solution of 1.7 g (8.3 mmol) of pyridine 33 free base dissolved in 40 mL of THF. The resulting reaction solution was stirred at room temperature for 18 h and then heated to 50° C. and stirred an additional 3 h. The reaction solution was allowed to cool and then 50 mL of water was added and the aqueous layer was extracted 2× with 100 mL of ethyl acteate. The combined organic layers were dried and concentrated under reduced pressure to provide the crude product which was purified by chromatography eluting with 20 to 100% ethyl acetate in hexanes to provide 1.5 g (51%) of caprolactam 34 as an oil.

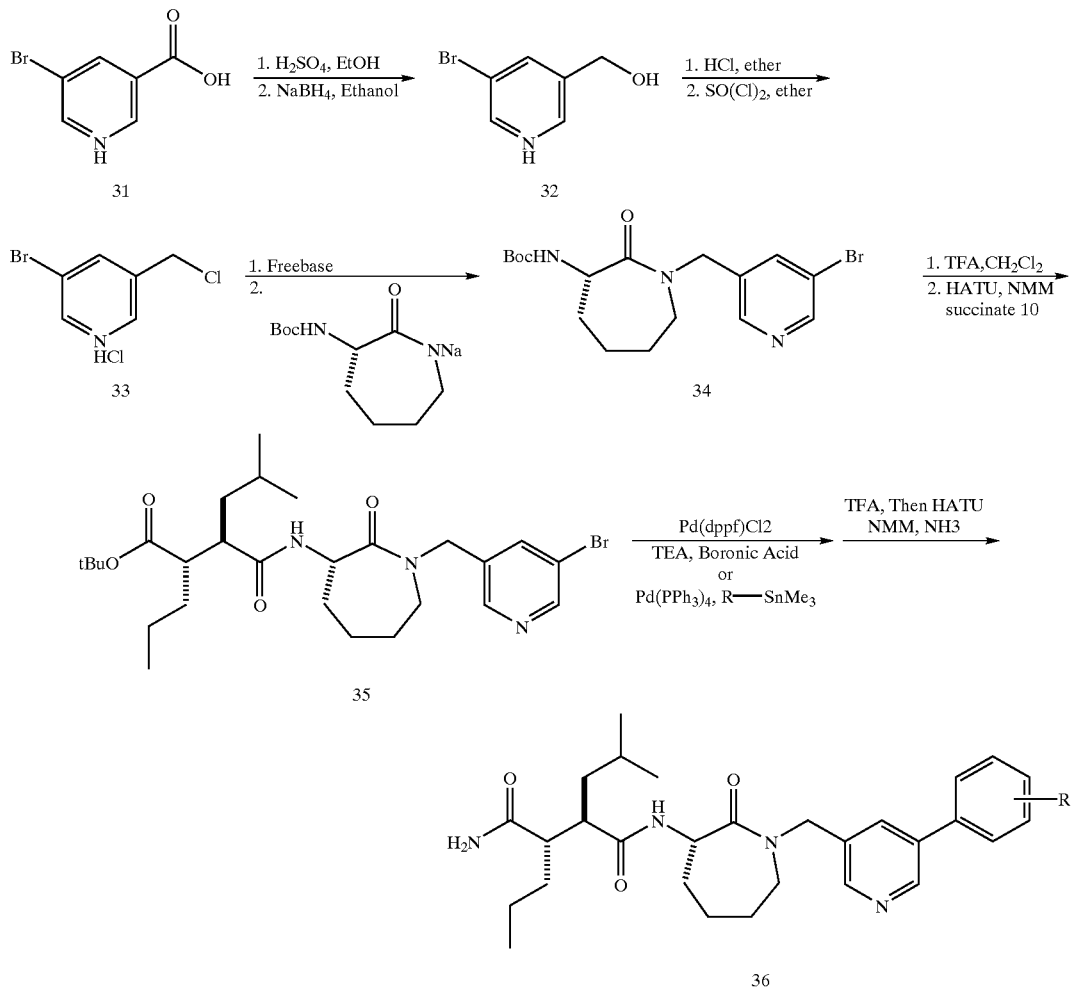

Scheme 7

General Procedure for Synthesis According to Scheme 7

The chloromethyl pyidine HCl salt 33 is prepared using a known procedure reported in Nutaitis, Charles F.; Ledeboer, Mark W. Org. Prep. Proced. Int. (1992), 24(2), 143–6.

Caprolactam 34:

Pyridine HCl salt 33 (2.0 g, 8.3 mmol) is dissolved in 50 mL of a saturated NaHCO3 solution and the solution is Amide 35:

Caprolactam 34 (0.40 g, 1.0 mmol) is dissolved in 20 mL of 50% trifluoroacetic acid in $CH_2Cl_2$ and stirred at room temperature for 30 min. The solvents were then removed under reduced pressure and the resulting oil was redissolved in 5 mL of toluene and reconcentrated to remove residual TFA. Separately, 0.270 g (1.0 mmol) of succinate 10 was dissolved in 5.0 mL of dry DMF and 0.44 mL (4 mmol) of N-methylmorpholine was added followed by 0.50 g (1.3 mmol) of HATU and the resulting solution was stirred at room temperature for 30 min. The crude deprotected caprolactam from above was dissolved in 5.0 mL of dry DMF and added to the succinate solution and the resulting solution was heated to 50° C. and stirred for 2 days. The solution was then diluted with 20 mL of water and extracted with 3 50 mL portions of ethyl acetate. The combined organic layers were dried and concentrated under reduced pressure to provide an oil which was purified by chromatography eluting with 20 to 50% ethyl acetate in hexanes to provide 0.40 g (70%) of the Amide 35.

Additional examples can be prepared by the method shown in Scheme 8. Coupling of an amine onto a commercially available aldehyde-derived resin 37 under conditions for reductive amination such as sodium tris(acetoxy) borohydride in $CH_2Cl_2$ containing 1% acetic provides a support-bound amine 38. The carboxylic acid 39 can then be coupled to the support-bound amine generating an amide 40 which can be liberated from the support employing trifluoroacetic acid in $CH_2Cl_2$.

acetic acid (30 uL, 1%) are added and the reaction is shaken on a shaker table for 16 h at room temperature. The solvents were removed by filtration and the resin 38 was rinsed 3× with 20 mL of DMF, 3× with 20 mL of methanol, and 3× with 20 mL of $CH_2Cl_2$. and dried in vacuo.

Products 40 of Scheme 8:

Carboxylic acid 39 (23 mg, 0.045 mmol), diisopropylethylamine (13 mL, 0.075 mmol) and HATU (17.1 mg, 0.045 mmol) were mixed in 0.5 mL of DMF for 30 min. Amine-derived resins 38 (30 mg, 0.015 mmol) were then added and the suspension was shaken at room temperature for 16 h. . The solvents were removed by filtration and the resins were rinsed 3× with 20 mL of DMF, 3× with 20 mL of methanol, and 3× with 20 mL of $CH_2Cl_2$. The isolated resins were then cleaved by the addition of 0.50 mL of trifluoroacetic acid. The product solutions were concentrated and redissolved in 0.5 mL of methanol and reconcentrated 2× to remove residual TFA. Product yields ranged from 0–100% based on the structure of the amine.

The compounds of Formula (I) of the present invention can also be prepared from aminolactam 42 and succinic acid

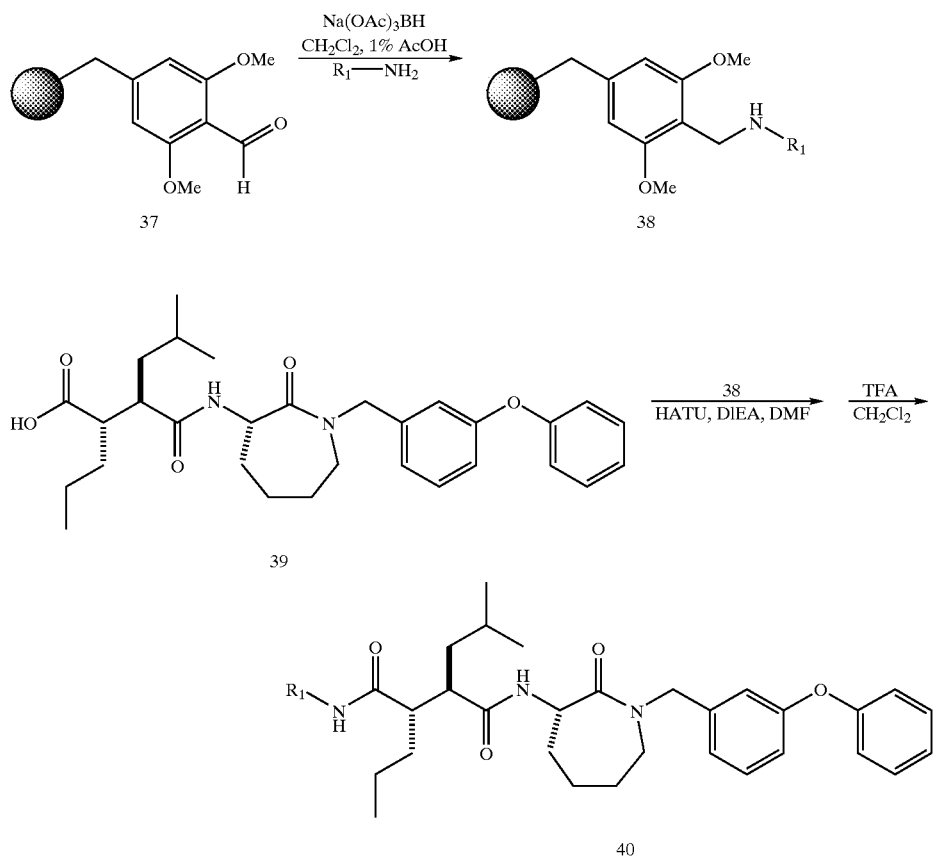

General Procedure for Solid-phase Synthesis According to Scheme 8

Resin 38 of Scheme 5:

Aldehyde-derived resin 37 (200 mg, 0.5 mmol/g, 0.1 mmol) is purchased from Perkin Elmer Biosystems and swelled in 3 ml of $CH_2Cl_2$ for 1 hour. An amine (1.0 mmol), sodium tris(acetoxy)borohydride (106 mg, 0.5 mmol) and derivatives 41 using amide bond syntheses known in the art, including methods commonly used in peptide syntheses, such as HATU, TBTU, BOP, pyBOP, EDC, CDI, DCC, hydroxysuccinimide, mixed carboxylic anhydride, and phenyl ester mediated couplings, as illustrated in Scheme 9 for the synthesis of aminolactam 43, an embodiment of the present invention.

Scheme 9

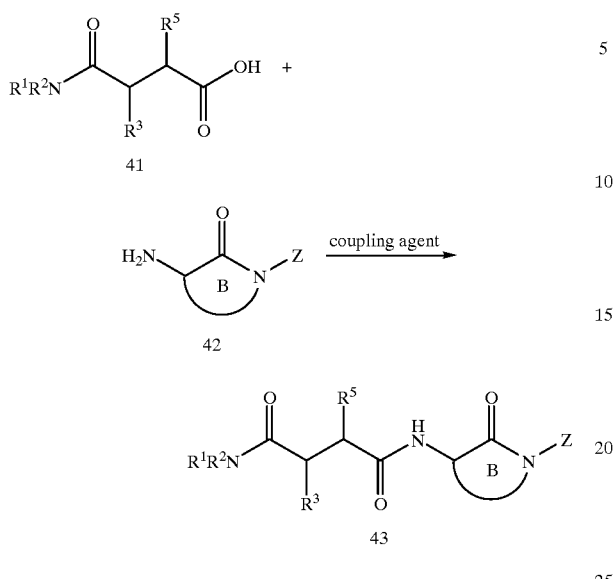

Depending on the structure of the final product, it is appreciated by those skilled in the art that protecting groups or precursor functionality convertable to the desired groups may be desireable. Protecting groups and their use in synthesis are described in Green and Wuts, *Protective Groups in Organic Synthesis*, (Wiley 1991). The use of protecting groups is further illustrated in Scheme 10, in which the succinate half-ester 44 (Becket et al., Synlett 1993, 137–138) is coupled to the aminobenzodiazepine 45 (Sherrill and Sugg, J. Org. Chem. 1995, 60, 730–734; Bock et al., J. Med. Chem., 1993, 36, 4276–4292) to give ester 46, followed by conversion of the ester group to the primary amide 47.

Scheme 10

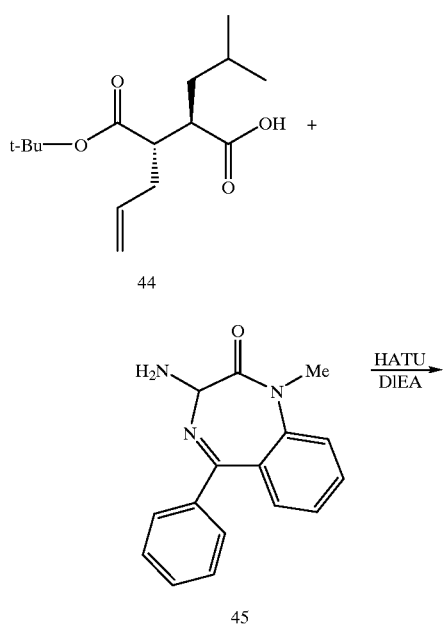

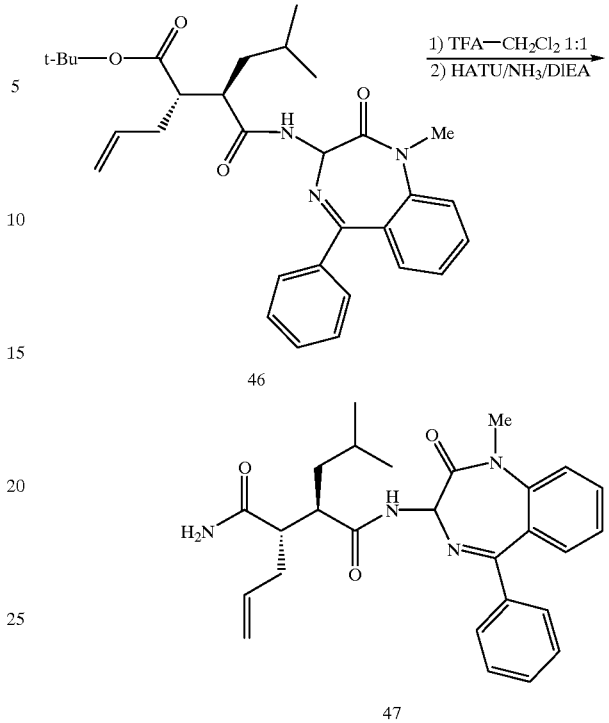

Methods for the synthesis of lactams as contemplated by the present invention in lactam ring B in Formula (I), including amino benzodiazepines, are known in the art and are disclosed in a number of references including PCT publication number WO 98/28268, which is hereby incorporated by reference. Additional references include Bock, et al, J. Org. Chem., 1987, 52, 3232–3239 and Sherrill et al, J. Org. Chem., 1995, 60, 730–734; Walsh, D. A., Synthesis, September 1980, p.677.

The carbocyclic and heterocyclic B groups can be synthesized using methods described in WO 98/28268, W099/32453, and WO/99/67221 and references cited therein. The synthetic disclosures of WO 98/28268, W099/32453, and WO/99/67221, and the references which are cited within these references, are hereby incorporated by reference.

EXAMPLES

Example 1

Representative Procedure for 4-butyl-3-oxo-2,3,4,8,9,10-hexahydronaphtho[1,8-ef][1,4]diazepine Core 1.

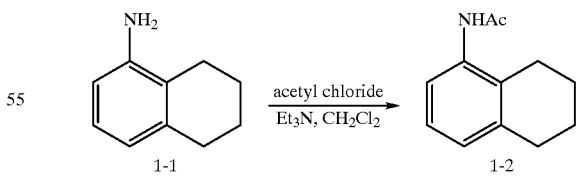

5,6,7,8-Tetrahydro-1-naphthylamine (1-1, 24.0 g, 163 mmol) and triethylamine (33.4 g, 330 mmol) were dissolved in CH$_2$Cl$_2$ (120 mL). The solution was cooled to 0 C in an ice-water bath. Acetyl chloride (19.5 g, 248 mmol) was added dropwise over 30 min. The reaction mixture was warmed to room temperature. After the solvent was removed in vacuo, the slurry was filtered. The solid was washed with water and dried under high vacuum to provide 1-2 (28.68 g, 93% yield). $^1$H NMR (300 MHz, CDCl$_3$) 67.59 (d, J=7.7 Hz, 1H), 7.12 (t, J=7.7 Hz, 1H), 6.94(m, 2H), 2.78 (t, J=6.1 Hz, 2H), 2.59 (t, J=6.0 Hz, 2H), 2.20 (s, 3H), 1.80 (m, 4H). [M. Sugimori et al J. Med. Chem. 1998, 41,2308]

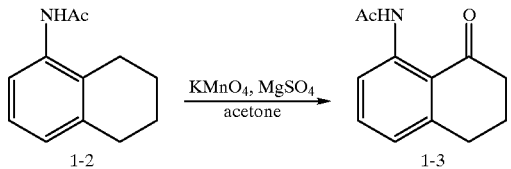

To a solution of 1-2 (28.0 g, 148 mmol) in a mixture of acetone (1.5 L) and 15% aqueous MgSO$_4$ (133 mL) was added KMnO$_4$ (70.0 g, 444 mmol) in portions at 0° C. The reaction mixture was stirred for 12 h at room temperature and diluted with water. After removal of the volatile in vacuo, the mixture was extracted with CH$_2$Cl$_2$, and the organic phase was washed successively with saturated NaHSO$_3$,1 N NaOH, brine and dried (MgSO$_4$). Evaporation of the solvent provided 1-3 as a yellow solid (17.0 g, 57% yield). $^1$H NMR (300 MHz, CDCl$_3$) 8 8.59 (d, J=8.4 Hz, 1H), 7.44 (t, J=8.0 Hz, 1H), 6.92 (d, J=7.7 Hz, 1H), 2.97 (t, J=6.0 Hz, 2H), 2.70 (t, J=6.6 Hz, 2H), 2.23 (s, 3H), 2.09 (m, 2H).

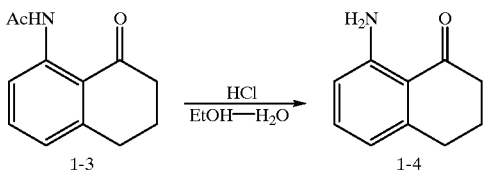

A solution of 1-3 (17.0 g, 83.6 mmol) in a mixture of EtOH (150 mL) and 6 N HCl (70 mL) was heated to 100° C. for 6 h. After the reaction mixture was cooled to room temperature, it was neutralized with NaOH to pH=13 and extracted with EtOAc. The organic layer was washed with brine, dried (Na$_2$SO$_4$) and evaporated. Flash column chromatography (10% EtOAc/hexane) of the reside gave 1-4 (10.0 g, 42.0% yield). $^1$H NMR (300 MHz, CDCl$_3$) δ 7.15 (t, J=8.0 Hz, 1H), 6.46 (m, 4H), 2.87 (t, J=6.0 Hz, 2 H), 2.63 (t, J=6.6 Hz, 2H), 2.04 (m, 2H); MS (ESI, MH) 162.2.

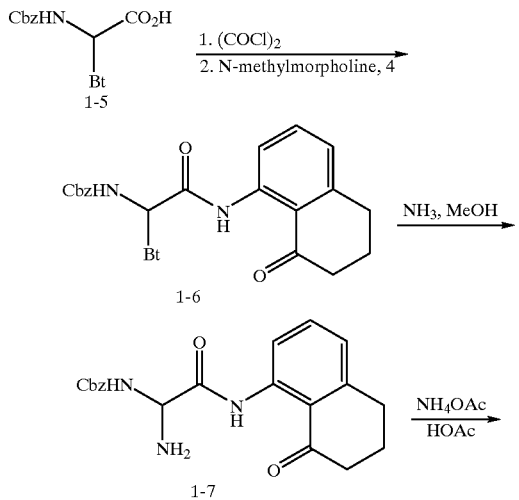

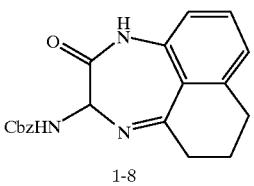

A solution of 2-(benzotriazol-1-yl)-N-(benzyloxycarbonyl)glycine (1–5, 22.25 g, 68.2 mmol) in anhydrous THF (200 mL) and CH$_2$Cl$_2$ (35 mL) under N$_2$ was cooled to 0° C with an ice-water bath. Oxalyl chloride (8.66 g, 68.2 mmol) was added followed by anhydrous DMF (0.2 mL). After maintaining the reaction mixture at 0–5° C. for 2 h, a solution of 1-4 (10.0 g, 62.0 mmol) and N-methylmorpholine (13.8 g, 136 mmol) in THF (80 mL) was added dropwise over 30 min. The mixture was allowed to warm to room temperature and the reaction slurry was filtered. The solid was washed with minimum amount of cold THF. The mother liquor containing 1–6 was saturated with ammonia gas and stirred overnight. Following solvent displacement into CHCl$_3$, the solution of crude 1–7 was washed with 1 N NaOH, brine, dried (MgSO$_4$) and concentrated in vacuo.

The crude 1-7 was dissolved in glacial acetic acid (300 mL), combined with ammonium acetate (15.0 g), was stirred at room temperature overnight. The reaction mixture was concentrated and suspended in EtOAc and Et$_2$O. Aqueous NaOH was added until the pH >9. The resulting slurry was cooled to 0–5° C. in an ice-water bath and then filtered. The solid was washed consecutively with water and Et$_2$O and dried under high vacuum to provide 1-8 (12.5 g, 53% yield) as a crystalline solid. $^1$H NMR (300 MHz, CDCl$_3$) δ 8.93 (br s, 1H), 7.25–7.45 (m, 6H), 7.05 (d, J=7.3 Hz, 1H), 6.92 (d, J=8.1 Hz, 1H), 6.54 (d, J=8.4 Hz, 1H), 5.05–5.30 (m, 3H), 2.65–3.00 (m, 4H), 2.05–2.20 (m, 1H), 1.90–2.05 (m, 1H); MS (ESI, MH) 350.4.

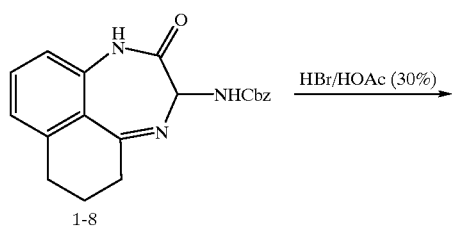

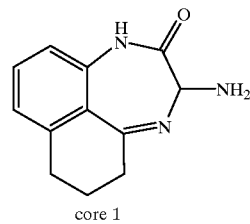

1-8 (2.0 g, 5.7 mmol) was dissolved in HBr/HOAc (30%, 30 mL) and stirred for 5 h at ambient temperature. The reaction mixture was then diluted with ether (200 mL). The precipitate was filtered under nitrogen atmosphere and washed thoroughly with ether to give a yellow solid. The solid was dissolved in H$_2$O, saturated with K$_2$CO$_3$, and extracted with ethyl acetate. The organic phase was dried (Na$_2$SO$_4$). Evaporation of the solvent gave core 1 (900 mg, 73%) as a yellow solid. MS m/z 216.1 (MH$^+$).

Example 1a

Representative Procedure: (2R,3S)-3-allyl-2-isobutyl-$N^1$-(4-butyl-3-oxo-2,3,4,8,9,10-hexahydronaphtho[1,8-ef][1,4diazepin-2-yl)butanediamide (Example 1a)

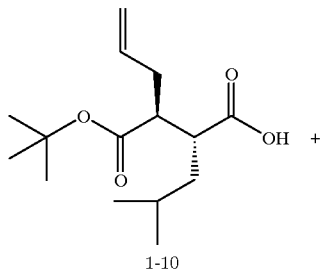

1-10

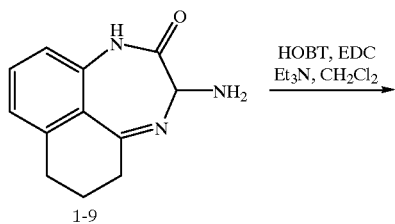

1-9

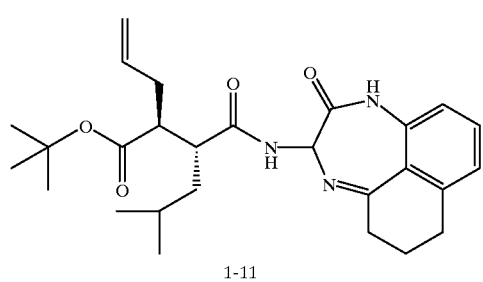

1-11

1-9 (880 mg, 4.10 mmol), 1-10 (1.10 g, 4.10 mmol), 1-hydroxybenzotriazole hydrate (HOBT, 665 mg, 4.92 mmol) were suspended in CH$_2$Cl$_2$, and cooled to 0° C. 1-(3-dimethylaminopropyl)-3-ethylcarbodiimide hydrochloride (EDC-HCl, 1.18 g, 6.15 mmol) and triethylamine (0.86 mL, 6.15 mmol) were added subsequently. After being stirred for 24 h at ambient temperature, the reaction mixture was diluted with ethyl acetate. The organic layer was washed with water, brine and dried (Na$_2$SO$_4$). After evaporation of the solvent, the residue was purified on silica gel (5% methanol/methylene chloride) to afford 1-11 (1.51 g, 79%). MS m/z 468.5 (MH$^+$).

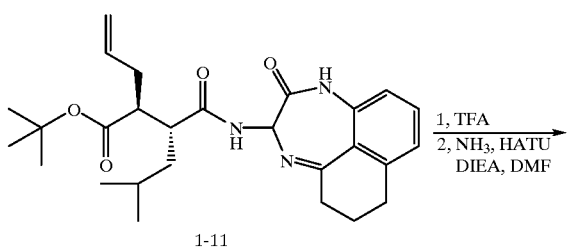

1-11

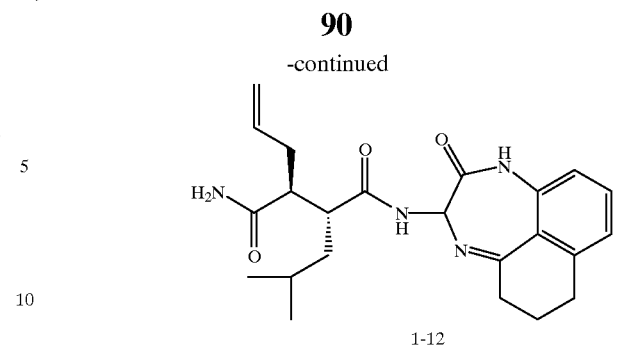

1-12

1-11 (1.93 g, 4.10 mmol) was dissolved in CH$_2$Cl$_2$/TFA (8 mL, 1:1) and stirred for 4 h at ambient temperature. Solvent was removed by rotovap, and the residue was dissolved in DMF (10 mL) and cooled to 0° C. To the above solution was added HATU (1.87 g, 4.90 mmol), diisopropylethylamine (0.26 mL, 6.15 mmol) and bubbled with anhydrous ammonia for 20 min. Stirring was continued overnight. DMF was removed in vacuo, the residue was diluted with ethyl acetate, washed with water, brine, and dried (MgSO$_4$). After evaporation of the solvent, the residue was purified on silica gel (5% methanol/methylene chloride) to afford product 1-12 (745 mg, 44%) as a white solid. MS m/z 411.3 (MH$^+$).

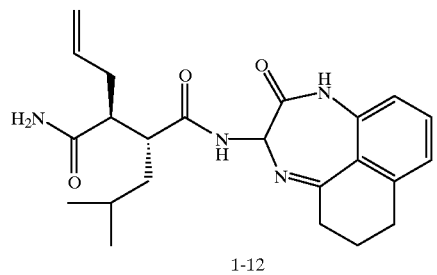

1-12

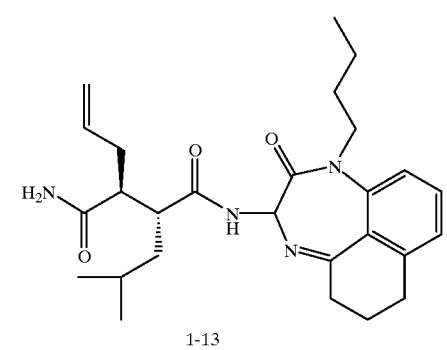

1-13

A mixture of 1-12 (410.5 mg, 1.0 mmol), iodobutane (552.1 mg, 3.0 mmol), and potassium carbonate (276.4 mg, 2.0 mmol) in anhydrous DMF (3 mL) was stirred at ambient temperature for 20 h. The reaction mixture was diluted with ethyl acetate. The organic layer was washed with 5% aqueous LiCl, brine, and dried (MgSO$_4$). Fter the solvent was evaporated, the residue was purified on silica gel (3% methanol/methylene chloride) to provide 1-13 (384 mg, 82%) as a white solid. This mixture of two diastereoisomers was separated on chiral AD column with methanol/isopropanol/hexane to give Example 1a' and Example 1a".

Example 1a'

¹H NMR (300 MHz, CDCl₃) δ 0.75–0.95 (m, 9H), 1.08–b 1.60 (m, br, 6H), 1.65–1.80 (m, 1H), 1.90–2.02 (m, 1H), 2.15–2.35 (m, 2H), 2.45–2.65 (m, 2H), 2.70-3.10 (m, br, 5H), 3.58–3.70 (m, 1H), 4.20–4.30 (m, 1H), 5.08 (d, J=10 Hz, 1H), 5.14 (d, J=17 Hz, 1H), 5.32 (s, br, 1H), 5.40 (d, J=7 Hz, 1H), 5.78–5.85 (m, 1H), 7.15 (d, J=8 Hz, 1H), 7.24–7.26 (m, 1H), 7.39 (d, J=8 Hz, 1H), 7.50–7.60 (m, 1H); MS m/z 467.5 (MH⁺).

Example 1a"

¹H NMR (300 MHz, CDCl₃) δ 0.75–0.95 (m, 9H), 1.08–2.05 (m, 10H), 2.15–2.35 (m, 2H), 2.40–2.60 (m, 1H), 2.60–2.75 (m, 1H), 2.80–3.15 (m, 3H), 3.58-3.70 (m, 1H), 4.15–4.26 (m, 1H), 5.06 (d, J=10 Hz, 1H), 5.13 (d, J=15 Hz, 1H), 5.32-5.42 (m, br, 2H), 5.78–5.85 (m, 1H), 7.15 (d, J=7 Hz, 1H), 7.24–7.26 (m, 2H), 7.50–7.60 (m, 1H); MS m/z 467.5 (MH⁺).

Example 1b (2R,3S)-3-allyl-2-isobutyl-N¹-(4-methyl-3-oxo-2,3,4,8,9,10-hexahydronaphtho[1,8-ef] [1,4]diazepin-2-yl)butanediamide (Example 1b)

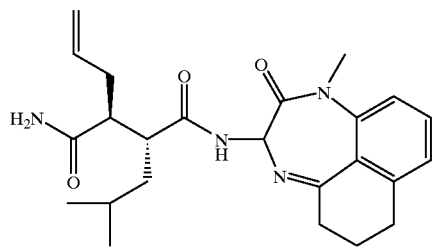

Ex. 1b (2R,3S)-3-allyl-2-isobutyl-N¹-(4-methyl-3-oxo-2,3,4,8,9,10-hexahydronaphtho[1,8-ef] [1,4]diazepin-2-yl)butanediamide (1b) was prepared in the similar manner by alkylation of 1-12 with iodomethane. MS m/z 425.5 (MH⁺).

Example 1c (2R,3S)-3-allyl-2-isobutyl-N¹-(4-(pyrid-2-ylmethyl)-3-oxo-2,3,4,8,9,10-hexahydronaphtho[1,8-ef] [1,4]diazepin-2-yl)butanediamide (Example 1c)

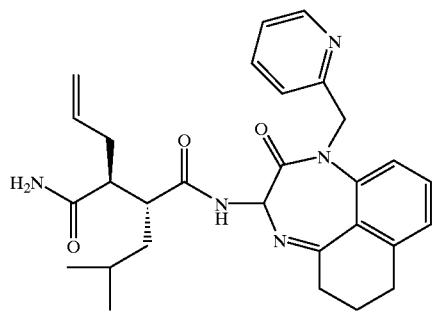

Ex. 1c (2R,3S)-3-allyl-2-isobutyl-N¹-(3-oxo-4-(2-pyridinylmethyl)-2,3,4,8,9,10-hexahydronaphtho[1,8-ef] [1,4]diazepin-2-yl)butanediamide (Example 1c) was prepared in the similar manner by alkylation of 1-12 with 2-(bromomethyl)pyridine. MS mlz 502.5 (MH⁺).

Example 1d (2R, 3S)-3-allyl-2-isobutyl-N¹-(4-(2-(diethylamino)ethyl)-3-oxo-2,3,4,8,9,10-hexahydronaphtho[1,8-ef] [1,4]diazepin-2-yl)butanediamide (Example 1d)

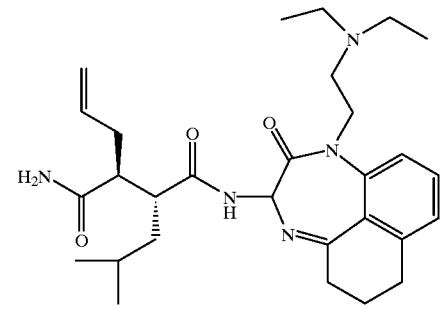

Ex. 1d (2R, 3S)-3-allyl-2-isobutyl-N¹-{4-[2-(diethylaminoethyl)]-3-oxo-2,3,4,8,9,10-hexahydronaphtho[1,8-ef] [1,4]diazepin-2-yl}-3-isobutylbutanediamide (1d) was prepared in the similar manner by alkylation of 1-12 with 2-bromo-N,N-diethylethylamine. MS m/z 510.5 (MH⁺).

Example 2

Representative Procedure for 4-oxo-1-phenyl-3,4,6,7-tetrahydrof[1,4]diazepino[6,7,1-hi]indole Core 2.

2,3-Dihydro-1H-indol-7-ylphenyl)methanone (2-17) was prepared according to the procedure of Y. Satoh et al Chem. Pharm. Bull. 1994, 42, 2071.

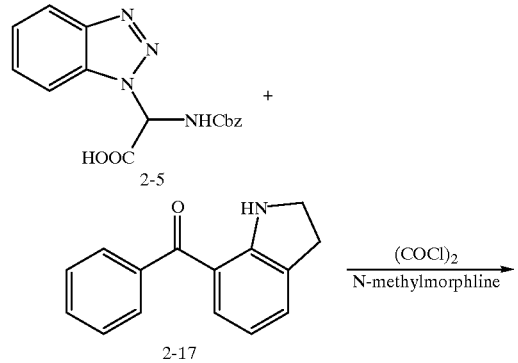

2-17

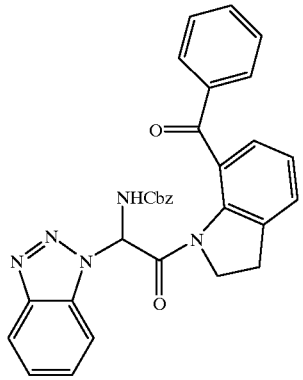

2-18

To a solution of 2-(benzotriazol-1-yl)-N-(benzoloxycarbonyl)glycine (2-5, 28.1 g, 86.0 mmol) in anhydrous THF (200 mL) at 0° C. was added oxalyl chloride (7.4 mL, 86 mmol) via syringe over 5 min., followed by addition of anhydrous DMF (1 mL). Stirring was continued for 3 h at 0° C. A solution of 2-17 (17.50 g, 78 mmol) and N-methylmorpholine (18.96 mL, 172 mmol) in anhydrous THF (120 mL) was added over ca. 30 min. The reaction mixture was slowly warmed to room temperature and stirred overnight. The precipitate was filtered and washed with cold THF. The mother liquor was evaporated, and the residue was purified on silica gel (50% ethyl acetate/hexane) to give 2-18 (7.5 g, 18%) as a yellow solid. MS m/z 554.4 (M+Na)+, 530.4 (M−H)+

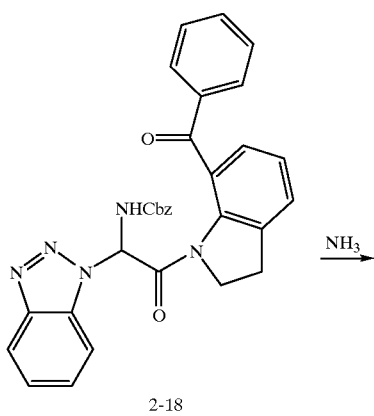

2-18

2-18 (7.7 g, 14.5 mmol) was dissolved in THF (100 mL) and methanol (30 mL). The mixture was bubbled with anhydrous ammonia for 4 h and stirred overnight. The reaction mixture was concentrated and purified on silica gel (10% ethyl acetate/hexane) to give 2-19 (1.41 g, 24%). MS m/z 412.4 (M+H)+, 434.4 (M+Na)+, 410.4 (M−H)+.

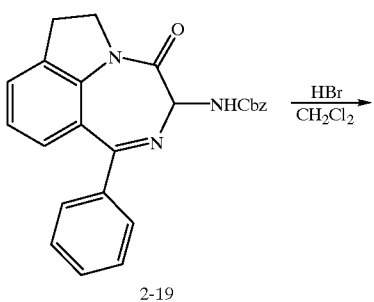

2-19

-continued

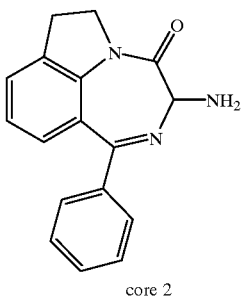

core 2

A solution of 2-19 (1.40 g, 3.4 mmol) in CH$_2$Cl$_2$ (5 mL) was saturated with anhydrous HBr gas for 2 h. The reaction mixture was then diluted with ether, and the precipitate was washed with ether by decantation. To the solid was added saturated aqueous Na$_2$CO$_3$ until pH>10. The aqueous layer was extracted with EtOAc. The organic extracts were combined, washed with brine, and dried (Na$_2$SO4). Evaporation of the solvent provided core 2 (270 mg, 29%) as a yellow oil. MS m/z 278.3 (M+H)+, 276.3 (M−H)+.

Example 2a (2R,3S)-3-allyl-2-isobutyl-N$^1$-(4-oxo-1-phenyl-3,4,6,7-tetrahydro[1,4]diazepino[6,7,1-hi]indol-3-yl)butandiamide (Example 2a)

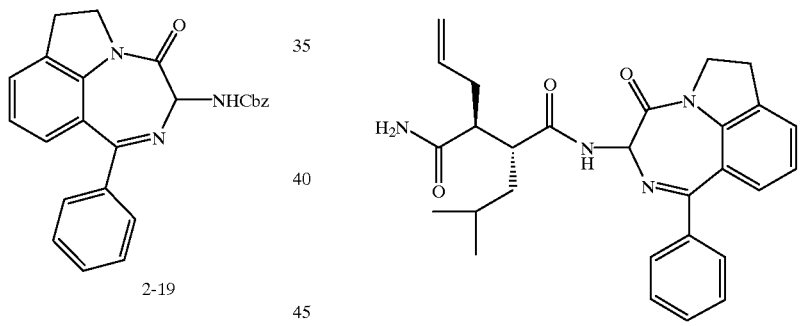

Ex. 2a (2R, 3S)-3-allyl-2-isobutyl-N$^1$-(4-oxo-1-phenyl-3,4,6,7-tetrahydro[1,4]diazepino[6,7,1-hi]indol-3-yl)butandiamide (Ex. 2a) can be prepared from core 2 and 1-10 as illustrated in the synthesis of 1-12.

Example 3

Representative Procedure for 4-oxo-1,2,4,5,6,7-hexahydro-azepino[3,2,1-hi]indole Core.

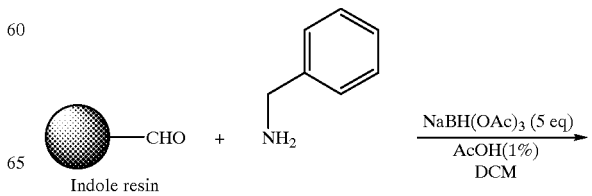

95
-continued

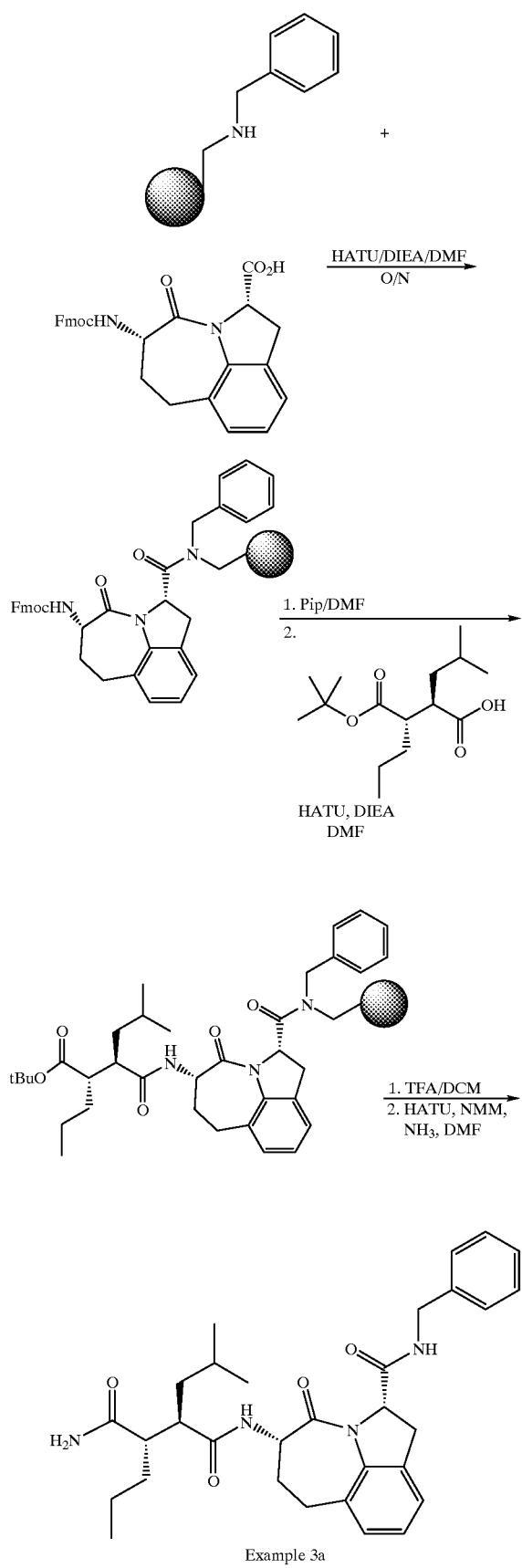

Example 3a

Example 3a

N1-(2-Benzylcarbamoyl-4-oxo-1,2,4,5,6,7-hexahydro-azepino[3,2,1-hi]indol-5-yl)-2-isobutyl-3-propyl-succinamide.

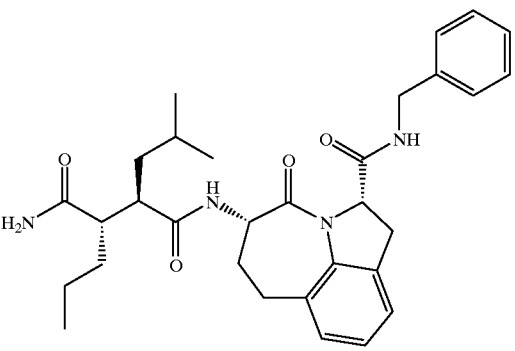

A portion of (3-formylindolyl)acetamidomethyl polystyrene resin (0.100 g, 0.75 mmol / g, 0.075 mmol, Novabiochem, Inc. ) was washed and suspended in about 2 mL $CH_2Cl_2$. Then 5 eq (0.375 mmoles, M.W.=107.16, d=0.781, 51.5 μL) of benzylamine was added followed by 5 eq (0.375 mmoles, M.W.=212, 80 mg) of $NaBH(OAc)_3$ and 1% AcOH (v/v, 20 μL) and the reaction suspension was allowed to shake overnight. Next day, a small sample was checked with Chloranil test (positive).

The resin was washed thoroughly with $CH_2Cl_2$, MeOH, DMF and suspended in DMF. Then 5 eq (0.375 mmoles, M.W.=468.5, 176 mg) of Fmoc-Haic (Neosystems, Inc., or see Tetrahedron Letters, 1994, 35, (41), 7513–7516) was added followed by 5 eq (0.375 mmoles, M.W.=380.2, 143 mg) of HATU and 10 eq (0.75 mmoles, M.W.=129.25, d=0.742, 131 μL) of DIEA. The reaction suspension was allowed to shake overnight. Next day, a small sample was monitored by Chloranil test (negative).

The resin was washed thoroughly with DMF, MeOH, $CH_2Cl_2$, DMF and the Fmoc group was deprotected with 50% Piperidine/DMF for 10 min and the resin was washed again as above. Then 50 mg of resin was taken and suspended in DMF and coupled with 5 eq (0.19 mmoles, M.W.=272.4, 52 mg) of Succinic acid 10 (Scheme 2) followed by 5 eq (0.19 mmoles, M.W.=380.2,72 mg) of HATU and 10 eq (0.38 mmoles, M.W.=129.25, d =0.742, 66 μL) of DIEA was added and the resin was allowed to shake overnight. Next day, a small sample was monitored by Ninhydrin test (negative).

The resin was washed thoroughly with DMF, MeOH and $CH_2Cl_2$ and dried well under vacuum. The resin was treated with a mixture of $TFA/CH_2Cl_2$(9: 1) for 3 h, filtered and concentrated in vacuum and azeotroped with dichloromethane and hexane to remove the residual TFA. The residue was triturated with Ether/hexane mixture to give the carboxylic acid. The acid (0.034 g, 0.064 mmol) was dissolved in 1 ml of DMF and HATU (0.032 g, 0.032 mmol) and 4-Methylmorpholine were added and stirred for 15 min. Then $NH_3$ (g) was bubbled for a min. and stirred for 2 h. The reaction mixture was diluted with water and extracted with ethyl acetate. The organic layer was washed with satd. brine soln., dried over anhydrous $Na_2SO_4$, evaporated under high vacuum and dried under vacuum to give the crude amide. Purification by reverse phase HPLC provided the title compound of Example 3a as a white powder (12 mg). MS $(M+H)^+$=533.5.

Example 3b
N1-[2-(1-Benzyl-pyrrolidin-3-ylcarbamoyl)-4-oxo-1,2,4,5,6,7-hexahydro-azepino[3,2,1-hi]indol-5-yl]-2-isobutyl-3-propyl-succinamide.

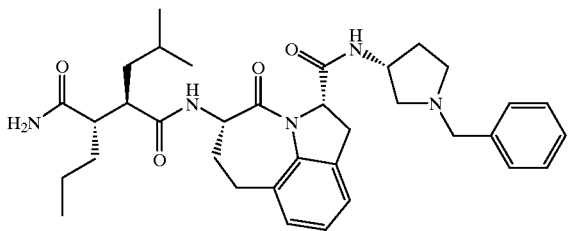

The compound of Example 3b was synthesized in a manner similar to the synthesis of the compound of Example 3a, but using (R)-3-amino-1-benzylpyrrolidine as the amine in the last step. Cleavage of 100 mg of functionalized resin (0.52 mmol/g) and purification by RP-HPLC provided 10.5 mg (30%) of the title compound as a white powder. MS (M+H)$^+$=602.5.

Example 3c
N1-[2-(1-Benzyl-pyrrolidin-3-ylcarbamoyl)-4-oxo-1,2,4,5,6,7-hexahydro-azepino[3,2,1-hi]indol-5-yl]-2-isobutyl-3-propyl-succinamide.

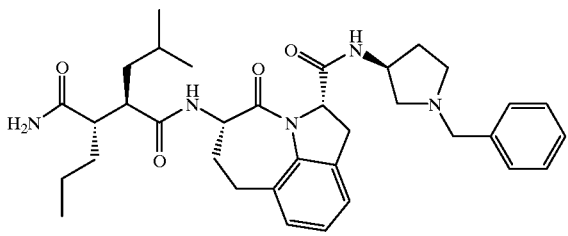

The compound of Example 3c was synthesized in a manner similar to the synthesis of the compound of Example 3a, but using (S)-3-aminol-benzylpyrrolidine as the amine in the last step. Cleavage of 100 mg of functionalized resin (0.52 mmol/g) and purification by RP-HPLC provided 7.0 mg (22%) of the title compound as a white powder. MS (M+H)$^+$=602.5.

Example 3d
2-Isobutyl-N1-[2-(4-methoxy-benzylcarbamoyl)-4-oxo-1,2,4,5,6,7-hexahydroazepino[3,2,1-hi]indol-5-yl]-3-propyl-succinamide.

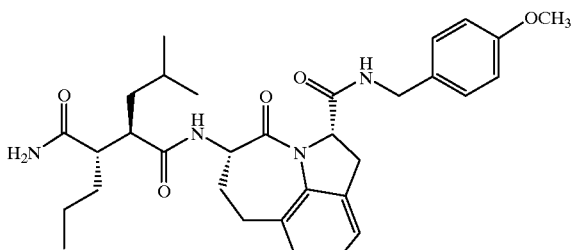

The compound of Example 3d was synthesized in a manner similar to the synthesis of the compound of Example 3a, but using 4-methoxybenzylamine as the amine in the last step. Cleavage of 100 mg of functionalized resin (0.53 mmol/g) and purification by RP-HPLC provided 12.0 mg (40%) of the title compound as a white powder. MS (M+H)$^+$=563.43.

Example 3e
2-Isobutyl-N 1-[2-(3-methoxy-benzylcarbamoyl)-4-oxo-1,2,4,5,6,7-hexahydroazepino[3,2,1-hi]indol-5-yl]-3-propyl-succinamide.

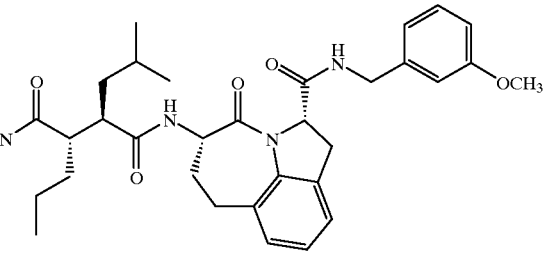

The compound of Example 3e was synthesized in a manner similar to the synthesis of the compound of Example 3a, but using 3-methoxybenzylamine as the amine in the last step. Cleavage of 100 mg of functionalized resin (0.53 mmol/g) and purification by RP-HPLC provided 17.0 mg (56%) of the title compound as a white powder. MS (M+H)$^+$=563.43.

Example 3f.
N1-[2-(Cyclohexylmethyl-carbamoyl)-4-oxo-1,2,4,5,6,7-hexahydro-azepino[3,2,1-hi]indol-5-yl]-2-isobutyl-3-propyl-succinamide.

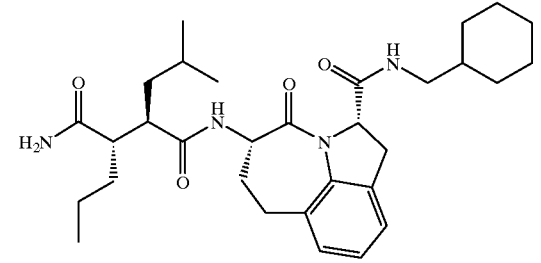

The compound of Example 3f was synthesized in a manner similar to the synthesis of the compound of Example 3a, but using cyclohexylmethylamine as the amine in the last step. Cleavage of 100 mg of functionalized resin (0.53 mmol/g) and purification by RP-HPLC provided 9.0 mg (32%) of the title compound as a white powder. MS (M+H)$^+$=539.5.

Example 3g.
2-Isobutyl-N1-(2-isopropylcarbamoyl-4-oxo-1,2,4,5,6,7-hexahydro-azepino[3,2,1-hi]indol-5-yl)-3-propyl-succinamide.

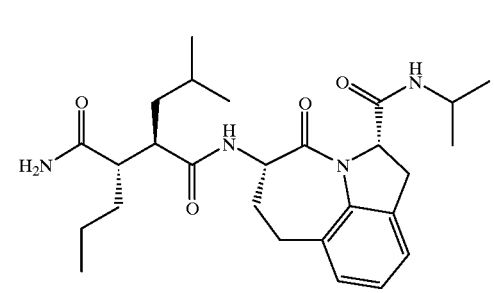

The compound of Example 3g was synthesized in a manner similar to the synthesis of the compound of Example 3a, but using isopropylamine as the amine in the last step. Cleavage of 100 mg of functionalized resin (0.55 mmol/g) and purification by RP-HPLC provided 15.5 mg (60%) of the title compound as a white powder. MS (M+H)$^+$=485.5.

Example 3h
2-Isobutyl-N1-(4-oxo-2-phenylcarbamoyl-1,2,4,5,6,7-hexahydro-azepino[3,2,1-hi]indol-5-yl)-3-propyl-succinamide.

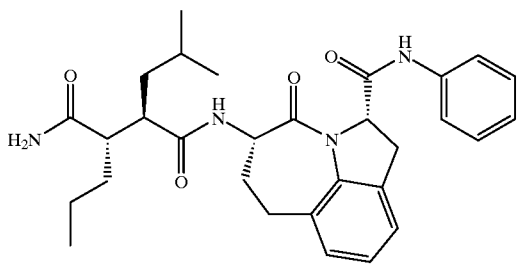

The compound of Example 3h was synthesized in a manner similar to the synthesis of the compound of Example 3a, but using aniline as the amine in the last step. Cleavage of 50 mg of functionalized resin (0.54 mmol/g) and purification by RP-HPLC provided 4.0 mg (38%) of the title compound as a white powder. MS (M+H)$^+$=519.4.

Example 4
tert-Butyl 2-isobutyl-N1-(10,11-dihydro-5H-dibenzo[a,d]cycloheptene-5-yl)-3-allyl-succinate or 2-Isobutyl-N1-(dibenzosuberan-5-yl)-3-allyl-succinate tert-butyl ester.
Compound 4-3 was made according to P. Melloni et al *J. Med. Chem.* 1979, 22(2), 183-191.

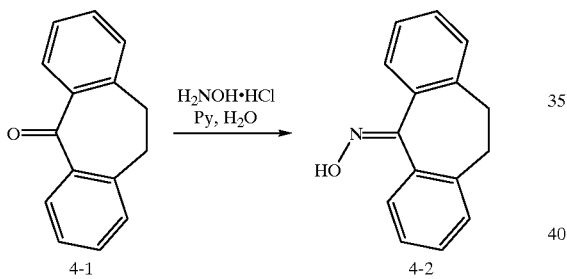

A mixture of hydroxylamine hydrochloride (8.35 g, 120 mmol) and dibenzosuberone (4-1, 10 g, 48 mmol) in pyridine (30 mL) and H$_2$O (30 mL) was refluxed for 3 days. Pyridine was removed from the reaction mixture in vacuo. The residue was extracted with ethyl acetate. The organic extracts were combined and washed with water, brine, and dried (Na$_2$SO$_4$). The solvent was evaporated, and the residue was crystallized from ethyl acetate and hexane to give 4-2 (2.95 g, 28%) as a white crystalline. MS m/z 224.1 (MH$^+$).

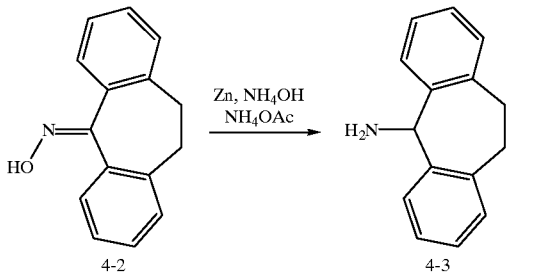

To a solution of 4-2 (2.95 g, 13 mmol) in ethanol (20 mL) and DMF (3 mL) was added zinc powder (4.2 g, 6.5 mmol), ammonium acetate (0.5 g, 6.5 mmol), and ammonium hydroxide (65 mL) sequentially. The reaction mixture was refluxed for 3 h, and then cooled to room temperature. After diluted with ether (100 mL), the reaction mixture was made basic (pH>10) with 35% NaOH, and extracted with ether. The organic extracts were combined, washed with water, brine, and dried (K$_2$CO$_3$). Evaporation of the solvent provided 4-3 (2.27 g, 83%) as a white solid. $^1$H NMR (300 MHz, CDCl$_3$) δ 7.10–7.50 (m, 8H), 5.47 (s, 1H), 3.30–3.50 (m, 2H), 3.10–3.25 (m, 2H), 2.53 (br s, 2H).

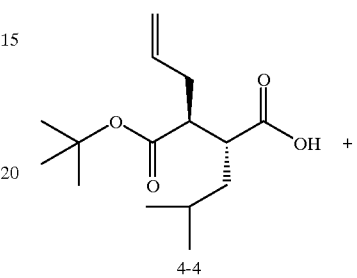

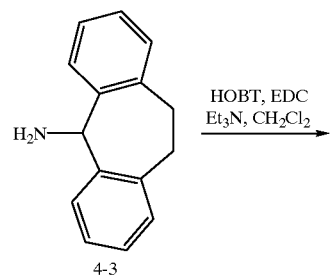

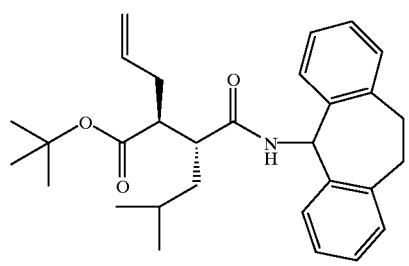

Example 4

Compound 4-4 (135 mg, 0.500 mmol), 4-3 (105 mg, 0.500 mmol) and 1-hydroxybenzotriazole hydrate (HOBT, 81 mg, 0.60 mmol) were suspended in CH$_2$Cl$_2$, and cooled to 0° C. To this mixture 1-(3-dimethylaminopropyl)-3-ethylcarbodiimide hydrochloride (EDC HCl, 192 mg, 1.00 mmol) and triethylamine (0.10 mL, 0.75 mmol) were added. After being stirred for 20 h at ambient temperature, the reaction mixture was diluted with ethyl acetate. The organic layer was washed with water, brine and dried (Na$_2$SO$_4$). After evaporation of the solvent, the solid obtained was recrystallized from ethyl acetate and hexane to afford Example 4 (200 mg, 87%). MS m/z 462.3 (MH$^+$).

Example 5

(2R,3S)-3-Allyl-N¹-[(7S)-2-benzyl-6-oxo-1,2,3,4,6,7,8,10a-octahydropyrazino[1,2-a]azepin-7-yl]-2-isobutylbutanediamide.

Preparation of tert-butyl (1S)-1-[(4-benzyl-2-vinyl-1-piperazinyl)carbonyl]-3-butenylcarbamate.

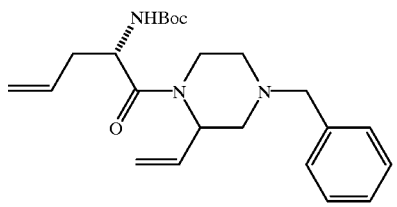

(2S)-2-[(tert-butoxycarbonyl)amino]-4-pentenoic acid (466 mg, 2.17 mmol) and 1-benzyl-3-vinylpiperazine (436 mg, 2.17 mmol) and 1-(3-dimethylaminopropyl)-3-ethylcarbodiinide hydrochloride (HOBT, 622 mg, 3.26 mmol) were combined with anhydrous $CH_2Cl_2$ (10 mL) at room temperature. $Et_3N$ (0.74 mL, 5.43 mmol) was added in one portion. The resulted solution was maintained at room temperature for 18 h at which time it was concentrated in vacuo to a volume of approximately 5 mL. Then the solution was purified by silica gel chromatography (SGC) eluting with 2:1 hex-EtOAc. The title compound (a pair of diastereomers) was obtained (171 mg, 20%) as a pale-yellow oil. $^1H$ NMR (300 MHz, $CDCl_3$) δ 7.31 (s, 5H), 5.99–5.82 (m, 1H), 5.81–5.65 (m, 1H), 5.50–5.00 (m, 6H), 4.75–4.23 (m, 2H), 3.70–3.37 (m, 3H), 3.11–2.79 (m, 2H), 2.59-2.00 (m, 4H), 1.42 (s, 9H) ppm. MS (CI) 400.6 (M+H).

Preparation of tert-butyl (7S)-2-benzyl-6-oxo-1,2,3,4,6,7,8,10a-octahydropyrazino[1,2-a]azepin-7-ylcarbamate.

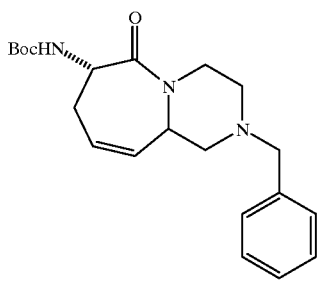

tert-Butyl (1S)-1-[(4-benzyl-2-vinyl-1-piperazinyl)carbonyl]-3-butenylcarbamate (250 mg, 0.63 mmol) and Grubb's catalyst (26 mg, 0.03 mmol) were combined in toluene (32 mL) at room temperature. This mixture was degassed via vacuum-argon three times at room temperature. Then $CH_2Cl_2$ (32 mL) was added in one portion. The reaction mixture was heated at reflux for 5 days, then concentrated in vacuo. The residue was purified by SGC (4:1 hex-EtOAc) to give the title product (103 mg, 44%) as a yellow powder. The $^1H$ NMR spectrum was consistent with the presence of one diastereomer, not assigned. (300 MHz, $CDCl_3$) δ 7.35–7.27 (m, 5H), 5.76–5.72 (m, 2H), 5.67–5.58 (m, 1H), 5.35–5.01 (m, 1H), 4.68 (br s, 1H), 4.00 (m, 1H), 3.64 (d, 1H, J=13.1 Hz), 3.42 (d, 1H, J=13.2 Hz), 3.09 (dt, 1H, J=13.5, 4.1 Hz), 2.91–2.86 (m, 1H), 2.76-2.72 (m, 2H), 2.26–2.00 (m, 3H), 1.44 (s, 9H) ppm.

Preparation of (7S)-7-Amino-2-benzyl-1,3,4,7,8,10a-hexahydropyrazino[1,2-a]azepin-6(2H)-one.

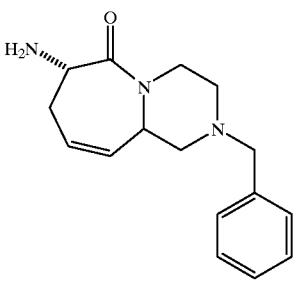

tert-Butyl (7S)-2-benzyl-6-oxo-1,2,3,4,6,7,8,10a-octahydropyrazino[1,2-a]azepin-7-ylcarbamate (140 mg, 0.38 mmol) was dissolved in 4 mL $CH_2Cl_2$ at room temperature. Trifluoroacetic acid (TFA, 2 mL) was added in 3 portions. The reaction mixture was maintained at room temperature for 18 h at which time it was concentrated in vacuo to give the bis-TFA salt (103 mg, 100%) of the title compound as a brown heavy oil. Part of this crude sample (73 mg, 0.15 mmol) was suspended in 5 mL of $CHCl_3$ at room temperature. A saturated aqueous solution of $K_2CO_3$ (5 mL) was added in one portion. The two-phase mixture was stirred vigorously at room temperature for 2 h, then diluted with 20 mL of $H_2O$. The resulting mixture was extracted with $CHCl_3$ (3×20 mL). The organic layers were combined and washed with brine (50 mL), dried over $MgSO_4$ and concentrated in vacuo. The title free amine was isolated (39 mg, 100%) as a tan colored powder. $^1H$ NMR (300 MHz, $CDCl_3$) δ 7.35–7.28 (m, 5H), 5.75–5.74 (m, 1H), 5.64–5.58 (m, 1H), 4.66 (br s, 1H), 4.45 (dd, 1H, J=12.8, 5.8 Hz), 4.00 (dt, 1H, J=13.5, 10.9, 1.1 Hz), 3.64 (d, 1H, J=13.2 Hz), 3.43 (d, 1H, J=13.2 Hz), 3.09 (dt, 1H, J=13.5, 4.1 Hz), 2.91–2.88 (m, 1H), 2.79–2.72 (m, 1H), 2.61–2.52 (m, 1H), 2.28–1.90 (m, 5H) ppm.

Preparation of tert-butyl (2S)-2-[(1)-1-({[(7S)-2-benzyl-6-oxo-1,2,3,4,6,7,8,10a-octahydropyrazino[1,2-a]azepin-7-yl]amino}carbonyl)-3-methylbutyl]-4-pentenoate.

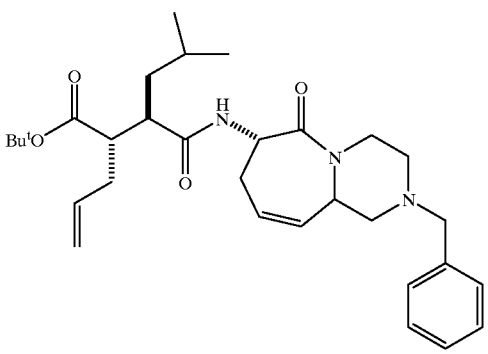

(7S)-7-Amino-2-benzyl-1,3,4,7,8,10a-hexahydropyrazino[1,2-a]azepin-6(2H)-one bis-trifluoroacetic acid salt (73 mg, 0.27 mmol), succinate 1-10 (90 mg, 0.32 mmol), and HATU (133 mg, 0.35 mmol) were combined with 1 mL of DMF at room temperature. This solution was stirred at room temperature for 5 min at which time diisopropylethyl amine (55 mg, 0.43 mmol) was added in one portion. The reaction was maintained at room temperature for 18 h and concentrated in vacuo at 60° C. The residue was purified by SGC (4:1 hex-EtOAc) to provide the title compound (101 mg, 71%) as a pale-yellow heavy oil. $^1$H NMR (300 MHz, CDCl$_3$) δ 7.35–7.27 (m, 5H), 6.94 (d, 1H, J=6.9 Hz), 5.80–5.45 (m, 4H), 5.05–4.98 (m, 2H), 4.69 (br s, 1H), 4.07–3.99 (m, 1H), 3.64 (d, 1H, J=13.1 Hz), 3.44 (d, 1H, J=13.1 Hz), 3.11 (dt, 1H, J=13.4,4.0 Hz), 2.95–2.72 (m, 2H), 2.60–2.38 (m, 2H), 2.30–2.14 (m, 4H), 2.12–1.96 (m, 1H), 1.79–1.50 (m, 3H), 1.44 (s, 9H), 1.15–1.00 (m, 1H), 0.91–0.84(m, 6H) ppm.

Preparation of (2R,3S)-3-allyl-N$^1$-[(7S)-2-benzyl-6-oxo-1,2,3,4,6,7,8,10a-octahydropyrazino[1,2-a]azepin-7-yl]-2-isobutylbutanediamide (Example 5).

Example 5

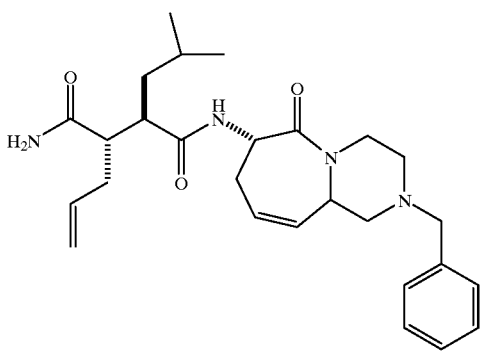

tert-Butyl (2S)-2-[(1S)-1-({[(7S)-2-benzyl-6-oxo-1,2,3,4,6,7,8,10a-octahydropyrazino[1,2-a]azepin-7-yl]amino}carbonyl)-3-methylbutyl]-4-pentenoate (90 mg, 0. 17 mmo) was dissolved in 2 mL of CH$_2$Cl$_2$ at room temperature. With stirring 1 mL of TFA was added in three portions. The solution was maintained at room temperature for 18 h, then concentrated in vacuo. The residue was combined with HATU (109 mg, 1.08 mmol), diisopropylethyl amine (109 mg, 0.84 mmol) and 1 mL of DMF. To this solution at room temperature was intoduced a stream of ammonia for 4 min. Additional 1 mL of DMF was added, and the mixture was was heated at 100° C. until the precipitate dissolved. This solution was then maintained at room temperature for 18 h at which time it was concentrated in vacuo at 60° C. The residue was purified by SGC (79:1 CH$_2$C$_{12}$-MeOH) to give the title compound (50 mg, 63%) as a tan colored foam. $^1$H NMR (300 MHz, CDCl$_3$) δ 7.35–7.27 (m, 5H), 7.11 (d, 1H, J=6.6 Hz), 6.11 (br s, 1H), 5.79–5.44 (m, 5H), 5.10–5.02 (m, 2H), 4.70 (br s, 1H), 4.20–3.99 (m, 1H), 3.64 (d, 1H, J=13.2 Hz), 3.44 (d, 1H, J=13.2 Hz), 3.10 (dt, 1H, J=13.5,4.1 Hz), 2.95–2.72 (m, 3H), 2.60–2.45 (m, 2H), 2.40–1.99 (m, 5H), 1.72–1.16 (m, 3H), 0.90–0.85 (m, 6H) ppm.

Example 7

Representative Preparation for 4-amino-hexahydro-pyrrolo[1,2-a][1,4]diazepine-1,5-dione Core 7.

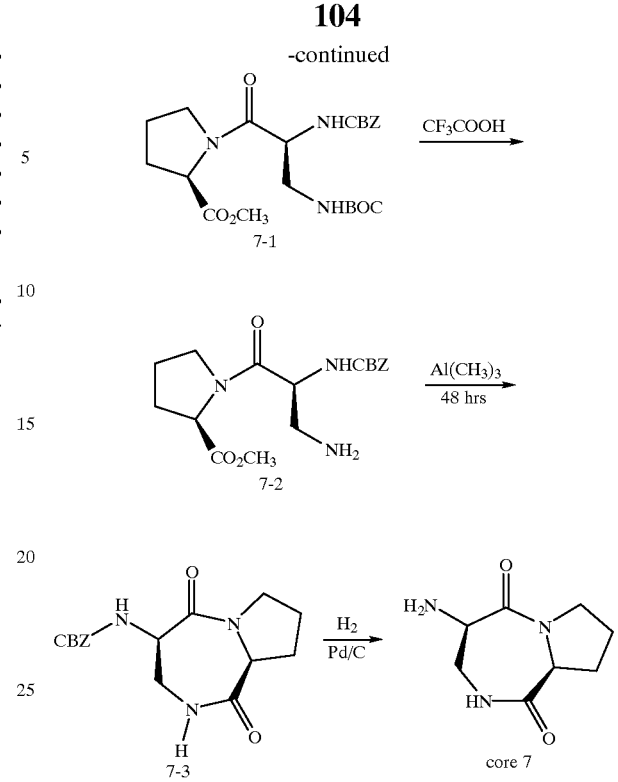

To a solution of N-α-Cbz-N-β-Boc-1-diaminopropionic acid dicyclohexylamine salt (14 g, 26.9 mmol) in 300 ml CH$_2$C$_{12}$ was added D-proline methylester HCl (5.0 g, 31.2 mmol), followed by 1-(3-dimethylaminopropyl)-3-ethylcarbodiimide HCl (EDC, 8.0 g, 41.7 mmol, 1.5 eq.), 1-hydroxybenzotriazole hydrate (HOBT, 7.5 g, 55.5 mmol, 2.0 eq.) and triethylamine (10 ml, 72 mmol, 2.6 eq.). The mixture was stirred overnight. The solvents were removed under reduced pressure to give a white solid, which was taken up in EtOAc and water. The organic layer was washed with water, brine and dried over Na$_2$SO$_4$. The solution was concentrated to give the crude product as a solid, which was purified by column chromatography on silica gel using EtOAc:hexane (7:3) to give 7-1 as a white solid (12.1 g, 100%). MS: $^1$HNMR(300 MHz, CDCl$_3$) 1.4 (s, 9H), 1.9–2.3 (m, 3H), 3.3–3.5 (m, 2H), 3.7 (s, 3H), 3.7–3.9 (m, 1H), 4.4 (m, 1H), 4.6–4.7 (m, 1H), 5.0-5.2 (m, 3H), 5.8–6.0 (m, 1H), 7.2–7.4 (m, 5H). MS: 450.2 (M+H), 472.3 (M+Na).

Compound 7–1 (3.5 g, 7.8 mmol) was dissolved in 100 ml of 50% trifluoroacetic acid (TFA) in CH$_2$Cl$_2$ and stirred at ambient temperature for one hour. The solvents were then removed under reduced pressure and the resulting oil was redissolved in 30 ml of toluene and reconcentrated to remove residual TFA. The product (7–2) was obtained as a slightly yellow solid 7-2 (2.5 g, 92%). $^1$HNMR (300 MHz, CDCl$_3$) 1.8–2.0 (m, 2H), 2.0–2.2 (m, 1H), 3.2–3.8 (m, 6H), 4.3–4.9 (m, 3H), 4.9–5.1 (m, 3H), 7.2–7.4 (m, 5H). MS: 350.3 (M+H), 372.2 (M+Na).

Trimethylaluminum (22 mmol, 1.0M in hexane) was added to a solution of 7-2 (2.5 g, 7.2 mmol) in 50 ml 1,2-dichloroethane at room temperature and the reaction mixture was heated to 75° C. for 48 hours. The reaction was quenched with water and then enough 1.0 N HCl solution was added to the mixture to give a clear solution. The aqueous solution was extracted with CHCl$_3$ (2×200 ml). The combined organic layers were dried with brine and Na$_2$SO$_4$. Evaporation of the organic solvent gave a sticky oil which was purified by column chromatography on silica gel with 100% EtOAc to give a white solid (7-3, 800 mg, 35%). ¹HNMR (300 MHz, CDCl₃) 1.7–1.9 (m, 2H), 2.0–2.2 (m, 1H), 2.6–2.8 (m, 1H), 3.2–3.4 (m, 1H), 3.4–3.7 (m, 3H), 4.4–4.6 (m, 1H), 4.8–5.0 (m, 1H), 5.0–5.2 (m, 2H), 6.2 (m, 1H), 6.4–6.5 (s, 1H), 7.2–7.4 (m, 5H). MS: 318.2 (M+H).

A solution of 7-3 (4.0 g, 12.6 mmol) in 100 ml EtOAc was shaken with 1.0 g Pd/C (5% on activated carbon) under H₂ (~50psi) for 2 hrs. The reaction mixture was filtered and the solvent was removed under reduced pressure to give a white solid 7 (1.8 g, 9.8 mmol, 78%). MS: 184.3 (M+H).

Example 7a 3-(1,5-Dioxo-octahydro-pyrrolo[1,2-a] [1,4]diazepin-4-ylcarbamoyl)-5-methyl-2-propyl-hexanoic Acid tert-butyl Ester.

Example 7a

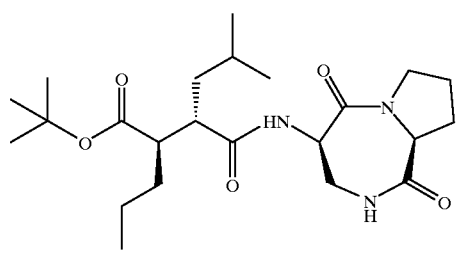

To a solution of core 7 (350 mg, 1.9 mmol) in 20 ml DMF at room temperature was added propyl-succinate X (510 mg, 1.9 mmol), o-(7-azabenzotriazol-1-yl)-N,N,N,N,-tetramethyluronium hexafluorophosphate (HATU, 900 mg, 2.4 mmol) and then diisopropylethylamine (DIPEA, 0.4 ml, 2.3 mmol). The mixture was stirred at room temperature overnight. The reaction was quenched with 10 ml water. The solvents were removed under reduced pressure to give a viscous oil which was taken up in EtOAc and water (1:1). The organic layer was washed with water, brine and Na₂SO₄. The solvents were evaporated under reduced pressure to give an oily crude product which was purified by column chromatography in 5% methanol/CH₂Cl₂ to give Example 7a as a white solid (230 mg, 0.53 mmol, 28%). MS: 438.4 (M+H).

Example 7b 3-(1,5-Dioxo-octahydro-pyrrolo[1,2-a] [1,4]diazepin-4-ylcarbamoyl)-5-methyl-2-propyl-hexanoic Acid.

Example 7b

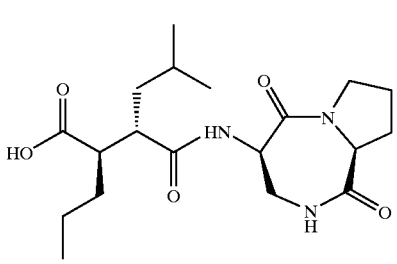

Example 7a (230 mg, 0.53 mmol) was dissolved in 20 ml of 50% TFA in CH₂C₁₂ and stirred at room temperature for 2 hrs. The solvents were removed under reduced pressure and the resulting oil was taken up in 20 ml toluene and concentrated to give Example 7b as a slightly yellow solid (190 mg, 0.50 mmol). MS: 380.2 (M−H).

Example 7c

N1-(1,5-Dioxo-octahydro-pyrrolo[1,2-a] [1,4]diazepin-4-yl)-2-isobutyl-3-propyl-succinamide.

Example 7c

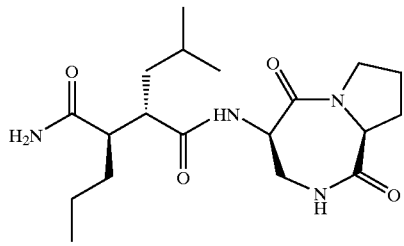

To a solution of Example 7b (190 mg, 0.50 mmol) in 20 ml DMF was added HATU (250 mg, 0.56 mmol), followed by DIPEA (0.3 ml, 1.7 mmol). After the reaction mixture was treated with ammonia gas for 5 minutes, the reaction was stirred at room temperature overnight. After quenching the reaction was with 10 ml water, the solvents were removed under reduced pressure and the resulting oil was taken into EtOAc and water (1: 1). The organic layer was washed with brine and dried over Na₂SO₄. Evaporation of solvents and purification by column chromatography on silica gel with 10% methanol in CH₂Cl₂ provided Example 7c as a white solid (3 mg, 0.008 mmol, 1.6%). ¹HNMR (300 MHz, CD₃OD) 0.8–1.0 (m, 9H), 1.0–1.7 (m, 7H), 1.8–2.1 (m, 3H), 2.2–2.5 (m, 3H), 3.2 (m, 1H), 3.4–3.8 (m, 5H), 3.9–4.0 (m, 1H), 4.2–4.3 (m, 1H). MS: 381.2 (M+H), 403.2 (M+Na).

Example 9

Representative preparation for the 1,2,3,6,7,9a-hexahydro-pyrrolo[1,2-a]azepin-5-one Core 9.

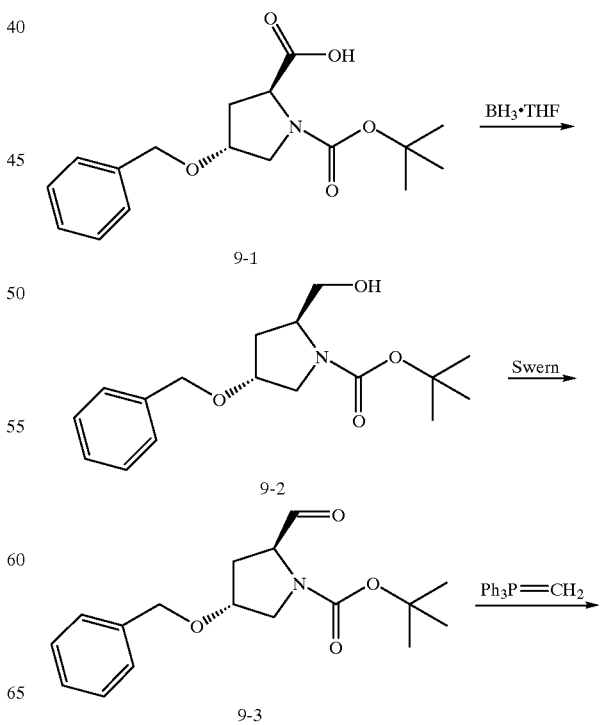

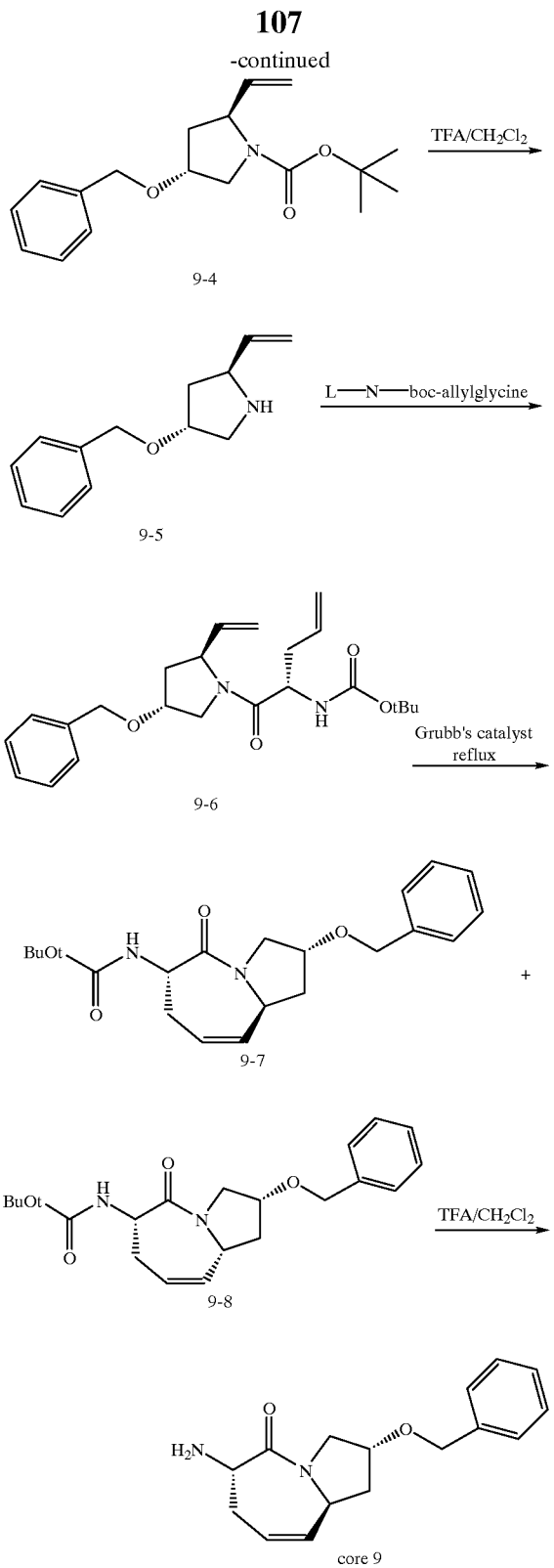

A solution of 9-1 (17.0 g, 53 mmol) in 100 ml THF was added to a solution of BH$_3$-THF (100 ml, 100 mmol) over a period of 30 minutes under nitrogen at 0° C. After the mixture was stirred for an additional one hour at 0° C., the reaction was quenched with 25 ml of 10% HOAc in methanol solution, and the solvents were evaporated under reduced pressure to give a viscous oil. The crude product was taken up in EtOAc, washed with 1.0N HCl, water and saturated NaHCO$_3$, and then dried over brine and Na$_2$SO$_4$. Evaporation of solvents provided a colorless oil 9-2 (16.5 g, 100%) which was directly used in the next step without purification. $^1$HNMR (300 MHz, CDCl$_3$) 1.48 (s, 9H), 1.6–1.8(m, 1H), 2.1–2.3(m, 1H), 3.3–3.5 (m, 1H), 3.5–3.8 (m, 3H), 4.0–4.2 (m, 2H), 4.4–4.6 (m, 2H), 5.0 (m, 1H), 7.2–7.4 (m, 5H). MS: 308.2 (M+H), 371.2 (M+Na+CH$_3$CN), 637.3 (2M+Na).

In a 1000 ml three-neck flask, a solution of oxalyl chloride (11.0 g, 86.7 mmol) in 50 ml CH$_2$Cl$_2$ was cooled in dry-ice bath. To this solution, a solution of DMSO (12 ml, 170 mmol) in 100 ml CH$_2$Cl$_2$ was added slowly. After 10 minutes, the solution of 9–2 (16.3 g, 53 mmol) in 200 ml CH$_2$Cl$_2$ was added into the above solution dropwise over 10 minutes. After the reaction mixture was stirred in a dry-ice bath for additional 30 minutes, N-methylmorpholine (34.3 g, 339 mmol) was added. The reaction was stirred for another 10 minutes in a dry-ice bath before warming to zero degrees in an ice bath. After 20 minutes, the yellow slurry solution was poured into ice water. The aqueous solution was extracted with CH$_2$C$_{12}$ (2×200 ml). The combined organic extracts were washed with 1.0N NaOH (3×100 ml), and then saturated NaHCO$_3$ (2×100 ml). The solution was dried with brine and Na$_2$SO$_4$. Concentration provided 9-3 as a yellow oil, which was used directly in the next step without purification. $^1$HNMR (300 MHz, CDCl$_3$) 1.4–1.6(d, 9H), 1.9–2.0 (m, 1H), 2.2–2.4 (m, 1H), 3.4–3.8 (m, 2H), 4.0–4.4 (m, 2H), 4.4–4.6 (m, 2H), 7.2-7.4 (m, 5H), 9.4–9.6 (m, 1H).

A solution of sodium bis(trimethylsilyl)amide (12.0 g, 62.2 mmol) in 200 ml THF was added into a suspension of methyltriphenylphosphonium bromide (22.8 g, 63.8 mmol) in 200 ml THF at zero degree over 30 minutes to give a yellow slurry which was stirred at zero degree for additional 30 minutes. A solution of 9-3 in 100 ml THF was added to the slurry above over a period of 30 minutes. After addition, the reaction was complete in 10 minutes (TLC). The reaction mixture was poured into ice water and the aqueous layer was adjusted to pH 7 with 1.0 N HCl. The mixture was extracted with 3×100 mL EtOAc. The combined organic layers were washed with saturated NaHCO$_3$ and brine, then dried over Na$_2$SO$_4$. The organic solvent was evaporated under reduced pressure to give the crude product as an oil, which was purified by column chromatography on silica gel in 10% EtOAc/hexane to give 9-4 as a slightly yellow oil (12 g, 39.6 mmol, 75%). $^1$HNMR (300 MHZ, CDCl$_3$) 1.4 (s, 9H), 1.8–2.0 (m, 1H), 2.2–2.3 (m, 1H), 3.4–3.8 (m, 2H), 4.0–4.6 (m, 4H), 5.0–5.2 (m, 2H), 5.6–5.8 (m, 1H), 7.2–7.4 (m, 5H). MS: 326.2 (M+H), 367.2 (M+Na+CH$_3$CN).

A solution of 9-4 in 100 ml of 50% TFA in CH$_2$Cl$_2$ was stirred at room temperature for 2 hrs. The solvents were removed under reduced pressure and the resulting oil was redissolved in 50 ml of toluene and concentrated to give 9-5 as a dark oil (8.0 g, 39.4 mmol, 100%). $^1$HNMR (300 MHz, CDCl$_3$) 1.9–2.1 (m, 1H), 2.3–2.4 (m, 1H), 3.4–3.7 (m, 2H), 4.2–4.4 (m, 2H), 4.4–4.6 (s, 2H), 5.4–5.6 (m, 2H), 5.8–6.0 (m, 1H), 7.2-7.4 (m, 5H). MS: 204.3 (M+H).

To a solution of 9-5 (8.0 g, 39.4 mmol) in 200 ml CH$_2$C$_{12}$ was added L-N-boc-allylglycine (9.0 g, 42 mmol), EDC (12.0 g, 62.2 mmol), HOBT (8.0 g, 59.2 mmol) and triethylamine (8 ml, 57.3 mmol). The reaction mixture was stirred at ambient temperature overnight. The reaction mixture was concentrated to give a viscous oil which was taken up in EtOAc and water. The organic layer was washed with water, brine and dried over Na$_2$SO$_4$. The solvent was evaporated and the oily crude product was purified by column chromatography on silica gel in 20% EtOAc/hexane to give 9-6 as a colorless oil (10.0 g, 25 mmol, 60%). ¹HNMR (300 MHz, CDCl₃) 1.4 (s, 9H), 1.8–2.0 (m, 1H), 2.2–2.6 (m, 3H), 3.4–3.6 (m, 1H), 3.7–3.9 (m, 1H), 4.0–4.2 (m, 1H), 4.4–4.8 (m, 3H), 5.0–5.2 (m, 4H), 5.3–5.5 (m, 1H), 5.6–5.9 (m, 2H), 7.2–7.4 (m, 5H). MS: 401.2 (M+H), 423.2 (M+Na).

To a solution of 9-6 (10.0 g, 25 mmol) in 1000 ml of 50% CH₂Cl₂ in toluene at 100 degree was added 1.0 g, (1.2 mmol) bis(tricyclohexylphosphine)benzylidine ruthenium (IV) dichloride (Grubb's catalyst). After an interval of 4 hours, an identical portion of catalyst was added. After an additional interval of 4 hours, an additional 500 mg of catalyst was added prior to heating overnight. The reaction mixture was then cooled to room temperature and filtered through a layer of celite. The solvents were removed to give a dark oil. GC-MS analysis suggested the presence of approximately 5% of the epimer 9-8. The crude oil was purified by column chromatography on silica gel in 5% methanol/ CH₂Cl₂, which provided the major product 9-7 (3.7 g, 9.95 mmol, 40%). ¹HNMR (300 MHz, CDCl₃) 1.4 (s, 9H), 1.8–2.0 (m, 1H), 2.4–2.6 (m, 2H), 2.6–2.8 (m, 1H), 3.5–3.7 (m, 1H), 3.8–4.2 (m, 3H), 4.4–4.6 (m, 2H), 4.7–4.9 (m, 1H), 5.6–5.8 (m, 2H), 7.2–7.4 (m, 5H). MS: 373.2 (M+H), 767.5 (2M+Na).

Compound 9-7 was dissolved in 100 ml of 50% TFA in CH₂Cl₂ was stirred at room temperature for 2 hrs. The solvents were removed under reduced pressure and the resulting oil was redissolved in 50 ml of toluene and concentrated to give bicyclic core 9. ¹HNMR (300 MHz, CDCl₃) 1.8–2.0 (m, 1H), 2.3–2.5 (m, 1H), 2.6–2.8 (m, 1H), 2.8–3.0 (m, 1H), 3.6–3.8 (m, 2H), 3.8–4.0 (m, 1H), 4.0–4.1 (m, 1H), 4.4–4.6 (m, 2H), 4.6–4.8 (m, 1H), 5.8–6.0 (m, 1H), 6.0–6.2 (m, 1H), 7.0–7.4 (m, 5H). MS: 273.3 (M+H).

Example 9a 3-(2-Benzyloxy-5-oxo-2,3,5,6,7,9a-hexahydro-1H-pyrrolo[1,2-a]azepin-6-ylcarbamoyl)-5-methyl-2-propyl-hexanoic Acid tert-butyl Ester.

Example 9a

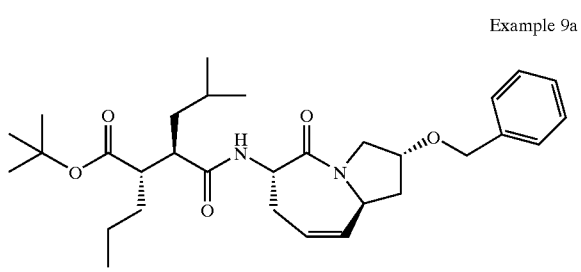

To a solution of bicyclic core 9 (2.0 g, 7.4 mmol) in 50 ml DMF was added the appropriate propyl-succinate t-butyl ester (2.0 g, 7.4 mmol), HATU(3.7 g, 9.7 mmol), and DIPEA (2.5 ml, 14.3 mmol). The reaction mixture was stirred at room temperature overnight, then quenched with 10 ml water. The solvents were removed under reduced pressure to give a viscous oil which was taken into EtOAc and water. The organic layer was washed with water and dried over brine and Na₂SO₄. The solvents were evaporated under reduced pressure to give the crude product, which was purified by column chromatography on silica gel in 5% methanol/CH₂Cl₂ to give Example 9a as a solid (2.1 g, 4.0 mmol, 54%). ¹HNMR (300 MHz, CDCl₃) 0.7–0.9 (m, 9H), 1.0–2.0 (m, 17H), 2.3–2.6 (m, 4H), 2.8 (m, 1H), 3.5–3.7 (m, 1H), 3.8–4.2 (m, 2H), 4.4–4.6 (m, 2H), 4.6–4.8 (m, 1H), 5.7–5.9 (m, 2H), 6.2–6.4 (m, 1H), 7.2–7.4 (m, 5H). MS: 527.3 (M+H), 549.3 (M+Na).

Example 9b 3-(2-Benzyloxy-5-oxo-2,3,5,6,7,9a-hexahydro-1H-pyrrolo[1,2-a]azepin-6-ylcarbamoyl)-5-methyl-2-propyl-hexanoic Acid.

Example 9b

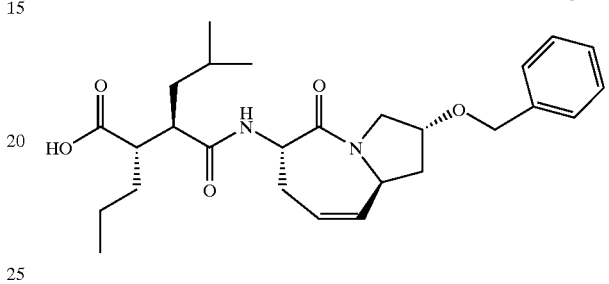

Example 9a (2.0 g, 3.8 mmol) was dissolved in 50 ml of 50% TFA in CH₂C₁₂ and stirred at room temperature for 2 hours. The solvents were removed under reduced pressure and the resulting oil was redissolved in 50 ml of toluene and concentrated to give acid Example 9b (1.7 g, 3.6 mmol), which was used without purification.

Example 9c

N1-(2-Benzyloxy-5-oxo-2,3,5,6,7,9a-hexahydro-1H-pyrrolo[1,2-a]azepin-6-yl)-2-isobutyl-3-propyl-succinamide.

Example 9c

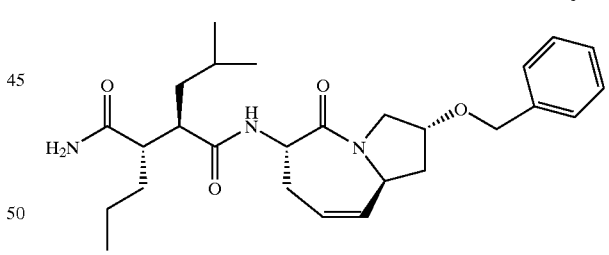

To a solution of Example 9b (1.7 g, 3.6 mmol) in 100 ml DMF was added HATU (1.5 g, 3.9 mmol), followed by DIPEA (0.8 ml, 4.6 mmol). The solution was treated with ammonia gas for 5 minutes, the the reaction mixture was stirred overnight. The solvents were removed under reduced pressure and the resulting solid was purified by column chromatography on silica gel using 5% methanol/CH₂Cl₂ to give Example 9c as a white solid (920 mg, 1.96 mmol, 54%). ¹HNMR (300 MHz, CDCl₃) 0.7–0.9 (m, 9H), 1.2–2.0(m, 8H), 2.4–2.6 (m, 4H), 2.8 (m, 1H), 3.6 (m, 1H), 3.8–3.9(m, 1H), 4.0–4.1 (m, 1H), 4.51 (s, 2H), 4.55–4.65 (m, 1H), 4.8 (m, 1H), 5.6–5.8(m, 3H), 6.0–6.1 (s, 1H), 6.5 (d, 1H), 7.2–7.4 (m, 5H). MS: 470.3 (M+H), 492.2 (M+Na).

Example 10a

N1-(2-Benzyloxy-5-oxo-octahydro-pyrrolo[1,2-a]azepin-6-yl)-2-isobutyl-3-propyl-succinamide.

Example 10a

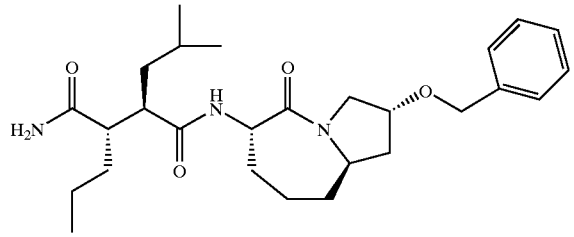

A solution of Example 9c (100 mg, 0.21 mmol) in 30 ml ethanol with 10 mg Wilkinson's catalyst, (chlorotris (triphenylphosphine)rhodium(I)), was shaken under $H_2$ (~50psi) overnight. The solvent was removed under reduced pressure to give a slightly yellow solid. The crude product was purified by column chromatography on silica gel in 5% methanoll $CH_2Cl_2$ to give Example 10a as a white solid (60 mg, 0.13 mmol, 60%). $^1$HNMR (300 MHz, $CD_3OD$) 0.7–0.9 (m, 9H), 0.9–1.1 (m, 1H), 1.1–1.4 (m, 3H), 1.4–1.6 (m, 4H), 1.6–2.0 (m, 5H), 2.0–2.2 (m, 1H), 2.3–2.4 (m, 2H), 2.4–2.6 (m, 1H), 3.4–3.6 (m, 1H), 3.6–3.8 (m, 1H), 4.0–4.2 (m, 2H), 4.4–4.6 (m, 3H), 7.2–7.4 (m, 5H). MS: 472.3 (M+H), 494.3 (M+Na).

Example 10b

N1-(2-Hydroxy-5-oxo-octahydro-pyrrolo[1,2-a]azepin-6-yl)-2-isobutyl-3-propyl-succinamide.

Example 10b

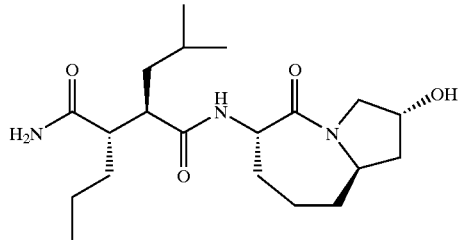

A solution of Example 10a (50 mg, 0.11 mmol) in 30 ml ethanol was shaken under $H_2$ (~50psi) for 2 hrs in the presence of 5 mg Pd/C (5% on activated carbon). The reaction mixture was filtered, the solvent was removed under reduced pressure, and the crude product was purified by column chromatography on silica gel in 5% methanol/ $CH_2Cl_2$ to give alcohol Example 10b as a white solid (40 mg, 0.10 mmol, 90%). $^1$HNMR (300 MHz, $CD_3OD$) 0.8–0.9 (m, 9H), 1.0–2.0 (m, 15H), 2.0–2.2 (m, 2H), 2.2–2.4 (m, 1H), 2.5–2.7 (m, 1H), 3.4–3.6 (m, 3H), 4.0–4.2 (m, 1H), 4.3 (s, 1H), 4.5 (d, 1H). MS: 382.3 (M+H), 404.2 (M+Na).

For Examples 91–105, HPLC analyses were obtained using a Rainin Dynamax® $C_{18}$ column with UV detection at 223 nm using a standard solvent gradient program unless specified otherwise.

Example 96

Preparation of 2-allyl-3-[3-(4-bromo-phenyl)-6,7,8,9-tetrahydro-5H-[1,2,4]triazolo[4,3-a]azepin-9-ylcarbamoyl]-5-methyl-hexanoic Acid tert-butyl Ester.

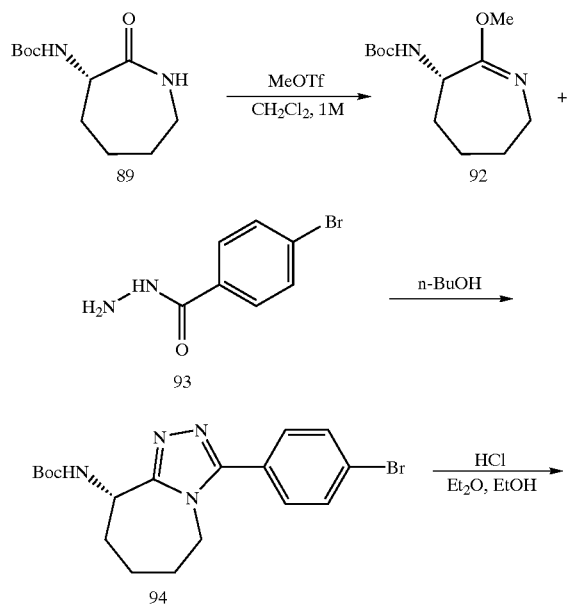

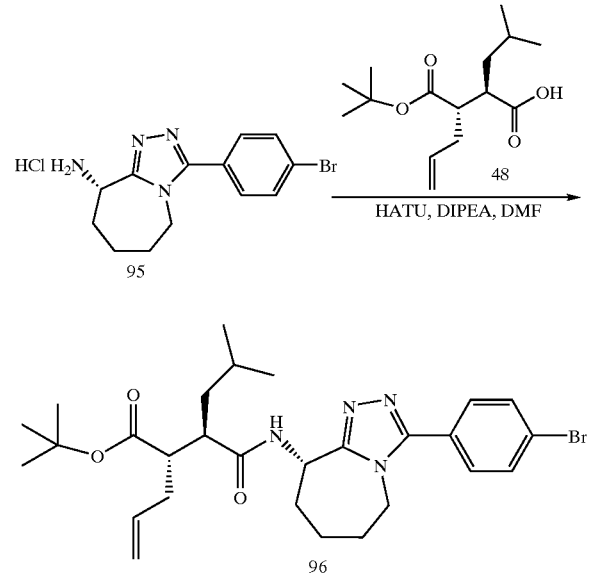

Preparation of Compound 92.

To a solution of compound 89 (16.8 g, 73.7 mmol) in $CH_2Cl_2$ (75 mL) at room temperature was added MeOTf (14.1 g, 85.9 mmol) and the solution was stirred for 6 h under $N_2$. The solution was then diluted with additional $CH_2C_{12}$ (200 mL), washed with sat. $NaHCO_3$ (3×300 mL), brine, and dried over anhydrous $Na_2SO_4$. The solution was filtered and concentrated to yield 92 (15.8 g, 88%) as a light yellow, viscous oil that was used without additional purification: $^1$H NMR (300 MHz, $CDCl_3$) δ 5.42 (m, 1H), 4.59 (m, 1H), 3.71 (m, 4H), 3.22 (t, J=13.7 Hz, 1H), 2.01–1.22 (m, 15H); ESI MS m/z=243 $[C_{13}H_{22}NO_3+H]^+$.

Preparation of Compound 94.

A solution of compound 92 (3.6 g, 14.7 mmol) and 4-bromobenzoic hydrazide, 93, (3.0 g 13.9 mmol) in n-BuOH (100 mL) was heated at reflux for 24 h. The solvent was removed under reduced pressure and the resulting residue was purified by column chromatography (silica gel, 98:2 $CH_2Cl_2$/MeOH) to yield 94 (3.6 g, 60%) as a pale green solid: $^1$H NMR (300 MHz, $CDCl_3$) δ 7.78–7.39 (m, 4H), 6.26 (s, 1H), 4.86 (m, 1H), 4.27 (m, 1H), 3.74 (t, J=13.7 Hz, 1H), 2.47–1.41 (m, 15H); ESI MS m/z=407 $[C_{18}H_{23}BrN_4O_2+H]^+$.

Preparation of Compound 95.

A solution of compound 94 (1.2 g, 2.9 mmol), in ethanol (75 mL) and a 1 N solution of HCl in ether (75 mL) were stirred for 3 h. The solution was concentrated under reduced pressure and ether was added to the residue. The solid that precipitated was collected and dried under vacuum to yield 95 (0.81 g, 91%) as a tan solid: $^1$H NMR (300 MHz, $CD_3OD$) δ 7.99–7.60 (m, 4H), 4.47 (m, 1H), 4.14 (m, 2H), 2.39–1.35 (m, 6 H); ESI MS m/z=307 $[C_{13}H_{15}BrN_4+H]^+$.

Preparation of Example 96.

To a solution of 95 (1 g, 2.9 mmol), DIPEA (2.0 mL, 11.6 mmol) and 48 (0.63 g, 2.3 mmol) in DMF (30 mL) was added HATU (1.3 g, 3.5 mmol) and the solution was stirred at room temperature for 18 h. The resulting solution was partitioned between EtOAc (200 mL) and 5% LiCl (200 mL), the layers separated, the organic layer washed with 5% LiCl (2×100 mL), 0.1 N HCl (2×100 mL), sat. $NaHCO_3$ (2×100 mL), brine (1×100 mL), and dried over anhydrous $Na_2SO_4$. The resulting solution was filtered and concentrated to yield an oily solid. This residue was further purified by column chromatography (silica gel, 70:30 EtOAc/hexanes) to yield 96 (0.66 g, 51%) as a white powder: mp 75–82° C.; $^1$H NMR (300 MHz, $CDCl_3$) δ 7.74–7.42 (m, 4H), 5.77 (m, 1H), 5.19–5.02 (m, 3H), 4.23 (m, 1H), 3.76 (t, J=14.1 Hz, 1H), 2.62–1.03 (m, 13H), 0.95 (d, J=7.0 Hz, 3H), 0.87 (d, J=7.0 Hz, 3H); IR (KBr) 3406,2932, 1726, 1671, 1490 cm$^{-1}$; ESI MS m/z=559 $[C_{28}H_{39}BrN_4O_3+H]^+$; HPLC 100%, $t_r$=22.68 min.

Example 91a

3-Allyl-$N^1$-[3-(4-bromo-phenyl)-6,7,8,9-tetrahydro-5H-[1,2,4]triazolo[4,3-a]azepin-9-yl]-2-isobutyl-succinamide.

91a

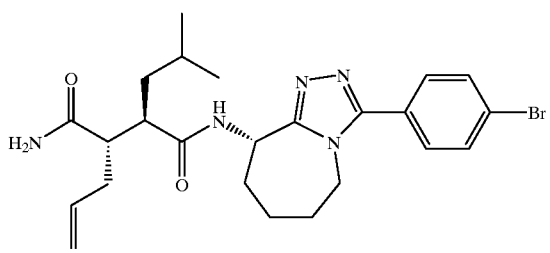

To a solution of Example 96 (0.21 mg, 0.37 mmol) in $CH_2Cl_2$ (7 mL) was added TFA (7 mL) and the solution was allowed to stir for 24 h at room temperature. The solution was concentrated under reduced pressure, the residue was dissolved in $CH_2C_{12}$ (150 mL) and the solution was washed with $NaHCO_3$ (2×150 mL), dried over anhydrous $Na_2SO_4$, filtered, and concentrated to yield a residue. Ammonia gas was bubbled through a solution of the foregoing residue (90 mg, 0.2 mmol) with DIPEA (0.12 mL, 0.71 mmol), HATU (82 mg, 0.214 mmol) in DMF for 30 min and the solution was allowed to stir for 24 h at room temperature. The contents of the flask were partitioned between EtOAc and a 5% LiCl solution (150 mL each), the organic phase washed with 5% LiCl (3×50 mL), and dried over anhydrous $Na_2SO_4$. The resulting solution was filtered and concentrated to yield a white solid. This was further purified by column chromatography (silica gel, 97:3 EtOAc/MeOH) to yield 91a (45 mg, 24%) as a white powder: mp 159–166° C.; $^1$H NMR (300 MHz, $CDCl_3$) δ 7.88 (s, 1H), 7.78-7.44 (m, 4H), 6.49 (s, 1H), 6.07 (m, 1H), 5.82 (m, 1H), 5.31–4.96 (m, 3H), 4.31 (m, 1 H) 3.86 (t, J=14.1 Hz, 1H), 2.89–1.22 (m, 13H), 0.95 (d, J=7.1 Hz, 3H), 0.87 (d, J=7.1 Hz, 3H); IR (KBr) 3334, 2953, 1663, 1490, 1438 cm$^{-1}$; ESI MS m/z=502 $[C_{24}H_{32}BrN_5O_2+H]^+$; HPLC 100%, $t^r$=20.12 min.

Example 91b

3-Allyl-$N^1$-[3-(4-phenyl-phenyl)-6,7,8,9-tetrahydro-5H-[1,2,4]triazolo[4,3-a]azepin-9-yl]-2-isobutyl-succinamide.

91b

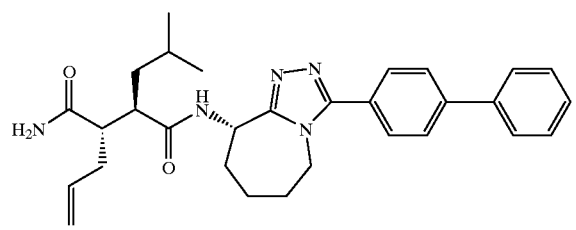

Preparation of 2-allyl-3-[3-(4-phenyl-phenyl)-6,7,8,9-tetrahydro-5H-[1,2,4]triazolo[4,3-a]azepin-9-ylcarbamoyl]-5-methyl-hexanoic Acid tert-butyl Ester.

To a solution of 96 (0.14 g, 0.24 mmol), $Ph_3P$ (38 mg, 0.15 mmol), $K_3PO_4$ (0.26 g, 1.21 mmol), $PhB(OH)_2$ (44 mg, 0.36 mmol) in DMF/$H_2O$ (5 mL: 1 mL) was added $Pd(Ph_3P)_2Cl_2$ (50 mg, 0,07 mmol), and argon was bubbled through the solution for 30 min. The solution was heated to 70° C. for 10 h under Ar. The resulting solution was diluted with EtOAc (100 mL) washed with 5% LiCl (3×100 mL), and dried over anhydrous $Na_2SO_4$. The resulting solution was filtered and concentrated to yield a pale yellow waxy solid. This solid was further purified by column chromatography (silica gel, 50:50 EtOAc/hexanes) to yield 98b (48 mg, 36%) as a white powder: $^1$H NMR (300 MHz, $CDCl_3$) δ 7.81–7.41 (m, 10H), 5.73 (m, 1H), 5.21–5.05 (m, 3H), 4.42 (m, 1H), 3.73 (t, J=14.0 Hz, 1H), 2.89–1.22 (m, 22H), 0.92 (m, 6H); ESI MS m/z=557 $[C_{34}H_{44}N_4O_3+H]^+$.

Preparation of Example 91b.

To a solution of 98b (45 mg, 0.08 mmol) in $CH_2Cl_2$ (5 mL) was added TFA (0.12 mL) and the solution was allowed to stir for 24 h at room temperature. The solution was concentrated under reduced pressure, the residue was redissolved in toluene and concentrated (3×10 mL). Ammonia gas was bubbled through a solution of the foregoing residue (30 mg, 0.06 mmol), DIPEA (0.05 mL, 0.3 mmol), HATU (46 mg, 0.12 mmol) in DMF (5 mL) for 30 min and the solution was allowed to stir for 24 h at room temperature. The contents of the flask were partitioned between EtOAc and a 5% LiCl solution (150 mL each), the organic phase washed with 5% LiCl (3×50 mL), and dried over anhydrous Na$_2$SO$_4$. The resulting solution was filtered and concentrated to yield a white solid. This was further purified by column chromatography (silica gel, 97:3 EtOAc/MeOH) to yield 91b (20 mg, 50%) as a white powder: mp 272–275° C.; $^1$H NMR (300 MHz, CDCl$_3$) δ 7.82–7.38 (m, 10H), 6.28 (s, 1H), 5.84 (m, 1H), 5.62 (s, 1 H), 5.28–4.99 (m, 3H), 4.30 (m, 1H), 3.87 (t, J=14.0 Hz, 1H), 2.89–1.22 (m, 13H), 0.95 (d, J=7.1 Hz, 3H), 0.87 (d, J=7.1 Hz, 3H); IR (KBr) 3390, 2921, 1654, 1483, 1438 cm$^{-1}$; ESI MS m/z=500 [C$_{30}$H$_{37}$N$_5$O$_2$+H]$^+$; HPLC 95.3%, t$_r$=16.84 min.

Example 91c

3-Allyl-N$^1$-[3-(4-benzofuran-2-yl-phenyl)-6,7,8,9-tetrahydro-5H-[1,2,4]triazolo[4,3-a]azepin-9-yl]-2-isobutyl-succinamide.

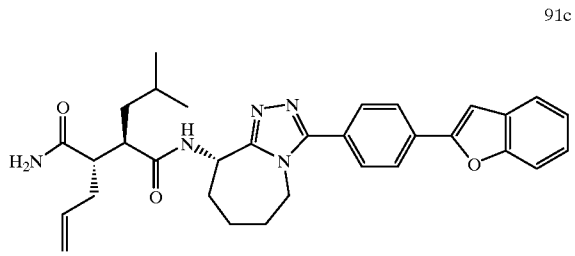

91c

Preparation of 2-allyl-3-[3-(4-benzofuran-2-yl -phenyl)-6,7,8,9-tetrahydro-5H-[1,2,4]triazolo[4,3-a]azepin-9-ylcarbamoyl]-5-methyl-hexanoic acid tert-butyl ester.

To a solution of 96 (0.112 g, 0.2 mmol), Ph$_3$P (10 mg, 0.04 mmol), K$_3$PO$_4$ (0.21 g, 1.0 mmol), benzo[b]furan-2-boronic acid (65 mg, 0.4 mmol) in DMF/H$_2$O (4 mL:1 mL) was added Pd(Ph$_3$P)$_2$Cl$_2$ (28 mg, 0.04 mmol), and argon was bubbled through the solution for 30 min. The solution was heated to 70° C. for 10 h under Ar. The resulting solution was diluted with EtOAc (100 mL), washed with 5% LiCl (3×100 mL), and dried over anhydrous Na$_2$SO$_4$. The resulting solution was filtered and concentrated to yield a white oily solid. This solid was further purified by column chromatography (silica gel, 50:50 EtOAc/hexanes) to yield 98c (47 mg, 39%) as a white powder: $^1$H NMR (300 MHz, CDCl$_3$) 67.97 (m, 2H), 7.62–7.17 (m, 8H), 5.63 (m, 1H), 5.09–4.90 (m, 3H), 4.25 (m, 1H), 3.69 (t, J=13.8 Hz, 1H), 2.59–1.09 (m, 22H), 0.88 (d, J=6.9 Hz, 3H); 0.81 (d, J=6.9 Hz, 3H); ESI MS m/z=597 [C$_{36}$H44N$_4$O$_4$+H]$^+$.

Preparation of Example 91c.

To a solution of 98c (41 mg, 0.069 mmol) in CH$_2$Cl$_2$ (4 mL) was added TFA (4 mL) and the solution was allowed to stir for 24 h at room temperature. The solution was concentrated under reduced pressure, the residue was redissolved in toluene and concentrated (3×10 mL). Ammonia gas was bubbled through a solution of the foregoing residue (30 mg, 0.06 mmol), DIPEA (0.06 mL, 0.3 mmol), and HATU (29 mg, 0.08 mmol) in DMF (5 mL) for 30 min and the solution was allowed to stir for 24 h at room temperature. After the contents of the flask were partitioned between EtOAc and a 5% LiCl solution (50 mL each), the organic phase was washed with 5% LiCl (3×50 mL), and dried over anhydrous Na$_2$SO$_4$. Concentration gave a white solid which was further purified by column chromatography (silica gel, 97:3 EtOAc/MeOH) to yield 91c (22 mg, 59%) as a white powder: mp 281–284° C.; $^1$H NMR (500 MHz, CDCl$_3$) δ 8.02 (m, 2H), 7.82–7.38 (m, 8H), 6.07 (s, 1H), 5.82 (m, 1H), 5.37 (s, 1H), 5.18–5.09 (m, 3H), 4.42 (m, 1H) 3.87 (t, J=14.2 Hz, 1H), 2.71–1.39 (m, 13H), 1.00 (d, J=7.1 Hz, 3 H), 0.92 (d, J=7.1 Hz, 3H); IR (KBr) 3303, 2928, 1664, 1641, 1438 cm$^{-1}$; ESI MS m/z=540 [C$_{32}$H$_{37}$N$_5$O$_2$+H]$^+$; HPLC 96.2%, t$_r$=17.72 min.

Example 91d

3-Allyl-N$^1$-[3-(4-(4-chloro-phenyl)-phenyl)-6,7,8,9-tetrahydro-5H-[1,2,4]triazolo[4,3-a]azepin-9-yl]-2-isobutyl-succinamide.

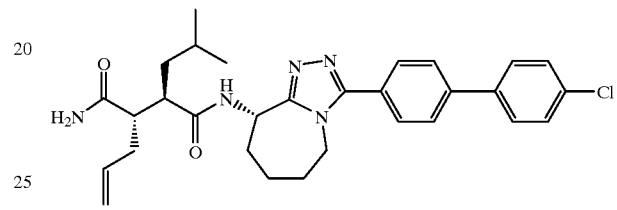

91d

Preparation of 2-allyl-3 -[3-(4-(4-chloro-phenyl)-phenyl)-6,7,8,9-tetrahydro-5H-[1,2,4]triazolo[4,3-a]azepin-9-ylcarbamoyl]-5-methyl-hexanoic acid tert-butyl ester.

To a solution of 96 (0.15 g, 0.25 mmol), Ph$_3$P (20 mg, 0.08 mmol), K$_3$PO$_4$ (0.27 g, 1.3 mmol), and 4-chlorophenyl boronic acid (59 mg, 0.38 mmol) in DMF/H$_2$0 (8 mL:2 mL) was added Pd(Ph$_3$P)$_2$C$_{12}$ (53 mg, 0.07 mmol). Argon was bubbled through the solution for 30 min. The solution was heated to 70° C. for 10 h under Ar, then cooled, was diluted with EtOAc (100 mL), washed with 5% LiCl (3×100 mL), and dried over anhydrous Na$_2$SO$_4$. Filtration and concentration gave a light brown waxy solid. This solid was further purified by column chromatography (silica gel, 50:50 EtOAc/hexanes) to yield 98d (68 mg, 46%) as a white powder: $^1$H NMR (300 MHz, CDCl$_3$) δ 7.83–7.41 (m, 10H), 5.78 (m, 1H), 5.20–5.02 (m, 3H), 4.38 (m, 1H), 3.76 (t, J=14.0 Hz, 1H), 2.59–1.02 (m, 22H), 0.93 (d, J=6.7Hz, 3H); 0.86 (d, J=6.7Hz, 3H); ESI MS m/z=591 [C$_{34}$H$_{43}$ClN$_4$O$_3$+H]$^+$.

Preparation of Example 91d.

To a solution of 98d (65 mg, 0.11 mmol) in CH$_2$Cl$_2$ (6 mL) was added TFA (2 mL) and the solution was allowed to stir for 24 h at room temperature. The solution was concentrated under reduced pressure, and the residue was redissolved in toluene and concentrated (3×10 mL). Ammonia gas was bubbled through a solution of the foregoing residue (55 mg, 0.1 mmol), DIPEA (0.1 mL, 0.59 mmol), HATU (90 mg, 0.24 mmol) in DMF (5 mL) for 30 min and the solution was allowed to stir for 24 h at room temperature. The contents of the flask were partitioned between EtOAc and a 5% LiCl solution (50 mL each), the organic phase washed with 5% LiCl (3×50 mL), and dried over anhydrous Na$_2$SO$_4$. The resulting solution was filtered and concentrated to yield a white solid. This was further purified by column chromatography (silica gel, 97:3 CH$_2$Cl$_2$/MeOH) to yield 91d (33 mg, 56%) as a white powder: mp 262–267° C.; ¹H NMR (300 MHz, CD₃OD) δ 8.82 (m, 1H), 7.72–7.39 (m, 8H), 5.53 (m, 1H), 5.11 (s, 1H), 4.92–4.75 (m, 3H), 4.10 (m, 1H), 3.87 (m, 1H), 2.58–0.92 (m, 13H), 0.79 (d, J=7.2 Hz, 3H), 0.71 (d, J=7.2 Hz, 3H); IR (KBr) 3405, 2954, 1655, 1486, 1467 cm⁻; ESI MS m/z=534 [C₃₀H₃₆ClN₅O₂+H]⁺; HPLC 95.8%, t$_r$=16.56 min.

Example 91e

3-Allyl-N¹-[3-(4-(3,5-dimethylisoxazol-4-yl)phenyl)-6,7,8,9-tetrahydro-5H-[1,2,4]triazolo[4,3-a]azepin-9-yl]-2-isobutyl-succinamide.

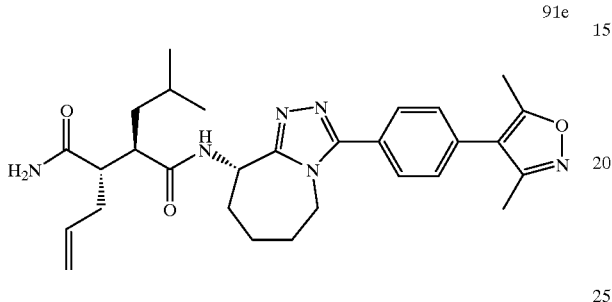

Preparation of 2-allyl-3-[3-(4-(3,5-dimethylisoxazol-4-yl)phenyl)-6,7,8,9-tetrahydro-5H-[1,2,4]triazolo[4,3-a]azepin-9-ylcarbamoyl]-5-methyl-hexanoic Acid tert-butyl Ester.

To a solution of 96 (0.12 g, 0.21 mmol), Ph₃P (11 mg, 0.04 mmol), K₃PO4 (0.23 g, 1.1 mmol), and 3,5-dimethylisoxazole-4-boronic acid (60 mg, 0.43 mmol) in DMF/H₂O (5 mL: 1 mL) was added Pd(Ph₃P)₂C₁₂ (50 mg, 0,07 mmol), and argon was bubbled through the solution for 30 min. The solution was heated to 70° C. for 10 h under Ar, then cooled, diluted with EtOAc (100 mL), washed with 5% LiCl (3×100 mL), and dried over anhydrous Na₂SO₄. The resulting solution was filtered and concentrated to yield a tan granular solid which was further purified by column chromatography (silica gel, 50:50 EtOAc/hexanes) to yield 98e (48 mg, 40%) as a white powder: ¹H NMR (300 MHz, CDCl₃) δ 7.71–7.49 (m, 5H), 5.82 (m, 1H), 5.20–4.98 (m, 3H), 4.36 (m, 1H), 3.79 (t, J=13.9Hz, 1H), 2.67–1.12 (m, 28H), 0.98 (d, J=6.9Hz, 3H); 0.91 (d, J=6.9 Hz, 3H); ESI MS m/z=576 [C₃₃H₄₅N₅O₄+H]⁺. Preparation of Example 91e.

To a solution of 98e (48 mg, 0.08 mmol) in CH₂Cl₂ (6 mL) was added TFA (1 mL) and the solution was allowed to stir for 24 h at room temperature. The solution was concentrated under reduced pressure, the residue was redissolved in toluene and concentrated (3×10 mL). Ammonia gas was bubbled through a solution of the foregoing residue (30 mg, 0.05 mmol), DIPEA (0.044 mL, 0.25 mmol), and HATU (38 mg, 0.1 mmol) in DMF (5 mL) for 30 min and the solution was allowed to stir for 24 h at room temperature. The contents of the flask were partitioned between EtOAc and 5% LiCl solution (50 mL each), and the organic phase washed with 5% LiCl (3×50 mL), then dried over anhydrous Na₂SO₄. The resulting solution was filtered and concentrated to yield a white solid. This was further purified by column chromatography (silica gel, 97:3 CH₂Cl₂/MeOH) to yield 91e (12 mg, 29%) as a white powder: mp 154–162° C.; ¹H NMR (500 MHz, CDCl₃) δ 7.72–7.39 (m, 5H), 6.08 (m, 1H), 5.80–5.76 (m, 1H), 5.46 (m, 1H), 5.16–5.04 (m, 3H), 4.39 (m, 1H), 3.81 (t, J=13.8 Hz, 1H), 2.68–1.25 (m, 19 H), 0.96 (d, J=6.7 Hz, 3H), 0.89 (d, J=6.7 Hz, 3H); IR (KBr) 3406, 2954, 2928, 1663, 1490 cm⁻¹; ESI MS m/z=519 [C₂₉H₃₈N₆O₃+H]⁺; HPLC 95.6%, t$_r$=16.70 min.

Example 102

Preparation of 2-allyl-3-[3-(3-bromo-phenyl)-6,7,8,9-tetrahydro-5H-[1,2,4]triazolo[4,3-a]azepin-9-ylcarbamoyl]-5-methyl-hexanoic Acid tert-butyl Ester.

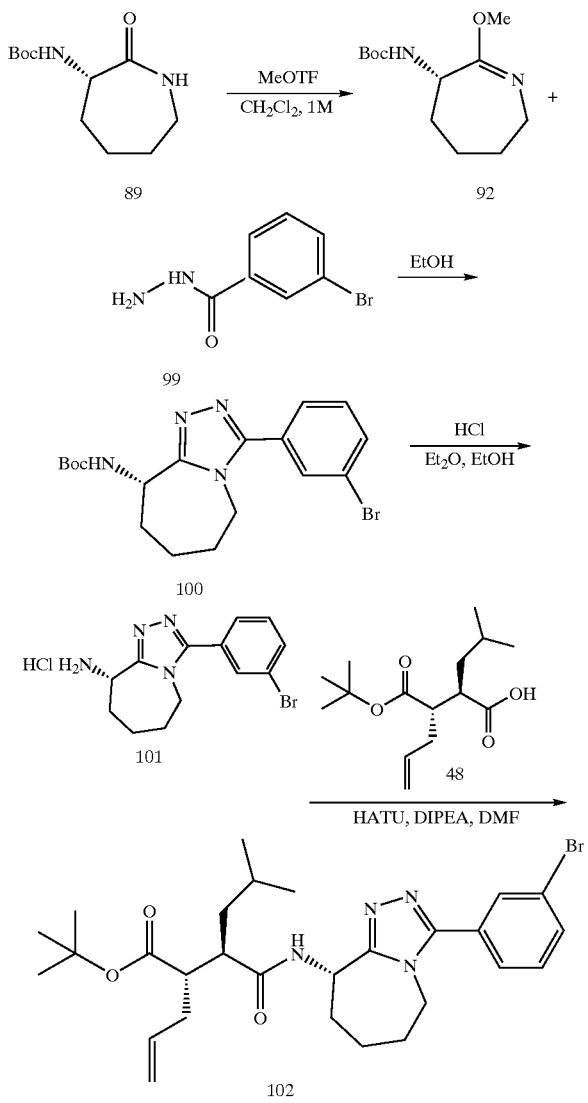

Preparation of Compound 100.

A solution of compound 92 (3.8 g, 14.7 mmol) and 3-bromobenzoic hydrazide, 99, (3.0 g, 13.9 mmol) in EtOH (100 mL) was heated at reflux for 24 h. The solvent was removed under reduced pressure and the resulting residue was purified by column chromatography (silica gel, 98:2 CH₂Cl₂/MeOH) to yield 100 (4.0 g, 62%) as a pale green solid: ¹H NMR (300 MHz, CDCl₃) 7.71–7.38 (m, 4H), 6.26 (s, 1H), 4.91 (m, 1 H), 4.26 (m, 1H), 3.73 (t, J=14.1 Hz, 1H), 2.47–1.41 (m, 15H); ESI MS m/z=407 [C₁₈H₂₃BrN₄O₂+H]⁺.

Preparation of Compound 101.

A solution of compound 100 (3.3 g, 8.3 mmol), in ethanol (100 mL) was stirred with a 1 N solution of HCl in ether (150 mL) for 36 h. The solution was concentrated under reduced pressure and ether was added to the residue. The solid that precipitated was filtered and dried under vacuum to yield 101 (2.3 g, 89%) as a tan solid: ¹H NMR (300 MHz, CD₃OD) 8.03–7.75 (m, 4H), 4.47 (m, 1H), 4.14 (m, 2H), 2.39–1.35 (m, 6 H); ESI MS m/z=307 [C₁₃H₁₅BrN₄+H]⁺.

Preparation of Example 102.

To a solution of 95 (1 g, 2.9 mmol), DIPEA (2.0 mL, 11.6 mmol) and 48 (0.63 g, 2.3 mmol), in DMF (30 mL) was added HATU (1.3 g, 3.5 mmol). The solution was stirred at room temperature for 18 h, then partitioned between EtOAc (200 mL) and 5% LiCl (200 mL). The organic layer washed with 5% LiCl (2×100 mL), 0.1 N HCl (2×100 mL), sat. NaHCO$_3$ (2×100 mL), brine (1×100 mL), and dried over anhydrous Na$_2$SO$_4$. The resulting solution was filtered and concentrated to yield an oily solid. This residue was further purified by column chromatography (silica gel, 70:30 EtOAc/hexanes) to yield 102 (0.66 g, 51%) as a white powder: mp 75–82° C.; $^1$H NMR (300 MHz, CDCl$_3$) δ 7.74–7.42 (m, 4H), 5.77 (m, 1H), 5.19–5.02 (m, 3H), 4.23 (m, 1 H), 3.76 (t, J=14.1 Hz, 1H), 2.62–1.03 (m, 13H), 0.95 (d, J=7.0 Hz, 3H), 0.87 (d, J=7.0 Hz, 3H); ESI MS m/z=559 [C$_{28}$H$_{39}$BrN$_4$O$_3$+H]$^+$.

Example 103

3-Allyl-N$^1$-[3-(3-bromo-phenyl)-6,7,8,9-tetrahydro-5H-[1,2,4]triazolo[4,3-a]azepin-9-yl]-2-isobutyl-succinamide.

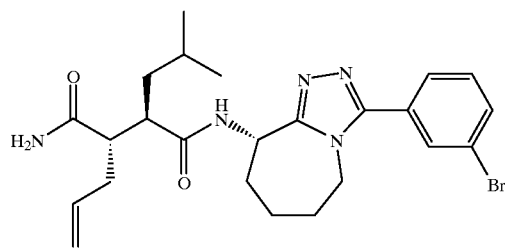

103

Example 103 was prepared using the procedures described for Example 91a. ESI MS m/z=502 [C$_{24}$H$_{32}$BrN$_5$O$_2$+H]$^+$.

Example 105a

3-Allyl-N$^1$-[3-(3-phenyl-phenyl)-6,7,8,9-tetrahydro-5H-[1,2,4]triazolo[4,3-a]azepin-9-yl]-2-isobutyl-succinamide.

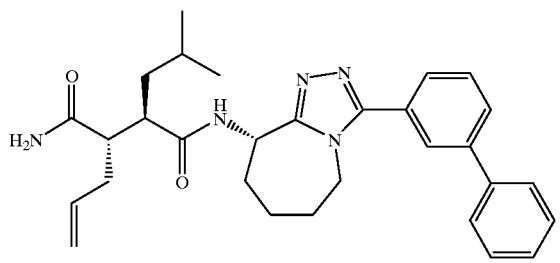

105a

Example 105a was prepared in a manner similar to Example 91c starting from compound 102. Using the procedures disclosed in Example 91b, compound 102 was reacted with phenyl boronic acid to form 2-allyl-3-[3-(3-phenyl-phenyl)-6,7,8,9-tetrahydro-5H-[1,2,4]triazolo[4,3-a]azepin-9-ylcarbamoyl]-5-methyl-hexanoic acid tert-butyl ester; which was subsequently converted to the amide 105a. ESI MS m/z=500 [C$_{30}$H$_{37}$N$_5$O$_2$+H]$^+$.

Example 105b

3-Allyl-N$^1$-[3-(3-benzofuran-2-yl-phenyl)-6,7,8,9-tetrahydro-5H-[1,2,4]triazolo[4,3-a]azepin-9-yl]-2-isobutyl-succinamide.

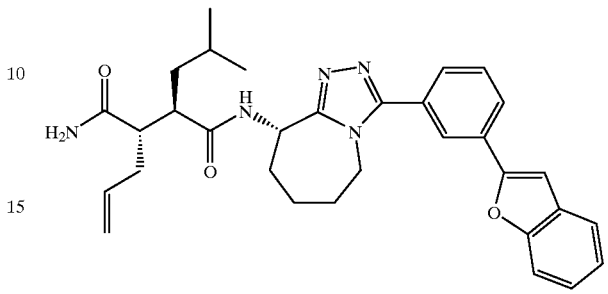

105b

Example 105b was prepared in a manner similar to Example 91c starting from compound 102. Using the procedures disclosed in Example 91c, compound 102 was reacted with benzo[b]furan-2-boronic acid to form 2-allyl-3-[3-(3-phenyl-phenyl)-6,7,8,9-tetrahydro-5H-[1,2,4]triazolo[4,3-a]azepin-9-ylcarbamoyl]-5-methyl-hex anoic acid tert-butyl ester; which was subsequently converted to the amide 105b. ESI MS m/z=540 [C$_{32}$H$_{37}$N$_5$O$_2$+H]$^+$.

UTILITY

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of 3 amyloid precursor protein. Compounds that inhibit β or γ secretase activity, either directly or indirectly, control the production of Aβ. Such inhibition of P or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. No. 5,703,129 and U.S. Pat. No. 5,593,846; all hereby incorporated by reference.

The compounds of the present invention have utility for the prevention and treatment of disorders involving Aβ production, such as cerebrovascular disorders.

Compounds of the present invention have been shown to inhibit Aβ production, as determined by the secretase inhibition assay described below.

Compounds of the present invention have been shown to inhibit AP production, utilizing the C-terminus β amyloid precursor protein accumulation assay described below.

Compounds of Formula (I) are expected to possess y secretase inhibitory activity. The y secretase inhibitory activity of the compounds of the present invention is demonstrated using assays for such activity, for Example, using the assay described below. Compounds of the present invention have been shown to inhibit the activity of γ secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetato.

A compound is considered to be active if it has an $IC_{50}$ or $K_i$ value of less than about 100 μM for the inhibition of Aβ production or inhibition of proteolytic activity leading to Aβ production. Compounds, as demonstrated by use of the invention, have demonstrated $IC_{50}$ values, for the inhibition of Aβ production, of less than about 100 μM. Preferably compounds, as demonstrated by use of the invention, demonstrate $IC_{50}$ values, for the inhibition of Aβ production, of less than about 1 μM. More preferably compounds, as demonstrated by use of the invention, demonstrate $IC_{50}$ values, for the inhibition of AD production, of less than about 100 nM. Even more preferably compounds, as demonstrated by use of the invention, demonstrate $IC_{50}$ values, for the inhibition of Aβ production, of less than about 50 nM.

β Amyloid Precursor Protein Accumulation Assay (β APPA assay)

An assay to evaluate the accumulation of AP protein was developed to detect potential inhibitors of secretases. The assay uses the N 9 cell line, characterized for expression of exogenous APP by immunoblotting and immunoprecipitation.

The effect of test compounds on the accumulation of AP in the conditioned medium is tested by immunoprecipitation. N 9 cells are grown to confluency in 6-well plates and washed twice with 1× Hank's buffered salt solution. The cells are starved in methionine/cysteine deficient media for 30 min., followed by replacement with fresh deficient media containing 150 uCi Tran35S-LABEL™ (ICN). Test compounds dissolved in DMSO (final concentration 1%) are added, over a range of 1 picomolar to 100 micromolar, together with the addition of the fresh media containing Tran35S-LABEL™. The cells are incubated for 4 h at 37° C. in a tissue culture incubator.

At the end of the incubation period, the conditioned medium is harvested and pre-cleared by the addition of 5 μl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing Sug of a monoclonal antibody (examples of antibodies include but are not limited by, clone 1101.1, directed against an internal peptide sequence in Aβ; or 6E10 from Senetek; or 4G8 from Senetek; additionally polyclonals from rabbit antihuman Aβ from Boehringer Mannheim) and 50 μl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 50 mM NaCl, 5 mM EDTA, 0.5% Nonidet P-40), and three times with 10 mM Tris, pH 7.5. The pellet after the last wash is resuspended in SDS sample buffer (Laemmli U.K. Cleavage of structural proteins during the assembly of the head of bacteriphage T4. Nature 227, 680–5, 1970.) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβpolypeptides. The steady-state level of Aβ in the presence of a test compound is compared to wells treated with DMSO (1%) alone. A typical test compound in this assay blocks AP accumulation in the conditioned medium, and is considered active with an $IC_{50}$ less than 100 μM.

C-Terminus b Amyloid Precursor Protein Accumulation Assay (CTF assay)

The effect of test compounds on the accumulation of C-terminal fragments is determined by immunoprecipitation of APP and fragments thereof from cell lysates. N 9 cells are metabolically labeled, as above, with media containing Tran35S-LABEL™, in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% $NaN_3$). Again, lysates are precleared with 5 ul normal rabbit serum/50 ul protein A Sepharose, followed by the addition of BC-1 antiserum (15μl;) and 50μl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound in this assay stimulates C-terminal fragment accumulation in the cell lysates, and is considered active with an $IC_{50}$ less than 100 μM. Accumulation-Release Assay This immunoprecipitation assay is specific for g secretase activity (i.e., proteolytic activity required to generate the C-terminal end of Aβ either by direct cleavage or generating a C-terminal extended species which is subsequently further proteolyzed). N 9 cells are pulse labeled with media containing Tran35S-LABELTM in the presence of a reported g secretase inhibitor (MDL 28170; Higaki J, Quon D, Zhong Z, Cordell B. Inhibition of beta-amyloid formation identifies proteolytic precursors and subcellular site of catabolism. Neuron 14, 651–659, 1995) for 1 h, followed by washing to remove 35S radiolabel and MDL 28170. The media is replaced and test compounds are added over a dose range (for example 0.1 nM to 100 uM). The cells are chased for increasing periods of times and Aβ is isolated from the conditioned medium and C-terminal fragments from cell lysates (see accumulation assay above). The activity of test compounds are characterized by whether a stabilization of C-terminal fragments is observed and whether Aβ is generated from these accumulated precursor. A typical test compound in this assay prevents the generation of Aβ out of accumulated C-terminal fragments and is considered active with an $IC_{50}$ less than 100 μM.

Dosage and Formulation

The compounds determined from the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds determined from the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds determined from the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

Advantageously, compounds determined from the present invention may be administered in a single daily dose, or the total daily dosage may be administered in divided doses of two, three, or four times daily.

The compounds identified using the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β▽ lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds determined from the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds determined from the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Table 1 demonstrates representative compounds envisaged within the scope of the present invention. Each formulae at the start of Table 1 are intended to be paired with each entry in the table which follows. The formulae are generated by combining each fragment from Group A with each fragment with Group B.

TABLE 1
Group A (each fragment in Group A has a -W-X-Y-Z group attached thereto, the fragment can be attached at any point on the multi-ring system)
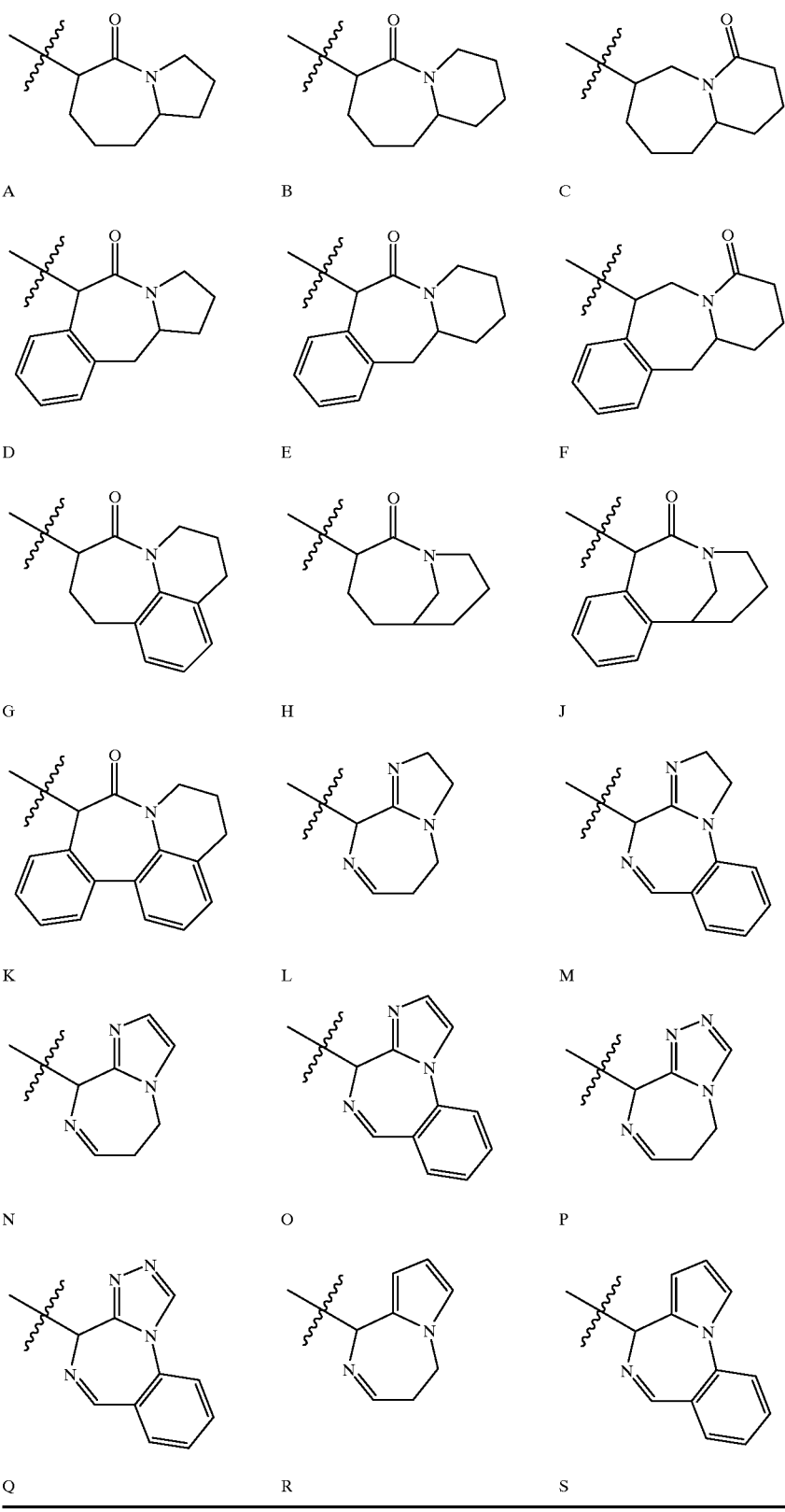

TABLE 1-continued
Group B
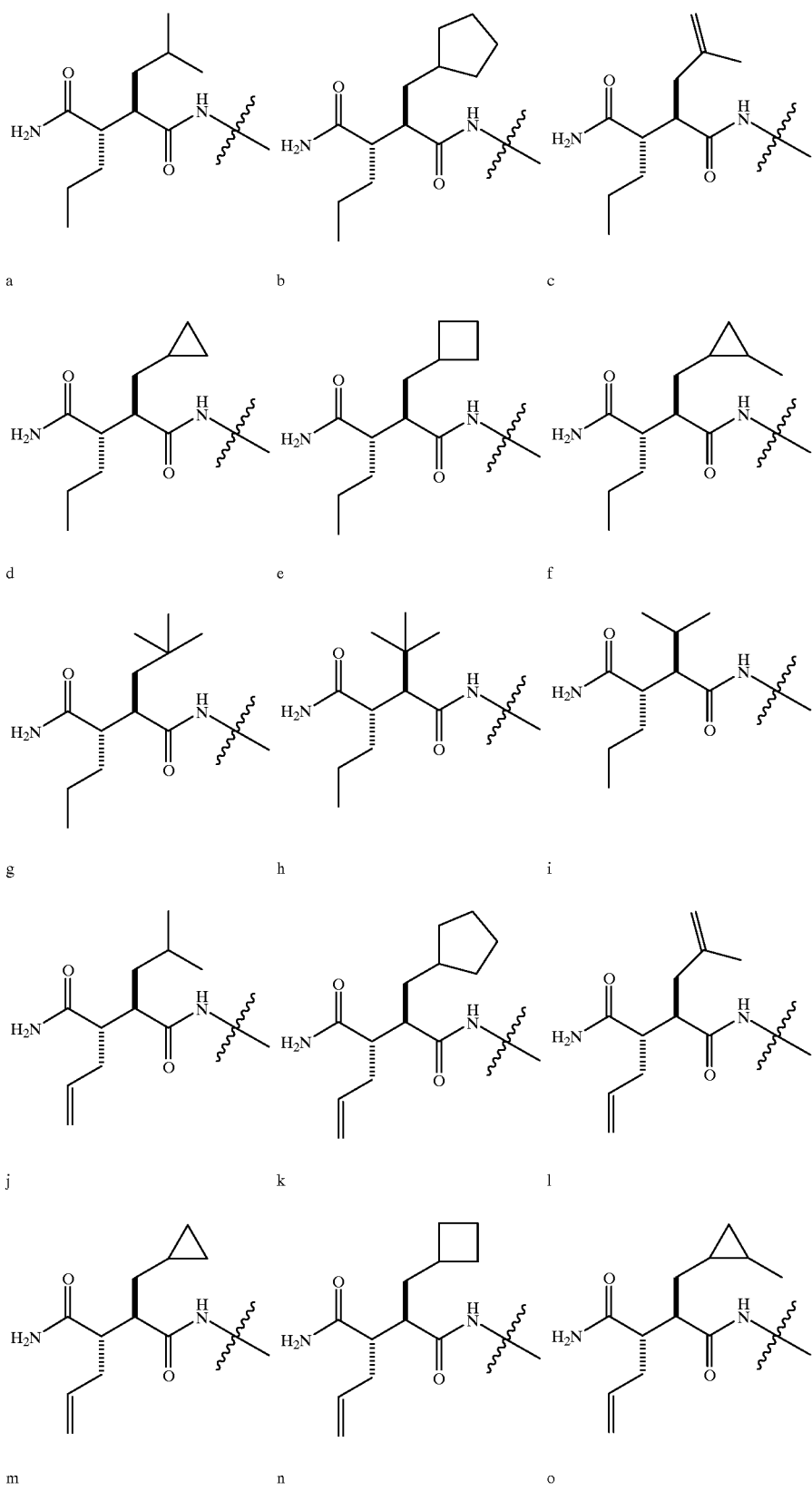
a b c
d e f
g h i
j k l
m n o

TABLE 1-continued
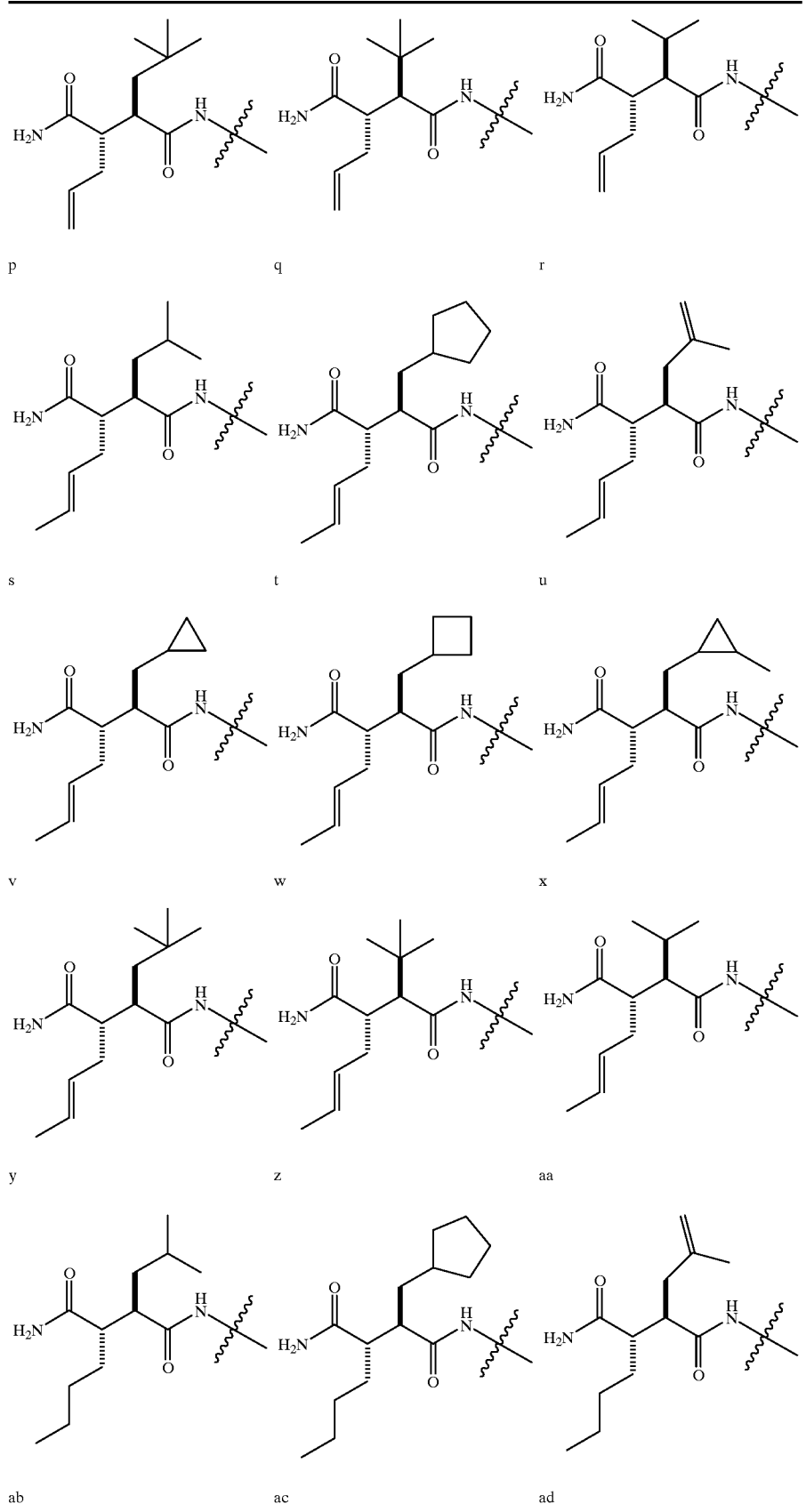
p  q  r
s  t  u
v  w  x
y  z  aa
ab  ac  ad

TABLE 1-continued
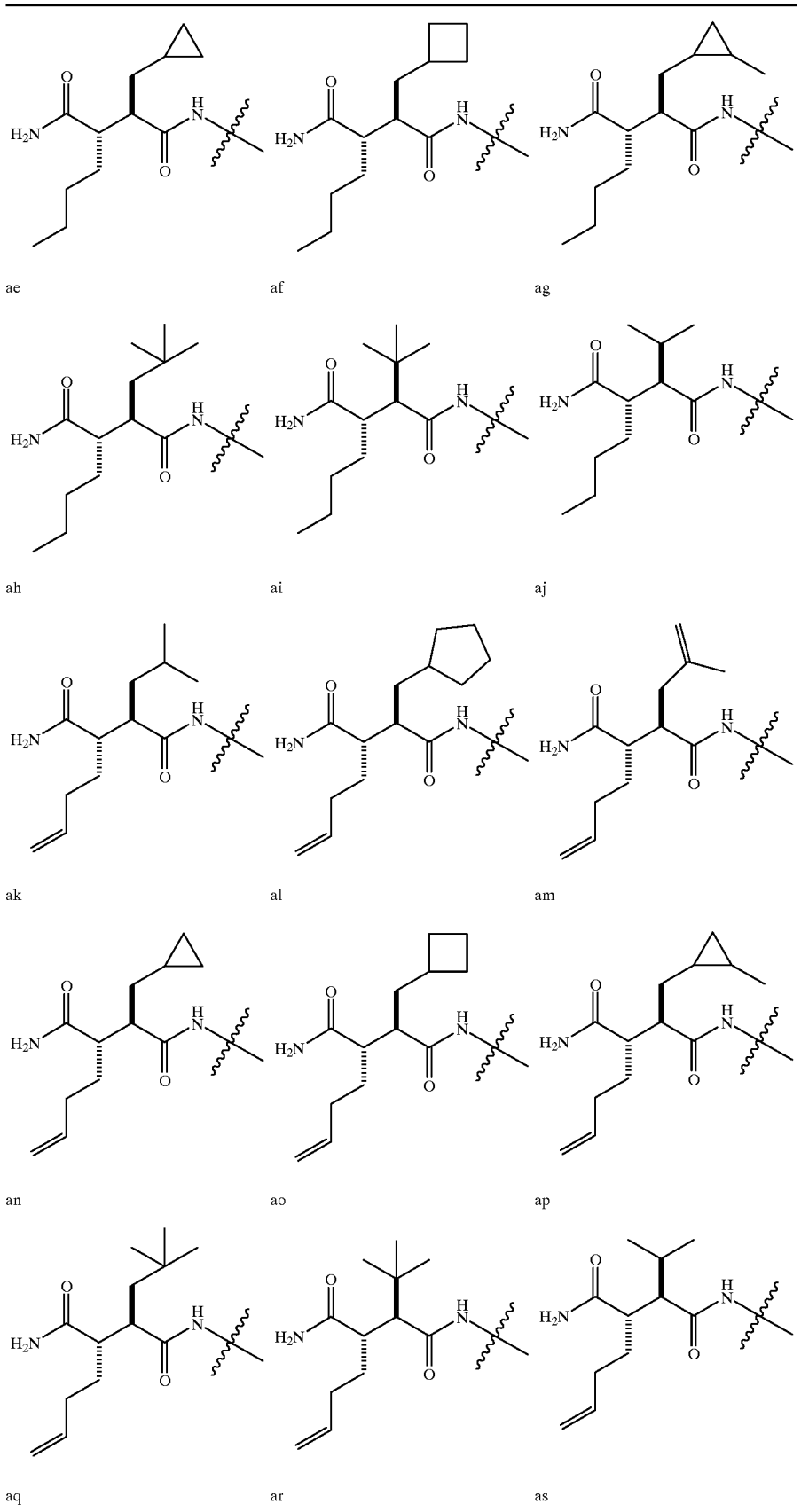

TABLE 1-continued
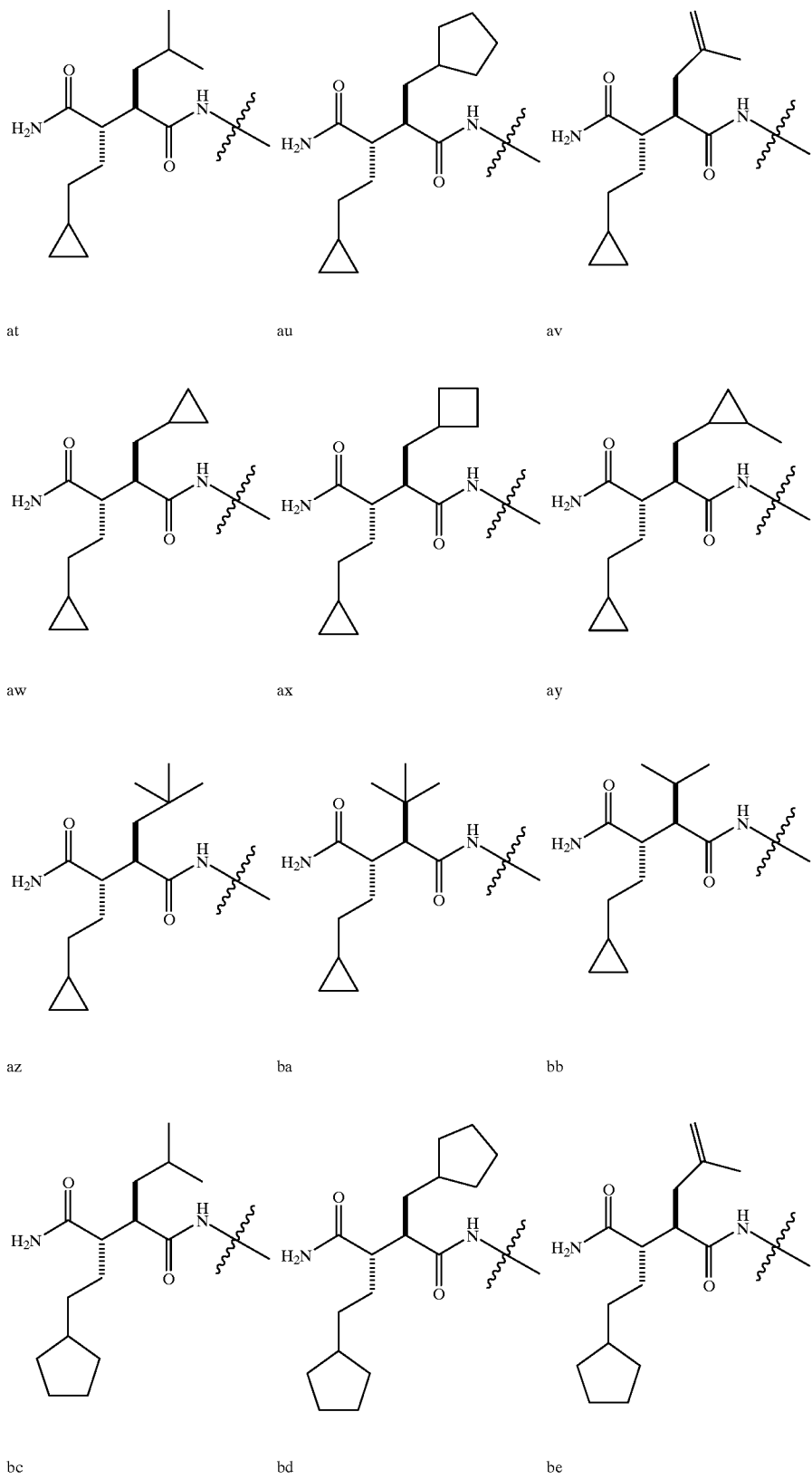
at au av
aw ax ay
az ba bb
bc bd be

TABLE 1-continued
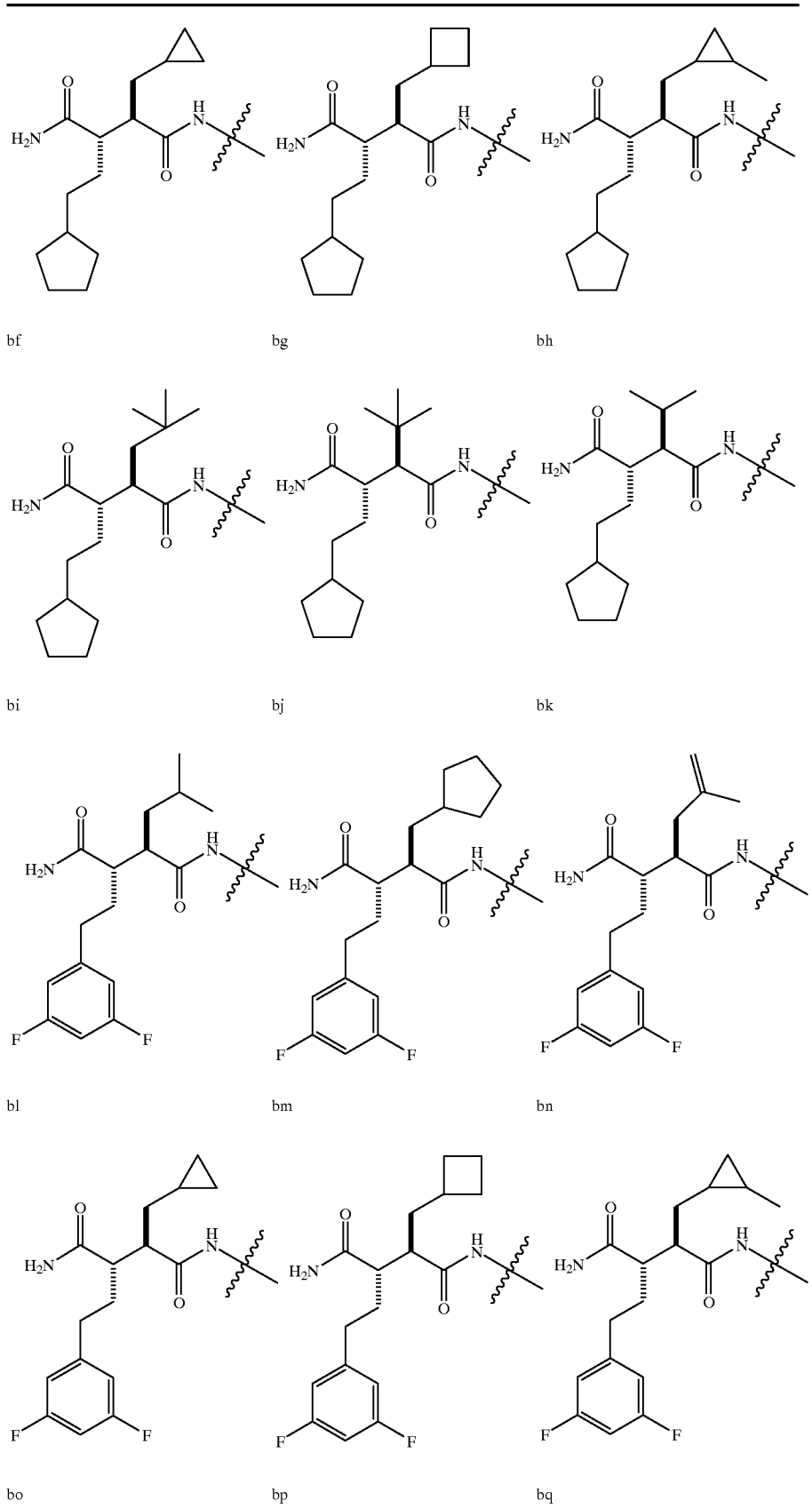

TABLE 1-continued

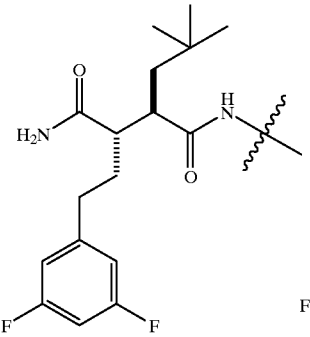

br          bs          bt

| Ex # | W | X | Y | Z |
|---|---|---|---|---|
| 100 | —CH$_2$— | phen-1,3-diyl | bond | phenyl |
| 101 | —CH$_2$— | phen-1,3-diyl | bond | 3,3-diphenylmethyl |
| 102 | —CH$_2$— | phen-1,3-diyl | bond | 2-F-phenyl |
| 103 | —CH$_2$— | phen-1,3-diyl | bond | 3-F-phenyl |
| 104 | —CH$_2$— | phen-1,3-diyl | bond | 4-F-phenyl |
| 105 | —CH$_2$— | phen-1,3-diyl | bond | 2-Cl-phenyl |
| 106 | —CH$_2$— | phen-1,3-diyl | bond | 3-Cl-phenyl |
| 107 | —CH$_2$— | phen-1,3-diyl | bond | 4-Cl-phenyl |
| 108 | —CH$_2$— | phen-1,3-diyl | bond | 2-Me-phenyl |
| 109 | —CH$_2$— | phen-1,3-diyl | bond | 3-Me-phenyl |
| 110 | —CH$_2$— | phen-1,3-diyl | bond | 4-Me-phenyl |
| 111 | —CH$_2$— | phen-1,3-diyl | bond | 2-MeO-phenyl |
| 112 | —CH$_2$— | phen-1,3-diyl | bond | 3-MeO-phenyl |
| 113 | —CH$_2$— | phen-1,3-diyl | bond | 4-MeO-phenyl |
| 114 | —CH$_2$— | phen-1,3-diyl | bond | 2-MeS-phenyl |
| 115 | —CH$_2$— | phen-1,3-diyl | bond | 3-MeS-phenyl |
| 116 | —CH$_2$— | phen-1,3-diyl | bond | 4-MeS-phenyl |
| 117 | —CH$_2$— | phen-1,3-diyl | bond | 2-F$_3$C-phenyl |
| 118 | —CH$_2$— | phen-1,3-diyl | bond | 3-F$_3$C-phenyl |
| 119 | —CH$_2$— | phen-1,3-diyl | bond | 4-F$_3$C-phenyl |
| 120 | —CH$_2$— | phen-1,3-diyl | bond | 2,3-diF-phenyl |
| 121 | —CH$_2$— | phen-1,3-diyl | bond | 2,4-diF-phenyl |
| 122 | —CH$_2$— | phen-1,3-diyl | bond | 2,5-diF-phenyl |
| 123 | —CH$_2$— | phen-1,3-diyl | bond | 2,6-diF-phenyl |
| 124 | —CH$_2$— | phen-1,3-diyl | bond | 3,4-diF-phenyl |
| 125 | —CH$_2$— | phen-1,3-diyl | bond | 3,5-diF-phenyl |
| 126 | —CH$_2$— | phen-1,3-diyl | bond | 2,3-diCl-phenyl |
| 127 | —CH$_2$— | phen-1,3-diyl | bond | 2,4-diCl-phenyl |
| 128 | —CH$_2$— | phen-1,3-diyl | bond | 2,5-diCl-phenyl |
| 129 | —CH$_2$— | phen-1,3-diyl | bond | 2,6-diCl-phenyl |
| 130 | —CH$_2$— | phen-1,3-diyl | bond | 3,4-diCl-phenyl |
| 131 | —CH$_2$— | phen-1,3-diyl | bond | 3,5-diCl-phenyl |
| 132 | —CH$_2$— | phen-1,3-diyl | bond | 2-Cl-3-F-phenyl |
| 133 | —CH$_2$— | phen-1,3-diyl | bond | 2-Cl-4-F-phenyl |
| 134 | —CH$_2$— | phen-1,3-diyl | bond | 2-Cl-5-F-phenyl |
| 135 | —CH$_2$— | phen-1,3-diyl | bond | 3-Cl-4-F-phenyl |
| 136 | —CH$_2$— | phen-1,3-diyl | bond | 3-Cl-5-F-phenyl |
| 137 | —CH$_2$— | phen-1,3-diyl | bond | 4-Cl-2-F-phenyl |
| 138 | —CH$_2$— | phen-1,3-diyl | bond | 4-Cl-3-F-phenyl |
| 139 | —CH$_2$— | phen-1,3-diyl | bond | 2,3-diMeO-phenyl |
| 140 | —CH$_2$— | phen-1,3-diyl | bond | 2,4-diMeO-phenyl |
| 141 | —CH$_2$— | phen-1,3-diyl | bond | 2,5-diMeO-phenyl |
| 142 | —CH$_2$— | phen-1,3-diyl | bond | 2,6-diMeO-phenyl |
| 143 | —CH$_2$— | phen-1,3-diyl | bond | 3,4-diMeO-phenyl |
| 144 | —CH$_2$— | phen-1,3-diyl | bond | 3,5-diMeO-phenyl |
| 145 | —CH$_2$— | phen-1,3-diyl | bond | cyclopropyl |
| 146 | —CH$_2$— | phen-1,3-diyl | bond | cyclobutyl |
| 147 | —CH$_2$— | phen-1,3-diyl | bond | cyclopentyl |
| 148 | —CH$_2$— | phen-1,3-diyl | bond | cyclohexyl |
| 149 | —CH$_2$— | phen-1,3-diyl | bond | 2-furanyl |
| 150 | —CH$_2$— | phen-1,3-diyl | bond | 2-thienyl |
| 151 | —CH$_2$— | phen-1,3-diyl | bond | 2-imidazolyl |
| 152 | —CH$_2$— | phen-1,3-diyl | bond | 2-pyridyl |
| 153 | —CH$_2$— | phen-1,3-diyl | bond | 3-pyridyl |
| 154 | —CH$_2$— | phen-1,3-diyl | bond | 4-pyridyl |
| 155 | —CH$_2$— | phen-1,3-diyl | bond | N-morpholinyl |
| 156 | —CH$_2$— | phen-1,3-diyl | bond | N-piperidinyl |

TABLE 1-continued

| | | | | |
|---|---|---|---|---|
| 157 | —CH$_2$— | phen-1,3-diyl | bond | 3-Me-2-pyridyl |
| 158 | —CH$_2$— | phen-1,3-diyl | bond | 4-Me-2-pyridyl |
| 159 | —CH$_2$— | phen-1,3-diyl | bond | 1-indolyl |
| 160 | —CH$_2$— | phen-1,3-diyl | bond | 2-benzothienyl |
| 161 | —CH$_2$— | phen-1,3-diyl | bond | 2-benzofuranyl |
| 162 | —CH$_2$— | phen-1,3-diyl | bond | 1-benzimidazole |
| 163 | —CH$_2$— | phen-1,3-diyl | bond | 2-naphthyl |
| 164 | —CH$_2$— | pyridin-3,5-diyl | bond | phenyl |
| 165 | —CH$_2$— | pyridin-3,5-diyl | bond | 3,3-diphenylmethyl |
| 166 | —CH$_2$— | pyridin-3,5-diyl | bond | 2-F-phenyl |
| 167 | —CH$_2$— | pyridin-3,5-diyl | bond | 3-F-phenyl |
| 168 | —CH$_2$— | pyridin-3,5-diyl | bond | 4-F-phenyl |
| 169 | —CH$_2$— | pyridin-3,5-diyl | bond | 2-Cl-phenyl |
| 170 | —CH$_2$— | pyridin-3,5-diyl | bond | 3-Cl-phenyl |
| 171 | —CH$_2$— | pyridin-3,5-diyl | bond | 4-Cl-phenyl |
| 172 | —CH$_2$— | pyridin-3,5-diyl | bond | 2-Me-phenyl |
| 173 | —CH$_2$— | pyridin-3,5-diyl | bond | 3-Me-phenyl |
| 174 | —CH$_2$— | pyridin-3,5-diyl | bond | 4-Me-phenyl |
| 175 | —CH$_2$— | pyridin-3,5-diyl | bond | 2-MeO-phenyl |
| 176 | —CH$_2$— | pyridin-3,5-diyl | bond | 3-MeO-phenyl |
| 177 | —CH$_2$— | pyridin-3,5-diyl | bond | 4-MeO-phenyl |
| 178 | —CH$_2$— | pyridin-3,5-diyl | bond | 2-MeS-phenyl |
| 179 | —CH$_2$— | pyridin-3,5-diyl | bond | 3-MeS-phenyl |
| 180 | —CH$_2$— | pyridin-3,5-diyl | bond | 4-MeS-phenyl |
| 181 | —CH$_2$— | pyridin-3,5-diyl | bond | 2-F$_3$C-phenyl |
| 182 | —CH$_2$— | pyridin-3,5-diyl | bond | 3-F$_3$C-phenyl |
| 183 | —CH$_2$— | pyridin-3,5-diyl | bond | 4-F$_3$C-phenyl |
| 184 | —CH$_2$— | pyridin-3,5-diyl | bond | 2,3-diF-phenyl |
| 185 | —CH$_2$— | pyridin-3,5-diyl | bond | 2,4-diF-phenyl |
| 186 | —CH$_2$— | pyridin-3,5-diyl | bond | 2,5-diF-phenyl |
| 187 | —CH$_2$— | pyridin-3,5-diyl | bond | 2,6-diF-phenyl |
| 188 | —CH$_2$— | pyridin-3,5-diyl | bond | 3,4-diF-phenyl |
| 189 | —CH$_2$— | pyridin-3,5-diyl | bond | 3,5-diF-phenyl |
| 190 | —CH$_2$— | pyridin-3,5-diyl | bond | 2,3-diCl-phenyl |
| 191 | —CH$_2$— | pyridin-3,5-diyl | bond | 2,4-diCl-phenyl |
| 192 | —CH$_2$— | pyridin-3,5-diyl | bond | 2,5-diCl-phenyl |
| 193 | —CH$_2$— | pyridin-3,5-diyl | bond | 2,6-diCl-phenyl |
| 194 | —CH$_2$— | pyridin-3,5-diyl | bond | 3,4-diCl-phenyl |
| 195 | —CH$_2$— | pyridin-3,5-diyl | bond | 3,5-diCl-phenyl |
| 196 | —CH$_2$— | pyridin-3,5-diyl | bond | 2-Cl-3-F-phenyl |
| 197 | —CH$_2$— | pyridin-3,5-diyl | bond | 2-Cl-4-F-phenyl |
| 198 | —CH$_2$— | pyridin-3,5-diyl | bond | 2-Cl-5-F-phenyl |
| 199 | —CH$_2$— | pyridin-3,5-diyl | bond | 3-Cl-4-F-phenyl |
| 200 | —CH$_2$— | pyridin-3,5-diyl | bond | 3-Cl-5-F-phenyl |
| 201 | —CH$_2$— | pyridin-3,5-diyl | bond | 4-Cl-2-F-phenyl |
| 202 | —CH$_2$— | pyridin-3,5-diyl | bond | 4-Cl-3-F-phenyl |
| 203 | —CH$_2$— | pyridin-3,5-diyl | bond | 2,3-diMeO-phenyl |
| 204 | —CH$_2$— | pyridin-3,5-diyl | bond | 2,4-diMeO-phenyl |
| 205 | —CH$_2$— | pyridin-3,5-diyl | bond | 2,5-diMeO-phenyl |
| 206 | —CH$_2$— | pyridin-3,5-diyl | bond | 2,6-diMeO-phenyl |
| 207 | —CH$_2$— | pyridin-3,5-diyl | bond | 3,4-diMeO-phenyl |
| 208 | —CH$_2$— | pyridin-3,5-diyl | bond | 3,5-diMeO-phenyl |
| 209 | —CH$_2$— | pyridin-3,5-diyl | bond | cyclopropyl |
| 210 | —CH$_2$— | pyridin-3,5-diyl | bond | cyclobutyl |
| 211 | —CH$_2$— | pyridin-3,5-diyl | bond | cyclopentyl |
| 212 | —CH$_2$— | pyridin-3,5-diyl | bond | cyclohexyl |
| 213 | —CH$_2$— | pyridin-3,5-diyl | bond | 2-furanyl |
| 214 | —CH$_2$— | pyridin-3,5-diyl | bond | 2-thienyl |
| 215 | —CH$_2$— | pyridin-3,5-diyl | bond | 2-imidazolyl |
| 216 | —CH$_2$— | pyridin-3,5-diyl | bond | 2-pyridyl |
| 217 | —CH$_2$— | pyridin-3,5-diyl | bond | 3-pyridyl |
| 218 | —CH$_2$— | pyridin-3,5-diyl | bond | 4-pyridyl |
| 219 | —CH$_2$— | pyridin-3,5-diyl | bond | N-morpholinyl |
| 220 | —CH$_2$— | pyridin-3,5-diyl | bond | N-piperidinyl |
| 221 | —CH$_2$— | pyridin-3,5-diyl | bond | 3-Me-2-pyridyl |
| 222 | —CH$_2$— | pyridin-3,5-diyl | bond | 4-Me-2-pyridyl |
| 223 | —CH$_2$— | pyridin-3,5-diyl | bond | 1-indolyl |
| 224 | —CH$_2$— | pyridin-3,5-diyl | bond | 2-benzothienyl |
| 225 | —CH$_2$— | pyridin-3,5-diyl | bond | 2-benzofuranyl |
| 226 | —CH$_2$— | pyridin-3,5-diyl | bond | 1-benzimidazole |
| 227 | —CH$_2$— | pyridin-3,5-diyl | bond | 2-naphthyl |
| 228 | —CH$_2$— | pyridin-2,6-diyl | bond | phenyl |
| 229 | —CH$_2$— | pyridin-2,6-diyl | bond | 3,3-diphenylmethyl |
| 230 | —CH$_2$— | pyridin-2,6-diyl | bond | 2-F-phenyl |
| 231 | —CH$_2$— | pyridin-2,6-diyl | bond | 3-F-phenyl |
| 232 | —CH$_2$— | pyridin-2,6-diyl | bond | 4-F-phenyl |
| 233 | —CH$_2$— | pyridin-2,6-diyl | bond | 2-Cl-phenyl |
| 234 | —CH$_2$— | pyridin-2,6-diyl | bond | 3-Cl-phenyl |
| 235 | —CH$_2$— | pyridin-2,6-diyl | bond | 4-Cl-phenyl |

TABLE 1-continued

| | | | | |
|---|---|---|---|---|
| 236 | —CH₂— | pyridin-2,6-diyl | bond | 2-Me-phenyl |
| 237 | —CH₂— | pyridin-2,6-diyl | bond | 3-Me-phenyl |
| 238 | —CH₂— | pyridin-2,6-diyl | bond | 4-Me-phenyl |
| 239 | —CH₂— | pyridin-2,6-diyl | bond | 2-MeO-phenyl |
| 240 | —CH₂— | pyridin-2,6-diyl | bond | 3-MeO-phenyl |
| 241 | —CH₂— | pyridin-2,6-diyl | bond | 4-MeO-phenyl |
| 242 | —CH₂— | pyridin-2,6-diyl | bond | 2-MeS-phenyl |
| 243 | —CH₂— | pyridin-2,6-diyl | bond | 3-MeS-phenyl |
| 244 | —CH₂— | pyridin-2,6-diyl | bond | 4-MeS-phenyl |
| 245 | —CH₂— | pyridin-2,6-diyl | bond | 2-F₃C-phenyl |
| 246 | —CH₂— | pyridin-2,6-diyl | bond | 3-F₃C-phenyl |
| 247 | —CH₂— | pyridin-2,6-diyl | bond | 4-F₃C-phenyl |
| 248 | —CH₂— | pyridin-2,6-diyl | bond | 2,3-diF-phenyl |
| 249 | —CH₂— | pyridin-2,6-diyl | bond | 2,4-diF-phenyl |
| 250 | —CH₂— | pyridin-2,6-diyl | bond | 2,5-diF-phenyl |
| 251 | —CH₂— | pyridin-2,6-diyl | bond | 2,6-diF-phenyl |
| 252 | —CH₂— | pyridin-2,6-diyl | bond | 3,4-diF-phenyl |
| 253 | —CH₂— | pyridin-2,6-diyl | bond | 3,5-diF-phenyl |
| 254 | —CH₂— | pyridin-2,6-diyl | bond | 2,3-diCl-phenyl |
| 255 | —CH₂— | pyridin-2,6-diyl | bond | 2,4-diCl-phenyl |
| 256 | —CH₂— | pyridin-2,6-diyl | bond | 2,5-diCl-phenyl |
| 257 | —CH₂— | pyridin-2,6-diyl | bond | 2,6-diCl-phenyl |
| 258 | —CH₂— | pyridin-2,6-diyl | bond | 3,4-diCl-phenyl |
| 259 | —CH₂— | pyridin-2,6-diyl | bond | 3,5-diCl-phenyl |
| 260 | —CH₂— | pyridin-2,6-diyl | bond | 2-Cl-3-F-phenyl |
| 261 | —CH₂— | pyridin-2,6-diyl | bond | 2-Cl-4-F-phenyl |
| 262 | —CH₂— | pyridin-2,6-diyl | bond | 2-Cl-5-F-phenyl |
| 263 | —CH₂— | pyridin-2,6-diyl | bond | 3-Cl-4-F-phenyl |
| 264 | —CH₂— | pyridin-2,6-diyl | bond | 3-Cl-5-F-phenyl |
| 265 | —CH₂— | pyridin-2,6-diyl | bond | 4-Cl-2-F-phenyl |
| 266 | —CH₂— | pyridin-2,6-diyl | bond | 4-Cl-3-F-phenyl |
| 267 | —CH₂— | pyridin-2,6-diyl | bond | 2,3-diMeO-phenyl |
| 268 | —CH₂— | pyridin-2,6-diyl | bond | 2,4-diMeO-phenyl |
| 269 | —CH₂— | pyridin-2,6-diyl | bond | 2,5-diMeO-phenyl |
| 270 | —CH₂— | pyridin-2,6-diyl | bond | 2,6-diMeO-phenyl |
| 271 | —CH₂— | pyridin-2,6-diyl | bond | 3,4-diMeO-phenyl |
| 272 | —CH₂— | pyridin-2,6-diyl | bond | 3,5-diMeO-phenyl |
| 273 | —CH₂— | pyridin-2,6-diyl | bond | cyclopropyl |
| 274 | —CH₂— | pyridin-2,6-diyl | bond | cyclobutyl |
| 275 | —CH₂— | pyridin-2,6-diyl | bond | cyclopentyl |
| 276 | —CH₂— | pyridin-2,6-diyl | bond | cyclohexyl |
| 277 | —CH₂— | pyridin-2,6-diyl | bond | 2-furanyl |
| 278 | —CH₂— | pyridin-2,6-diyl | bond | 2-thienyl |
| 279 | —CH₂— | pyridin-2,6-diyl | bond | 2-imidazolyl |
| 280 | —CH₂— | pyridin-2,6-diyl | bond | 2-pyridyl |
| 281 | —CH₂— | pyridin-2,6-diyl | bond | 3-pyridyl |
| 282 | —CH₂— | pyridin-2,6-diyl | bond | 4-pyridyl |
| 283 | —CH₂— | pyridin-2,6-diyl | bond | N-morpholinyl |
| 284 | —CH₂— | pyridin-2,6-diyl | bond | N-piperidinyl |
| 285 | —CH₂— | pyridin-2,6-diyl | bond | 3-Me-2-pyridyl |
| 286 | —CH₂— | pyridin-2,6-diyl | bond | 4-Me-2-pyridyl |
| 287 | —CH₂— | pyridin-2,6-diyl | bond | 1-indolyl |
| 288 | —CH₂— | pyridin-2,6-diyl | bond | 2-benzothienyl |
| 289 | —CH₂— | pyridin-2,6-diyl | bond | 2-benzofuranyl |
| 290 | —CH₂— | pyridin-2,6-diyl | bond | 1-benzimidazole |
| 291 | —CH₂— | pyridin-2,6-diyl | bond | 2-naphthyl |
| 292 | —CH₂— | pyridin-2,4-diyl | bond | phenyl |
| 293 | —CH₂— | pyridin-2,4-diyl | bond | 3,3-diphenylmethyl |
| 294 | —CH₂— | pyridin-2,4-diyl | bond | 2-F-phenyl |
| 295 | —CH₂— | pyridin-2,4-diyl | bond | 3-F-phenyl |
| 296 | —CH₂— | pyridin-2,4-diyl | bond | 4-F-phenyl |
| 297 | —CH₂— | pyridin-2,4-diyl | bond | 2-Cl-phenyl |
| 298 | —CH₂— | pyridin-2,4-diyl | bond | 3-Cl-phenyl |
| 299 | —CH₂— | pyridin-2,4-diyl | bond | 4-Cl-phenyl |
| 300 | —CH₂— | pyridin-2,4-diyl | bond | 2-Me-phenyl |
| 301 | —CH₂— | pyridin-2,4-diyl | bond | 3-Me-phenyl |
| 302 | —CH₂— | pyridin-2,4-diyl | bond | 4-Me-phenyl |
| 303 | —CH₂— | pyridin-2,4-diyl | bond | 2-MeO-phenyl |
| 304 | —CH₂— | pyridin-2,4-diyl | bond | 3-MeO-phenyl |
| 305 | —CH₂— | pyridin-2,4-diyl | bond | 4-MeO-phenyl |
| 306 | —CH₂— | pyridin-2,4-diyl | bond | 2-MeS-phenyl |
| 307 | —CH₂— | pyridin-2,4-diyl | bond | 3-MeS-phenyl |
| 308 | —CH₂— | pyridin-2,4-diyl | bond | 4-MeS-phenyl |
| 309 | —CH₂— | pyridin-2,4-diyl | bond | 2-F₃C-phenyl |
| 310 | —CH₂— | pyridin-2,4-diyl | bond | 3-F₃C-phenyl |
| 311 | —CH₂— | pyridin-2,4-diyl | bond | 4-F₃C-phenyl |
| 312 | —CH₂— | pyridin-2,4-diyl | bond | 2,3-diF-phenyl |
| 313 | —CH₂— | pyridin-2,4-diyl | bond | 2,4-diF-phenyl |
| 314 | —CH₂— | pyridin-2,4-diyl | bond | 2,5-diF-phenyl |

TABLE 1-continued

| | | | | |
|---|---|---|---|---|
| 315 | —CH$_2$— | pyridin-2,4-diyl | bond | 2,6-diF-phenyl |
| 316 | —CH$_2$— | pyridin-2,4-diyl | bond | 3,4-diF-phenyl |
| 317 | —CH$_2$— | pyridin-2,4-diyl | bond | 3,5-diF-phenyl |
| 318 | —CH$_2$— | pyridin-2,4-diyl | bond | 2,3-diCl-phenyl |
| 319 | —CH$_2$— | pyridin-2,4-diyl | bond | 2,4-diCl-phenyl |
| 320 | —CH$_2$— | pyridin-2,4-diyl | bond | 2,5-diCl-phenyl |
| 321 | —CH$_2$— | pyridin-2,4-diyl | bond | 2,6-diCl-phenyl |
| 322 | —CH$_2$— | pyridin-2,4-diyl | bond | 3,4-diCl-phenyl |
| 323 | —CH$_2$— | pyridin-2,4-diyl | bond | 3,5-diCl-phenyl |
| 324 | —CH$_2$— | pyridin-2,4-diyl | bond | 2-Cl-3-F-phenyl |
| 325 | —CH$_2$— | pyridin-2,4-diyl | bond | 2-Cl-4-F-phenyl |
| 326 | —CH$_2$— | pyridin-2,4-diyl | bond | 2-Cl-5-F-phenyl |
| 327 | —CH$_2$— | pyridin-2,4-diyl | bond | 3-Cl-4-F-phenyl |
| 328 | —CH$_2$— | pyridin-2,4-diyl | bond | 3-Cl-5-F-phenyl |
| 329 | —CH$_2$— | pyridin-2,4-diyl | bond | 4-Cl-2-F-phenyl |
| 330 | —CH$_2$— | pyridin-2,4-diyl | bond | 4-Cl-3-F-phenyl |
| 331 | —CH$_2$— | pyridin-2,4-diyl | bond | 2,3-diMeO-phenyl |
| 332 | —CH$_2$— | pyridin-2,4-diyl | bond | 2,4-diMeO-phenyl |
| 333 | —CH$_2$— | pyridin-2,4-diyl | bond | 2,5-diMeO-phenyl |
| 334 | —CH$_2$— | pyridin-2,4-diyl | bond | 2,6-diMeO-phenyl |
| 335 | —CH$_2$— | pyridin-2,4-diyl | bond | 3,4-diMeO-phenyl |
| 336 | —CH$_2$— | pyridin-2,4-diyl | bond | 3,5-diMeO-phenyl |
| 337 | —CH$_2$— | pyridin-2,4-diyl | bond | cyclopropyl |
| 338 | —CH$_2$— | pyridin-2,4-diyl | bond | cyclobutyl |
| 339 | —CH$_2$— | pyridin-2,4-diyl | bond | cyclopentyl |
| 340 | —CH$_2$— | pyridin-2,4-diyl | bond | cyclohexyl |
| 341 | —CH$_2$— | pyridin-2,4-diyl | bond | 2-furanyl |
| 342 | —CH$_2$— | pyridin-2,4-diyl | bond | 2-thienyl |
| 343 | —CH$_2$— | pyridin-2,4-diyl | bond | 2-imidazolyl |
| 344 | —CH$_2$— | pyridin-2,4-diyl | bond | 2-pyridyl |
| 345 | —CH$_2$— | pyridin-2,4-diyl | bond | 3-pyridyl |
| 346 | —CH$_2$— | pyridin-2,4-diyl | bond | 4-pyridyl |
| 347 | —CH$_2$— | pyridin-2,4-diyl | bond | N-morpholinyl |
| 348 | —CH$_2$— | pyridin-2,4-diyl | bond | N-piperidinyl |
| 349 | —CH$_2$— | pyridin-2,4-diyl | bond | 3-Me-2-pyridyl |
| 350 | —CH$_2$— | pyridin-2,4-diyl | bond | 4-Me-2-pyridyl |
| 351 | —CH$_2$— | pyridin-2,4-diyl | bond | 1-indolyl |
| 352 | —CH$_2$— | pyridin-2,4-diyl | bond | 2-benzothienyl |
| 353 | —CH$_2$— | pyridin-2,4-diyl | bond | 2-benzofuranyl |
| 354 | —CH$_2$— | pyridin-2,4-diyl | bond | 1-benzimidazole |
| 355 | —CH$_2$— | pyridin-2,4-diyl | bond | 2-naphthyl |
| 356 | —CH$_2$— | pyridin-4,2-diyl | bond | phenyl |
| 357 | —CH$_2$— | pyridin-4,2-diyl | bond | 3,3-diphenylmethyl |
| 358 | —CH$_2$— | pyridin-4,2-diyl | bond | 2-F-phenyl |
| 359 | —CH$_2$— | pyridin-4,2-diyl | bond | 3-F-phenyl |
| 360 | —CH$_2$— | pyridin-4,2-diyl | bond | 4-F-phenyl |
| 361 | —CH$_2$— | pyridin-4,2-diyl | bond | 2-Cl-phenyl |
| 362 | —CH$_2$— | pyridin-4,2-diyl | bond | 3-Cl-phenyl |
| 363 | —CH$_2$— | pyridin-4,2-diyl | bond | 4-Cl-phenyl |
| 364 | —CH$_2$— | pyridin-4,2-diyl | bond | 2-Me-phenyl |
| 365 | —CH$_2$— | pyridin-4,2-diyl | bond | 3-Me-phenyl |
| 366 | —CH$_2$— | pyridin-4,2-diyl | bond | 4-Me-phenyl |
| 367 | —CH$_2$— | pyridin-4,2-diyl | bond | 2-MeO-phenyl |
| 368 | —CH$_2$— | pyridin-4,2-diyl | bond | 3-MeO-phenyl |
| 369 | —CH$_2$— | pyridin-4,2-diyl | bond | 4-MeO-phenyl |
| 370 | —CH$_2$— | pyridin-4,2-diyl | bond | 2-MeS-phenyl |
| 371 | —CH$_2$— | pyridin-4,2-diyl | bond | 3-MeS-phenyl |
| 372 | —CH$_2$— | pyridin-4,2-diyl | bond | 4-MeS-phenyl |
| 373 | —CH$_2$— | pyridin-4,2-diyl | bond | 2-F$_3$C-phenyl |
| 374 | —CH$_2$— | pyridin-4,2-diyl | bond | 3-F$_3$C-phenyl |
| 375 | —CH$_2$— | pyridin-4,2-diyl | bond | 4-F$_3$C-phenyl |
| 376 | —CH$_2$— | pyridin-4,2-diyl | bond | 2,3-diF-phenyl |
| 377 | —CH$_2$— | pyridin-4,2-diyl | bond | 2,4-diF-phenyl |
| 378 | —CH$_2$— | pyridin-4,2-diyl | bond | 2,5-diF-phenyl |
| 379 | —CH$_2$— | pyridin-4,2-diyl | bond | 2,6-diF-phenyl |
| 380 | —CH$_2$— | pyridin-4,2-diyl | bond | 3,4-diF-phenyl |
| 381 | —CH$_2$— | pyridin-4,2-diyl | bond | 3,5-diF-phenyl |
| 382 | —CH$_2$— | pyridin-4,2-diyl | bond | 2,3-diCl-phenyl |
| 383 | —CH$_2$— | pyridin-4,2-diyl | bond | 2,4-diCl-phenyl |
| 384 | —CH$_2$— | pyridin-4,2-diyl | bond | 2,5-diCl-phenyl |
| 385 | —CH$_2$— | pyridin-4,2-diyl | bond | 2,6-diCl-phenyl |
| 386 | —CH$_2$— | pyridin-4,2-diyl | bond | 3,4-diCl-phenyl |
| 387 | —CH$_2$— | pyridin-4,2-diyl | bond | 3,5-diCl-phenyl |
| 388 | —CH$_2$— | pyridin-4,2-diyl | bond | 2-Cl-3-F-phenyl |
| 389 | —CH$_2$— | pyridin-4,2-diyl | bond | 2-Cl-4-F-phenyl |
| 390 | —CH$_2$— | pyridin-4,2-diyl | bond | 2-Cl-5-F-phenyl |
| 391 | —CH$_2$— | pyridin-4,2-diyl | bond | 3-Cl-4-F-phenyl |
| 392 | —CH$_2$— | pyridin-4,2-diyl | bond | 3-Cl-5-F-phenyl |
| 393 | —CH$_2$— | pyridin-4,2-diyl | bond | 4-Cl-2-F-phenyl |

TABLE 1-continued

| | | | | |
|---|---|---|---|---|
| 394 | —CH₂— | pyridin-4,2-diyl | bond | 4-Cl-3-F-phenyl |
| 395 | —CH₂— | pyridin-4,2-diyl | bond | 2,3-diMeO-phenyl |
| 396 | —CH₂— | pyridin-4,2-diyl | bond | 2,4-diMeO-phenyl |
| 397 | —CH₂— | pyridin-4,2-diyl | bond | 2,5-diMeO-phenyl |
| 398 | —CH₂— | pyridin-4,2-diyl | bond | 2,6-diMeO-phenyl |
| 399 | —CH₂— | pyridin-4,2-diyl | bond | 3,4-diMeO-phenyl |
| 400 | —CH₂— | pyridin-4,2-diyl | bond | 3,5-diMeO-phenyl |
| 401 | —CH₂— | pyridin-4,2-diyl | bond | cyclopropyl |
| 402 | —CH₂— | pyridin-4,2-diyl | bond | cyclobutyl |
| 403 | —CH₂— | pyridin-4,2-diyl | bond | cyclopentyl |
| 404 | —CH₂— | pyridin-4,2-diyl | bond | cyclohexyl |
| 405 | —CH₂— | pyridin-4,2-diyl | bond | 2-furanyl |
| 406 | —CH₂— | pyridin-4,2-diyl | bond | 2-thienyl |
| 407 | —CH₂— | pyridin-4,2-diyl | bond | 2-imidazolyl |
| 408 | —CH₂— | pyridin-4,2-diyl | bond | 2-pyridyl |
| 409 | —CH₂— | pyridin-4,2-diyl | bond | 3-pyridyl |
| 410 | —CH₂— | pyridin-4,2-diyl | bond | 4-pyridyl |
| 411 | —CH₂— | pyridin-4,2-diyl | bond | N-morpholinyl |
| 412 | —CH₂— | pyridin-4,2-diyl | bond | N-piperidinyl |
| 413 | —CH₂— | pyridin-4,2-diyl | bond | 3-Me-2-pyridyl |
| 414 | —CH₂— | pyridin-4,2-diyl | bond | 4-Me-2-pyridyl |
| 415 | —CH₂— | pyridin-4,2-diyl | bond | 1-indolyl |
| 416 | —CH₂— | pyridin-4,2-diyl | bond | 2-benzothienyl |
| 417 | —CH₂— | pyridin-4,2-diyl | bond | 2-benzofuranyl |
| 418 | —CH₂— | pyridin-4,2-diyl | bond | 1-benzimidazole |
| 419 | —CH₂— | pyridin-4,2-diyl | bond | 2-naphthyl |
| 420 | —CH₂— | piperidin-1,3-diyl | bond | phenyl |
| 421 | —CH₂— | piperidin-1,3-diyl | bond | 3,3-diphenylmethyl |
| 422 | —CH₂— | piperidin-1,3-diyl | bond | 2-F-phenyl |
| 423 | —CH₂— | piperidin-1,3-diyl | bond | 3-F-phenyl |
| 424 | —CH₂— | piperidin-1,3-diyl | bond | 4-F-phenyl |
| 425 | —CH₂— | piperidin-1,3-diyl | bond | 2-Cl-phenyl |
| 426 | —CH₂— | piperidin-1,3-diyl | bond | 3-Cl-phenyl |
| 427 | —CH₂— | piperidin-1,3-diyl | bond | 4-Cl-phenyl |
| 428 | —CH₂— | piperidin-1,3-diyl | bond | 2-Me-phenyl |
| 429 | —CH₂— | piperidin-1,3-diyl | bond | 3-Me-phenyl |
| 430 | —CH₂— | piperidin-1,3-diyl | bond | 4-Me-phenyl |
| 431 | —CH₂— | piperidin-1,3-diyl | bond | 2-MeO-phenyl |
| 432 | —CH₂— | piperidin-1,3-diyl | bond | 3-MeO-phenyl |
| 433 | —CH₂— | piperidin-1,3-diyl | bond | 4-MeO-phenyl |
| 434 | —CH₂— | piperidin-1,3-diyl | bond | 2-MeS-phenyl |
| 435 | —CH₂— | piperidin-1,3-diyl | bond | 3-MeS-phenyl |
| 436 | —CH₂— | piperidin-1,3-diyl | bond | 4-MeS-phenyl |
| 437 | —CH₂— | piperidin-1,3-diyl | bond | 2-F₃C-phenyl |
| 438 | —CH₂— | piperidin-1,3-diyl | bond | 3-F₃C-phenyl |
| 439 | —CH₂— | piperidin-1,3-diyl | bond | 4-F₃C-phenyl |
| 440 | —CH₂— | piperidin-1,3-diyl | bond | 2,3-diF-phenyl |
| 441 | —CH₂— | piperidin-1,3-diyl | bond | 2,4-diF-phenyl |
| 442 | —CH₂— | piperidin-1,3-diyl | bond | 2,5-diF-phenyl |
| 443 | —CH₂— | piperidin-1,3-diyl | bond | 2,6-diF-phenyl |
| 444 | —CH₂— | piperidin-1,3-diyl | bond | 3,4-diF-phenyl |
| 445 | —CH₂— | piperidin-1,3-diyl | bond | 3,5-diF-phenyl |
| 446 | —CH₂— | piperidin-1,3-diyl | bond | 2,3-diCl-phenyl |
| 447 | —CH₂— | piperidin-1,3-diyl | bond | 2,4-diCl-phenyl |
| 448 | —CH₂— | piperidin-1,3-diyl | bond | 2,5-diCl-phenyl |
| 449 | —CH₂— | piperidin-1,3-diyl | bond | 2,6-diCl-phenyl |
| 450 | —CH₂— | piperidin-1,3-diyl | bond | 3,4-diCl-phenyl |
| 451 | —CH₂— | piperidin-1,3-diyl | bond | 3,5-diCl-phenyl |
| 452 | —CH₂— | piperidin-1,3-diyl | bond | 2-Cl-3-F-phenyl |
| 453 | —CH₂— | piperidin-1,3-diyl | bond | 2-Cl-4-F-phenyl |
| 454 | —CH₂— | piperidin-1,3-diyl | bond | 2-Cl-5-F-phenyl |
| 455 | —CH₂— | piperidin-1,3-diyl | bond | 3-Cl-4-F-phenyl |
| 456 | —CH₂— | piperidin-1,3-diyl | bond | 3-Cl-5-F-phenyl |
| 457 | —CH₂— | piperidin-1,3-diyl | bond | 4-Cl-2-F-phenyl |
| 458 | —CH₂— | piperidin-1,3-diyl | bond | 4-Cl-3-F-phenyl |
| 459 | —CH₂— | piperidin-1,3-diyl | bond | 2,3-diMeO-phenyl |
| 460 | —CH₂— | piperidin-1,3-diyl | bond | 2,4-diMeO-phenyl |
| 461 | —CH₂— | piperidin-1,3-diyl | bond | 2,5-diMeO-phenyl |
| 462 | —CH₂— | piperidin-1,3-diyl | bond | 2,6-diMeO-phenyl |
| 463 | —CH₂— | piperidin-1,3-diyl | bond | 3,4-diMeO-phenyl |
| 464 | —CH₂— | piperidin-1,3-diyl | bond | 3,5-diMeO-phenyl |
| 465 | —CH₂— | piperidin-1,3-diyl | bond | cyclopropyl |
| 466 | —CH₂— | piperidin-1,3-diyl | bond | cyclobutyl |
| 467 | —CH₂— | piperidin-1,3-diyl | bond | cyclopentyl |
| 468 | —CH₂— | piperidin-1,3-diyl | bond | cyclohexyl |
| 469 | —CH₂— | piperidin-1,3-diyl | bond | 2-furanyl |
| 470 | —CH₂— | piperidin-1,3-diyl | bond | 2-thienyl |
| 471 | —CH₂— | piperidin-1,3-diyl | bond | 2-imidazolyl |
| 472 | —CH₂— | piperidin-1,3-diyl | bond | 2-pyridyl |

TABLE 1-continued

| | | | | |
|---|---|---|---|---|
| 473 | —CH$_2$— | piperidin-1,3-diyl | bond | 3-pyridyl |
| 474 | —CH$_2$— | piperidin-1,3-diyl | bond | 4-pyridyl |
| 475 | —CH$_2$— | piperidin-1,3-diyl | bond | N-morpholinyl |
| 476 | —CH$_2$— | piperidin-1,3-diyl | bond | N-piperidinyl |
| 477 | —CH$_2$— | piperidin-1,3-diyl | bond | 3-Me-2-pyridyl |
| 478 | —CH$_2$— | piperidin-1,3-diyl | bond | 4-Me-2-pyridyl |
| 479 | —CH$_2$— | piperidin-1,3-diyl | bond | 1-indolyl |
| 480 | —CH$_2$— | piperidin-1,3-diyl | bond | 2-benzothienyl |
| 481 | —CH$_2$— | piperidin-1,3-diyl | bond | 2-benzofuranyl |
| 482 | —CH$_2$— | piperidin-1,3-diyl | bond | 1-benzimidazole |
| 483 | —CH$_2$— | piperidin-1,3-diyl | bond | 2-naphthyl |
| 484 | —CH$_2$— | piperidin-3,1-diyl | bond | phenyl |
| 485 | —CH$_2$— | piperidin-3,1-diyl | bond | 3,3-diphenylmethyl |
| 486 | —CH$_2$— | piperidin-3,1-diyl | bond | 2-F-phenyl |
| 487 | —CH$_2$— | piperidin-3,1-diyl | bond | 3-F-phenyl |
| 488 | —CH$_2$— | piperidin-3,1-diyl | bond | 4-F-phenyl |
| 489 | —CH$_2$— | piperidin-3,1-diyl | bond | 2-Cl-phenyl |
| 490 | —CH$_2$— | piperidin-3,1-diyl | bond | 3-Cl-phenyl |
| 491 | —CH$_2$— | piperidin-3,1-diyl | bond | 4-Cl-phenyl |
| 492 | —CH$_2$— | piperidin-3,1-diyl | bond | 2-Me-phenyl |
| 493 | —CH$_2$— | piperidin-3,1-diyl | bond | 3-Me-phenyl |
| 494 | —CH$_2$— | piperidin-3,1-diyl | bond | 4-Me-phenyl |
| 495 | —CH$_2$— | piperidin-3,1-diyl | bond | 2-MeO-phenyl |
| 496 | —CH$_2$— | piperidin-3,1-diyl | bond | 3-MeO-phenyl |
| 497 | —CH$_2$— | piperidin-3,1-diyl | bond | 4-MeO-phenyl |
| 498 | —CH$_2$— | piperidin-3,1-diyl | bond | 2-MeS-phenyl |
| 499 | —CH$_2$— | piperidin-3,1-diyl | bond | 3-MeS-phenyl |
| 500 | —CH$_2$— | piperidin-3,1-diyl | bond | 4-MeS-phenyl |
| 501 | —CH$_2$— | piperidin-3,1-diyl | bond | 2-F$_3$C-phenyl |
| 502 | —CH$_2$— | piperidin-3,1-diyl | bond | 3-F$_3$C-phenyl |
| 503 | —CH$_2$— | piperidin-3,1-diyl | bond | 4-F$_3$C-phenyl |
| 504 | —CH$_2$— | piperidin-3,1-diyl | bond | 2,3-diF-phenyl |
| 505 | —CH$_2$— | piperidin-3,1-diyl | bond | 2,4-diF-phenyl |
| 506 | —CH$_2$— | piperidin-3,1-diyl | bond | 2,5-diF-phenyl |
| 507 | —CH$_2$— | piperidin-3,1-diyl | bond | 2,6-diF-phenyl |
| 508 | —CH$_2$— | piperidin-3,1-diyl | bond | 3,4-diF-phenyl |
| 509 | —CH$_2$— | piperidin-3,1-diyl | bond | 3,5-diF-phenyl |
| 510 | —CH$_2$— | piperidin-3,1-diyl | bond | 2,3-diCl-phenyl |
| 511 | —CH$_2$— | piperidin-3,1-diyl | bond | 2,4-diCl-phenyl |
| 512 | —CH$_2$— | piperidin-3,1-diyl | bond | 2,5-diCl-phenyl |
| 513 | —CH$_2$— | piperidin-3,1-diyl | bond | 2,6-diCl-phenyl |
| 514 | —CH$_2$— | piperidin-3,1-diyl | bond | 3,4-diCl-phenyl |
| 515 | —CH$_2$— | piperidin-3,1-diyl | bond | 3,5-diCl-phenyl |
| 516 | —CH$_2$— | piperidin-3,1-diyl | bond | 2-Cl-3-F-phenyl |
| 517 | —CH$_2$— | piperidin-3,1-diyl | bond | 2-Cl-4-F-phenyl |
| 518 | —CH$_2$— | piperidin-3,1-diyl | bond | 2-Cl-5-F-phenyl |
| 519 | —CH$_2$— | piperidin-3,1-diyl | bond | 3-Cl-4-F-phenyl |
| 520 | —CH$_2$— | piperidin-3,1-diyl | bond | 3-Cl-5-F-phenyl |
| 521 | —CH$_2$— | piperidin-3,1-diyl | bond | 4-Cl-2-F-phenyl |
| 522 | —CH$_2$— | piperidin-3,1-diyl | bond | 4-Cl-3-F-phenyl |
| 523 | —CH$_2$— | piperidin-3,1-diyl | bond | 2,3-diMeO-phenyl |
| 524 | —CH$_2$— | piperidin-3,1-diyl | bond | 2,4-diMeO-phenyl |
| 525 | —CH$_2$— | piperidin-3,1-diyl | bond | 2,5-diMeO-phenyl |
| 526 | —CH$_2$— | piperidin-3,1-diyl | bond | 2,6-diMeO-phenyl |
| 527 | —CH$_2$— | piperidin-3,1-diyl | bond | 3,4-diMeO-phenyl |
| 528 | —CH$_2$— | piperidin-3,1-diyl | bond | 3,5-diMeO-phenyl |
| 529 | —CH$_2$— | piperidin-3,1-diyl | bond | cyclopropyl |
| 530 | —CH$_2$— | piperidin-3,1-diyl | bond | cyclobutyl |
| 531 | —CH$_2$— | piperidin-3,1-diyl | bond | cyclopentyl |
| 532 | —CH$_2$— | piperidin-3,1-diyl | bond | cyclohexyl |
| 533 | —CH$_2$— | piperidin-3,1-diyl | bond | 2-furanyl |
| 534 | —CH$_2$— | piperidin-3,1-diyl | bond | 2-thienyl |
| 535 | —CH$_2$— | piperidin-3,1-diyl | bond | 2-imidazolyl |
| 536 | —CH$_2$— | piperidin-3,1-diyl | bond | 2-pyridyl |
| 537 | —CH$_2$— | piperidin-3,1-diyl | bond | 3-pyridyl |
| 538 | —CH$_2$— | piperidin-3,1-diyl | bond | 4-pyridyl |
| 539 | —CH$_2$— | piperidin-3,1-diyl | bond | N-morpholinyl |
| 540 | —CH$_2$— | piperidin-3,1-diyl | bond | N-piperidinyl |
| 541 | —CH$_2$— | piperidin-3,1-diyl | bond | 3-Me-2-pyridyl |
| 542 | —CH$_2$— | piperidin-3,1-diyl | bond | 4-Me-2-pyridyl |
| 543 | —CH$_2$— | piperidin-3,1-diyl | bond | 1-indolyl |
| 544 | —CH$_2$— | piperidin-3,1-diyl | bond | 2-benzothienyl |
| 545 | —CH$_2$— | piperidin-3,1-diyl | bond | 2-benzofuranyl |
| 546 | —CH$_2$— | piperidin-3,1-diyl | bond | 1-benzimidazole |
| 547 | —CH$_2$— | piperidin-3,1-diyl | bond | 2-naphthyl |
| 548 | —CH$_2$— | cyclohex-1,3-diyl | bond | phenyl |
| 549 | —CH$_2$— | cyclohex-1,3-diyl | bond | 3,3-diphenylmethyl |
| 550 | —CH$_2$— | cyclohex-1,3-diyl | bond | 2-F-phenyl |
| 551 | —CH$_2$— | cyclohex-1,3-diyl | bond | 3-F-phenyl |

TABLE 1-continued

| | | | | |
|---|---|---|---|---|
| 552 | —CH$_2$— | cyclohex-1,3-diyl | bond | 4-F-phenyl |
| 553 | —CH$_2$— | cyclohex-1,3-diyl | bond | 2-Cl-phenyl |
| 554 | —CH$_2$— | cyclohex-1,3-diyl | bond | 3-Cl-phenyl |
| 555 | —CH$_2$— | cyclohex-1,3-diyl | bond | 4-Cl-phenyl |
| 556 | —CH$_2$— | cyclohex-1,3-diyl | bond | 2-Me-phenyl |
| 557 | —CH$_2$— | cyclohex-1,3-diyl | bond | 3-Me-phenyl |
| 558 | —CH$_2$— | cyclohex-1,3-diyl | bond | 4-Me-phenyl |
| 559 | —CH$_2$— | cyclohex-1,3-diyl | bond | 2-MeO-phenyl |
| 560 | —CH$_2$— | cyclohex-1,3-diyl | bond | 3-MeO-phenyl |
| 561 | —CH$_2$— | cyclohex-1,3-diyl | bond | 4-MeO-phenyl |
| 562 | —CH$_2$— | cyclohex-1,3-diyl | bond | 2-MeS-phenyl |
| 563 | —CH$_2$— | cyclohex-1,3-diyl | bond | 3-MeS-phenyl |
| 564 | —CH$_2$— | cyclohex-1,3-diyl | bond | 4-MeS-phenyl |
| 565 | —CH$_2$— | cyclohex-1,3-diyl | bond | 2-F$_3$C-phenyl |
| 566 | —CH$_2$— | cyclohex-1,3-diyl | bond | 3-F$_3$C-phenyl |
| 567 | —CH$_2$— | cyclohex-1,3-diyl | bond | 4-F$_3$C-phenyl |
| 568 | —CH$_2$— | cyclohex-1,3-diyl | bond | 2,3-diF-phenyl |
| 569 | —CH$_2$— | cyclohex-1,3-diyl | bond | 2,4-diF-phenyl |
| 570 | —CH$_2$— | cyclohex-1,3-diyl | bond | 2,5-diF-phenyl |
| 571 | —CH$_2$— | cyclohex-1,3-diyl | bond | 2,6-diF-phenyl |
| 572 | —CH$_2$— | cyclohex-1,3-diyl | bond | 3,4-diF-phenyl |
| 573 | —CH$_2$— | cyclohex-1,3-diyl | bond | 3,5-diF-phenyl |
| 574 | —CH$_2$— | cyclohex-1,3-diyl | bond | 2,3-diCl-phenyl |
| 575 | —CH$_2$— | cyclohex-1,3-diyl | bond | 2,4-diCl-phenyl |
| 576 | —CH$_2$— | cyclohex-1,3-diyl | bond | 2,5-diCl-phenyl |
| 577 | —CH$_2$— | cyclohex-1,3-diyl | bond | 2,6-diCl-phenyl |
| 578 | —CH$_2$— | cyclohex-1,3-diyl | bond | 3,4-diCl-phenyl |
| 579 | —CH$_2$— | cyclohex-1,3-diyl | bond | 3,5-diCl-phenyl |
| 580 | —CH$_2$— | cyclohex-1,3-diyl | bond | 2-Cl-3-F-phenyl |
| 581 | —CH$_2$— | cyclohex-1,3-diyl | bond | 2-Cl-4-F-phenyl |
| 582 | —CH$_2$— | cyclohex-1,3-diyl | bond | 2-Cl-5-F-phenyl |
| 583 | —CH$_2$— | cyclohex-1,3-diyl | bond | 3-Cl-4-F-phenyl |
| 584 | —CH$_2$— | cyclohex-1,3-diyl | bond | 3-Cl-5-F-phenyl |
| 585 | —CH$_2$— | cyclohex-1,3-diyl | bond | 4-Cl-2-F-phenyl |
| 586 | —CH$_2$— | cyclohex-1,3-diyl | bond | 4-Cl-3-F-phenyl |
| 587 | —CH$_2$— | cyclohex-1,3-diyl | bond | 2,3-diMeO-phenyl |
| 588 | —CH$_2$— | cyclohex-1,3-diyl | bond | 2,4-diMeO-phenyl |
| 589 | —CH$_2$— | cyclohex-1,3-diyl | bond | 2,5-diMeO-phenyl |
| 590 | —CH$_2$— | cyclohex-1,3-diyl | bond | 2,6-diMeO-phenyl |
| 591 | —CH$_2$— | cyclohex-1,3-diyl | bond | 3,4-diMeO-phenyl |
| 592 | —CH$_2$— | cyclohex-1,3-diyl | bond | 3,5-diMeO-phenyl |
| 593 | —CH$_2$— | cyclohex-1,3-diyl | bond | cyclopropyl |
| 594 | —CH$_2$— | cyclohex-1,3-diyl | bond | cyclobutyl |
| 595 | —CH$_2$— | cyclohex-1,3-diyl | bond | cyclopentyl |
| 596 | —CH$_2$— | cyclohex-1,3-diyl | bond | cyclohexyl |
| 597 | —CH$_2$— | cyclohex-1,3-diyl | bond | 2-furanyl |
| 598 | —CH$_2$— | cyclohex-1,3-diyl | bond | 2-thienyl |
| 599 | —CH$_2$— | cyclohex-1,3-diyl | bond | 2-imidazolyl |
| 600 | —CH$_2$— | cyclohex-1,3-diyl | bond | 2-pyridyl |
| 601 | —CH$_2$— | cyclohex-1,3-diyl | bond | 3-pyridyl |
| 602 | —CH$_2$— | cyclohex-1,3-diyl | bond | 4-pyridyl |
| 603 | —CH$_2$— | cyclohex-1,3-diyl | bond | N-morpholinyl |
| 604 | —CH$_2$— | cyclohex-1,3-diyl | bond | N-piperidinyl |
| 605 | —CH$_2$— | cyclohex-1,3-diyl | bond | 3-Me-2-pyridyl |
| 606 | —CH$_2$— | cyclohex-1,3-diyl | bond | 4-Me-2-pyridyl |
| 607 | —CH$_2$— | cyclohex-1,3-diyl | bond | 1-indolyl |
| 608 | —CH$_2$— | cyclohex-1,3-diyl | bond | 2-benzothienyl |
| 609 | —CH$_2$— | cyclohex-1,3-diyl | bond | 2-benzofuranyl |
| 610 | —CH$_2$— | cyclohex-1,3-diyl | bond | 1-benzimidazole |
| 611 | —CH$_2$— | cyclohex-1,3-diyl | bond | 2-naphthyl |
| 612 | —CH$_2$— | cyclopropan-1,2-diyl | bond | phenyl |
| 613 | —CH$_2$— | cyclopropan-1,2-diyl | bond | 3,3-diphenylmethyl |
| 614 | —CH$_2$— | cyclopropan-1,2-diyl | bond | 2-F-phenyl |
| 615 | —CH$_2$— | cyclopropan-1,2-diyl | bond | 3-F-phenyl |
| 616 | —CH$_2$— | cyclopropan-1,2-diyl | bond | 4-F-phenyl |
| 617 | —CH$_2$— | cyclopropan-1,2-diyl | bond | 2-Cl-phenyl |
| 618 | —CH$_2$— | cyclopropan-1,2-diyl | bond | 3-Cl-phenyl |
| 619 | —CH$_2$— | cyclopropan-1,2-diyl | bond | 4-Cl-phenyl |
| 620 | —CH$_2$— | cyclopropan-1,2-diyl | bond | 2-Me-phenyl |
| 621 | —CH$_2$— | cyclopropan-1,2-diyl | bond | 3-Me-phenyl |
| 622 | —CH$_2$— | cyclopropan-1,2-diyl | bond | 4-Me-phenyl |
| 623 | —CH$_2$— | cyclopropan-1,2-diyl | bond | 2-MeO-phenyl |
| 624 | —CH$_2$— | cyclopropan-1,2-diyl | bond | 3-MeO-phenyl |
| 625 | —CH$_2$— | cyclopropan-1,2-diyl | bond | 4-MeO-phenyl |
| 626 | —CH$_2$— | cyclopropan-1,2-diyl | bond | 2-MeS-phenyl |
| 627 | —CH$_2$— | cyclopropan-1,2-diyl | bond | 3-MeS-phenyl |
| 628 | —CH$_2$— | cyclopropan-1,2-diyl | bond | 4-MeS-phenyl |
| 629 | —CH$_2$— | cyclopropan-1,2-diyl | bond | 2-F$_3$C-phenyl |
| 630 | —CH$_2$— | cyclopropan-1,2-diyl | bond | 3-F$_3$C-phenyl |

TABLE 1-continued

| | | | | |
|---|---|---|---|---|
| 631 | —CH$_2$— | cyclopropan-1,2-diyl | bond | 4-F$_3$C-phenyl |
| 632 | —CH$_2$— | cyclopropan-1,2-diyl | bond | 2,3-diF-phenyl |
| 633 | —CH$_2$— | cyclopropan-1,2-diyl | bond | 2,4-diF-phenyl |
| 634 | —CH$_2$— | cyclopropan-1,2-diyl | bond | 2,5-diF-phenyl |
| 635 | —CH$_2$— | cyclopropan-1,2-diyl | bond | 2,6-diF-phenyl |
| 636 | —CH$_2$— | cyclopropan-1,2-diyl | bond | 3,4-diF-phenyl |
| 637 | —CH$_2$— | cyclopropan-1,2-diyl | bond | 3,5-diF-phenyl |
| 638 | —CH$_2$— | cyclopropan-1,2-diyl | bond | 2,3-diCl-phenyl |
| 639 | —CH$_2$— | cyclopropan-1,2-diyl | bond | 2,4-diCl-phenyl |
| 640 | —CH$_2$— | cyclopropan-1,2-diyl | bond | 2,5-diCl-phenyl |
| 641 | —CH$_2$— | cyclopropan-1,2-diyl | bond | 2,6-diCl-phenyl |
| 642 | —CH$_2$— | cyclopropan-1,2-diyl | bond | 3,4-diCl-phenyl |
| 643 | —CH$_2$— | cyclopropan-1,2-diyl | bond | 3,5-diCl-phenyl |
| 644 | —CH$_2$— | cyclopropan-1,2-diyl | bond | 2-Cl-3-F-phenyl |
| 645 | —CH$_2$— | cyclopropan-1,2-diyl | bond | 2-Cl-4-F-phenyl |
| 646 | —CH$_2$— | cyclopropan-1,2-diyl | bond | 2-Cl-5-F-phenyl |
| 647 | —CH$_2$— | cyclopropan-1,2-diyl | bond | 3-Cl-4-F-phenyl |
| 648 | —CH$_2$— | cyclopropan-1,2-diyl | bond | 3-Cl-5-F-phenyl |
| 649 | —CH$_2$— | cyclopropan-1,2-diyl | bond | 4-Cl-2-F-phenyl |
| 650 | —CH$_2$— | cyclopropan-1,2-diyl | bond | 4-Cl-3-F-phenyl |
| 651 | —CH$_2$— | cyclopropan-1,2-diyl | bond | 2,3-diMeO-phenyl |
| 652 | —CH$_2$— | cyclopropan-1,2-diyl | bond | 2,4-diMeO-phenyl |
| 653 | —CH$_2$— | cyclopropan-1,2-diyl | bond | 2,5-diMeO-phenyl |
| 654 | —CH$_2$— | cyclopropan-1,2-diyl | bond | 2,6-diMeO-phenyl |
| 655 | —CH$_2$— | cyclopropan-1,2-diyl | bond | 3,4-diMeO-phenyl |
| 656 | —CH$_2$— | cyclopropan-1,2-diyl | bond | 3,5-diMeO-phenyl |
| 657 | —CH$_2$— | cyclopropan-1,2-diyl | bond | cyclopropyl |
| 658 | —CH$_2$— | cyclopropan-1,2-diyl | bond | cyclobutyl |
| 659 | —CH$_2$— | cyclopropan-1,2-diyl | bond | cyclopentyl |
| 660 | —CH$_2$— | cyclopropan-1,2-diyl | bond | cyclohexyl |
| 661 | —CH$_2$— | cyclopropan-1,2-diyl | bond | 2-furanyl |
| 662 | —CH$_2$— | cyclopropan-1,2-diyl | bond | 2-thienyl |
| 663 | —CH$_2$— | cyclopropan-1,2-diyl | bond | 2-imidazolyl |
| 664 | —CH$_2$— | cyclopropan-1,2-diyl | bond | 2-pyridyl |
| 665 | —CH$_2$— | cyclopropan-1,2-diyl | bond | 3-pyridyl |
| 666 | —CH$_2$— | cyclopropan-1,2-diyl | bond | 4-pyridyl |
| 667 | —CH$_2$— | cyclopropan-1,2-diyl | bond | N-morpholinyl |
| 668 | —CH$_2$— | cyclopropan-1,2-diyl | bond | N-piperidinyl |
| 669 | —CH$_2$— | cyclopropan-1,2-diyl | bond | 3-Me-2-pyridyl |
| 670 | —CH$_2$— | cyclopropan-1,2-diyl | bond | 4-Me-2-pyridyl |
| 671 | —CH$_2$— | cyclopropan-1,2-diyl | bond | 1-indolyl |
| 672 | —CH$_2$— | cyclopropan-1,2-diyl | bond | 2-benzothienyl |
| 673 | —CH$_2$— | cyclopropan-1,2-diyl | bond | 2-benzofuranyl |
| 674 | —CH$_2$— | cyclopropan-1,2-diyl | bond | 1-benzimidazole |
| 675 | —CH$_2$— | cyclopropan-1,2-diyl | bond | 2-naphthyl |
| 676 | —CH$_2$— | cyclopentan-1,3-diyl | bond | phenyl |
| 677 | —CH$_2$— | cyclopentan-1,3-diyl | bond | 3,3-diphenylmethyl |
| 678 | —CH$_2$— | cyclopentan-1,3-diyl | bond | 2-F-phenyl |
| 679 | —CH$_2$— | cyclopentan-1,3-diyl | bond | 3-F-phenyl |
| 680 | —CH$_2$— | cyclopentan-1,3-diyl | bond | 4-F-phenyl |
| 681 | —CH$_2$— | cyclopentan-1,3-diyl | bond | 2-Cl-phenyl |
| 682 | —CH$_2$— | cyclopentan-1,3-diyl | bond | 3-Cl-phenyl |
| 683 | —CH$_2$— | cyclopentan-1,3-diyl | bond | 4-Cl-phenyl |
| 684 | —CH$_2$— | cyclopentan-1,3-diyl | bond | 2-Me-phenyl |
| 685 | —CH$_2$— | cyclopentan-1,3-diyl | bond | 3-Me-phenyl |
| 686 | —CH$_2$— | cyclopentan-1,3-diyl | bond | 4-Me-phenyl |
| 687 | —CH$_2$— | cyclopentan-1,3-diyl | bond | 2-MeO-phenyl |
| 688 | —CH$_2$— | cyclopentan-1,3-diyl | bond | 3-MeO-phenyl |
| 689 | —CH$_2$— | cyclopentan-1,3-diyl | bond | 4-MeO-phenyl |
| 690 | —CH$_2$— | cyclopentan-1,3-diyl | bond | 2-MeS-phenyl |
| 691 | —CH$_2$— | cyclopentan-1,3-diyl | bond | 3-MeS-phenyl |
| 692 | —CH$_2$— | cyclopentan-1,3-diyl | bond | 4-MeS-phenyl |
| 693 | —CH$_2$— | cyclopentan-1,3-diyl | bond | 2-F$_3$C-phenyl |
| 694 | —CH$_2$— | cyclopentan-1,3-diyl | bond | 3-F$_3$C-phenyl |
| 695 | —CH$_2$— | cyclopentan-1,3-diyl | bond | 4-F$_3$C-phenyl |
| 696 | —CH$_2$— | cyclopentan-1,3-diyl | bond | 2,3-diF-phenyl |
| 697 | —CH$_2$— | cyclopentan-1,3-diyl | bond | 2,4-diF-phenyl |
| 698 | —CH$_2$— | cyclopentan-1,3-diyl | bond | 2,5-diF-phenyl |
| 699 | —CH$_2$— | cyclopentan-1,3-diyl | bond | 2,6-diF-phenyl |
| 700 | —CH$_2$— | cyclopentan-1,3-diyl | bond | 3,4-diF-phenyl |
| 701 | —CH$_2$— | cyclopentan-1,3-diyl | bond | 3,5-diF-phenyl |
| 702 | —CH$_2$— | cyclopentan-1,3-diyl | bond | 2,3-diCl-phenyl |
| 703 | —CH$_2$— | cyclopentan-1,3-diyl | bond | 2,4-diCl-phenyl |
| 704 | —CH$_2$— | cyclopentan-1,3-diyl | bond | 2,5-diCl-phenyl |
| 705 | —CH$_2$— | cyclopentan-1,3-diyl | bond | 2,6-diCl-phenyl |
| 706 | —CH$_2$— | cyclopentan-1,3-diyl | bond | 3,4-diCl-phenyl |
| 707 | —CH$_2$— | cyclopentan-1,3-diyl | bond | 3,5-diCl-phenyl |
| 708 | —CH$_2$— | cyclopentan-1,3-diyl | bond | 2-Cl-3-F-phenyl |
| 709 | —CH$_2$— | cyclopentan-1,3-diyl | bond | 2-Cl-4-F-phenyl |

TABLE 1-continued

| | | | | |
|---|---|---|---|---|
| 710 | —CH$_2$— | cyclopentan-1,3-diyl | bond | 2-Cl-5-F-phenyl |
| 711 | —CH$_2$— | cyclopentan-1,3-diyl | bond | 3-Cl-4-F-phenyl |
| 712 | —CH$_2$— | cyclopentan-1,3-diyl | bond | 3-Cl-5-F-phenyl |
| 713 | —CH$_2$— | cyclopentan-1,3-diyl | bond | 4-Cl-2-F-phenyl |
| 714 | —CH$_2$— | cyclopentan-1,3-diyl | bond | 4-Cl-3-F-phenyl |
| 715 | —CH$_2$— | cyclopentan-1,3-diyl | bond | 2,3-diMeO-phenyl |
| 716 | —CH$_2$— | cyclopentan-1,3-diyl | bond | 2,4-diMeO-phenyl |
| 717 | —CH$_2$— | cyclopentan-1,3-diyl | bond | 2,5-diMeO-phenyl |
| 718 | —CH$_2$— | cyclopentan-1,3-diyl | bond | 2,6-diMeO-phenyl |
| 719 | —CH$_2$— | cyclopentan-1,3-diyl | bond | 3,4-diMeO-phenyl |
| 720 | —CH$_2$— | cyclopentan-1,3-diyl | bond | 3,5-diMeO-phenyl |
| 721 | —CH$_2$— | cyclopentan-1,3-diyl | bond | cyclopropyl |
| 722 | —CH$_2$— | cyclopentan-1,3-diyl | bond | cyclobutyl |
| 723 | —CH$_2$— | cyclopentan-1,3-diyl | bond | cyclopentyl |
| 724 | —CH$_2$— | cyclopentan-1,3-diyl | bond | cyclohexyl |
| 725 | —CH$_2$— | cyclopentan-1,3-diyl | bond | 2-furanyl |
| 726 | —CH$_2$— | cyclopentan-1,3-diyl | bond | 2-thienyl |
| 727 | —CH$_2$— | cyclopentan-1,3-diyl | bond | 2-imidazolyl |
| 728 | —CH$_2$— | cyclopentan-1,3-diyl | bond | 2-pyridyl |
| 729 | —CH$_2$— | cyclopentan-1,3-diyl | bond | 3-pyridyl |
| 730 | —CH$_2$— | cyclopentan-1,3-diyl | bond | 4-pyridyl |
| 731 | —CH$_2$— | cyclopentan-1,3-diyl | bond | N-morpholinyl |
| 732 | —CH$_2$— | cyclopentan-1,3-diyl | bond | N-piperidinyl |
| 733 | —CH$_2$— | cyclopentan-1,3-diyl | bond | 3-Me-2-pyridyl |
| 734 | —CH$_2$— | cyclopentan-1,3-diyl | bond | 4-Me-2-pyridyl |
| 735 | —CH$_2$— | cyclopentan-1,3-diyl | bond | 1-indolyl |
| 736 | —CH$_2$— | cyclopentan-1,3-diyl | bond | 2-benzothienyl |
| 737 | —CH$_2$— | cyclopentan-1,3-diyl | bond | 2-benzofuranyl |
| 738 | —CH$_2$— | cyclopentan-1,3-diyl | bond | 1-benzimidazole |
| 739 | —CH$_2$— | cyclopentan-1,3-diyl | bond | 2-naphthyl |
| 740 | —CH$_2$— | phen-1,3-diyl | —O— | phenyl |
| 741 | —CH$_2$— | phen-1,3-diyl | —O— | 3,3-diphenylmethyl |
| 742 | —CH$_2$— | phen-1,3-diyl | —O— | 2-F-phenyl |
| 743 | —CH$_2$— | phen-1,3-diyl | —O— | 3-F-phenyl |
| 744 | —CH$_2$— | phen-1,3-diyl | —O— | 4-F-phenyl |
| 745 | —CH$_2$— | phen-1,3-diyl | —O— | 2-Cl-phenyl |
| 746 | —CH$_2$— | phen-1,3-diyl | —O— | 3-Cl-phenyl |
| 747 | —CH$_2$— | phen-1,3-diyl | —O— | 4-Cl-phenyl |
| 748 | —CH$_2$— | phen-1,3-diyl | —O— | 2-Me-phenyl |
| 749 | —CH$_2$— | phen-1,3-diyl | —O— | 3-Me-phenyl |
| 750 | —CH$_2$— | phen-1,3-diyl | —O— | 4-Me-phenyl |
| 751 | —CH$_2$— | phen-1,3-diyl | —O— | 2-MeO-phenyl |
| 752 | —CH$_2$— | phen-1,3-diyl | —O— | 3-MeO-phenyl |
| 753 | —CH$_2$— | phen-1,3-diyl | —O— | 4-MeO-phenyl |
| 754 | —CH$_2$— | phen-1,3-diyl | —O— | 2-MeS-phenyl |
| 755 | —CH$_2$— | phen-1,3-diyl | —O— | 3-MeS-phenyl |
| 756 | —CH$_2$— | phen-1,3-diyl | —O— | 4-MeS-phenyl |
| 757 | —CH$_2$— | phen-1,3-diyl | —O— | 2-F$_3$C-phenyl |
| 758 | —CH$_2$— | phen-1,3-diyl | —O— | 3-F$_3$C-phenyl |
| 759 | —CH$_2$— | phen-1,3-diyl | —O— | 4-F$_3$C-phenyl |
| 760 | —CH$_2$— | phen-1,3-diyl | —O— | 2,3-diF-phenyl |
| 761 | —CH$_2$— | phen-1,3-diyl | —O— | 2,4-diF-phenyl |
| 762 | —CH$_2$— | phen-1,3-diyl | —O— | 2,5-diF-phenyl |
| 763 | —CH$_2$— | phen-1,3-diyl | —O— | 2,6-diF-phenyl |
| 764 | —CH$_2$— | phen-1,3-diyl | —O— | 3,4-diF-phenyl |
| 765 | —CH$_2$— | phen-1,3-diyl | —O— | 3,5-diF-phenyl |
| 766 | —CH$_2$— | phen-1,3-diyl | —O— | 2,3-diCl-phenyl |
| 767 | —CH$_2$— | phen-1,3-diyl | —O— | 2,4-diCl-phenyl |
| 768 | —CH$_2$— | phen-1,3-diyl | —O— | 2,5-diCl-phenyl |
| 769 | —CH$_2$— | phen-1,3-diyl | —O— | 2,6-diCl-phenyl |
| 770 | —CH$_2$— | phen-1,3-diyl | —O— | 3,4-diCl-phenyl |
| 771 | —CH$_2$— | phen-1,3-diyl | —O— | 3,5-diCl-phenyl |
| 772 | —CH$_2$— | phen-1,3-diyl | —O— | 2-Cl-3-F-phenyl |
| 773 | —CH$_2$— | phen-1,3-diyl | —O— | 2-Cl-4-F-phenyl |
| 774 | —CH$_2$— | phen-1,3-diyl | —O— | 2-Cl-5-F-phenyl |
| 775 | —CH$_2$— | phen-1,3-diyl | —O— | 3-Cl-4-F-phenyl |
| 776 | —CH$_2$— | phen-1,3-diyl | —O— | 3-Cl-5-F-phenyl |
| 777 | —CH$_2$— | phen-1,3-diyl | —O— | 4-Cl-2-F-phenyl |
| 778 | —CH$_2$— | phen-1,3-diyl | —O— | 4-Cl-3-F-phenyl |
| 779 | —CH$_2$— | phen-1,3-diyl | —O— | 2,3-diMeO-phenyl |
| 780 | —CH$_2$— | phen-1,3-diyl | —O— | 2,4-diMeO-phenyl |
| 781 | —CH$_2$— | phen-1,3-diyl | —O— | 2,5-diMeO-phenyl |
| 782 | —CH$_2$— | phen-1,3-diyl | —O— | 2,6-diMeO-phenyl |
| 783 | —CH$_2$— | phen-1,3-diyl | —O— | 3,4-diMeO-phenyl |
| 784 | —CH$_2$— | phen-1,3-diyl | —O— | 3,5-diMeO-phenyl |
| 785 | —CH$_2$— | phen-1,3-diyl | —O— | cyclopropyl |
| 786 | —CH$_2$— | phen-1,3-diyl | —O— | cyclobutyl |
| 787 | —CH$_2$— | phen-1,3-diyl | —O— | cyclopentyl |
| 788 | —CH$_2$— | phen-1,3-diyl | —O— | cyclohexyl |

TABLE 1-continued

| | | | | |
|---|---|---|---|---|
| 789 | —CH$_2$— | phen-1,3-diyl | —O— | 2-furanyl |
| 790 | —CH$_2$— | phen-1,3-diyl | —O— | 2-thienyl |
| 791 | —CH$_2$— | phen-1,3-diyl | CH$_2$CH$_2$ | 2-imidazolyl |
| 792 | —CH$_2$— | phen-1,3-diyl | —O— | 2-pyridyl |
| 793 | —CH$_2$— | phen-1,3-diyl | —O— | 3-pyridyl |
| 794 | —CH$_2$— | phen-1,3-diyl | —O— | 4-pyridyl |
| 795 | —CH$_2$— | phen-1,3-diyl | CH$_2$CH$_2$ | N-morpholinyl |
| 796 | —CH$_2$— | phen-1,3-diyl | CH$_2$CH$_2$ | N-piperidinyl |
| 797 | —CH$_2$— | phen-1,3-diyl | —O— | 3-Me-2-pyridyl |
| 798 | —CH$_2$— | phen-1,3-diyl | —O— | 4-Me-2-pyridyl |
| 799 | —CH$_2$— | phen-1,3-diyl | CH$_2$CH$_2$ | 1-indolyl |
| 800 | —CH$_2$— | phen-1,3-diyl | —O— | 2-benzothienyl |
| 801 | —CH$_2$— | phen-1,3-diyl | —O— | 2-benzofuranyl |
| 802 | —CH$_2$— | phen-1,3-diyl | CH$_2$CH$_2$ | 1-benzimidazole |
| 803 | —CH$_2$— | phen-1,3-diyl | —O— | 2-naphthyl |
| 804 | —CH$_2$— | pyridin-3,5-diyl | —O— | phenyl |
| 805 | —CH$_2$— | pyridin-3,5-diyl | —O— | 3,3-diphenylmethyl |
| 806 | —CH$_2$— | pyridin-3,5-diyl | —O— | 2-F-phenyl |
| 807 | —CH$_2$— | pyridin-3,5-diyl | —O— | 3-F-phenyl |
| 808 | —CH$_2$— | pyridin-3,5-diyl | —O— | 4-F-phenyl |
| 809 | —CH$_2$— | pyridin-3,5-diyl | —O— | 2-Cl-phenyl |
| 810 | —CH$_2$— | pyridin-3,5-diyl | —O— | 3-Cl-phenyl |
| 811 | —CH$_2$— | pyridin-3,5-diyl | —O— | 4-Cl-phenyl |
| 812 | —CH$_2$— | pyridin-3,5-diyl | —O— | 2-Me-phenyl |
| 813 | —CH$_2$— | pyridin-3,5-diyl | —O— | 3-Me-phenyl |
| 814 | —CH$_2$— | pyridin-3,5-diyl | —O— | 4-Me-phenyl |
| 815 | —CH$_2$— | pyridin-3,5-diyl | —O— | 2-MeO-phenyl |
| 816 | —CH$_2$— | pyridin-3,5-diyl | —O— | 3-MeO-phenyl |
| 817 | —CH$_2$— | pyridin-3,5-diyl | —O— | 4-MeO-phenyl |
| 818 | —CH$_2$— | pyridin-3,5-diyl | —O— | 2-MeS-phenyl |
| 819 | —CH$_2$— | pyridin-3,5-diyl | —O— | 3-MeS-phenyl |
| 820 | —CH$_2$— | pyridin-3,5-diyl | —O— | 4-MeS-phenyl |
| 821 | —CH$_2$— | pyridin-3,5-diyl | —O— | 2-F$_3$C-phenyl |
| 822 | —CH$_2$— | pyridin-3,5-diyl | —O— | 3-F$_3$C-phenyl |
| 823 | —CH$_2$— | pyridin-3,5-diyl | —O— | 4-F$_3$C-phenyl |
| 824 | —CH$_2$— | pyridin-3,5-diyl | —O— | 2,3-diF-phenyl |
| 825 | —CH$_2$— | pyridin-3,5-diyl | —O— | 2,4-diF-phenyl |
| 826 | —CH$_2$— | pyridin-3,5-diyl | —O— | 2,5-diF-phenyl |
| 827 | —CH$_2$— | pyridin-3,5-diyl | —O— | 2,6-diF-phenyl |
| 828 | —CH$_2$— | pyridin-3,5-diyl | —O— | 3,4-diF-phenyl |
| 829 | —CH$_2$— | pyridin-3,5-diyl | —O— | 3,5-diF-phenyl |
| 830 | —CH$_2$— | pyridin-3,5-diyl | —O— | 2,3-diCl-phenyl |
| 831 | —CH$_2$— | pyridin-3,5-diyl | —O— | 2,4-diCl-phenyl |
| 832 | —CH$_2$— | pyridin-3,5-diyl | —O— | 2,5-diCl-phenyl |
| 833 | —CH$_2$— | pyridin-3,5-diyl | —O— | 2,6-diCl-phenyl |
| 834 | —CH$_2$— | pyridin-3,5-diyl | —O— | 3,4-diCl-phenyl |
| 835 | —CH$_2$— | pyridin-3,5-diyl | —O— | 3,5-diCl-phenyl |
| 836 | —CH$_2$— | pyridin-3,5-diyl | —O— | 2-Cl-3-F-phenyl |
| 837 | —CH$_2$— | pyridin-3,5-diyl | —O— | 2-Cl-4-F-phenyl |
| 838 | —CH$_2$— | pyridin-3,5-diyl | —O— | 2-Cl-5-F-phenyl |
| 839 | —CH$_2$— | pyridin-3,5-diyl | —O— | 3-Cl-4-F-phenyl |
| 840 | —CH$_2$— | pyridin-3,5-diyl | —O— | 3-Cl-5-F-phenyl |
| 841 | —CH$_2$— | pyridin-3,5-diyl | —O— | 4-Cl-2-F-phenyl |
| 842 | —CH$_2$— | pyridin-3,5-diyl | —O— | 4-Cl-3-F-phenyl |
| 843 | —CH$_2$— | pyridin-3,5-diyl | —O— | 2,3-diMeO-phenyl |
| 844 | —CH$_2$— | pyridin-3,5-diyl | —O— | 2,4-diMeO-phenyl |
| 845 | —CH$_2$— | pyridin-3,5-diyl | —O— | 2,5-diMeO-phenyl |
| 846 | —CH$_2$— | pyridin-3,5-diyl | —O— | 2,6-diMeO-phenyl |
| 847 | —CH$_2$— | pyridin-3,5-diyl | —O— | 3,4-diMeO-phenyl |
| 848 | —CH$_2$— | pyridin-3,5-diyl | —O— | 3,5-diMeO-phenyl |
| 849 | —CH$_2$— | pyridin-3,5-diyl | —O— | cyclopropyl |
| 850 | —CH$_2$— | pyridin-3,5-diyl | —O— | cyclobutyl |
| 851 | —CH$_2$— | pyridin-3,5-diyl | —O— | cyclopentyl |
| 852 | —CH$_2$— | pyridin-3,5-diyl | —O— | cyclohexyl |
| 853 | —CH$_2$— | pyridin-3,5-diyl | —O— | 2-furanyl |
| 854 | —CH$_2$— | pyridin-3,5-diyl | —O— | 2-thienyl |
| 855 | —CH$_2$— | pyridin-3,5-diyl | CH$_2$CH$_2$ | 2-imidazolyl |
| 856 | —CH$_2$— | pyridin-3,5-diyl | —O— | 2-pyridyl |
| 857 | —CH$_2$— | pyridin-3,5-diyl | —O— | 3-pyridyl |
| 858 | —CH$_2$— | pyridin-3,5-diyl | —O— | 4-pyridyl |
| 859 | —CH$_2$— | pyridin-3,5-diyl | CH$_2$CH$_2$ | N-morpholinyl |
| 860 | —CH$_2$— | pyridin-3,5-diyl | CH$_2$CH$_2$ | N-piperidinyl |
| 861 | —CH$_2$— | pyridin-3,5-diyl | —O— | 3-Me-2-pyridyl |
| 862 | —CH$_2$— | pyridin-3,5-diyl | —O— | 4-Me-2-pyridyl |
| 863 | —CH$_2$— | pyridin-3,5-diyl | CH$_2$CH$_2$ | 1-indolyl |
| 864 | —CH$_2$— | pyridin-3,5-diyl | —O— | 2-benzothienyl |
| 865 | —CH$_2$— | pyridin-3,5-diyl | —O— | 2-benzofuranyl |
| 866 | —CH$_2$— | pyridin-3,5-diyl | CH$_2$CH$_2$ | 1-benzimidazole |
| 867 | —CH$_2$— | pyridin-3,5-diyl | —O— | 2-naphthyl |

TABLE 1-continued

| | | | | |
|---|---|---|---|---|
| 868 | —CH₂— | pyridin-2,6-diyl | —O— | phenyl |
| 869 | —CH₂— | pyridin-2,6-diyl | —O— | 3,3-diphenylmethyl |
| 870 | —CH₂— | pyridin-2,6-diyl | —O— | 2-F-phenyl |
| 871 | —CH₂— | pyridin-2,6-diyl | —O— | 3-F-phenyl |
| 872 | —CH₂— | pyridin-2,6-diyl | —O— | 4-F-phenyl |
| 873 | —CH₂— | pyridin-2,6-diyl | —O— | 2-Cl-phenyl |
| 874 | —CH₂— | pyridin-2,6-diyl | —O— | 3-Cl-phenyl |
| 875 | —CH₂— | pyridin-2,6-diyl | —O— | 4-Cl-phenyl |
| 876 | —CH₂— | pyridin-2,6-diyl | —O— | 2-Me-phenyl |
| 877 | —CH₂— | pyridin-2,6-diyl | —O— | 3-Me-phenyl |
| 878 | —CH₂— | pyridin-2,6-diyl | —O— | 4-Me-phenyl |
| 879 | —CH₂— | pyridin-2,6-diyl | —O— | 2-MeO-phenyl |
| 880 | —CH₂— | pyridin-2,6-diyl | —O— | 3-MeO-phenyl |
| 881 | —CH₂— | pyridin-2,6-diyl | —O— | 4-MeO-phenyl |
| 882 | —CH₂— | pyridin-2,6-diyl | —O— | 2-MeS-phenyl |
| 883 | —CH₂— | pyridin-2,6-diyl | —O— | 3-MeS-phenyl |
| 884 | —CH₂— | pyridin-2,6-diyl | —O— | 4-MeS-phenyl |
| 885 | —CH₂— | pyridin-2,6-diyl | —O— | 2-F₃C-phenyl |
| 886 | —CH₂— | pyridin-2,6-diyl | —O— | 3-F₃C-phenyl |
| 887 | —CH₂— | pyridin-2,6-diyl | —O— | 4-F₃C-phenyl |
| 888 | —CH₂— | pyridin-2,6-diyl | —O— | 2,3-diF-phenyl |
| 889 | —CH₂— | pyridin-2,6-diyl | —O— | 2,4-diF-phenyl |
| 890 | —CH₂— | pyridin-2,6-diyl | —O— | 2,5-diF-phenyl |
| 891 | —CH₂— | pyridin-2,6-diyl | —O— | 2,6-diF-phenyl |
| 892 | —CH₂— | pyridin-2,6-diyl | —O— | 3,4-diF-phenyl |
| 893 | —CH₂— | pyridin-2,6-diyl | —O— | 3,5-diF-phenyl |
| 894 | —CH₂— | pyridin-2,6-diyl | —O— | 2,3-diCl-phenyl |
| 895 | —CH₂— | pyridin-2,6-diyl | —O— | 2,4-diCl-phenyl |
| 896 | —CH₂— | pyridin-2,6-diyl | —O— | 2,5-diCl-phenyl |
| 897 | —CH₂— | pyridin-2,6-diyl | —O— | 2,6-diCl-phenyl |
| 898 | —CH₂— | pyridin-2,6-diyl | —O— | 3,4-diCl-phenyl |
| 899 | —CH₂— | pyridin-2,6-diyl | —O— | 3,5-diCl-phenyl |
| 900 | —CH₂— | pyridin-2,6-diyl | —O— | 2-Cl-3-F-phenyl |
| 901 | —CH₂— | pyridin-2,6-diyl | —O— | 2-Cl-4-F-phenyl |
| 902 | —CH₂— | pyridin-2,6-diyl | —O— | 2-Cl-5-F-phenyl |
| 903 | —CH₂— | pyridin-2,6-diyl | —O— | 3-Cl-4-F-phenyl |
| 904 | —CH₂— | pyridin-2,6-diyl | —O— | 3-Cl-5-F-phenyl |
| 905 | —CH₂— | pyridin-2,6-diyl | —O— | 4-Cl-2-F-phenyl |
| 906 | —CH₂— | pyridin-2,6-diyl | —O— | 4-Cl-3-F-phenyl |
| 907 | —CH₂— | pyridin-2,6-diyl | —O— | 2,3-diMeO-phenyl |
| 908 | —CH₂— | pyridin-2,6-diyl | —O— | 2,4-diMeO-phenyl |
| 909 | —CH₂— | pyridin-2,6-diyl | —O— | 2,5-diMeO-phenyl |
| 910 | —CH₂— | pyridin-2,6-diyl | —O— | 2,6-diMeO-phenyl |
| 911 | —CH₂— | pyridin-2,6-diyl | —O— | 3,4-diMeO-phenyl |
| 912 | —CH₂— | pyridin-2,6-diyl | —O— | 3,5-diMeO-phenyl |
| 913 | —CH₂— | pyridin-2,6-diyl | —O— | cyclopropyl |
| 914 | —CH₂— | pyridin-2,6-diyl | —O— | cyclobutyl |
| 915 | —CH₂— | pyridin-2,6-diyl | —O— | cyclopentyl |
| 916 | —CH₂— | pyridin-2,6-diyl | —O— | cyclohexyl |
| 917 | —CH₂— | pyridin-2,6-diyl | —O— | 2-furanyl |
| 918 | —CH₂— | pyridin-2,6-diyl | —O— | 2-thienyl |
| 919 | —CH₂— | pyridin-2,6-diyl | CH₂CH₂ | 2-imidazolyl |
| 920 | —CH₂— | pyridin-2,6-diyl | —O— | 2-pyridyl |
| 921 | —CH₂— | pyridin-2,6-diyl | —O— | 3-pyridyl |
| 922 | —CH₂— | pyridin-2,6-diyl | —O— | 4-pyridyl |
| 923 | —CH₂— | pyridin-2,6-diyl | CH₂CH₂ | N-morpholinyl |
| 924 | —CH₂— | pyridin-2,6-diyl | CH₂CH₂ | N-piperidinyl |
| 925 | —CH₂— | pyridin-2,6-diyl | —O— | 3-Me-2-pyridyl |
| 926 | —CH₂— | pyridin-2,6-diyl | —O— | 4-Me-2-pyridyl |
| 927 | —CH₂— | pyridin-2,6-diyl | CH₂CH₂ | 1-indolyl |
| 928 | —CH₂— | pyridin-2,6-diyl | —O— | 2-benzothienyl |
| 929 | —CH₂— | pyridin-2,6-diyl | —O— | 2-benzofuranyl |
| 930 | —CH₂— | pyridin-2,6-diyl | CH₂CH₂ | 1-benzimidazole |
| 931 | —CH₂— | pyridin-2,6-diyl | —O— | 2-naphthyl |
| 932 | —CH₂— | pyridin-2,4-diyl | —O— | phenyl |
| 933 | —CH₂— | pyridin-2,4-diyl | —O— | 3,3-diphenylmethyl |
| 934 | —CH₂— | pyridin-2,4-diyl | —O— | 2-F-phenyl |
| 935 | —CH₂— | pyridin-2,4-diyl | —O— | 3-F-phenyl |
| 936 | —CH₂— | pyridin-2,4-diyl | —O— | 4-F-phenyl |
| 937 | —CH₂— | pyridin-2,4-diyl | —O— | 2-Cl-phenyl |
| 938 | —CH₂— | pyridin-2,4-diyl | —O— | 3-Cl-phenyl |
| 939 | —CH₂— | pyridin-2,4-diyl | —O— | 4-Cl-phenyl |
| 940 | —CH₂— | pyridin-2,4-diyl | —O— | 2-Me-phenyl |
| 941 | —CH₂— | pyridin-2,4-diyl | —O— | 3-Me-phenyl |
| 942 | —CH₂— | pyridin-2,4-diyl | —O— | 4-Me-phenyl |
| 943 | —CH₂— | pyridin-2,4-diyl | —O— | 2-MeO-phenyl |
| 944 | —CH₂— | pyridin-2,4-diyl | —O— | 3-MeO-phenyl |
| 945 | —CH₂— | pyridin-2,4-diyl | —O— | 4-MeO-phenyl |
| 946 | —CH₂— | pyridin-2,4-diyl | —O— | 2-MeS-phenyl |

TABLE 1-continued

| | | | |
|---|---|---|---|
| 947 —CH$_2$— | pyridin-2,4-diyl | —O— | 3-MeS-phenyl |
| 948 —CH$_2$— | pyridin-2,4-diyl | —O— | 4-MeS-phenyl |
| 949 —CH$_2$— | pyridin-2,4-diyl | —O— | 2-F$_3$C-phenyl |
| 950 —CH$_2$— | pyridin-2,4-diyl | —O— | 3-F$_3$C-phenyl |
| 951 —CH$_2$— | pyridin-2,4-diyl | —O— | 4-F$_3$C-phenyl |
| 952 —CH$_2$— | pyridin-2,4-diyl | —O— | 2,3-diF-phenyl |
| 953 —CH$_2$— | pyridin-2,4-diyl | —O— | 2,4-diF-phenyl |
| 954 —CH$_2$— | pyridin-2,4-diyl | —O— | 2,5-diF-phenyl |
| 955 —CH$_2$— | pyridin-2,4-diyl | —O— | 2,6-diF-phenyl |
| 956 —CH$_2$— | pyridin-2,4-diyl | —O— | 3,4-diF-phenyl |
| 957 —CH$_2$— | pyridin-2,4-diyl | —O— | 3,5-diF-phenyl |
| 958 —CH$_2$— | pyridin-2,4-diyl | —O— | 2,3-diCl-phenyl |
| 959 —CH$_2$— | pyridin-2,4-diyl | —O— | 2,4-diCl-phenyl |
| 960 —CH$_2$— | pyridin-2,4-diyl | —O— | 2,5-diCl-phenyl |
| 961 —CH$_2$— | pyridin-2,4-diyl | —O— | 2,6-diCl-phenyl |
| 962 —CH$_2$— | pyridin-2,4-diyl | —O— | 3,4-diCl-phenyl |
| 963 —CH$_2$— | pyridin-2,4-diyl | —O— | 3,5-diCl-phenyl |
| 964 —CH$_2$— | pyridin-2,4-diyl | —O— | 2-Cl-3-F-phenyl |
| 965 —CH$_2$— | pyridin-2,4-diyl | —O— | 2-Cl-4-F-phenyl |
| 966 —CH$_2$— | pyridin-2,4-diyl | —O— | 2-Cl-5-F-phenyl |
| 967 —CH$_2$— | pyridin-2,4-diyl | —O— | 3-Cl-4-F-phenyl |
| 968 —CH$_2$— | pyridin-2,4-diyl | —O— | 3-Cl-5-F-phenyl |
| 969 —CH$_2$— | pyridin-2,4-diyl | —O— | 4-Cl-2-F-phenyl |
| 970 —CH$_2$— | pyridin-2,4-diyl | —O— | 4-Cl-3-F-phenyl |
| 971 —CH$_2$— | pyridin-2,4-diyl | —O— | 2,3-diMeO-phenyl |
| 972 —CH$_2$— | pyridin-2,4-diyl | —O— | 2,4-diMeO-phenyl |
| 973 —CH$_2$— | pyridin-2,4-diyl | —O— | 2,5-diMeO-phenyl |
| 974 —CH$_2$— | pyridin-2,4-diyl | —O— | 2,6-diMeO-phenyl |
| 975 —CH$_2$— | pyridin-2,4-diyl | —O— | 3,4-diMeO-phenyl |
| 976 —CH$_2$— | pyridin-2,4-diyl | —O— | 3,5-diMeO-phenyl |
| 977 —CH$_2$— | pyridin-2,4-diyl | —O— | cyclopropyl |
| 978 —CH$_2$— | pyridin-2,4-diyl | —O— | cyclobutyl |
| 979 —CH$_2$— | pyridin-2,4-diyl | —O— | cyclopentyl |
| 980 —CH$_2$— | pyridin-2,4-diyl | —O— | cyclohexyl |
| 981 —CH$_2$— | pyridin-2,4-diyl | —O— | 2-furanyl |
| 982 —CH$_2$— | pyridin-2,4-diyl | —O— | 2-thienyl |
| 983 —CH$_2$— | pyridin-2,4-diyl | CH$_2$CH$_2$ | 2-imidazolyl |
| 984 —CH$_2$— | pyridin-2,4-diyl | —O— | 2-pyridyl |
| 985 —CH$_2$— | pyridin-2,4-diyl | —O— | 3-pyridyl |
| 986 —CH$_2$— | pyridin-2,4-diyl | —O— | 4-pyridyl |
| 987 —CH$_2$— | pyridin-2,4-diyl | CH$_2$CH$_2$ | N-morpholinyl |
| 988 —CH$_2$— | pyridin-2,4-diyl | CH$_2$CH$_2$ | N-piperidinyl |
| 989 —CH$_2$— | pyridin-2,4-diyl | —O— | 3-Me-2-pyridyl |
| 990 —CH$_2$— | pyridin-2,4-diyl | —O— | 4-Me-2-pyridyl |
| 991 —CH$_2$— | pyridin-2,4-diyl | CH$_2$CH$_2$ | 1-indolyl |
| 992 —CH$_2$— | pyridin-2,4-diyl | —O— | 2-benzothienyl |
| 993 —CH$_2$— | pyridin-2,4-diyl | —O— | 2-benzofuranyl |
| 994 —CH$_2$— | pyridin-2,4-diyl | CH$_2$CH$_2$ | 1-benzimidazole |
| 995 —CH$_2$— | pyridin-2,4-diyl | —O— | 2-naphthyl |
| 996 —CH$_2$— | pyridin-4,2-diyl | —O— | phenyl |
| 997 —CH$_2$— | pyridin-4,2-diyl | —O— | 3,3-diphenylmethyl |
| 998 —CH$_2$— | pyridin-4,2-diyl | —O— | 2-F-phenyl |
| 999 —CH$_2$— | pyridin-4,2-diyl | —O— | 3-F-phenyl |
| 1000 —CH$_2$— | pyridin-4,2-diyl | —O— | 4-F-phenyl |
| 1001 —CH$_2$— | pyridin-4,2-diyl | —O— | 2-Cl-phenyl |
| 1002 —CH$_2$— | pyridin-4,2-diyl | —O— | 3-Cl-phenyl |
| 1003 —CH$_2$— | pyridin-4,2-diyl | —O— | 4-Cl-phenyl |
| 1004 —CH$_2$— | pyridin-4,2-diyl | —O— | 2-Me-phenyl |
| 1005 —CH$_2$— | pyridin-4,2-diyl | —O— | 3-Me-phenyl |
| 1006 —CH$_2$— | pyridin-4,2-diyl | —O— | 4-Me-phenyl |
| 1007 —CH$_2$— | pyridin-4,2-diyl | —O— | 2-MeO-phenyl |
| 1008 —CH$_2$— | pyridin-4,2-diyl | —O— | 3-MeO-phenyl |
| 1009 —CH$_2$— | pyridin-4,2-diyl | —O— | 4-MeO-phenyl |
| 1010 —CH$_2$— | pyridin-4,2-diyl | —O— | 2-MeS-phenyl |
| 1011 —CH$_2$— | pyridin-4,2-diyl | —O— | 3-MeS-phenyl |
| 1012 —CH$_2$— | pyridin-4,2-diyl | —O— | 4-MeS-phenyl |
| 1013 —CH$_2$— | pyridin-4,2-diyl | —O— | 2-F$_3$C-phenyl |
| 1014 —CH$_2$— | pyridin-4,2-diyl | —O— | 3-F$_3$C-phenyl |
| 1015 —CH$_2$— | pyridin-4,2-diyl | —O— | 4-F$_3$C-phenyl |
| 1016 —CH$_2$— | pyridin-4,2-diyl | —O— | 2,3-diF-phenyl |
| 1017 —CH$_2$— | pyridin-4,2-diyl | —O— | 2,4-diF-phenyl |
| 1018 —CH$_2$— | pyridin-4,2-diyl | —O— | 2,5-diF-phenyl |
| 1019 —CH$_2$— | pyridin-4,2-diyl | —O— | 2,6-diF-phenyl |
| 1020 —CH$_2$— | pyridin-4,2-diyl | —O— | 3,4-diF-phenyl |
| 1021 —CH$_2$— | pyridin-4,2-diyl | —O— | 3,5-diF-phenyl |
| 1022 —CH$_2$— | pyridin-4,2-diyl | —O— | 2,3-diCl-phenyl |
| 1023 —CH$_2$— | pyridin-4,2-diyl | —O— | 2,4-diCl-phenyl |
| 1024 —CH$_2$— | pyridin-4,2-diyl | —O— | 2,5-diCl-phenyl |
| 1025 —CH$_2$— | pyridin-4,2-diyl | —O— | 2,6-diCl-phenyl |

TABLE 1-continued

| | | | | |
|---|---|---|---|---|
| 1026 | —CH₂— | pyridin-4,2-diyl | —O— | 3,4-diCl-phenyl |
| 1027 | —CH₂— | pyridin-4,2-diyl | —O— | 3,5-diCl-phenyl |
| 1028 | —CH₂— | pyridin-4,2-diyl | —O— | 2-Cl-3-F-phenyl |
| 1029 | —CH₂— | pyridin-4,2-diyl | —O— | 2-Cl-4-F-phenyl |
| 1030 | —CH₂— | pyridin-4,2-diyl | —O— | 2-Cl-5-F-phenyl |
| 1031 | —CH₂— | pyridin-4,2-diyl | —O— | 3-Cl-4-F-phenyl |
| 1032 | —CH₂— | pyridin-4,2-diyl | —O— | 3-Cl-5-F-phenyl |
| 1033 | —CH₂— | pyridin-4,2-diyl | —O— | 4-Cl-2-F-phenyl |
| 1034 | —CH₂— | pyridin-4,2-diyl | —O— | 4-Cl-3-F-phenyl |
| 1035 | —CH₂— | pyridin-4,2-diyl | —O— | 2,3-diMeO-phenyl |
| 1036 | —CH₂— | pyridin-4,2-diyl | —O— | 2,4-diMeO-phenyl |
| 1037 | —CH₂— | pyridin-4,2-diyl | —O— | 2,5-diMeO-phenyl |
| 1038 | —CH₂— | pyridin-4,2-diyl | —O— | 2,6-diMeO-phenyl |
| 1039 | —CH₂— | pyridin-4,2-diyl | —O— | 3,4-diMeO-phenyl |
| 1040 | —CH₂— | pyridin-4,2-diyl | —O— | 3,5-diMeO-phenyl |
| 1041 | —CH₂— | pyridin-4,2-diyl | —O— | cyclopropyl |
| 1042 | —CH₂— | pyridin-4,2-diyl | —O— | cyclobutyl |
| 1043 | —CH₂— | pyridin-4,2-diyl | —O— | cyclopentyl |
| 1044 | —CH₂— | pyridin-4,2-diyl | —O— | cyclohexyl |
| 1045 | —CH₂— | pyridin-4,2-diyl | —O— | 2-furanyl |
| 1046 | —CH₂— | pyridin-4,2-diyl | —O— | 2-thienyl |
| 1047 | —CH₂— | pyridin-4,2-diyl | CH₂CH₂ | 2-imidazolyl |
| 1048 | —CH₂— | pyridin-4,2-diyl | —O— | 2-pyridyl |
| 1049 | —CH₂— | pyridin-4,2-diyl | —O— | 3-pyridyl |
| 1050 | —CH₂— | pyridin-4,2-diyl | —O— | 4-pyridyl |
| 1051 | —CH₂— | pyridin-4,2-diyl | CH₂CH₂ | N-morpholinyl |
| 1052 | —CH₂— | pyridin-4,2-diyl | CH₂CH₂ | N-piperidinyl |
| 1053 | —CH₂— | pyridin-4,2-diyl | —O— | 3-Me-2-pyridyl |
| 1054 | —CH₂— | pyridin-4,2-diyl | —O— | 4-Me-2-pyridyl |
| 1055 | —CH₂— | pyridin-4,2-diyl | CH₂CH₂ | 1-indolyl |
| 1056 | —CH₂— | pyridin-4,2-diyl | —O— | 2-benzothienyl |
| 1057 | —CH₂— | pyridin-4,2-diyl | —O— | 2-benzofuranyl |
| 1058 | —CH₂— | pyridin-4,2-diyl | CH₂CH₂ | 1-benzimidazole |
| 1059 | —CH₂— | pyridin-4,2-diyl | —O— | 2-naphthyl |
| 1060 | —CH₂— | piperidin-1,3-diyl | —O— | phenyl |
| 1061 | —CH₂— | piperidin-1,3-diyl | —O— | 3,3-diphenylmethyl |
| 1062 | —CH₂— | piperidin-1,3-diyl | —O— | 2-F-phenyl |
| 1063 | —CH₂— | piperidin-1,3-diyl | —O— | 3-F-phenyl |
| 1064 | —CH₂— | piperidin-1,3-diyl | —O— | 4-F-phenyl |
| 1065 | —CH₂— | piperidin-1,3-diyl | —O— | 2-Cl-phenyl |
| 1066 | —CH₂— | piperidin-1,3-diyl | —O— | 3-Cl-phenyl |
| 1067 | —CH₂— | piperidin-1,3-diyl | —O— | 4-Cl-phenyl |
| 1068 | —CH₂— | piperidin-1,3-diyl | —O— | 2-Me-phenyl |
| 1069 | —CH₂— | piperidin-1,3-diyl | —O— | 3-Me-phenyl |
| 1070 | —CH₂— | piperidin-1,3-diyl | —O— | 4-Me-phenyl |
| 1071 | —CH₂— | piperidin-1,3-diyl | —O— | 2-MeO-phenyl |
| 1072 | —CH₂— | piperidin-1,3-diyl | —O— | 3-MeO-phenyl |
| 1073 | —CH₂— | piperidin-1,3-diyl | —O— | 4-MeO-phenyl |
| 1074 | —CH₂— | piperidin-1,3-diyl | —O— | 2-MeS-phenyl |
| 1075 | —CH₂— | piperidin-1,3-diyl | —O— | 3-MeS-phenyl |
| 1076 | —CH₂— | piperidin-1,3-diyl | —O— | 4-MeS-phenyl |
| 1077 | —CH₂— | piperidin-1,3-diyl | —O— | 2-F₃C-phenyl |
| 1078 | —CH₂— | piperidin-1,3-diyl | —O— | 3-F₃C-phenyl |
| 1079 | —CH₂— | piperidin-1,3-diyl | —O— | 4-F₃C-phenyl |
| 1080 | —CH₂— | piperidin-1,3-diyl | —O— | 2,3-diF-phenyl |
| 1081 | —CH₂— | piperidin-1,3-diyl | —O— | 2,4-diF-phenyl |
| 1082 | —CH₂— | piperidin-1,3-diyl | —O— | 2,5-diF-phenyl |
| 1083 | —CH₂— | piperidin-1,3-diyl | —O— | 2,6-diF-phenyl |
| 1084 | —CH₂— | piperidin-1,3-diyl | —O— | 3,4-diF-phenyl |
| 1085 | —CH₂— | piperidin-1,3-diyl | —O— | 3,5-diF-phenyl |
| 1086 | —CH₂— | piperidin-1,3-diyl | —O— | 2,3-diCl-phenyl |
| 1087 | —CH₂— | piperidin-1,3-diyl | —O— | 2,4-diCl-phenyl |
| 1088 | —CH₂— | piperidin-1,3-diyl | —O— | 2,5-diCl-phenyl |
| 1089 | —CH₂— | piperidin-1,3-diyl | —O— | 2,6-diCl-phenyl |
| 1090 | —CH₂— | piperidin-1,3-diyl | —O— | 3,4-diCl-phenyl |
| 1091 | —CH₂— | piperidin-1,3-diyl | —O— | 3,5-diCl-phenyl |
| 1092 | —CH₂— | piperidin-1,3-diyl | —O— | 2-Cl-3-F-phenyl |
| 1093 | —CH₂— | piperidin-1,3-diyl | —O— | 2-Cl-4-F-phenyl |
| 1094 | —CH₂— | piperidin-1,3-diyl | —O— | 2-Cl-5-F-phenyl |
| 1095 | —CH₂— | piperidin-1,3-diyl | —O— | 3-Cl-4-F-phenyl |
| 1096 | —CH₂— | piperidin-1,3-diyl | —O— | 3-Cl-5-F-phenyl |
| 1097 | —CH₂— | piperidin-1,3-diyl | —O— | 4-Cl-2-F-phenyl |
| 1098 | —CH₂— | piperidin-1,3-diyl | —O— | 4-Cl-3-F-phenyl |
| 1099 | —CH₂— | piperidin-1,3-diyl | —O— | 2,3-diMeO-phenyl |
| 1100 | —CH₂— | piperidin-1,3-diyl | —O— | 2,4-diMeO-phenyl |
| 1101 | —CH₂— | piperidin-1,3-diyl | —O— | 2,5-diMeO-phenyl |
| 1102 | —CH₂— | piperidin-1,3-diyl | —O— | 2,6-diMeO-phenyl |
| 1103 | —CH₂— | piperidin-1,3-diyl | —O— | 3,4-diMeO-phenyl |
| 1104 | —CH₂— | piperidin-1,3-diyl | —O— | 3,5-diMeO-phenyl |

TABLE 1-continued

| | | | | |
|---|---|---|---|---|
| 1105 | —CH₂— | piperidin-1,3-diyl | —O— | Cyclopropyl |
| 1106 | —CH₂— | piperidin-1,3-diyl | —O— | Cyclobutyl |
| 1107 | —CH₂— | piperidin-1,3-diyl | —O— | Cyclopentyl |
| 1108 | —CH₂— | piperidin-1,3-diyl | —O— | Cyclohexyl |
| 1109 | —CH₂— | piperidin-1,3-diyl | —O— | 2-furanyl |
| 1110 | —CH₂— | piperidin-1,3-diyl | —O— | 2-thienyl |
| 1111 | —CH₂— | piperidin-1,3-diyl | CH₂CH₂ | 2-imidazolyl |
| 1112 | —CH₂— | piperidin-1,3-diyl | —O— | 2-pyridyl |
| 1113 | —CH₂— | piperidin-1,3-diyl | —O— | 3-pyridyl |
| 1114 | —CH₂— | piperidin-1,3-diyl | —O— | 4-pyridyl |
| 1115 | —CH₂— | piperidin-1,3-diyl | CH₂CH₂ | N-morpholinyl |
| 1116 | —CH₂— | piperidin-1,3-diyl | CH₂CH₂ | N-piperidinyl |
| 1117 | —CH₂— | piperidin-1,3-diyl | —O— | 3-Me-2-pyridyl |
| 1118 | —CH₂— | piperidin-1,3-diyl | —O— | 4-Me-2-pyridyl |
| 1119 | —CH₂— | piperidin-1,3-diyl | CH₂CH₂ | 1-indolyl |
| 1120 | —CH₂— | piperidin-1,3-diyl | —O— | 2-benzothienyl |
| 1121 | —CH₂— | piperidin-1,3-diyl | —O— | 2-benzofuranyl |
| 1122 | —CH₂— | piperidin-1,3-diyl | CH₂CH₂ | 1-benzimidazole |
| 1123 | —CH₂— | piperidin-1,3-diyl | —O— | 2-naphthyl |
| 1124 | —CH₂— | piperidin-3,1-diyl | —O— | Phenyl |
| 1125 | —CH₂— | piperidin-3,1-diyl | —O— | 3,3-diphenylmethyl |
| 1126 | —CH₂— | piperidin-3,1-diyl | —O— | 2-F-phenyl |
| 1127 | —CH₂— | piperidin-3,1-diyl | —O— | 3-F-phenyl |
| 1128 | —CH₂— | piperidin-3,1-diyl | —O— | 4-F-phenyl |
| 1129 | —CH₂— | piperidin-3,1-diyl | —O— | 2-Cl-phenyl |
| 1130 | —CH₂— | piperidin-3,1-diyl | —O— | 3-Cl-phenyl |
| 1131 | —CH₂— | piperidin-3,1-diyl | —O— | 4-Cl-phenyl |
| 1132 | —CH₂— | piperidin-3,1-diyl | —O— | 2-Me-phenyl |
| 1133 | —CH₂— | piperidin-3,1-diyl | —O— | 3-Me-phenyl |
| 1134 | —CH₂— | piperidin-3,1-diyl | —O— | 4-Me-phenyl |
| 1135 | —CH₂— | piperidin-3,1-diyl | —O— | 2-MeO-phenyl |
| 1136 | —CH₂— | piperidin-3,1-diyl | —O— | 3-MeO-phenyl |
| 1137 | —CH₂— | piperidin-3,1-diyl | —O— | 4-MeO-phenyl |
| 1138 | —CH₂— | piperidin-3,1-diyl | —O— | 2-MeS-phenyl |
| 1139 | —CH₂— | piperidin-3,1-diyl | —O— | 3-MeS-phenyl |
| 1140 | —CH₂— | piperidin-3,1-diyl | —O— | 4-MeS-phenyl |
| 1141 | —CH₂— | piperidin-3,1-diyl | —O— | 2-F₃C-phenyl |
| 1142 | —CH₂— | piperidin-3,1-diyl | —O— | 3-F₃C-phenyl |
| 1143 | —CH₂— | piperidin-3,1-diyl | —O— | 4-F₃C-phenyl |
| 1144 | —CH₂— | piperidin-3,1-diyl | —O— | 2,3-diF-phenyl |
| 1145 | —CH₂— | piperidin-3,1-diyl | —O— | 2,4-diF-phenyl |
| 1146 | —CH₂— | piperidin-3,1-diyl | —O— | 2,5-diF-phenyl |
| 1147 | —CH₂— | piperidin-3,1-diyl | —O— | 2,6-diF-phenyl |
| 1148 | —CH₂— | piperidin-3,1-diyl | —O— | 3,4-diF-phenyl |
| 1149 | —CH₂— | piperidin-3,1-diyl | —O— | 3,5-diF-phenyl |
| 1150 | —CH₂— | piperidin-3,1-diyl | —O— | 2,3-diCl-phenyl |
| 1151 | —CH₂— | piperidin-3,1-diyl | —O— | 2,4-diCl-phenyl |
| 1152 | —CH₂— | piperidin-3,1-diyl | —O— | 2,5-diCl-phenyl |
| 1153 | —CH₂— | piperidin-3,1-diyl | —O— | 2,6-diCl-phenyl |
| 1154 | —CH₂— | piperidin-3,1-diyl | —O— | 3,4-diCl-phenyl |
| 1155 | —CH₂— | piperidin-3,1-diyl | —O— | 3,5-diCl-phenyl |
| 1156 | —CH₂— | piperidin-3,1-diyl | —O— | 2-Cl-3-F-phenyl |
| 1157 | —CH₂— | piperidin-3,1-diyl | —O— | 2-Cl-4-F-phenyl |
| 1158 | —CH₂— | piperidin-3,1-diyl | —O— | 2-Cl-5-F-phenyl |
| 1159 | —CH₂— | piperidin-3,1-diyl | —O— | 3-Cl-4-F-phenyl |
| 1160 | —CH₂— | piperidin-3,1-diyl | —O— | 3-Cl-5-F-phenyl |
| 1161 | —CH₂— | piperidin-3,1-diyl | —O— | 4-Cl-2-F-phenyl |
| 1162 | —CH₂— | piperidin-3,1-diyl | —O— | 4-Cl-3-F-phenyl |
| 1163 | —CH₂— | piperidin-3,1-diyl | —O— | 2,3-diMeO-phenyl |
| 1164 | —CH₂— | piperidin-3,1-diyl | —O— | 2,4-diMeO-phenyl |
| 1165 | —CH₂— | piperidin-3,1-diyl | —O— | 2,5-diMeO-phenyl |
| 1166 | —CH₂— | piperidin-3,1-diyl | —O— | 2,6-diMeO-phenyl |
| 1167 | —CH₂— | piperidin-3,1-diyl | —O— | 3,4-diMeO-phenyl |
| 1168 | —CH₂— | piperidin-3,1-diyl | —O— | 3,5-diMeO-phenyl |
| 1169 | —CH₂— | piperidin-3,1-diyl | —O— | Cyclopropyl |
| 1170 | —CH₂— | piperidin-3,1-diyl | —O— | Cyclobutyl |
| 1171 | —CH₂— | piperidin-3,1-diyl | —O— | Cyclopentyl |
| 1172 | —CH₂— | piperidin-3,1-diyl | —O— | Cyclohexyl |
| 1173 | —CH₂— | piperidin-3,1-diyl | —O— | 2-furanyl |
| 1174 | —CH₂— | piperidin-3,1-diyl | —O— | 2-thienyl |
| 1175 | —CH₂— | piperidin-3,1-diyl | CH₂CH₂ | 2-imidazolyl |
| 1176 | —CH₂— | piperidin-3,1-diyl | —O— | 2-pyridyl |
| 1177 | —CH₂— | piperidin-3,1-diyl | —O— | 3-pyridyl |
| 1178 | —CH₂— | piperidin-3,1-diyl | —O— | 4-pyridyl |
| 1179 | —CH₂— | piperidin-3,1-diyl | CH₂CH₂ | N-morpholinyl |
| 1180 | —CH₂— | piperidin-3,1-diyl | CH₂CH₂ | N-piperidinyl |
| 1181 | —CH₂— | piperidin-3,1-diyl | —O— | 3-Me-2-pyridyl |
| 1182 | —CH₂— | piperidin-3,1-diyl | —O— | 4-Me-2-pyridyl |
| 1183 | —CH₂— | piperidin-3,1-diyl | CH₂CH₂ | 1-indolyl |

TABLE 1-continued

| | | | | |
|---|---|---|---|---|
| 1184 | —CH$_2$— | piperidin-3,1-diyl | —O— | 2-benzothienyl |
| 1185 | —CH$_2$— | piperidin-3,1-diyl | —O— | 2-benzofuranyl |
| 1186 | —CH$_2$— | piperidin-3,1-diyl | CH$_2$CH$_2$ | 1-benzimidazole |
| 1187 | —CH$_2$— | piperidin-3,1-diyl | —O— | 2-naphthyl |
| 1188 | —CH$_2$— | cyclohex-1,3-diyl | —O— | Phenyl |
| 1189 | —CH$_2$— | cyclohex-1,3-diyl | —O— | 3,3-diphenylmethyl |
| 1190 | —CH$_2$— | cyclohex-1,3-diyl | —O— | 2-F-phenyl |
| 1191 | —CH$_2$— | cyclohex-1,3-diyl | —O— | 3-F-phenyl |
| 1192 | —CH$_2$— | cyclohex-1,3-diyl | —O— | 4-F-phenyl |
| 1193 | —CH$_2$— | cyclohex-1,3-diyl | —O— | 2-Cl-phenyl |
| 1194 | —CH$_2$— | cyclohex-1,3-diyl | —O— | 3-Cl-phenyl |
| 1195 | —CH$_2$— | cyclohex-1,3-diyl | —O— | 4-Cl-phenyl |
| 1196 | —CH$_2$— | cyclohex-1,3-diyl | —O— | 2-Me-phenyl |
| 1197 | —CH$_2$— | cyclohex-1,3-diyl | —O— | 3-Me-phenyl |
| 1198 | —CH$_2$— | cyclohex-1,3-diyl | —O— | 4-Me-phenyl |
| 1199 | —CH$_2$— | cyclohex-1,3-diyl | —O— | 2-MeO-phenyl |
| 1200 | —CH$_2$— | cyclohex-1,3-diyl | —O— | 3-MeO-phenyl |
| 1201 | —CH$_2$— | cyclohex-1,3-diyl | —O— | 4-MeO-phenyl |
| 1202 | —CH$_2$— | cyclohex-1,3-diyl | —O— | 2-MeS-phenyl |
| 1203 | —CH$_2$— | cyclohex-1,3-diyl | —O— | 3-MeS-phenyl |
| 1204 | —CH$_2$— | cyclohex-1,3-diyl | —O— | 4-MeS-phenyl |
| 1205 | —CH$_2$— | cyclohex-1,3-diyl | —O— | 2-F$_3$C-phenyl |
| 1206 | —CH$_2$— | cyclohex-1,3-diyl | —O— | 3-F$_3$C-phenyl |
| 1207 | —CH$_2$— | cyclohex-1,3-diyl | —O— | 4-F$_3$C-phenyl |
| 1208 | —CH$_2$— | cyclohex-1,3-diyl | —O— | 2,3-diF-phenyl |
| 1209 | —CH$_2$— | cyclohex-1,3-diyl | —O— | 2,4-diF-phenyl |
| 1210 | —CH$_2$— | cyclohex-1,3-diyl | —O— | 2,5-diF-phenyl |
| 1211 | —CH$_2$— | cyclohex-1,3-diyl | —O— | 2,6-diF-phenyl |
| 1212 | —CH$_2$— | cyclohex-1,3-diyl | —O— | 3,4-diF-phenyl |
| 1213 | —CH$_2$— | cyclohex-1,3-diyl | —O— | 3,5-diF-phenyl |
| 1214 | —CH$_2$— | cyclohex-1,3-diyl | —O— | 2,3-diCl-phenyl |
| 1215 | —CH$_2$— | cyclohex-1,3-diyl | —O— | 2,4-diCl-phenyl |
| 1216 | —CH$_2$— | cyclohex-1,3-diyl | —O— | 2,5-diCl-phenyl |
| 1217 | —CH$_2$— | cyclohex-1,3-diyl | —O— | 2,6-diCl-phenyl |
| 1218 | —CH$_2$— | cyclohex-1,3-diyl | —O— | 3,4-diCl-phenyl |
| 1219 | —CH$_2$— | cyclohex-1,3-diyl | —O— | 3,5-diCl-phenyl |
| 1220 | —CH$_2$— | cyclohex-1,3-diyl | —O— | 2-Cl-3-F-phenyl |
| 1221 | —CH$_2$— | cyclohex-1,3-diyl | —O— | 2-Cl-4-F-phenyl |
| 1222 | —CH$_2$— | cyclohex-1,3-diyl | —O— | 2-Cl-5-F-phenyl |
| 1223 | —CH$_2$— | cyclohex-1,3-diyl | —O— | 3-Cl-4-F-phenyl |
| 1224 | —CH$_2$— | cyclohex-1,3-diyl | —O— | 3-Cl-5-F-phenyl |
| 1225 | —CH$_2$— | cyclohex-1,3-diyl | —O— | 4-Cl-2-F-phenyl |
| 1226 | —CH$_2$— | cyclohex-1,3-diyl | —O— | 4-Cl-3-F-phenyl |
| 1227 | —CH$_2$— | cyclohex-1,3-diyl | —O— | 2,3-diMeO-phenyl |
| 1228 | —CH$_2$— | cyclohex-1,3-diyl | —O— | 2,4-diMeO-phenyl |
| 1229 | —CH$_2$— | cyclohex-1,3-diyl | —O— | 2,5-diMeO-phenyl |
| 1230 | —CH$_2$— | cyclohex-1,3-diyl | —O— | 2,6-diMeO-phenyl |
| 1231 | —CH$_2$— | cyclohex-1,3-diyl | —O— | 3,4-diMeO-phenyl |
| 1232 | —CH$_2$— | cyclohex-1,3-diyl | —O— | 3,5-diMeO-phenyl |
| 1233 | —CH$_2$— | cyclohex-1,3-diyl | —O— | Cyclopropyl |
| 1234 | —CH$_2$— | cyclohex-1,3-diyl | —O— | Cyclobutyl |
| 1235 | —CH$_2$— | cyclohex-1,3-diyl | —O— | Cyclopentyl |
| 1236 | —CH$_2$— | cyclohex-1,3-diyl | —O— | Cyclohexyl |
| 1237 | —CH$_2$— | cyclohex-1,3-diyl | —O— | 2-furanyl |
| 1238 | —CH$_2$— | cyclohex-1,3-diyl | —O— | 2-thienyl |
| 1239 | —CH$_2$— | cyclohex-1,3-diyl | CH$_2$CH$_2$ | 2-imidazolyl |
| 1240 | —CH$_2$— | cyclohex-1,3-diyl | —O— | 2-pyridyl |
| 1241 | —CH$_2$— | cyclohex-1,3-diyl | —O— | 3-pyridyl |
| 1242 | —CH$_2$— | cyclohex-1,3-diyl | —O— | 4-pyridyl |
| 1243 | —CH$_2$— | cyclohex-1,3-diyl | CH$_2$CH$_2$ | N-morpholinyl |
| 1244 | —CH$_2$— | cyclohex-1,3-diyl | CH$_2$CH$_2$ | N-piperidinyl |
| 1245 | —CH$_2$— | cyclohex-1,3-diyl | —O— | 3-Me-2-pyridyl |
| 1246 | —CH$_2$— | cyclohex-1,3-diyl | —O— | 4-Me-2-pyridyl |
| 1247 | —CH$_2$— | cyclohex-1,3-diyl | CH$_2$CH$_2$ | 1-indolyl |
| 1248 | —CH$_2$— | cyclohex-1,3-diyl | —O— | 2-benzothienyl |
| 1249 | —CH$_2$— | cyclohex-1,3-diyl | —O— | 2-benzofuranyl |
| 1250 | —CH$_2$— | cyclohex-1,3-diyl | CH$_2$CH$_2$ | 1-benzimidazole |
| 1251 | —CH$_2$— | cyclohex-1,3-diyl | —O— | 2-naphthyl |
| 1252 | —CH$_2$— | cyclopropan-1,2-diyl | —O— | Phenyl |
| 1253 | —CH$_2$— | cyclopropan-1,2-diyl | —O— | 3,3-diphenylmethyl |
| 1254 | —CH$_2$— | cyclopropan-1,2-diyl | —O— | 2-F-phenyl |
| 1255 | —CH$_2$— | cyclopropan-1,2-diyl | —O— | 3-F-phenyl |
| 1256 | —CH$_2$— | cyclopropan-1,2-diyl | —O— | 4-F-phenyl |
| 1257 | —CH$_2$— | cyclopropan-1,2-diyl | —O— | 2-Cl-phenyl |
| 1258 | —CH$_2$— | cyclopropan-1,2-diyl | —O— | 3-Cl-phenyl |
| 1259 | —CH$_2$— | cyclopropan-1,2-diyl | —O— | 4-Cl-phenyl |
| 1260 | —CH$_2$— | cyclopropan-1,2-diyl | —O— | 2-Me-phenyl |
| 1261 | —CH$_2$— | cyclopropan-1,2-diyl | —O— | 3-Me-phenyl |
| 1262 | —CH$_2$— | cyclopropan-1,2-diyl | —O— | 4-Me-phenyl |

TABLE 1-continued

| | | | | |
|---|---|---|---|---|
| 1263 | —CH$_2$— | cyclopropan-1,2-diyl | —O— | 2-MeO-phenyl |
| 1264 | —CH$_2$— | cyclopropan-1,2-diyl | —O— | 3-MeO-phenyl |
| 1265 | —CH$_2$— | cyclopropan-1,2-diyl | —O— | 4-MeO-phenyl |
| 1266 | —CH$_2$— | cyclopropan-1,2-diyl | —O— | 2-MeS-phenyl |
| 1267 | —CH$_2$— | cyclopropan-1,2-diyl | —O— | 3-MeS-phenyl |
| 1268 | —CH$_2$— | cyclopropan-1,2-diyl | —O— | 4-MeS-phenyl |
| 1269 | —CH$_2$— | cyclopropan-1,2-diyl | —O— | 2-F$_3$C-phenyl |
| 1270 | —CH$_2$— | cyclopropan-1,2-diyl | —O— | 3-F$_3$C-phenyl |
| 1271 | —CH$_2$— | cyclopropan-1,2-diyl | —O— | 4-F$_3$C-phenyl |
| 1272 | —CH$_2$— | cyclopropan-1,2-diyl | —O— | 2,3-diF-phenyl |
| 1273 | —CH$_2$— | cyclopropan-1,2-diyl | —O— | 2,4-diF-phenyl |
| 1274 | —CH$_2$— | cyclopropan-1,2-diyl | —O— | 2,5-diF-phenyl |
| 1275 | —CH$_2$— | cyclopropan-1,2-diyl | —O— | 2,6-diF-phenyl |
| 1276 | —CH$_2$— | cyclopropan-1,2-diyl | —O— | 3,4-diF-phenyl |
| 1277 | —CH$_2$— | cyclopropan-1,2-diyl | —O— | 3,5-diF-phenyl |
| 1278 | —CH$_2$— | cyclopropan-1,2-diyl | —O— | 2,3-diCl-phenyl |
| 1279 | —CH$_2$— | cyclopropan-1,2-diyl | —O— | 2,4-diCl-phenyl |
| 1280 | —CH$_2$— | cyclopropan-1,2-diyl | —O— | 2,5-diCl-phenyl |
| 1281 | —CH$_2$— | cyclopropan-1,2-diyl | —O— | 2,6-diCl-phenyl |
| 1282 | —CH$_2$— | cyclopropan-1,2-diyl | —O— | 3,4-diCl-phenyl |
| 1283 | —CH$_2$— | cyclopropan-1,2-diyl | —O— | 3,5-diCl-phenyl |
| 1284 | —CH$_2$— | cyclopropan-1,2-diyl | —O— | 2-Cl-3-F-phenyl |
| 1285 | —CH$_2$— | cyclopropan-1,2-diyl | —O— | 2-Cl-4-F-phenyl |
| 1286 | —CH$_2$— | cyclopropan-1,2-diyl | —O— | 2-Cl-5-F-phenyl |
| 1287 | —CH$_2$— | cyclopropan-1,2-diyl | —O— | 3-Cl-4-F-phenyl |
| 1288 | —CH$_2$— | cyclopropan-1,2-diyl | —O— | 3-Cl-5-F-phenyl |
| 1289 | —CH$_2$— | cyclopropan-1,2-diyl | —O— | 4-Cl-2-F-phenyl |
| 1290 | —CH$_2$— | cyclopropan-1,2-diyl | —O— | 4-Cl-3-F-phenyl |
| 1291 | —CH$_2$— | cyclopropan-1,2-diyl | —O— | 2,3-diMeO-phenyl |
| 1292 | —CH$_2$— | cyclopropan-1,2-diyl | —O— | 2,4-diMeO-phenyl |
| 1293 | —CH$_2$— | cyclopropan-1,2-diyl | —O— | 2,5-diMeO-phenyl |
| 1294 | —CH$_2$— | cyclopropan-1,2-diyl | —O— | 2,6-diMeO-phenyl |
| 1295 | —CH$_2$— | cyclopropan-1,2-diyl | —O— | 3,4-diMeO-phenyl |
| 1296 | —CH$_2$— | cyclopropan-1,2-diyl | —O— | 3,5-diMeO-phenyl |
| 1297 | —CH$_2$— | cyclopropan-1,2-diyl | —O— | Cyclopropyl |
| 1298 | —CH$_2$— | cyclopropan-1,2-diyl | —O— | Cyclobutyl |
| 1299 | —CH$_2$— | cyclopropan-1,2-diyl | —O— | Cyclopentyl |
| 1300 | —CH$_2$— | cyclopropan-1,2-diyl | —O— | Cyclohexyl |
| 1301 | —CH$_2$— | cyclopropan-1,2-diyl | —O— | 2-furanyl |
| 1302 | —CH$_2$— | cyclopropan-1,2-diyl | —O— | 2-thienyl |
| 1303 | —CH$_2$— | cyclopropan-1,2-diyl | CH$_2$CH$_2$ | 2-imidazolyl |
| 1304 | —CH$_2$— | cyclopropan-1,2-diyl | —O— | 2-pyridyl |
| 1305 | —CH$_2$— | cyclopropan-1,2-diyl | —O— | 3-pyridyl |
| 1306 | —CH$_2$— | cyclopropan-1,2-diyl | —O— | 4-pyridyl |
| 1307 | —CH$_2$— | cyclopropan-1,2-diyl | CH$_2$CH$_2$ | N-morpholinyl |
| 1308 | —CH$_2$— | cyclopropan-1,2-diyl | CH$_2$CH$_2$ | N-piperidinyl |
| 1309 | —CH$_2$— | cyclopropan-1,2-diyl | —O— | 3-Me-2-pyridyl |
| 1310 | —CH$_2$— | cyclopropan-1,2-diyl | —O— | 4-Me-2-pyridyl |
| 1311 | —CH$_2$— | cyclopropan-1,2-diyl | CH$_2$CH$_2$ | 1-indolyl |
| 1312 | —CH$_2$— | cyclopropan-1,2-diyl | —O— | 2-benzothienyl |
| 1313 | —CH$_2$— | cyclopropan-1,2-diyl | —O— | 2-benzofuranyl |
| 1314 | —CH$_2$— | cyclopropan-1,2-diyl | CH$_2$CH$_2$ | 1-benzimidazole |
| 1315 | —CH$_2$— | cyclopropan-1,2-diyl | —O— | 2-naphthyl |
| 1316 | —CH$_2$— | cyclopentan-1,3-diyl | —O— | Phenyl |
| 1317 | —CH$_2$— | cyclopentan-1,3-diyl | —O— | 3,3-diphenylmethyl |
| 1318 | —CH$_2$— | cyclopentan-1,3-diyl | —O— | 2-F-phenyl |
| 1319 | —CH$_2$— | cyclopentan-1,3-diyl | —O— | 3-F-phenyl |
| 1320 | —CH$_2$— | cyclopentan-1,3-diyl | —O— | 4-F-phenyl |
| 1321 | —CH$_2$— | cyclopentan-1,3-diyl | —O— | 2-Cl-phenyl |
| 1322 | —CH$_2$— | cyclopentan-1,3-diyl | —O— | 3-Cl-phenyl |
| 1323 | —CH$_2$— | cyclopentan-1,3-diyl | —O— | 4-Cl-phenyl |
| 1324 | —CH$_2$— | cyclopentan-1,3-diyl | —O— | 2-Me-phenyl |
| 1325 | —CH$_2$— | cyclopentan-1,3-diyl | —O— | 3-Me-phenyl |
| 1326 | —CH$_2$— | cyclopentan-1,3-diyl | —O— | 4-Me-phenyl |
| 1327 | —CH$_2$— | cyclopentan-1,3-diyl | —O— | 2-MeO-phenyl |
| 1328 | —CH$_2$— | cyclopentan-1,3-diyl | —O— | 3-MeO-phenyl |
| 1329 | —CH$_2$— | cyclopentan-1,3-diyl | —O— | 4-MeO-phenyl |
| 1330 | —CH$_2$— | cyclopentan-1,3-diyl | —O— | 2-MeS-phenyl |
| 1331 | —CH$_2$— | cyclopentan-1,3-diyl | —O— | 3-MeS-phenyl |
| 1332 | —CH$_2$— | cyclopentan-1,3-diyl | —O— | 4-MeS-phenyl |
| 1333 | —CH$_2$— | cyclopentan-1,3-diyl | —O— | 2-F$_3$C-phenyl |
| 1334 | —CH$_2$— | cyclopentan-1,3-diyl | —O— | 3-F$_3$C-phenyl |
| 1335 | —CH$_2$— | cyclopentan-1,3-diyl | —O— | 4-F$_3$C-phenyl |
| 1336 | —CH$_2$— | cyclopentan-1,3-diyl | —O— | 2,3-diF-phenyl |
| 1337 | —CH$_2$— | cyclopentan-1,3-diyl | —O— | 2,4-diF-phenyl |
| 1338 | —CH$_2$— | cyclopentan-1,3-diyl | —O— | 2,5-diF-phenyl |
| 1339 | —CH$_2$— | cyclopentan-1,3-diyl | —O— | 2,6-diF-phenyl |
| 1340 | —CH$_2$— | cyclopentan-1,3-diyl | —O— | 3,4-diF-phenyl |
| 1341 | —CH$_2$— | cyclopentan-1,3-diyl | —O— | 3,5-diF-phenyl |

TABLE 1-continued

| | | | |
|---|---|---|---|
| 1342 —$CH_2$— | cyclopentan-1,3-diyl | —O— | 2,3-diCl-phenyl |
| 1343 —$CH_2$— | cyclopentan-1,3-diyl | —O— | 2,4-diCl-phenyl |
| 1344 —$CH_2$— | cyclopentan-1,3-diyl | —O— | 2,5-diCl-phenyl |
| 1345 —$CH_2$— | cyclopentan-1,3-diyl | —O— | 2,6-diCl-phenyl |
| 1346 —$CH_2$— | cyclopentan-1,3-diyl | —O— | 3,4-diCl-phenyl |
| 1347 —$CH_2$— | cyclopentan-1,3-diyl | —O— | 3,5-diCl-phenyl |
| 1348 —$CH_2$— | cyclopentan-1,3-diyl | —O— | 2-Cl-3-F-phenyl |
| 1349 —$CH_2$— | cyclopentan-1,3-diyl | —O— | 2-Cl-4-F-phenyl |
| 1350 —$CH_2$— | cyclopentan-1,3-diyl | —O— | 2-Cl-5-F-phenyl |
| 1351 —$CH_2$— | cyclopentan-1,3-diyl | —O— | 3-Cl-4-F-phenyl |
| 1352 —$CH_2$— | cyclopentan-1,3-diyl | —O— | 3-Cl-5-F-phenyl |
| 1353 —$CH_2$— | cyclopentan-1,3-diyl | —O— | 4-Cl-2-F-phenyl |
| 1354 —$CH_2$— | cyclopentan-1,3-diyl | —O— | 4-Cl-3-F-phenyl |
| 1355 —$CH_2$— | cyclopentan-1,3-diyl | —O— | 2,3-diMeO-phenyl |
| 1356 —$CH_2$— | cyclopentan-1,3-diyl | —O— | 2,4-diMeO-phenyl |
| 1357 —$CH_2$— | cyclopentan-1,3-diyl | —O— | 2,5-diMeO-phenyl |
| 1358 —$CH_2$— | cyclopentan-1,3-diyl | —O— | 2,6-diMeO-phenyl |
| 1359 —$CH_2$— | cyclopentan-1,3-diyl | —O— | 3,4-diMeO-phenyl |
| 1360 —$CH_2$— | cyclopentan-1,3-diyl | —O— | 3,5-diMeO-phenyl |
| 1361 —$CH_2$— | cyclopentan-1,3-diyl | —O— | Cyclopropyl |
| 1362 —$CH_2$— | cyclopentan-1,3-diyl | —O— | Cyclobutyl |
| 1363 —$CH_2$— | cyclopentan-1,3-diyl | —O— | Cyclopentyl |
| 1364 —$CH_2$— | cyclopentan-1,3-diyl | —O— | Cyclohexyl |
| 1365 —$CH_2$— | cyclopentan-1,3-diyl | —O— | 2-furanyl |
| 1366 —$CH_2$— | cyclopentan-1,3-diyl | —O— | 2-thienyl |
| 1367 —$CH_2$— | cyclopentan-1,3-diyl | $CH_2CH_2$ | 2-imidazolyl |
| 1368 —$CH_2$— | cyclopentan-1,3-diyl | —O— | 2-pyridyl |
| 1369 —$CH_2$— | cyclopentan-1,3-diyl | —O— | 3-pyridyl |
| 1370 —$CH_2$— | cyclopentan-1,3-diyl | —O— | 4-pyridyl |
| 1371 —$CH_2$— | cyclopentan-1,3-diyl | $CH_2CH_2$ | N-morpholinyl |
| 1372 —$CH_2$— | cyclopentan-1,3-diyl | $CH_2CH_2$ | N-piperidinyl |
| 1373 —$CH_2$— | cyclopentan-1,3-diyl | —O— | 3-Me-2-pyridyl |
| 1374 —$CH_2$— | cyclopentan-1,3-diyl | —O— | 4-Me-2-pyridyl |
| 1375 —$CH_2$— | cyclopentan-1,3-diyl | $CH_2CH_2$ | 1-indolyl |
| 1376 —$CH_2$— | cyclopentan-1,3-diyl | —O— | 2-benzothienyl |
| 1377 —$CH_2$— | cyclopentan-1,3-diyl | —O— | 2-benzofuranyl |
| 1378 —$CH_2$— | cyclopentan-1,3-diyl | $CH_2CH_2$ | 1-benzimidazole |
| 1379 —$CH_2$— | cyclopentan-1,3-diyl | —O— | 2-naphthyl |
| 1380 —$CH_2$— | bond | bond | phenyl |
| 1381 —$CH_2$— | bond | bond | 3,3-diphenyl |
| 1382 —$CH_2$— | bond | bond | 2-F-phenyl |
| 1383 —$CH_2$— | bond | bond | 3-F-phenyl |
| 1384 —$CH_2$— | bond | bond | 4-F-phenyl |
| 1385 —$CH_2$— | bond | bond | 2-Cl-phenyl |
| 1386 —$CH_2$— | bond | bond | 3-Cl-phenyl |
| 1387 —$CH_2$— | bond | bond | 4-Cl-phenyl |
| 1388 —$CH_2$— | bond | bond | 2-Me-phenyl |
| 1389 —$CH_2$— | bond | bond | 3-Me-phenyl |
| 1390 —$CH_2$— | bond | bond | 4-Me-phenyl |
| 1391 —$CH_2$— | bond | bond | 2-MeO-phenyl |
| 1392 —$CH_2$— | bond | bond | 3-MeO-phenyl |
| 1393 —$CH_2$— | bond | bond | 4-MeO-phenyl |
| 1394 —$CH_2$— | bond | bond | 2-MeS-phenyl |
| 1395 —$CH_2$— | bond | bond | 3-MeS-phenyl |
| 1396 —$CH_2$— | bond | bond | 4-MeS-phenyl |
| 1397 —$CH_2$— | bond | bond | 2-$F_3$C-phenyl |
| 1398 —$CH_2$— | bond | bond | 3-$F_3$C-phenyl |
| 1399 —$CH_2$— | bond | bond | 4-$F_3$C-phenyl |
| 1400 —$CH_2$— | bond | bond | 2,3-diF-phenyl |
| 1401 —$CH_2$— | bond | bond | 2,4-diF-phenyl |
| 1402 —$CH_2$— | bond | bond | 2,5-diF-phenyl |
| 1403 —$CH_2$— | bond | bond | 2,6-diF-phenyl |
| 1404 —$CH_2$— | bond | bond | 3,4-diF-phenyl |
| 1405 —$CH_2$— | bond | bond | 3,5-diF-phenyl |
| 1406 —$CH_2$— | bond | bond | 2,3-diCl-phenyl |
| 1407 —$CH_2$— | bond | bond | 2,4-diCl-phenyl |
| 1408 —$CH_2$— | bond | bond | 2,5-diCl-phenyl |
| 1409 —$CH_2$— | bond | bond | 2,6-diCl-phenyl |
| 1410 —$CH_2$— | bond | bond | 3,4-diCl-phenyl |
| 1411 —$CH_2$— | bond | bond | 3,5-diCl-phenyl |
| 1412 —$CH_2$— | bond | bond | 2-Cl-3-F-phenyl |
| 1413 —$CH_2$— | bond | bond | 2-Cl-4-F-phenyl |
| 1414 —$CH_2$— | bond | bond | 2-Cl-5-F-phenyl |
| 1415 —$CH_2$— | bond | bond | 3-Cl-4-F-phenyl |
| 1416 —$CH_2$— | bond | bond | 3-Cl-5-F-phenyl |
| 1417 —$CH_2$— | bond | bond | 4-Cl-2-F-phenyl |
| 1418 —$CH_2$— | bond | bond | 4-Cl-3-F-phenyl |
| 1419 —$CH_2$— | bond | bond | 2,3-diMeO-phenyl |
| 1420 —$CH_2$— | bond | bond | 2,4-diMeO-phenyl |

TABLE 1-continued

| | | | | |
|---|---|---|---|---|
| 1421 | —CH$_2$— | bond | bond | 2,5-diMeO-phenyl |
| 1422 | —CH$_2$— | bond | bond | 2,6-diMeO-phenyl |
| 1423 | —CH$_2$— | bond | bond | 3,4-diMeO-phenyl |
| 1424 | —CH$_2$— | bond | bond | 3,5-diMeO-phenyl |
| 1425 | —CH$_2$— | bond | bond | cyclopropyl |
| 1426 | —CH$_2$— | bond | bond | cyclobutyl |
| 1427 | —CH$_2$— | bond | bond | cyclopentyl |
| 1428 | —CH$_2$— | bond | bond | cyclohexyl |
| 1429 | —CH$_2$— | bond | bond | 2-furanyl |
| 1430 | —CH$_2$— | bond | bond | 2-thienyl |
| 1431 | —CH$_2$— | bond | bond | 2-imidazolyl |
| 1432 | —CH$_2$— | bond | bond | 2-pyridyl |
| 1433 | —CH$_2$— | bond | bond | 3-pyridyl |
| 1434 | —CH$_2$— | bond | bond | 4-pyridyl |
| 1435 | —CH$_2$— | bond | bond | N-morpholinyl |
| 1436 | —CH$_2$— | bond | bond | N-piperidinyl |
| 1437 | —CH$_2$— | bond | bond | 3-Me-2-pyridyl |
| 1438 | —CH$_2$— | bond | bond | 4-Me-2-pyridyl |
| 1439 | —CH$_2$— | bond | bond | 1-indolyl |
| 1440 | —CH$_2$— | bond | bond | 2-benzothienyl |
| 1441 | —CH$_2$— | bond | bond | 2-benzofuranyl |
| 1442 | —CH$_2$— | bond | bond | 1-benzimidazole |
| 1443 | —CH$_2$— | bond | bond | 2-naphthyl |
| 1444 | —CH$_2$CH$_2$— | bond | bond | phenyl |
| 1445 | —CH$_2$CH$_2$— | bond | bond | 3,3-diphenyl |
| 1446 | —CH$_2$CH$_2$— | bond | bond | 2-F-phenyl |
| 1447 | —CH$_2$CH$_2$— | bond | bond | 3-F-phenyl |
| 1448 | —CH$_2$CH$_2$— | bond | bond | 4-F-phenyl |
| 1449 | —CH$_2$CH$_2$— | bond | bond | 2-Cl-phenyl |
| 1450 | —CH$_2$CH$_2$— | bond | bond | 3-Cl-phenyl |
| 1451 | —CH$_2$CH$_2$— | bond | bond | 4-Cl-phenyl |
| 1452 | —CH$_2$CH$_2$— | bond | bond | 2-Me-phenyl |
| 1453 | —CH$_2$CH$_2$— | bond | bond | 3-Me-phenyl |
| 1454 | —CH$_2$CH$_2$— | bond | bond | 4-Me-phenyl |
| 1455 | —CH$_2$CH$_2$— | bond | bond | 2-MeO-phenyl |
| 1456 | —CH$_2$CH$_2$— | bond | bond | 3-MeO-phenyl |
| 1457 | —CH$_2$CH$_2$— | bond | bond | 4-MeO-phenyl |
| 1458 | —CH$_2$CH$_2$— | bond | bond | 2-MeS-phenyl |
| 1459 | —CH$_2$CH$_2$— | bond | bond | 3-MeS-phenyl |
| 1460 | —CH$_2$CH$_2$— | bond | bond | 4-MeS-phenyl |
| 1461 | —CH$_2$CH$_2$— | bond | bond | 2-F$_3$C-phenyl |
| 1462 | —CH$_2$CH$_2$— | bond | bond | 3-F$_3$C-phenyl |
| 1463 | —CH$_2$CH$_2$— | bond | bond | 4-F$_3$C-phenyl |
| 1464 | —CH$_2$CH$_2$— | bond | bond | 2,3-diF-phenyl |
| 1465 | —CH$_2$CH$_2$— | bond | bond | 2,4-diF-phenyl |
| 1466 | —CH$_2$CH$_2$— | bond | bond | 2,5-diF-phenyl |
| 1467 | —CH$_2$CH$_2$— | bond | bond | 2,6-diF-phenyl |
| 1468 | —CH$_2$CH$_2$— | bond | bond | 3,4-diF-phenyl |
| 1469 | —CH$_2$CH$_2$— | bond | bond | 3,5-diF-phenyl |
| 1470 | —CH$_2$CH$_2$— | bond | bond | 2,3-diCl-phenyl |
| 1471 | —CH$_2$CH$_2$— | bond | bond | 2,4-diCl-phenyl |
| 1472 | —CH$_2$CH$_2$— | bond | bond | 2,5-diCl-phenyl |
| 1473 | —CH$_2$CH$_2$— | bond | bond | 2,6-diCl-phenyl |
| 1474 | —CH$_2$CH$_2$— | bond | bond | 3,4-diCl-phenyl |
| 1475 | —CH$_2$CH$_2$— | bond | bond | 3,5-diCl-phenyl |
| 1476 | —CH$_2$CH$_2$— | bond | bond | 2-Cl-3-F-phenyl |
| 1477 | —CH$_2$CH$_2$— | bond | bond | 2-Cl-4-F-phenyl |
| 1478 | —CH$_2$CH$_2$— | bond | bond | 2-Cl-5-F-phenyl |
| 1479 | —CH$_2$CH$_2$— | bond | bond | 3-Cl-4-F-phenyl |
| 1480 | —CH$_2$CH$_2$— | bond | bond | 3-Cl-5-F-phenyl |
| 1481 | —CH$_2$CH$_2$— | bond | bond | 4-Cl-2-F-phenyl |
| 1482 | —CH$_2$CH$_2$— | bond | bond | 4-Cl-3-F-phenyl |
| 1483 | —CH$_2$CH$_2$— | bond | bond | 2,3-diMeO-phenyl |
| 1484 | —CH$_2$CH$_2$— | bond | bond | 2,4-diMeO-phenyl |
| 1485 | —CH$_2$CH$_2$— | bond | bond | 2,5-diMeO-phenyl |
| 1486 | —CH$_2$CH$_2$— | bond | bond | 2,6-diMeO-phenyl |
| 1487 | —CH$_2$CH$_2$— | bond | bond | 3,4-diMeO-phenyl |
| 1488 | —CH$_2$CH$_2$— | bond | bond | 3,5-diMeO-phenyl |
| 1489 | —CH$_2$CH$_2$— | bond | bond | cyclopropyl |
| 1490 | —CH$_2$CH$_2$— | bond | bond | cyclobutyl |
| 1491 | —CH$_2$CH$_2$— | bond | bond | cyclopentyl |
| 1492 | —CH$_2$CH$_2$— | bond | bond | cyclohexyl |
| 1493 | —CH$_2$CH$_2$— | bond | bond | 2-furanyl |
| 1494 | —CH$_2$CH$_2$— | bond | bond | 2-thienyl |
| 1495 | —CH$_2$CH$_2$— | bond | bond | 2-imidazolyl |
| 1496 | —CH$_2$CH$_2$— | bond | bond | 2-pyridyl |
| 1497 | —CH$_2$CH$_2$— | bond | bond | 3-pyridyl |
| 1498 | —CH$_2$CH$_2$— | bond | bond | 4-pyridyl |
| 1499 | —CH$_2$CH$_2$— | bond | bond | N-morpholinyl |

TABLE 1-continued

| | | | | |
|---|---|---|---|---|
| 1500 | —CH$_2$CH$_2$— | bond | bond | N-piperidinyl |
| 1501 | —CH$_2$CH$_2$— | bond | bond | 3-Me-2-pyridyl |
| 1502 | —CH$_2$CH$_2$— | bond | bond | 4-Me-2-pyridyl |
| 1503 | —CH$_2$CH$_2$— | bond | bond | 1-indolyl |
| 1504 | —CH$_2$CH$_2$— | bond | bond | 2-benzothienyl |
| 1505 | —CH$_2$CH$_2$— | bond | bond | 2-benzofuranyl |
| 1506 | —CH$_2$CH$_2$— | bond | bond | 1-benzimidazole |
| 1507 | —CH$_2$CH$_2$— | bond | bond | 2-naphthyl |
| 1508 | —CH$_2$CH$_2$CH$_2$— | bond | bond | phenyl |
| 1509 | —CH$_2$CH$_2$CH$_2$— | bond | bond | 3,3-diphenyl |
| 1510 | —CH$_2$CH$_2$CH$_2$— | bond | bond | 2-F-phenyl |
| 1511 | —CH$_2$CH$_2$CH$_2$— | bond | bond | 3-F-phenyl |
| 1512 | —CH$_2$CH$_2$CH$_2$— | bond | bond | 4-F-phenyl |
| 1513 | —CH$_2$CH$_2$CH$_2$— | bond | bond | 2-Cl-phenyl |
| 1514 | —CH$_2$CH$_2$CH$_2$— | bond | bond | 3-Cl-phenyl |
| 1515 | —CH$_2$CH$_2$CH$_2$— | bond | bond | 4-Cl-phenyl |
| 1516 | —CH$_2$CH$_2$CH$_2$— | bond | bond | 2-Me-phenyl |
| 1517 | —CH$_2$CH$_2$CH$_2$— | bond | bond | 3-Me-phenyl |
| 1518 | —CH$_2$CH$_2$CH$_2$— | bond | bond | 4-Me-phenyl |
| 1519 | —CH$_2$CH$_2$CH$_2$— | bond | bond | 2-MeO-phenyl |
| 1520 | —CH$_2$CH$_2$CH$_2$— | bond | bond | 3-MeO-phenyl |
| 1521 | —CH$_2$CH$_2$CH$_2$— | bond | bond | 4-MeO-phenyl |
| 1522 | —CH$_2$CH$_2$CH$_2$— | bond | bond | 2-MeS-phenyl |
| 1523 | —CH$_2$CH$_2$CH$_2$— | bond | bond | 3-MeS-phenyl |
| 1524 | —CH$_2$CH$_2$CH$_2$— | bond | bond | 4-MeS-phenyl |
| 1525 | —CH$_2$CH$_2$CH$_2$— | bond | bond | 2-F$_3$C-phenyl |
| 1526 | —CH$_2$CH$_2$CH$_2$— | bond | bond | 3-F$_3$C-phenyl |
| 1527 | —CH$_2$CH$_2$CH$_2$— | bond | bond | 4-F$_3$C-phenyl |
| 1528 | —CH$_2$CH$_2$CH$_2$— | bond | bond | 2,3-diF-phenyl |
| 1529 | —CH$_2$CH$_2$CH$_2$— | bond | bond | 2,4-diF-phenyl |
| 1530 | —CH$_2$CH$_2$CH$_2$— | bond | bond | 2,5-diF-phenyl |
| 1531 | —CH$_2$CH$_2$CH$_2$— | bond | bond | 2,6-diF-phenyl |
| 1532 | —CH$_2$CH$_2$CH$_2$— | bond | bond | 3,4-diF-phenyl |
| 1533 | —CH$_2$CH$_2$CH$_2$— | bond | bond | 3,5-diF-phenyl |
| 1534 | —CH$_2$CH$_2$CH$_2$— | bond | bond | 2,3-diCl-phenyl |
| 1535 | —CH$_2$CH$_2$CH$_2$— | bond | bond | 2,4-diCl-phenyl |
| 1536 | —CH$_2$CH$_2$CH$_2$— | bond | bond | 2,5-diCl-phenyl |
| 1537 | —CH$_2$CH$_2$CH$_2$— | bond | bond | 2,6-diCl-phenyl |
| 1538 | —CH$_2$CH$_2$CH$_2$— | bond | bond | 3,4-diCl-phenyl |
| 1539 | —CH$_2$CH$_2$CH$_2$— | bond | bond | 3,5-diCl-phenyl |
| 1540 | —CH$_2$CH$_2$CH$_2$— | bond | bond | 2-Cl-3-F-phenyl |
| 1541 | —CH$_2$CH$_2$CH$_2$— | bond | bond | 2-Cl-4-F-phenyl |
| 1542 | —CH$_2$CH$_2$CH$_2$— | bond | bond | 2-Cl-5-F-phenyl |
| 1543 | —CH$_2$CH$_2$CH$_2$— | bond | bond | 3-Cl-4-F-phenyl |
| 1544 | —CH$_2$CH$_2$CH$_2$— | bond | bond | 3-Cl-5-F-phenyl |
| 1545 | —CH$_2$CH$_2$CH$_2$— | bond | bond | 4-Cl-2-F-phenyl |
| 1546 | —CH$_2$CH$_2$CH$_2$— | bond | bond | 4-Cl-3-F-phenyl |
| 1547 | —CH$_2$CH$_2$CH$_2$— | bond | bond | 2,3-diMeO-phenyl |
| 1548 | —CH$_2$CH$_2$CH$_2$— | bond | bond | 2,4-diMeO-phenyl |
| 1549 | —CH$_2$CH$_2$CH$_2$— | bond | bond | 2,5-diMeO-phenyl |
| 1550 | —CH$_2$CH$_2$CH$_2$— | bond | bond | 2,6-diMeO-phenyl |
| 1551 | —CH$_2$CH$_2$CH$_2$— | bond | bond | 3,4-diMeO-phenyl |
| 1552 | —CH$_2$CH$_2$CH$_2$— | bond | bond | 3,5-diMeO-phenyl |
| 1553 | —CH$_2$CH$_2$CH$_2$— | bond | bond | cyclopropyl |
| 1554 | —CH$_2$CH$_2$CH$_2$— | bond | bond | cyclobutyl |
| 1555 | —CH$_2$CH$_2$CH$_2$— | bond | bond | cyclopentyl |
| 1556 | —CH$_2$CH$_2$CH$_2$— | bond | bond | cyclohexyl |
| 1557 | —CH$_2$CH$_2$CH$_2$— | bond | bond | 2-furanyl |
| 1558 | —CH$_2$CH$_2$CH$_2$— | bond | bond | 2-thienyl |
| 1559 | —CH$_2$CH$_2$CH$_2$— | bond | bond | 2-imidazolyl |
| 1560 | —CH$_2$CH$_2$CH$_2$— | bond | bond | 2-pyridyl |
| 1561 | —CH$_2$CH$_2$CH$_2$— | bond | bond | 3-pyridyl |
| 1562 | —CH$_2$CH$_2$CH$_2$— | bond | bond | 4-pyridyl |
| 1563 | —CH$_2$CH$_2$CH$_2$— | bond | bond | N-morpholinyl |
| 1564 | —CH$_2$CH$_2$CH$_2$— | bond | bond | N-piperidinyl |
| 1565 | —CH$_2$CH$_2$CH$_2$— | bond | bond | 3-Me-2-pyridyl |
| 1566 | —CH$_2$CH$_2$CH$_2$— | bond | bond | 4-Me-2-pyridyl |
| 1567 | —CH$_2$CH$_2$CH$_2$— | bond | bond | 1-indolyl |
| 1568 | —CH$_2$CH$_2$CH$_2$— | bond | bond | 2-benzothienyl |
| 1569 | —CH$_2$CH$_2$CH$_2$— | bond | bond | 2-benzofuranyl |
| 1570 | —CH$_2$CH$_2$CH$_2$— | bond | bond | 1-benzimidazole |
| 1571 | —CH$_2$CH$_2$CH$_2$— | bond | bond | 2-naphthyl |
| 1572 | —CH$_2$CH$_2$— | bond | —O— | phenyl |
| 1573 | —CH$_2$CH$_2$— | bond | —O— | 3,3-diphenylmethyl |
| 1574 | —CH$_2$CH$_2$— | bond | —O— | 2-F-phenyl |
| 1575 | —CH$_2$CH$_2$— | bond | —O— | 3-F-phenyl |
| 1576 | —CH$_2$CH$_2$— | bond | —O— | 4-F-phenyl |
| 1577 | —CH$_2$CH$_2$— | bond | —O— | 2-Cl-phenyl |
| 1578 | —CH$_2$CH$_2$— | bond | —O— | 3-Cl-phenyl |

TABLE 1-continued

| | | | | |
|---|---|---|---|---|
| 1579 | —CH$_2$CH$_2$— | bond | —O— | 4-Cl-phenyl |
| 1580 | —CH$_2$CH$_2$— | bond | —O— | 2-Me-phenyl |
| 1581 | —CH$_2$CH$_2$— | bond | —O— | 3-Me-phenyl |
| 1582 | —CH$_2$CH$_2$— | bond | —O— | 4-Me-phenyl |
| 1583 | —CH$_2$CH$_2$— | bond | —O— | 2-MeO-phenyl |
| 1584 | —CH$_2$CH$_2$— | bond | —O— | 3-MeO-phenyl |
| 1585 | —CH$_2$CH$_2$— | bond | —O— | 4-MeO-phenyl |
| 1586 | —CH$_2$CH$_2$— | bond | —O— | 2-MeS-phenyl |
| 1587 | —CH$_2$CH$_2$— | bond | —O— | 3-MeS-phenyl |
| 1588 | —CH$_2$CH$_2$— | bond | —O— | 4-MeS-phenyl |
| 1589 | —CH$_2$CH$_2$— | bond | —O— | 2-F$_3$C-phenyl |
| 1590 | —CH$_2$CH$_2$— | bond | —O— | 3-F$_3$C-phenyl |
| 1591 | —CH$_2$CH$_2$— | bond | —O— | 4-F$_3$C-phenyl |
| 1592 | —CH$_2$CH$_2$— | bond | —O— | 2,3-diF-phenyl |
| 1593 | —CH$_2$CH$_2$— | bond | —O— | 2,4-diF-phenyl |
| 1594 | —CH$_2$CH$_2$— | bond | —O— | 2,5-diF-phenyl |
| 1595 | —CH$_2$CH$_2$— | bond | —O— | 2,6-diF-phenyl |
| 1596 | —CH$_2$CH$_2$— | bond | —O— | 3,4-diF-phenyl |
| 1597 | —CH$_2$CH$_2$— | bond | —O— | 3,5-diF-phenyl |
| 1598 | —CH$_2$CH$_2$— | bond | —O— | 2,3-diCl-phenyl |
| 1599 | —CH$_2$CH$_2$— | bond | —O— | 2,4-diCl-phenyl |
| 1600 | —CH$_2$CH$_2$— | bond | —O— | 2,5-diCl-phenyl |
| 1601 | —CH$_2$CH$_2$— | bond | —O— | 2,6-diCl-phenyl |
| 1602 | —CH$_2$CH$_2$— | bond | —O— | 3,4-diCl-phenyl |
| 1603 | —CH$_2$CH$_2$— | bond | —O— | 3,5-diCl-phenyl |
| 1604 | —CH$_2$CH$_2$— | bond | —O— | 2-Cl-3-F-phenyl |
| 1605 | —CH$_2$CH$_2$— | bond | —O— | 2-Cl-4-F-phenyl |
| 1606 | —CH$_2$CH$_2$— | bond | —O— | 2-Cl-5-F-phenyl |
| 1607 | —CH$_2$CH$_2$— | bond | —O— | 3-Cl-4-F-phenyl |
| 1608 | —CH$_2$CH$_2$— | bond | —O— | 3-Cl-5-F-phenyl |
| 1609 | —CH$_2$CH$_2$— | bond | —O— | 4-Cl-2-F-phenyl |
| 1610 | —CH$_2$CH$_2$— | bond | —O— | 4-Cl-3-F-phenyl |
| 1611 | —CH$_2$CH$_2$— | bond | —O— | 2,3-diMeO-phenyl |
| 1612 | —CH$_2$CH$_2$— | bond | —O— | 2,4-diMeO-phenyl |
| 1613 | —CH$_2$CH$_2$— | bond | —O— | 2,5-diMeO-phenyl |
| 1614 | —CH$_2$CH$_2$— | bond | —O— | 2,6-diMeO-phenyl |
| 1615 | —CH$_2$CH$_2$— | bond | —O— | 3,4-diMeO-phenyl |
| 1616 | —CH$_2$CH$_2$— | bond | —O— | 3,5-diMeO-phenyl |
| 1617 | —CH$_2$CH$_2$— | bond | —O— | cyclopropyl |
| 1618 | —CH$_2$CH$_2$— | bond | —O— | cyclobutyl |
| 1619 | —CH$_2$CH$_2$— | bond | —O— | cyclopentyl |
| 1620 | —CH$_2$CH$_2$— | bond | —O— | cyclohexyl |
| 1621 | —CH$_2$CH$_2$— | bond | —O— | 2-furanyl |
| 1622 | —CH$_2$CH$_2$— | bond | —O— | 2-thienyl |
| 1623 | —CH$_2$CH$_2$— | bond | —O— | 2-pyridyl |
| 1624 | —CH$_2$CH$_2$— | bond | —O— | 3-pyridyl |
| 1625 | —CH$_2$CH$_2$— | bond | —O— | 4-pyridyl |
| 1626 | —CH$_2$CH$_2$— | bond | —O— | 3-Me-2-pyridyl |
| 1627 | —CH$_2$CH$_2$— | bond | —O— | 4-Me-2-pyridyl |
| 1628 | —CH$_2$CH$_2$— | bond | —O— | 2-benzothienyl |
| 1629 | —CH$_2$CH$_2$— | bond | —O— | 2-benzofuranyl |
| 1630 | —CH$_2$CH$_2$— | bond | —O— | 2-naphthyl |
| 1631 | —CH$_2$CH$_2$CH$_2$— | bond | —O— | phenyl |
| 1632 | —CH$_2$CH$_2$CH$_2$— | bond | —O— | 3,3-diphenylmethyl |
| 1633 | —CH$_2$CH$_2$CH$_2$— | bond | —O— | 2-F-phenyl |
| 1634 | —CH$_2$CH$_2$CH$_2$— | bond | —O— | 3-F-phenyl |
| 1635 | —CH$_2$CH$_2$CH$_2$— | bond | —O— | 4-F-phenyl |
| 1636 | —CH$_2$CH$_2$CH$_2$— | bond | —O— | 2-Cl-phenyl |
| 1637 | —CH$_2$CH$_2$CH$_2$— | bond | —O— | 3-Cl-phenyl |
| 1638 | —CH$_2$CH$_2$CH$_2$— | bond | —O— | 4-Cl-phenyl |
| 1639 | —CH$_2$CH$_2$CH$_2$— | bond | —O— | 2-Me-phenyl |
| 1640 | —CH$_2$CH$_2$CH$_2$— | bond | —O— | 3-Me-phenyl |
| 1641 | —CH$_2$CH$_2$CH$_2$— | bond | —O— | 4-Me-phenyl |
| 1642 | —CH$_2$CH$_2$CH$_2$— | bond | —O— | 2-MeO-phenyl |
| 1643 | —CH$_2$CH$_2$CH$_2$— | bond | —O— | 3-MeO-phenyl |
| 1644 | —CH$_2$CH$_2$CH$_2$— | bond | —O— | 4-MeO-phenyl |
| 1645 | —CH$_2$CH$_2$CH$_2$— | bond | —O— | 2-MeS-phenyl |
| 1646 | —CH$_2$CH$_2$CH$_2$— | bond | —O— | 3-MeS-phenyl |
| 1647 | —CH$_2$CH$_2$CH$_2$— | bond | —O— | 4-MeS-phenyl |
| 1648 | —CH$_2$CH$_2$CH$_2$— | bond | —O— | 2-F$_3$C-phenyl |
| 1649 | —CH$_2$CH$_2$CH$_2$— | bond | —O— | 3-F$_3$C-phenyl |
| 1650 | —CH$_2$CH$_2$CH$_2$— | bond | —O— | 4-F$_3$C-phenyl |
| 1651 | —CH$_2$CH$_2$CH$_2$— | bond | —O— | 2,3-diF-phenyl |
| 1652 | —CH$_2$CH$_2$CH$_2$— | bond | —O— | 2,4-diF-phenyl |
| 1653 | —CH$_2$CH$_2$CH$_2$— | bond | —O— | 2,5-diF-phenyl |
| 1654 | —CH$_2$CH$_2$CH$_2$— | bond | —O— | 2,6-diF-phenyl |
| 1655 | —CH$_2$CH$_2$CH$_2$— | bond | —O— | 3,4-diF-phenyl |
| 1656 | —CH$_2$CH$_2$CH$_2$— | bond | —O— | 3,5-diF-phenyl |
| 1657 | —CH$_2$CH$_2$CH$_2$— | bond | —O— | 2,3-diCl-phenyl |

TABLE 1-continued

| | | | | |
|---|---|---|---|---|
| 1658 | —CH₂CH₂CH₂— | bond | —O— | 2,4-diCl-phenyl |
| 1659 | —CH₂CH₂CH₂— | bond | —O— | 2,5-diCl-phenyl |
| 1660 | —CH₂CH₂CH₂— | bond | —O— | 2,6-diCl-phenyl |
| 1661 | —CH₂CH₂CH₂— | bond | —O— | 3,4-diCl-phenyl |
| 1662 | —CH₂CH₂CH₂— | bond | —O— | 3,5-diCl-phenyl |
| 1663 | —CH₂CH₂CH₂— | bond | —O— | 2-Cl-3-F-phenyl |
| 1664 | —CH₂CH₂CH₂— | bond | —O— | 2-Cl-4-F-phenyl |
| 1665 | —CH₂CH₂CH₂— | bond | —O— | 2-Cl-5-F-phenyl |
| 1666 | —CH₂CH₂CH₂— | bond | —O— | 3-Cl-4-F-phenyl |
| 1667 | —CH₂CH₂CH₂— | bond | —O— | 3-Cl-5-F-phenyl |
| 1668 | —CH₂CH₂CH₂— | bond | —O— | 4-Cl-2-F-phenyl |
| 1669 | —CH₂CH₂CH₂— | bond | —O— | 4-Cl-3-F-phenyl |
| 1670 | —CH₂CH₂CH₂— | bond | —O— | 2,3-diMeO-phenyl |
| 1671 | —CH₂CH₂CH₂— | bond | —O— | 2,4-diMeO-phenyl |
| 1672 | —CH₂CH₂CH₂— | bond | —O— | 2,5-diMeO-phenyl |
| 1673 | —CH₂CH₂CH₂— | bond | —O— | 2,6-diMeO-phenyl |
| 1674 | —CH₂CH₂CH₂— | bond | —O— | 3,4-diMeO-phenyl |
| 1675 | —CH₂CH₂CH₂— | bond | —O— | 3,5-diMeO-phenyl |
| 1676 | —CH₂CH₂CH₂— | bond | —O— | cyclopropyl |
| 1677 | —CH₂CH₂CH₂— | bond | —O— | cyclobutyl |
| 1678 | —CH₂CH₂CH₂— | bond | —O— | cyclopentyl |
| 1679 | —CH₂CH₂CH₂— | bond | —O— | cyclohexyl |
| 1680 | —CH₂CH₂CH₂— | bond | —O— | 2-furanyl |
| 1681 | —CH₂CH₂CH₂— | bond | —O— | 2-thienyl |
| 1682 | —CH₂CH₂CH₂— | bond | —O— | 2-pyridyl |
| 1683 | —CH₂CH₂CH₂— | bond | —O— | 3-pyridyl |
| 1684 | —CH₂CH₂CH₂— | bond | —O— | 4-pyridyl |
| 1685 | —CH₂CH₂CH₂— | bond | —O— | 3-Me-2-pyridyl |
| 1686 | —CH₂CH₂CH₂— | bond | —O— | 4-Me-2-pyridyl |
| 1687 | —CH₂CH₂CH₂— | bond | —O— | 2-benzothienyl |
| 1688 | —CH₂CH₂CH₂— | bond | —O— | 2-benzofuranyl |
| 1689 | —CH₂CH₂CH₂— | bond | —O— | 2-naphthyl |

What is claimed is:

1. A compound of Formula (I):

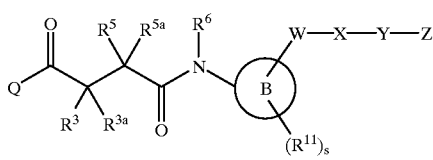

(I)

or a pharmaceutically acceptable salt thereof, wherein:
Q is —NR$^1$R$^2$;
ring B is

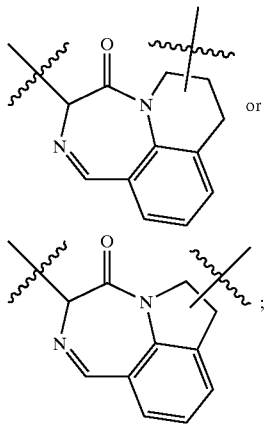

;

s is 0, 1, or 2;
R$^1$, at each occurrence, is independently selected from:
H;
C$_1$–C$_6$ alkyl substituted with 0–3 R$^{1a}$;
C$_2$–C$_6$ alkenyl substituted with 0–3 R$^{1a}$;
C$_3$–C$_{10}$ carbocycle substituted with 0–3 R$^{1b}$;
aryl substituted with 0–3 R$^{1b}$; and
5 to 10 membered heterocycle substituted with 0–3 R$^{1b}$;

R$^{1a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$;
C$_3$–C$_{10}$ carbocycle substituted with 0–3 R$^{1b}$;
aryl substituted with 0–3 R$^{1b}$; and
5 to 6 membered heterocycle substituted with 0–3 R$^{1b}$;

R$^{1b}$, at each occurrence, is independently selected from H, OH, Cl, F, Br, I, CN, NO$_2$, NR$^{15}$R$^{16}$, CF$_3$, C$_1$–C$_6$ alkyl, C$_1$–C$_4$ alkoxy, C$_1$–C$_4$ haloalkyl, and C$_1$–C$_4$ haloalkoxy;

R$^2$ is independently selected from H, NH$_2$, OH, C$_1$–C$_6$ alkyl, C$_1$–C$_6$ alkoxy, phenoxy, benzyloxy, C$_3$–C$_{10}$ carbocycle, aryl and 5 to 10 membered heterocycle;

R$^3$ is —(CR$^7$R$^{7a}$)$_n$—R$^4$,
—(CR$^7$R$^{7a}$)$_n$—S—(CR$^7$R$^{7a}$)$_m$—R$^4$,
—(CR$^7$R$^{7a}$)$_n$—O—(CR$^7$R$^{7a}$)$_m$—R$^4$,
—(CR$^7$R$^{7a}$)$_n$—N(R$^{7b}$)—(CR$^7$R$^{7a}$)$_m$—R$^4$,
—(CR$^7$R$^{7a}$)$_n$—S(=O)—(CR$^7$R$^{7a}$)$_m$—R$^4$,
—(CR$^7$R$^{7a}$)$_n$—S(=O)$_2$—(CR$^7$R$^{7a}$)$_m$—R$^4$,
—(CR$^7$R$^{7a}$)$_n$—C(=O)—(CR$^7$R$^{7a}$)$_m$—R$^4$,
—(CR$^7$R$^{7a}$)$_n$—N(R$^{7b}$)C(=O)—(CR$^7$R$^{7a}$)$_m$—R$^4$,
—(CR$^7$R$^{7a}$)$_n$—C(=O)N(R$^{7b}$)—(CR$^7$R$^{7a}$)$_m$—R$^4$,
—(CR$^7$R$^{7a}$)$_n$—N(R$^{7b}$)S(=O)$_2$—(CR$^7$R$^{7a}$)$_m$—R$^4$, or
—(CR$^7$R$^{7a}$)$_n$—S(=O)$_2$N(R$^{7b}$)—(CR$^7$R$^{7a}$)$_m$—R$^4$;

n is 0, 1, 2, or 3;
m is 0, 1, 2, or 3;
R$^{3a}$ is H, OH, C$_1$–C$_4$ alkyl, C$_1$–C$_4$ alkoxy, or C$_2$–C$_4$ alkenyloxy;
alternatively, R$^3$ and R$^{3a}$ may be combined to form a 3–7 membered carbocyclic moiety;
wherein said 3–7 membered carbocyclic moiety is saturated or partially unsaturated;

wherein said 3–7 membered carbocyclic moiety may optionally contain a heteroatom selected from —O—, —S—, —S(=O)—, —S(=O)$_2$—, —N=, —NH—, and —N(R$^{20}$)—, and wherein said 3–7 membered carbocyclic moiety is substituted with 0–4 R$^4$;

additionally, two R$^4$ substituents on adjacent atoms may be combined to form a benzo fused radical; wherein said benzo fused radical is substituted with 0–4 R$^{23}$;

additionally, two R$^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 R$^{23}$;

additionally, two R$^4$ substituents on the same or adjacent carbon atoms may be combined to form a C$_3$–C$_6$ carbocycle substituted with 0–3 R$^{23}$;

R$^4$ is H, OH, OR$^{14a}$,
C$_1$–C$_6$ alkyl substituted with 0–3 R$^{4a}$,
C$_2$–C$_6$ alkenyl substituted with 0–3 R$^{4a}$,
C$_2$–C$_6$ alkynyl substituted with 0–3 R$^{4a}$,
C$_3$–C$_{10}$ carbocycle substituted with 0–3 R$^{4b}$,
aryl substituted with 0–3 R$^{4b}$, or
5 to 10 membered heterocycle substituted with 0–3 R$^{4b}$;

R$^{4a}$, at each occurrence, is independently selected from is H, F, Cl, Br, I, CF$_3$,
C$_3$–C$_{10}$ carbocycle substituted with 0–3 R$^{4b}$,
aryl substituted with 0–3 R$^{4b}$, or
5 to 10 membered heterocycle substituted with 0–3 R$^{4b}$;

R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

R$^5$ is H, OR$^{14}$;
C$_1$–C$_6$ alkyl substituted with 0–3 R$^{5b}$;
C$_1$–C$_6$ alkoxy substituted with 0–3 R$^{5b}$;
C$_2$–C$_6$ alkenyl substituted with 0–3 R$^{5b}$;
C$_2$–C$_6$ alkynyl substituted with 0–3 R$^{5b}$;
C$_3$–C$_{10}$ carbocycle substituted with 0–3 R$^{5c}$;
aryl substituted with 0–3 R$^{5C}$; or
5 to 10 membered heterocycle substituted with 0–3 R$^{5C}$;

R$^{5a}$ is H, OH, C$_1$–C$_4$ alkyl, C$_1$–C$_4$ alkoxy, C$_2$–C$_4$ alkenyl, or C$_2$–C$_4$ alkenyloxy;

R$^{5b}$, at each occurrence, is independently selected from: H, C$_1$–C$_6$ alkyl, CF$_3$, OR$^{14}$, Cl, F, Br, I, =O, CN, NO$_2$, NR$^{15}$R$^{16}$;
C$_3$–C$_{10}$ carbocycle substituted with 0–3 R$^{5c}$;
aryl substituted with 0–3 R$^{5c}$; or
5 to 10 membered heterocycle substituted with 0–3 R$^{5c}$;

R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

alternatively, R$^5$ and R$^{5a}$ may be combined to form a 3–7 membered carbocyclic ring substituted with 0–3 R$^{5c}$; optionally the carbocyclic ring formed by combining R$^5$ and R$^{5a}$ may be benzo fused, wherein the benzo fused ring may be substituted with 0–3 R$^{5c}$;

R$^6$ is H;
C$_1$–C$_6$ alkyl substituted with 0–3 R$^{6a}$;
C$_3$–C$_{10}$ carbocycle substituted with 0–3 R$^{6b}$; or
aryl substituted with 0–3 R$^{6b}$;

R$^{6a}$, at each occurrence, is independently selected from H, C$_1$–C$_6$ alkyl, OR$^{14}$, Cl, F, Br, I, =O, CN, NO$_2$, NR$^{15}$R$^{16}$, phenyl or CF$_3$;

R$^{6b}$, at each occurrence, is independently selected from H, OH, Cl, F, Br, I, CN, NO$_2$, NR$^{15}$R$^{16}$, CF$_3$, C$_1$–C$_6$ alkyl, C$_1$–C$_4$ alkoxy, C$_1$–C$_4$ haloalkyl, and C$_1$–C$_4$ haloalkoxy;

R$^7$, at each occurrence, is independently selected from H, OH, Cl, F, Br, I, CN, NO$_2$, CF$_3$, and C$_1$–C$_4$ alkyl;

R$^{7a}$, at each occurrence, is independently selected from H, OH, Cl, F, Br, I, CN, NO$_2$, CF$_3$, aryl and C$_1$–C$_4$ alkyl;

R$^{7b}$ is independently selected from H and C$_1$–C$_4$ alkyl;

W is —(CR$^8$R$^{8a}$)$_p$—;

p is 0, 1, 2, 3, or 4;

R$^8$ and R$^{8a}$, at each occurrence, are independently selected from H, F, C$_1$–C$_4$ alkyl, C$_2$–C$_4$ alkenyl, C$_2$–C$_4$ alkynyl and C$_3$–C$_8$ cycloalkyl;

X is a bond;
aryl substituted with 0–3 R$^{Xb}$;
C$_3$–C$_{10}$ carbocycle substituted with 0–3 R$^{Xb}$; or
5 to 10 membered heterocycle substituted with 0–2 R$^{Xb}$;

R$^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

Y is a bond or —(CR$^9$R$^{9a}$)$_t$—V—(CR$^9$R$^{9a}$)$_u$—;

t is 0, 1, 2, or 3;

u is 0, 1, 2, or 3;

R$^9$ and R$^{9a}$, at each occurrence, are independently selected from H, F, C$_1$–C$_6$ alkyl or C$_3$–C$_8$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
C$_1$–C$_8$ alkyl substituted with 0–3 R$^{12a}$;
C$_2$–C$_4$ alkenyl substituted with 0–3 R$^{12a}$;
C$_2$–C$_4$ alkynyl substituted with 0–3 R$^{12a}$;
aryl substituted with 0–4 R$^{12a}$;
C$_3$–C$_{10}$ carbocycle substituted with 0–4 R$^{12a}$; or
5 to 10 membered heterocycle substituted with 0–3 R$^{12a}$;

R$^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl—S—, C$_1$–C$_3$ alkyl substituted with 0–1 R$^{12c}$;
aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl—S—;

R$^{12c}$, at each occurrence, is independently selected from aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{11}$, at each occurrence, is independently selected from H, C$_1$–C$_4$ alkoxy, Cl, F, Br, I, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$–C$_6$ alkyl substituted with 0–1 R$^{11a}$;
aryl substituted with 0–3 R$^{11b}$;
C$_3$–C$_{10}$ carbocycle substituted with 0–3 R$^{11b}$; or
5 to 10 membered heterocycle substituted with 0–3 R$^{11b}$;

R$^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or phenyl substituted with 0–3 R$^{11b}$;

R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

R$^{14}$, at each occurrence, is independently selected from H, phenyl, benzyl, C$_1$–C$_6$ alkyl, or C$_2$–C$_6$ alkoxyalkyl;

R$^{14a}$ is H, phenyl, benzyl, or C$_1$–C$_4$ alkyl;

R$^{15}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl);

R$^{16}$, at each occurrence, is independently selected from H, OH, C$_1$–C$_6$ alkyl, benzyl, phenethyl, —C(=O)—(C$_1$–C$_6$ alkyl) and —S(=O)$_2$—(C$_1$–C$_6$ alkyl);

R$^{17}$ is H, aryl, aryl-CH$_2$—, C$_1$–C$_6$ alkyl, or C$_2$–C$_6$ alkoxyalkyl;

R$^{18}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl); and R$^{19}$, at each occurrence, is independently selected from H, OH, C$_1$–C$_6$ alkyl, phenyl, benzyl, phenethyl, —C(=O)—(C$_1$–C$_6$ alkyl) and —S(=O)$_2$—(C$_1$–C$_6$ alkyl); and R$^{19b}$ is H, C$_1$–C$_6$ alkyl, C$_3$–C$_8$ cycloalkyl, phenyl, benzyl or phenethyl;

additionally, R$^{18}$ and R$^{19}$, when substituents on the same atom, may be combined to form a 3 to 7 membered heterocyclic ring;

R$^{20}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
C$_1$–C$_6$ alkyl optionally substituted with 0–3 R$^{20a}$; or
aryl substituted with 0–4 R$^{20b}$;

R$^{20a}$, at each occurrence, is independently selected from H, C$_1$–C$_4$ alkyl, OR$^{14}$, Cl, F, Br, I, =O, CN, NO$_2$, NR$^{15}$R$^{16}$, CF$_3$, or aryl substituted with 0–4 R$^{20b}$;

R$^{20b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_4$ alkoxy, C$_1$–C$_4$ haloalkyl, C$_1$–C$_4$ haloalkoxy, and C$_1$–C$_4$ haloalkyl—S—;

R$^{23}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$.

2. A compound of claim 1 of Formula (Ia):

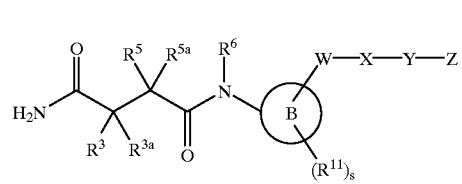

(Ia)

or a pharmaceutically acceptable salt thereof, wherein:
ring B is

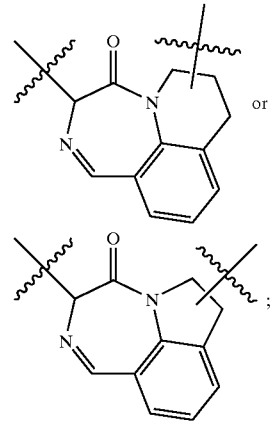

s is 0, 1, or 2;
R$^3$ is —(CR$^7$R$^{7a}$)$_n$—R$^4$,
—(CR$^7$R$^{7a}$)$_n$—S—R$^4$,
—(CR$^7$R$^{7a}$)$_n$—O—R$^4$,
—(CR$^7$R$^{7a}$)$_n$—N(R$^{7b}$)—R$^4$,
—(CR$^7$R$^{7a}$)$_n$—S(=O)—R$^4$,
—(CR$^7$R$^{7a}$)$_n$—S(=O)$_2$—R$^4$, or
—(CR$^7$R$^{7a}$)$_n$—C(=O)—R$^4$;

n is 0, 1, or 2;
R$^{3a}$ is H, OH, C$_1$–C$_4$ alkyl, C$_1$–C$_4$ alkoxy, or C$_2$–C$_4$ alkenyloxy;

alternatively, R$^3$ and R$^{3a}$ may be combined to form a 3–7 membered carbocyclic moiety;
wherein said 3–7 membered carbocyclic moiety is saturated or partially unsaturated;
wherein said 3–7 membered carbocyclic moiety may optionally contain a heteroatom selected from —O—, —S—, —S(=O)—, —S(=O)$_2$—, —N=, —NH—, and —N(R$^{20}$)—, and
wherein said 3–7 membered carbocyclic moiety is substituted with 0–4 R$^4$;

additionally, two R$^4$ substituents on adjacent atoms may be combined to form a benzo fused radical; wherein said benzo fused radical is substituted with 0–4 R$^{23}$;

additionally, two R$^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 R$^{23}$;

additionally, two R$^4$ substituents on the same or adjacent carbon atoms may be combined to form a C$_3$–C$_6$ carbocycle substituted with 0–3 R$^{23}$; p1 R$^4$ is H, OH, OR$^{14a}$,
C$_1$–C$_6$ alkyl substituted with 0–3 R$^{4a}$,
C$_2$–C$_6$ alkenyl substituted with 0–3 R$^{4a}$, $C_2$–$C_6$ alkynyl substituted with 0–3 $R^{4a}$,
$C_3$–$C_{10}$ carbocycle substituted with 0–3 $R^{4b}$,
aryl substituted with 0–3 $R^{4b}$, or
5 to 10 membered heterocycle substituted with 0–3 $R^{4b}$;

$R^{4a}$, at each occurrence, is independently selected from is H, F, Cl, Br, I, $CF_3$,
$C_3$–$C_{10}$ carbocycle substituted with 0–3 $R^{4b}$,
aryl substituted with 0–3 $R^{4b}$, or
5 to 10 membered heterocycle substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

$R^5$ is H;
 $C_1$–$C_6$ alkyl substituted with 0–3 $R^{5b}$;
 $C_2$–$C_6$ alkenyl substituted with 0–3 $R^{5b}$;
 $C_2$–$C_6$ alkynyl substituted with 0–3 $R^{5b}$;
 $C_3$–$C_{10}$ carbocycle substituted with 0–3 $R^{5c}$; or
 aryl substituted with 0–3 $R^{5c}$;

$R^{5a}$ is H, $C_1$–$C_4$ alkyl, or $C_2$–$C_4$ alkenyl;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
 $C_3$–$C_{10}$ carbocycle substituted with 0–3 $R^{5c}$;
 aryl substituted with 0–3 $R^{5c;\ or}$
 5 to 10 membered heterocycle substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

alternatively, $R^5$ and $R^{5a}$ may be combined to form a 3–7 membered carbocyclic ring substituted with 0–3 $R^{5c}$; optionally the carbocyclic ring formed by combining $R^5$ and $R^{5a}$ may be benzo fused, wherein the benzo fused ring may be substituted with 0–3 $R^{5c}$;

$R^6$ is H;
 $C_1$–$C_6$ alkyl substituted with 0–3 $R^{6a}$;
 $C_3$–$C_{10}$ carbocycle substituted with 0–3 $R^{6b}$; or
 aryl substituted with 0–3$R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, phenyl or $CF_3$;

$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

$R^7$, at each occurrence, is independently selected from H, OH, Cl, F, Br, I, CN, $NO_2$, $CF_3$, and $C_1$–$C_4$ alkyl;

$R^{7a}$, at each occurrence, is independently selected from H, OH, Cl, F, Br, I, CN, $NO_2$, $CF_3$, aryl and $C_1$–$C_4$ alkyl;

$R^{7b}$ is independently selected from H and $C_1$–$C_4$ alkyl;

W is —$(CR^8R^{8a})_p$—;

p is 0, 1, 2, or 3;

$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;

X is a bond;
 aryl substituted with 0–3 $R^{Xb}$;
 $C_3$–$C_{10}$ carbocycle substituted with 0–3 $R^{Xb}$; or
 5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

Y is a bond or —$(CR^9R^{9a})_t$—V—$(CR^9R^{9a})_u$—;

t is 0, 1, 2, or 3;

u is 0, 1, 2, or 3;

$R^9$ and $R^{9a}$, at each occurrence, are independently selected from H, F, $C_1$–$C_6$ alkyl or $C_3$–$C_8$ cycloalkyl;

V is a bond, —C(=O)—, —O—, —S—, —S(=O)—, —$S(=O)_2$—, —$N(R^{19})$—, —$C(=O)NR^{19b}$—, —$NR^{19b}C(=O)$—, —$NR^{19b}S(=O)_2$—, —$S(=O)_2NR^{19b}$—, —$NR^{19b}S(=O)$—, —$S(=O)NR^{19b}$—, —C(=O)O—, or —OC(=O)—;

Z is H;
 $C_1$–$C_8$ alkyl substituted with 0–3 $R^{12a}$;
 $C_2$–$C_4$ alkenyl substituted with 0–3 $R^{12a}$;
 $C_2$–$C_4$ alkynyl substituted with 0–3 $R^{12a}$;
 aryl substituted with 0–4 $R^{12a}$;
 $C_3$–$C_{10}$ carbocycle substituted with 0–4 $R^{12a}$; or
 5 to 10 membered heterocycle containing 1 to 4 heteroatoms selected from nitrogen, oxygen, and sulphur, wherein said 5 to 10 membered heterocycle is substituted with 0–3 $R^{12a}$; or $R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
 $C_1$–$C_6$ alkyl, $C_1$–$C_4$ alkoxy, $C_1$–$C_4$ haloalkyl,
 $C_1$–$C_4$ haloalkoxy, $C_1$–$C_4$ haloalkyl—S—,
 $C_1$–$C_3$ alkyl substituted with 0–1 $R^{12c}$;
 aryl substituted with 0–4 $R^{12b}$;
 $C_3$–$C_{10}$ carbocycle substituted with 0–4 $R^{12b}$; or
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF^3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

$R^{12c}$, at each occurrence, is independently selected from aryl substituted with 0–4 $R^{12b}$;
 $C_3$–$C_{10}$ carbocycle substituted with 0–4 $R^{12b}$; or
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{11}$, at each occurrence, is independently selected from H, $C_1$–$C_4$ alkoxy, Cl, F, Br, I, CN, $NO_2$, $NR^{18}R^{19}$, C(=O)$R^{17}$, C(=O)$OR^{17}$, C(=O)$NR^{18}R^{19}$, $S(=O)_2NR^{18}R^{19}$, $CF_3$;
 $C_1$–$C_6$ alkyl substituted with 0–1 $R^{11a}$;
 aryl substituted with 0–3 $R^{11b}$;
 $C_3$–$C_{10}$ carbocycle substituted with 0–3 $R^{11b}$; or
 5 to 10 membered heterocycle substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, SCH₃, S(=O)CH₃, S(=O)₂CH₃, C₁-C₆ alkyl, C₁-C₄ alkoxy, C₁-C₄ haloalkyl, C₁-C₄ haloalkoxy, and C₁-C₄ halothioalkoxy;

$R^{14}$, at each occurrence, is independently selected from H, phenyl, benzyl, C₁-C₆ alkyl, or C₂-C₆ alkoxyalkyl;

$R^{14a}$ is H, phenyl, benzyl, or C₁-C₄ alkyl;

$R^{15}$, at each occurrence, is independently selected from H, C₁-C₆ alkyl, benzyl, phenethyl, —C(=O)—(C₁-C₆ alkyl) and —S(=O)₂—(C₁-C₆ alkyl);

$R^{16}$, at each occurrence, is independently selected from H, OH, C₁-C₆ alkyl, benzyl, phenethyl, —C(=O)—(C₁-C₆ alkyl) and —S(=O)₂—(C₁-C₆ alkyl);

$R^{17}$ is H, aryl, aryl-CH₂—, C₁-C₆ alkyl, or C₂-C₆ alkoxyalkyl;

$R^{18}$, at each occurrence, is independently selected from H, C₁-C₆ alkyl, benzyl, phenethyl, —C(=O)—(C₁-C₆ alkyl) and —S(=O)₂—(C₁-C₆ alkyl); and $R^{19}$, at each occurrence, is independently selected from H, OH, C₁-C₆ alkyl, phenyl, benzyl, phenethyl, —C(=O)—(C₁-C₆ alkyl) and —S(=O)₂—(C₁-C₆ alkyl); and $R^{19b}$ is H, C₁-C₆ alkyl, C₃-C₈ cycloalkyl, phenyl, benzyl or phenethyl;

additionally, $R^{18}$ and $R^{19}$, when substituents on the same atom, may be combined to form a 3 to 7 membered heterocyclic ring;

$R^{20}$ is H, C(=O)$R^{17}$, C(=O)O$R^{17}$, C(=O)N$R^{18}R^{19}$, S(=O)₂N$R^{18}R^{19}$, S(=O)₂$R^{17}$;
C₁-C₆ alkyl optionally substituted with 0–3 $R^{20a}$; or aryl substituted with 0–4 $R^{20b}$;

$R^{20a}$, at each occurrence, is independently selected from H, C₁-C₄ alkyl, O$R^{14}$, Cl, F, Br, I, =O, CN, NO₂, N$R^{15}R^{16}$, CF₃, or aryl substituted with 0–4 $R^{20b}$;

$R^{20b}$, at each occurrence, is independently selected from H, OH, Cl, F, Br, I, CN, NO₂, N$R^{15}R^{16}$, CF₃, acetyl, SCH₃, S(=O)CH₃, S(=O)₂CH₃, C₁-C₄ alkyl, C₁-C₄ alkoxy, C₁-C₄ haloalkyl, C₁-C₄ haloalkoxy, and C₁-C₄ haloalkyl—S—;

$R^{23}$, at each occurrence, is independently selected from H, OH, C₁-C₆ alkyl, C₁-C₄ alkoxy, Cl, F, Br, I, CN, NO₂, N$R^{15}R^{16}$, and CF₃.

3. A compound of claim 2 of Formula (Ia):

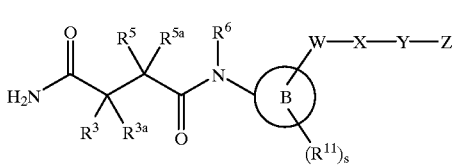

(Ia)

or a pharmaceutically acceptable salt thereof, wherein:
ring B is

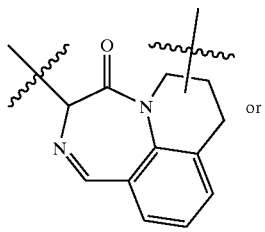 or

-continued

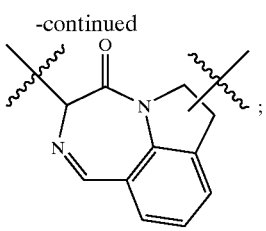;

s is 0, 1, or 2;

$R^3$ is —(CH₂)ₙ—$R^4$;

n is 0, 1, or 2;

$R^{3a}$ is H, OH, methyl, ethyl, propyl, butyl, methoxy, ethoxy, propoxy, or butoxy;

alternatively, $R^3$ and $R^{3a}$ may be combined to form a 3–7 membered carbocyclic moiety;
  wherein said 3–7 membered carbocyclic moiety is saturated or partially unsaturated;
  wherein said 3–7 membered carbocyclic moiety is substituted with 0–2 $R^4$;

$R^4$ is H, OH,
  C₁-C₄ alkyl substituted with 0–2 $R^{4a}$,
  C₂-C₄ alkenyl substituted with 0–2 $R^{4a}$,
  C₂-C₄ alkynyl substituted with 0–1 $R^{4a}$,
  C₃-C₆ cycloklyl substituted with 0–3 $R^{4b}$,
  aryl substituted with 0–3 $R^{4b}$, or
  5 to 6 membered heterocycle substituted with 0–3 $R^{4b}$;

$R^{4a}$, at each occurrence, is independently selected from is H, F, Cl, CF₃,
  C₃-C₆ cycloalkyl substituted with 0–3 $R^{4b}$,
  phenyl substituted with 0–3 $R^{4b}$, or
  5 to 6 membered heterocycle substituted with 0–3 $R^{4b}$;

$R^{4b}$, at each occurrence, is independently selected from H, OH, Cl, F, Br, I, CN, NO₂, N$R^{15}R^{16}$, CF₃, acetyl, SCH₃, S(=O)CH₃, S(=O)₂CH₃, C₁-C₄ alkyl, C₁-C₃ alkoxy, C₁-C₂ haloalkyl, and C₁-C₂ haloalkoxy;

$R^5$ is H;
  C₁-C₄ alkyl substituted with 0–2 $R^{5b}$;
  C₂-C₄ alkenyl substituted with 0–2 $R^{5b}$;
  C₂-C₄ alkynyl substituted with 0–2 $R^{5b}$;
  C₃-C₆ cycloalkyl substituted with 0–2 $R^{5c}$; or
  phenyl substituted with 0–3 $R^{5c}$;

$R^{5a}$ is H, methyl, ethyl, propyl, butyl, or allyl;

$R^{5b}$, at each occurrence, is independently selected from:
  H, methyl, ethyl, propyl, butyl, CF₃, O$R^{14}$,
  C₃-C₆ cycloalkyl substituted with 0–2 $R^{5c}$;
  phenyl substituted with 0–3 $R^{5c}$; or
  5 to 6 membered heterocycle substituted with 0–2 $R^{5c}$;

$R^{5c}$, at each occurrence, is independently selected from H, OH, Cl, F, Br, I, CN, NO₂, N$R^{15}R^{16}$, CF₃, acetyl, SCH₃, S(=O)CH₃, S(=O)₂CH₃, C₁-C₄ alkyl, C₁-C₃ alkoxy, C₁-C₂ haloalkyl, and C₁-C₂ haloalkoxy;

alternatively, $R^5$ and $R^{5a}$ may be combined to form a 3–7 membered carbocyclic ring substituted with 0–3 $R^{5c}$;

W is a bond, —CH₂—, —CH(CH₃)—, —CH₂CH₂— or —CH(CH₃)CH₂—;

X is a bond;
  phenyl substituted with 0–2 $R^{Xb}$;
  C₃-C₆ cycloalkyl substituted with 0–2 $R^{Xb}$; or
  5 to 6 membered heterocycle substituted with 0–2 $R^{Xb}$;

$R^{Xb}$, at each occurrence, is independently selected from H, OH, Cl, F, N$R^{15}R^{16}$, CF₃, acetyl, SCH₃, S(=O)CH₃, S(=O)₂CH₃, C₁-C₄ alkyl, C₁-C₃ alkoxy, C₁-C₂ haloalkyl, and C₁-C₂ haloalkoxy;

Y is a bond, —CH$_2$CH$_2$—V—, —CH$_2$—V—, or —V—;
V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —C(=O)O—, or —OC(=O)—;
Z is H;
C$_1$–C$_8$ alkyl substituted with 0–3 R$^{12a}$;
C$_2$–C$_4$ alkenyl substituted with 0–3 R$^{12a}$;
C$_2$–C$_4$ alkynyl substituted with 0–3 R$^{12a}$;
aryl substituted with 0–4 R$^{12a}$;
C$_3$–C$_{10}$ carbocycle substituted with 0–4 R$^{12a}$; or
5 to 10 membered heterocycle containing 1 to 4 heteroatoms selected from nitrogen, oxygen, and sulphur, wherein said 5 to 10 membered heterocycle is substituted with 0–3 R$^{12a}$; or R$^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$,
C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl—S—,
C$_1$–C$_3$ alkyl substituted with 0–1 R$^{12c}$;
aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_2$ haloalkyl, and C$_1$–C$_2$ haloalkoxy;

R$^{12c}$, at each occurrence, is independently selected from aryl substituted with 0–4 R$^{12b}$;
C$_3$–C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{11}$, at each occurrence, is independently selected from H, C$_1$–C$_4$ alkoxy, Cl, F, NR$^{18}$R$^{19}$, C(=O)R$^{17}$, C(=O)OR$^{17}$, CF$_3$;
C$_1$–C$_4$ alkyl substituted with 0–1 R$^{11a}$;
phenyl substituted with 0–3 R$^{11b}$;
C$_3$–C$_6$ carbocycle substituted with 0–3 R$^{11b}$; or
5 to 6 membered heterocycle substituted with 0–3 R$^{11b}$;

R$^{11a}$, at each occurrence, is independently selected from H, C$_1$–C$_4$ alkyl, OR$^{14}$, F, =O, NR$^{15}$R$^{16}$, CF$_3$, or phenyl substituted with 0–3 R$^{11b}$;

R$^{11b}$, at each occurrence, is independently selected from H, OH, Cl, F, NR$^{15}$R$^{16}$, CF$_3$, C$_1$–C$_4$ alkyl, C$_1$–C$_3$ alkoxy, C$_1$–C$_2$ haloalkyl, and C$_1$–C$_2$ haloalkoxy;

R$^{14}$ is H, phenyl, benzyl, C$_1$–C$_4$ alkyl, or C$_2$–C$_4$ alkoxyalkyl;

R$^{15}$, at each occurrence, is independently selected from H, C$_1$–C$_4$ alkyl, benzyl, phenethyl, —C(=O)—(C$_1$–C$_4$ alkyl) and —S(=O)$_2$—(C$_1$–C$_4$ alkyl);

R$^{16}$, at each occurrence, is independently selected from H, OH, C$_1$–C$_4$ alkyl, benzyl, phenethyl, —C(=O)—(C$_1$–C$_4$ alkyl) and —S(=O)$_2$—(C$_1$–C$_4$ alkyl);

R$^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;

R$^{18}$, at each occurrence, is independently selected from H, methyl, ethyl, propyl, butyl, phenyl, benzyl, and phenethyl; and R$^{19}$, at each occurrence, is independently selected from H, methyl, and ethyl;

R$^{19b}$ is H, mehyl, ethyl, propyl, butyl, cyclopropyl, cyclobutyl, cyclopentyl, phenyl, benzyl or phenethyl;

additionally, R$^{18}$ and R$^{19}$, when substituents on the same atom, may be combined to form a 3 to 7 membered heterocyclic ring.

4. A compound of claim 3 of Formula (I*a*):

or a pharmaceutically acceptable salt thereof, wherein:
ring B is s is 0, 1, or 2;
R$^3$ is —R$^4$, —CH$_2$—R$^4$, or —CH$_2$CH$_2$—R$^4$;
R$^{3a}$ is H;
alternatively, R$^3$ and R$^{3a}$ may be combined to form a cyclopropyl, cyclobutyl, cyclopentyl, or cyclohexyl moiety;
R$^4$ is H, C$_1$–C$_4$ alkyl, C$_2$–C$_4$ alkenyl, or C$_2$–C$_4$ alkynyl;
R$^5$ is C$_1$–C$_4$ alkyl substituted with 0–1 R$^{5b}$;
C$_2$–C$_4$ alkenyl substituted with 0–1 R$^{5b}$; or
C$_2$–C$_4$ alkynyl substituted with 0–1 R$^{5b}$;
R$^{5a}$ is H;
R$^{5b}$, at each occurrence, is independently selected from:
H, methyl, ethyl, propyl, butyl, CF$_3$, OR$^{14}$,
C$_3$–C$_6$ cycloalkyl substituted with 0–2 R$^{5c}$;
phenyl substituted with 0–3 R$^{5c}$; or
5 to 6 membered heterocycle substituted with 0–2 R$^{5c}$;
alternatively, R$^5$ and R$^{5a}$ may be combined to form a cyclopropyl, cyclobutyl, cyclopentyl, or cyclohexyl ring;
W is a bond, —CH$_2$—, —CH(CH$_3$)—, —CH$_2$CH$_2$— or —CH(CH$_3$)CH$_2$—;
X is a bond, phenyl, pyridyl, cyclopentyl, cyclohexyl, piperidinyl, or pyrrolidinyl;
Y is a bond, —CH$_2$CH$_2$—V—, —CH$_2$—V—, or —V—;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —C(=O)O—, or —OC(=O)—;

Z is H;

C$_1$-C$_8$ alkyl substituted with 0–3 R$^{12a}$;
C$_2$-C$_4$ alkenyl substituted with 0–3 R$^{12a}$;
C$_2$-C$_4$ alkynyl substituted with 0–3 R$^{12a}$;
aryl substituted with 0–2 R$^{12a}$;
C$_3$-C$_{10}$ carbocycle substituted with 0–4 R$^{12a}$; or
5 to 10 membered heterocycle containing 1 to 4 heteroatoms selected from nitrogen, oxygen, and sulphur, wherein said 5 to 10 membered heterocycle is substituted with 0–3 R$^{12a}$; or R$^{12a}$, at each occurrence, is independently selected from H, OH, Cl, F, Br, I, CN, NO$_2$, NR$^{15}$R$^{16}$, —C(=O) NR$^{15}$R$^{16}$, CF$_3$, acetyl, SCH$_3$, S(=O)CH$_3$, S(=O)$_2$CH$_3$,
C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl—S—,
C$_1$-C$_3$ alkyl substituted with 0–1 R$^{12C}$;
aryl substituted with 0–4 R$^{12b}$;
C$_3$-C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, NR$^{15}$R$^{16}$, CF$_3$, acetyl, SCH$_3$, S(=O) CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

R$^{12c}$, at each occurrence, is independently selected from aryl substituted with 0–4 R$^{12b}$;
C$_3$-C$_{10}$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{11}$, at each occurrence, is independently selected from H, C$_1$-C$_4$ alkoxy, Cl, F, =O, NR$^{18}$R$^{19}$, C(=O)R$^{17}$, C(=O)OR$^{17}$, CF$_3$;
C$_1$-C$_4$ alkyl substituted with 0–1 R$^{11a}$;
phenyl substituted with 0–3 R$^{11b}$;
C$_3$-C$_6$ carbocycle substituted with 0–3 R$^{11b}$; or
5 to 6 membered heterocycle substituted with 0–3 R$^{11b}$;

R$^{11a}$, at each occurrence, is independently selected from H, C$_1$-C$_4$ alkyl, OR$^{14}$, F, =O, NR$^{15}$R$^{16}$, CF$_3$, or phenyl substituted with 0–3 R$^{11b}$;

R$^{11b}$, at each occurrence, is independently selected from H, OH, Cl, F, NR$^{15}$R$^{16}$, CF$_3$, C$_1$-C$_4$ alkyl, C$_1$-C$_3$ alkoxy, C$_1$-C$_2$ haloalkyl, and C$_1$-C$_2$ haloalkoxy;

R$^{14}$ is H, phenyl, benzyl, C$_1$-C$_4$ alkyl, or C$_2$-C$_4$ alkoxyalkyl;

R$^{15}$, at each occurrence, is independently selected from H, C$_1$-C$_4$ alkyl, benzyl, phenethyl, —C(=O)—(C$_1$-C$_4$ alkyl) and —S(=O)$_2$—(C$_1$-C$_4$ alkyl);

R$^{16}$, at each occurrence, is independently selected from H, OH, C$_1$-C$_4$ alkyl, benzyl, phenethyl, —C(=O)—(C$_1$-C$_4$ alkyl) and —S(=O)$_2$—(C$_1$-C$_4$ alkyl);

R$^{17}$ is H, phenyl, 4-fluorophenyl, 4-chlorophenyl, 4-methylphenyl, 4-trifluorophenyl, (4-fluorophenyl)methyl, (4-chlorophenyl)methyl, (4-methylphenyl)methyl, (4-trifluorophenyl)methyl, methyl, ethyl, propyl, butyl, methoxymethyl, methyoxyethyl, ethoxymethyl, or ethoxyethyl;

R$^{18}$, at each occurrence, is independently selected from H, methyl, ethyl, propyl, butyl, phenyl, benzyl, and phenethyl; and R$^{19}$, at each occurrence, is independently selected from H, methyl, and ethyl;

R$^{19b}$ is H, mehyl, ethyl, propyl, butyl, cyclopropyl, cyclobutyl, cyclopentyl, phenyl, benzyl or phenethyl;

additionally, R$^{18}$ and R$^{19}$, when substituents on the same atom, may be combined to form a 3 to 7 membered heterocyclic ring.

5. A compound of claim 4 of Formula (Ic):

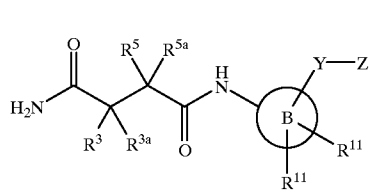

(Ic)

or a pharmaceutically acceptable salt thereof, wherein:

ring B is

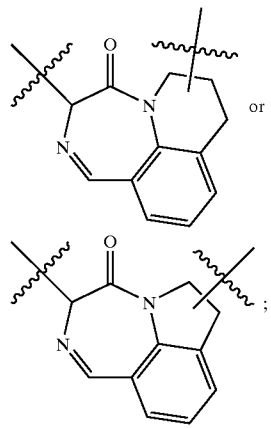

R$^3$ is —CH$_3$, —CH$_2$CH$_3$, —CH$_2$CH$_2$CH$_3$, —CH$_2$CH$_2$CH$_2$CH$_3$, —CH$_2$(CH$_3$)$_2$, —CH(CH$_3$) CH$_2$CH$_3$, —CH$_2$CH(CH$_3$)$_2$, —CH$_2$C(CH$_3$)$_3$, —CH=CH$_2$, —CH$_2$CH=CH$_2$, —CH$_2$C(CH$_3$)=CH$_2$, —CH$_2$CH=C(CH$_3$)$_2$, —CH$_2$CH$_2$CH=CH$_2$, —CH$_2$CH$_2$C(CH$_3$)=CH$_2$, —CH$_2$CH$_2$CH=C(CH$_3$)$_2$, cis-CH$_2$CH=CH(CH$_3$), cis-CH$_2$CH$_2$CH=CH(CH$_3$), trans-CH$_2$CH=CH(CH$_3$), trans-CH$_2$CH$_2$CH=CH (CH$_3$), —C≡CH, —CH$_2$C≡CH, or —CH$_2$C≡C (CH$_3$);

R$^{3a}$ is H;

alternatively, R$^3$ and R$^{3a}$ may be combined to form a cyclopropyl, cyclobutyl, cyclopentyl, or cyclohexyl moiety;

R$^5$ is —CH$_3$, —CH$_2$CH$_3$, —CH$_2$CH$_2$CH$_3$, —CH$_2$(CH$_3$)$_2$, —CH$_2$CH$_2$CH$_2$CH$_3$, —CH(CH$_3$)CH$_2$CH$_3$, —CH$_2$CH (CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, CH(CH$_2$CH$_3$)$_2$, —CH=CH$_2$, —CH$_2$CH=CH$_2$, —CH=CHCH$_3$, cis-CH$_2$CH=CH (CH$_3$), trans-CH$_2$CH=CH(CH$_3$), —CH$_2$CH=C (CH$_3$)$_2$, cis-CH$_2$CH=CHCH$_2$CH$_3$, trans-CH$_2$CH=CHCH$_2$CH$_3$, cis-CH$_2$CH$_2$CH=CH(CH$_3$), trans-CH$_2$CH$_2$CH=CH(CH$_3$), —C≡CH, —CH$_2$C≡CH, —CH$_2$C≡C(CH$_3$), CH$_2$CH$_2$C≡CH, or —CH$_2$CH$_2$C≡C(CH$_3$); R$^{5a}$ is H;

alternatively, R$^5$ and R$^{5a}$ may be combined to form a cyclopropyl, cyclobutyl, cyclopentyl, or cyclohexyl ring;

191

Y is a bond, —CH$_2$CH$_2$—V—, —CH$_2$—V—, or —V—;
V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —C(=O)O—, or —OC(=O)—;
Z is H;
  C$_1$–C$_4$ alkyl substituted with 0–1 R$^{12a}$;
  C$_2$–C$_4$ alkenyl substituted with 0–1 R$^{12a}$;
  C$_2$–C$_4$ alkynyl substituted with 0–1 R$^{12a}$;
  phenyl substituted with 0–2 R$^{12a}$;
  C$_3$–C$_6$ cycloalkyl, selected from cyclopropyl, cyclobutyl, cyclopentyl, and cyclohexyl; substituted with 0–2 R$^{12a}$; or
  5 to 10 membered heterocycle selected from pyridinyl, pyrimidinyl, triazinyl, furanyl, thienyl, thiazolyl, pyrrolyl, pyrrolidinyl, piperidinyl, N-piperinyl, pyrazolyl, imidazolyl, oxazolyl, isoxazolyl, tetrazolyl, morpholinyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl; wherein said 5 to 10 membered heterocycle is substituted with 0–2 R$^{12a}$;
R$^{12a}$, at each occurrence, is independently selected from H, OH, Cl, F, Br, CN, NO$_2$, NR$^{15}$R$^{16}$, —C(=O)NR$^{15}$R$^{16}$, CF$_3$, acetyl, SCH$_3$, SCF$_3$, S(=O)CH$_3$, S(=O)$_2$CH$_3$, methyl, ethyl, propyl, butyl, methoxy, ethoxy, propoxy, cyclopropyl, cyclobutyl, cyclopentyl, cyclohexyl, C$_1$–C$_2$ haloalkyl, C$_1$–C$_2$ haloalkoxy,
  C$_1$–C$_3$ alkyl substituted with R$^{12c}$;
  phenyl substituted with 0–3 R$^{12b}$;
  5 to 10 membered heterocycle selected from pyridinyl, pyrimidinyl, triazinyl, furanyl, thienyl, thiazolyl, pyrrolyl, pyrrolidinyl, piperidinyl, N-piperinyl, pyrazolyl, imidazolyl, oxazolyl, isoxazolyl, tetrazolyl, morpholinyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl; wherein said 5 to 10 membered heterocycle is substituted with 0–3 R$^{12b}$;
R$^{12b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;
R$^{12c}$, at each occurrence, is independently selected from phenyl substituted with 0–4 R$^{12b}$;
  C$_3$–C$_{10}$ cycloalkyl, selected from cyclopropyl, cyclobutyl, cyclopentyl, and cyclohexyl; substituted with 0–4 R$^{12b}$; or
  5 to 10 membered heterocycle selected from pyridinyl, pyrimidinyl, triazinyl, furanyl, thienyl, thiazolyl, pyrrolyl, pyrrolidinyl, piperidinyl, N-piperinyl, pyrazolyl, imidazolyl, oxazolyl, isoxazolyl, tetrazolyl, morpholinyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl; wherein said 5 to 10 membered heterocycle is substituted with 0–3 R$^{12b}$;
R$^{11}$, at each occurrence, is independently selected from H, Cl, F, NR$^{18}$R$^{19}$, methyl, ethyl, methoxy, ethoxy, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—; and

192

R$^{15}$, at each occurrence, is independently selected from H, methyl, ethyl, propyl, butyl, benzyl, phenethyl, methyl-C(=O)—, ethyl-C(=O)—, propyl-C(=O)—, butyl-C(=O)—, methyl-S(=O)$_2$—, ethyl-S(=O)$_2$—, propyl-S(=O)$_2$—, and butyl-S(=O)$_2$—;
R$^{16}$, at each occurrence, is independently selected from H, OH, methyl, ethyl, propyl, butyl, benzyl, phenethyl, methyl-C(=O)—, ethyl-C(=O)—, propyl-C(=O)—, butyl-C(=O)—, methyl-S(=O)$_2$—, ethyl-S(=O)$_2$—, propyl-S(=O)$_2$—, and butyl-S(=O)$_2$—;
R$^{18}$, at each occurrence, is independently selected from H, methyl, ethyl, propyl, butyl, phenyl, benzyl, and phenethyl; and
R$^{19}$, at each occurrence, is independently selected from H, methyl, and ethyl;
R$^{19b}$ is H, mehyl, ethyl, propyl, butyl, cyclopropyl, cyclobutyl, cyclopentyl, phenyl, benzyl or phenethyl; additionally, R$^{18}$ and R$^{19}$, when substituents on the same atom, may be combined to form a 3 to 7 membered heterocyclic ring selected from pyrrolidinyl, piperidinyl, homopiperidinyl, piperazinyl, and morpholinyl.

6. A compound selected from:
  (2R,3S)-3-allyl-2-isobutyl-N$^1$-(4-oxo-1-phenyl-3,4,6,7-tetrahydro[1,4]diazepino-[6,7,1-hi]indol-3-yl)butandiamide or a pharmaceutically acceptable salt thereof.

7. A pharmaceutical composition comprising a compound of claim 1 and a pharmaceutically acceptable carrier.

8. A pharmaceutical composition comprising a compound of claim 2 and a pharmaceutically acceptable carrier.

9. A pharmaceutical composition comprising a compound of claim 3 and a pharmaceutically acceptable carrier.

10. A pharmaceutical composition comprising a compound of claim 4 and a pharmaceutically acceptable carrier.

11. A pharmaceutical composition comprising a compound of claim 5 and a pharmaceutically acceptable carrier.

12. A pharmaceutical composition comprising a compound of claim 6 and a pharmaceutically acceptable carrier.

13. A method for the treatment of Alzheimer's Disease comprising administering to a host in need of such treatment a therapeutically effective amount of a compound of claim 1.

14. A method for the treatment of Alzheimer's Disease comprising administering to a host in need of such treatment a therapeutically effective amount of a compound of claim 2.

15. A method for the treatment of Alzheimer's Disease comprising administering to a host in need of such treatment a therapeutically effective amount of a compound of claim 3.

16. A method for the treatment of Alzheimer's Disease comprising administering to a host in need of such treatment a therapeutically effective amount of a compound of claim 4.

17. A method for the treatment of Alzheimer's Disease comprising administering to a host in need of such treatment a therapeutically effective amount of a compound of claim 5.

18. A method for the treatment of Alzheimer's Disease comprising administering to a host in need of such treatment a therapeutically effective amount of a compound of claim 6.

* * * * *